(12) United States Patent
Allen et al.

(10) Patent No.: US 11,548,903 B2
(45) Date of Patent: Jan. 10, 2023

(54) BICYCLIC THIAZINE AND OXAZINE DERIVATIVES AS BETA-SECRETASE INHIBITORS AND METHODS OF USE

(71) Applicant: AMGEN INC., Thousand Oaks, CA (US)

(72) Inventors: Jennifer R. Allen, Newbury Park, CA (US); Matthew P. Bourbeau, Woodland Hills, CA (US); Ning Chen, Thousand Oaks, CA (US); Qingyian Liu, Camarillo, CA (US); Liping H. Pettus, Thousand Oaks, CA (US); Aaron C. Siegmund, Ventura, CA (US)

(73) Assignee: Amgen Inc., Thousand Oaks, CA (US)

( * ) Notice: Subject to any disclaimer, the term of this patent is extended or adjusted under 35 U.S.C. 154(b) by 712 days.

(21) Appl. No.: 16/466,202

(22) PCT Filed: Dec. 13, 2017

(86) PCT No.: PCT/US2017/066180
§ 371 (c)(1),
(2) Date: Jun. 3, 2019

(87) PCT Pub. No.: WO2018/112084
PCT Pub. Date: Jun. 21, 2018

(65) Prior Publication Data
US 2020/0199153 A1   Jun. 25, 2020

Related U.S. Application Data

(60) Provisional application No. 62/570,429, filed on Oct. 10, 2017, provisional application No. 62/434,719, filed on Dec. 15, 2016.

(51) Int. Cl.
*C07D 513/04* (2006.01)
*C07D 498/04* (2006.01)
*A61P 25/28* (2006.01)

(52) U.S. Cl.
CPC ............ *C07D 513/04* (2013.01); *A61P 25/28* (2018.01); *C07D 498/04* (2013.01)

(58) Field of Classification Search
CPC .................. C07D 513/04; C07D 498/04
See application file for complete search history.

(56) References Cited

U.S. PATENT DOCUMENTS

| | | |
|---|---|---|
| 5,441,870 A | 8/1995 | Seubert et al. |
| 5,712,130 A | 1/1998 | Hajko et al. |
| 5,942,400 A | 8/1999 | Anderson et al. |
| 2009/0082560 A1 | 3/2009 | Kobayashi et al. |
| 2009/0209755 A1 | 8/2009 | Suzuki et al. |
| 2010/0075957 A1 | 3/2010 | Tamura et al. |
| 2010/0093999 A1 | 4/2010 | Motoki et al. |
| 2010/0160290 A1 | 6/2010 | Kobayashi et al. |
| 2011/0152253 A1 | 6/2011 | Motoki et al. |
| 2012/0238557 A1 | 9/2012 | Masui et al. |
| 2012/0245154 A1 | 9/2012 | Anan et al. |
| 2012/0245157 A1 | 9/2012 | Masui et al. |
| 2016/0046618 A1 | 2/2016 | Allen et al. |

FOREIGN PATENT DOCUMENTS

| | | |
|---|---|---|
| EP | 2 147 914 A1 | 1/2010 |
| EP | 2 151 435 A1 | 2/2010 |
| EP | 2 305 672 A1 | 4/2011 |
| EP | 2 703 401 A1 | 3/2014 |
| EP | 1 942 105 B1 | 4/2014 |
| WO | 2000/017369 A2 | 3/2000 |

(Continued)

OTHER PUBLICATIONS

Chen, et al. Amyloid beta:structure, biology and structure-based therapeutic development. Acta Pharmacologica Sinica 2017: 1205-1235.*

Alzheimer's disease [online] retrieved from the internet on Mar. 25, 2022 URL https://www.mayoclinic.org/diseases-conditions/alzheimers-disease/symptoms-causes/syc-20350447.*

Alzforum Networking for a Cure, "Barcelona: Out of Left Field—Hit to the Eye Kills Bace Inhibitor," pp. 1-7 (Mar. 31, 2011); access online: www.alzforum.org/news/conference-coverage/barcelona-out-left-field-hit-eye-kills-bace-inhibitor (last accessed Dec. 16, 2015).

Best, J. D. et al., "Quantitative Measurement of Changes in Amyloid-β(40) in the Rat Brain and Cerebrospinal Fluid Following Treatment with the γ-Secretase Inhibitor LY-411575 [N2-[(2S)-2-(3,5-Difluorophenyl)-2-hydroxyethanoyl]-N1-[(7S)-5-methyl-6-oxo-6,7-dihydro-5H-dibenzo[b,d]azepin-7-yl]-L-alaninamide]," Journal of Pharmacology and Experimental Therapeutics 313(2):902-908 (2005).

(Continued)

*Primary Examiner* — Shawquia Jackson
(74) *Attorney, Agent, or Firm* — Markus Bergauer

(57) ABSTRACT

The present disclosure provides a new class of compounds useful for the modulation of beta-secretase enzyme (BACE) activity. The compounds have a general Formula (I): (Formula (I)) wherein variables X, Y, $R^2$, $R^3$, $R^4$, $R^5$, $R^6$, and n of Formula (I) are defined herein. This disclosure also provides pharmaceutical compositions comprising the compounds, and uses of the compounds and compositions for treatment of disorders and/or conditions related to Aβ plaque formation and deposition, resulting from the biological activity of BACE. Such BACE mediated disorders include, for example, Alzheimer's disease, cognitive deficits, cognitive impairments, and other central nervous system conditions.

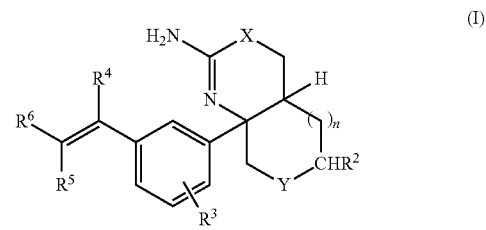

29 Claims, No Drawings

(56) References Cited

FOREIGN PATENT DOCUMENTS

| | | | |
|---|---|---|---|
| WO | 2009/134617 | A1 | 11/2009 |
| WO | 2009/151098 | A1 | 12/2009 |
| WO | 2010/013302 | A1 | 2/2010 |
| WO | 2010/013794 | A1 | 2/2010 |
| WO | 2011/005738 | A1 | 1/2011 |
| WO | 2011/009898 | A1 | 1/2011 |
| WO | 2011/029803 | A1 | 3/2011 |
| WO | 2011/044181 | A1 | 4/2011 |
| WO | 2011/069934 | A1 | 6/2011 |
| WO | 2012/095463 | A1 | 7/2012 |
| WO | 2012/095469 | A1 | 7/2012 |
| WO | 2012/098213 | A1 | 7/2012 |
| WO | 2012/098461 | A1 | 7/2012 |
| WO | 2012/138734 | A1 | 10/2012 |
| WO | 2012/139425 | A1 | 10/2012 |
| WO | 2012/147762 | A1 | 11/2012 |
| WO | 2012/156284 | A1 | 11/2012 |
| WO | 2012/162330 | A1 | 11/2012 |
| WO | 2012/162334 | A1 | 11/2012 |
| WO | 2013/004676 | A1 | 1/2013 |
| WO | 2013/027188 | A1 | 2/2013 |
| WO | 2013/028670 | A1 | 2/2013 |
| WO | 2013/030713 | A1 | 3/2013 |
| WO | 2013/142613 | A1 | 9/2013 |
| WO | 2013/164730 | A1 | 11/2013 |
| WO | 2013/182638 | A1 | 12/2013 |
| WO | 2014/013076 | A1 | 1/2014 |
| WO | 2014/045162 | A1 | 3/2014 |
| WO | 2014/062549 | A1 | 4/2014 |
| WO | 2014/062553 | A1 | 4/2014 |
| WO | 2014/065434 | A1 | 5/2014 |
| WO | 2014/066132 | A1 | 5/2014 |
| WO | 2014/093190 | A1 | 6/2014 |
| WO | 2014/097038 | A1 | 6/2014 |
| WO | 2014/098831 | A1 | 6/2014 |
| WO | 2014/099788 | A9 | 6/2014 |
| WO | 2014/099794 | A1 | 6/2014 |
| WO | 2014/138484 | A1 | 9/2014 |
| WO | 2014/143579 | A1 | 9/2014 |
| WO | 2016/022724 | A1 | 2/2016 |
| WO | 2016/172255 | A1 | 10/2016 |
| WO | 2017/024180 | A1 | 2/2017 |
| WO | 2018/112081 | A1 | 6/2018 |
| WO | 2018/112083 | A | 6/2018 |
| WO | 2018/112084 | A1 | 6/2018 |
| WO | 2018/112086 | A1 | 6/2018 |
| WO | 2018/112094 | A1 | 6/2018 |

OTHER PUBLICATIONS

Citron, M., "β-Secretase inhibition for the treatment of Alzheimer's disease—promise and challenge," Trends in Pharmacological Sciences 25(2):92-97 (2004).
Cole, S.L. and Vassar, R., "The Alzheimer's disease β-secretase enzyme, BACE1," Molecular Neurodegeneration 2(22):1-25 (2007).
De Meyer, G. et al., "Diagnosis-Independent Alzheimer Disease Biomarker Signature in Cognitively Normal Elderly People," Arch. Neurol. 67(8):949-956 (2010).
Dovey, H. F. et al., "Functional gamma-secretasae inhibitors reduce beta-amyloid peptide levels in brain," Journal of Neurochemistry 76:173-181 (2001).
Follo, C. et al., "Knock-Down of Cathepsin D Affects the Retinal Pigment Epithelium, Impairs Swim-Bladder Ontogenesis and Causes Premature Death in Zebrafish," PLoS One 6(7):e21908, pp. 1-13 (2011).
Games, D. et al., "Alzheimer-type neuropathology in transgenic mice overexpressing V717F β-amyloid precursor protein," Nature 373:523-527 (1995).
Götz, J. et al., "Transgenic animal models of Alzheimer's disease and related disorders: histopathology, behavior and therapy," Molecular Psychiatry 9:664-683 (2004).

Gulnik, S. V. et al., "Design of sensitive fluorogenic substrates for human cathepsin D," FEBS Lett. 413:379-384 (1997).
Harris, J. A. et al, "Transsynaptic Progression of Amyloid-β-Induced Neuronal Dysfunction within the Entorhinal-Hippocampal Network," Neuron 68:428-441 (2010).
Henley, D. B. et al., "Development of semagacestat (LY450139), a functional γ-secretase inhibitor, for the treatment of Alzheimer's disease," Expert Opin. Pharmacother. 10(10):1657-1664 (2009).
Hsia, A. Y. et al., "Plaque-independent disruption of neural circuits in Alzheimer's disease mouse models," Proc. Natl. Acad. Sci. USA 96:3228-3233 (1999).
Hsiao, K. et al., "Correlative Memory Deficits, Aβ Elevation, and Amyloid Plaques in Transgenic Mice," Science 274:99-102 (1996).
International Preliminary Report on Patentability and Written Opinion for International Patent Application No. PCT/US2017/066180, dated Jun. 18, 2019, pp. 1-6.
International Search Report for International Patent Application No. PCT/US2017/066180, dated Mar. 15, 2018, pp. 1-6.
Joachim, C. L. and Selkoe, D. J., "The Seminal Role of β-Amyloid in the Pathogenesis of Alzheimer Disease," Alzheimer Disease and Associated Disorders 6(1):7-34 (1992).
Koike, M. et al., "Involvement of two different cell death pathways in retinal atrophy of cathepsin D-deficient mice," Molecular and Cellular Neuroscience 22:146-161 (2003).
Luo, Y. et al., "Mice deficient in BACE1, the Alzheimer's β-secretase, have normal phenotype and abolished b-amyloid generation," Nature Neuroscience 4:231-232 (2001).
Palop, J. J. and Mucke, L., "Amyloid-β-induced neuronal in Alzheimer's disease: from synapses toward neural networks," Nature Neuroscience 13(7):812-818 (2010).
Sabbagh, M. N. et al., "β-Amyloid and Treatment Opportunities for Alzheimer's Disease," Alzheimer's Disease Review 3:1-19 (1997).
Selkoe, D. J., "Soluble oligomers of the amyloid β-protein impair synaptic plasticity and behavior," Behavioural Brain Research 192:106-113 (2008).
Selkoe, D. J., "The Molecular Pathology of Alzheimer's Disease," Neuron 6:487-498 (1991).
Seubert, P. et al., "Isolation and quantification of soluble Alzheimer's β-peptide from biological fluids," Nature 359:325-327 (1992).
Shacka, J. J. and Roth, K. A., "Cathepsin D Deficiency and NCL/Batten Disease: There's More to Death than Apoptosis," Autophagy, 3(5):474-476 (2007).
Shankar, G. M. et al., "Amyloid-β protein dimers isolated directly from Alzheimer's brains impair synaptic plasticity and memory," Nature Medicine 14(8):837-842 (2008).
Siemers, E. R. et al., "Effects of a γ-secretase inhibitor in a randomized study of patients with Alzheimer's disease," Neurology 66:602-604 (2006).
Siemers, E. R. et al., "Safety, Tolerability, and Effects on Plasma and Cerebrospinal Fluid Amyloid-β After Inhibition of γ-Secretase," Clin. Neuropharmacol. 30(6):317-325 (2007).
Sinha, S. et al., "Purification and cloning of amyloid precursor protein β-secretase from human brain," Nature 402:537-540 (1999).
Tanzi, R. E. and Bertram, L., "Twenty Years of the Alzheimer's Disease Amyloid Hypothesis: A Genetic Perspective," Cell 120(4):545-555 (2005).
Vassar, R. and Yan, R., "Targeting the β secretase BACE1 for Alzheimer's disease therapy," Lancet Neurology 13:319-329 (2014).
Walsh, D. M. and Selkoe, D. J., "Deciphering the Molecular Basis of Memory Failure in Alzheimer's Disease," Neuron 44(1):181-193 (2004).
Yasuda, Y. et al., "Characterization of New Fluorogenic Substrates for the Rapid and Sensitive Assay of Cathepsin E and Cathepsin D," J. Biochem. 125:1137-1143 (1999).
Yan R., "Stepping closer to treating Alzheimer's disease patients with BACE1 inhibitor drugs," Transl. Neurodegener. 5(13):1-11 (2016).
"A Study of CAD106 and CNP520 Versus Placebo in Participants at Risk for the Onset of Clinical Symptoms of Alzheimer's Disease (Generation S1)" https://clinicaltrials.gov/ct2/show/NCT02565511 (Nov 10, 2016—submitted date).

* cited by examiner

BICYCLIC THIAZINE AND OXAZINE DERIVATIVES AS BETA-SECRETASE INHIBITORS AND METHODS OF USE

CROSS-REFERENCE TO RELATED APPLICATIONS

This application is a national stage application under 35 U.S.C. § 371 of International Application No. PCT/US2017/066180, having an international filing date of Dec. 13, 2017, which claims the benefit of U.S. Provisional Patent Application No. 62/434,719, filed Dec. 15, 2016 and U.S. Provisional Patent Application No. 62/570,429, filed Oct. 10, 2017, each of which is incorporated by reference herein in its entirety.

FIELD

The present disclosure relates generally to pharmaceutically active compounds and pharmaceutical compositions thereof for the modulation of beta site amyloid precursor protein cleaving enzyme (BACE) activity. Provided herein are uses of these compounds and pharmaceutical compositions thereof for treatment of disorders and/or conditions related to beta-amyloid plaque formation and deposition, resulting from the biological activity of BACE. Such BACE mediated disorders include, for example, Alzheimer's disease, cognitive deficits, cognitive impairments, and other central nervous system conditions.

BACKGROUND

Alzheimer's disease (AD) affects greater than 12 million aging people worldwide, and, importantly, the number affected continues to grow. AD accounts for the majority of dementias clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to treat AD effectively upon diagnosis.

AD is characterized by two major physiological changes in the brain. The first change, beta amyloid plaque formation, supports the "amyloid cascade hypothesis" which conveys the thought that AD is caused by the formation of characteristic beta amyloid (Aβ) peptide deposits in the brain (commonly referred to as Aβ "plaques" or "plaque deposits") and in cerebral blood vessels (beta amyloid angiopathy). A wealth of evidence suggests that Aβ and accompanying amyloid plaque formation is central to the pathophysiology of AD and is likely to play an early role in this intractable neurodegenerative disorder. Yan et al., *Lancet Neurol.* 13(3):319-329 (2014). The second change in AD is the formation of intraneuronal tangles, consisting of an aggregate form of the microtubule-binding protein tau. Besides being found in patients with AD, intraneuronal tangles are also found in other dementia-inducing disorders. Joachim et al., *Alzheimer. Dis. Assoc. Disord.* 6(1):7-34 (1992).

Several lines of evidence indicate that progressive cerebral deposition of Aβ peptide plays a seminal role in the pathogenesis of AD and can precede cognitive symptoms by years or even decades. Selkoe, *Neuron* 6(4):487-498 (1991). Release of Aβ peptide from neuronal cells grown in culture and the presence of Aβ peptide in cerebrospinal fluid (CSF) of both normal individuals and AD patients has been demonstrated. Seubert et al., *Nature* 359:325-327 (1992). Autopsies of AD patients have revealed large numbers of lesions comprising Aβ and tau peptides in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that Aβ peptide formation is a causative precursor or factor in the development of AD. More specifically, deposition of Aβ peptide in areas of the brain responsible for cognition is believed to be a major factor in the development of AD. Aβ plaques are primarily composed of Aβ peptide. Aβ peptide is derived from the proteolytic cleavage of a large transmembrane amyloid precursor protein (APP), and is a peptide comprised of about 39-42 amino acid residues. Aβ 1-42 (42 amino acids long) is thought to be the major component of these plaque deposits in the brains of AD patients. Citron, *Trends Pharmacol. Sci.* 25(2):92-97 (2004).

Similar plaques appear in some variants of Lewy body dementia and in inclusion body myositis, a muscle disease. Aβ peptides also form aggregates coating cerebral blood vessels in cerebral amyloid angiopathy. These plaques are composed of fibrillar Aβ aggregates that display a characteristic β-sheet structure, a protein fold shared by other peptides such as prions associated with protein misfolding diseases. Research on laboratory rats suggest that the dimeric, soluble form of the peptide is a causative agent in the development of AD and is the smallest synaptotoxic species of soluble amyloid beta oligomer. Shankar et al., *Nat. Med.* 14(8):837-842 (2008).

Several aspartyl proteases, including β-secretase and γ-secretase, are involved in the processing or cleavage of APP, resulting in the formation of Aβ peptide. β-Secretase (BACE, also commonly referred to as memapsin) is the first to cleave APP to generate two fragments: (1) a first N-terminus fragment (sAPPβ) and (2) a second C-99 fragment, which is subsequently cleaved by γ-secretase to generate the Aβ peptide. APP has also been found to be cleaved by α-secretase to produce sAPPα, a secreted form of APP that does not result in Aβ plaque formation. This alternate pathway precludes the formation of Aβ peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the β-secretase specific cleavage site. BACE is present in two forms, BACE 1 and BACE 2, designated as such depending upon the specific cleavage site of APP. β-Secretase is described in Sinha et al., *Nature* 402:537-540 (1999) and International Patent Application Publication No. WO2000/017369. It has been proposed that Aβ peptide accumulates as a result of APP processing initiated by BACE. Moreover, in vivo processing of APP at the β-secretase cleavage site is thought to be a rate-limiting step in Aβ peptide production.

Sabbagh et al., *Alzheimer's Disease Review* 3:1-19 (1997). Thus, inhibition of the BACE enzyme activity is desirable for the treatment of AD.

Studies have shown that the inhibition of BACE may be linked to the treatment of AD. The BACE enzyme is essential for the generation of Aβ peptide. BACE knockout mice do not produce Aβ peptide and are free from AD associated pathologies including neuronal loss and certain memory deficits. Cole et al., *Molecular Neurodegeneration* 2:22, pages 1-25 (2007). When crossed with transgenic mice that over express APP, the progeny of BACE deficient mice show reduced amounts of Aβ peptide in brain extracts as compared with control animals. Luo et al., *Nat. Neurosci.* 4(3):231-232 (2001). The fact that BACE initiates the formation of Aβ peptide, and the observation that BACE levels are elevated in this disease provide direct and compelling reasons to develop therapies directed at BACE inhibition, thus, reducing Aβ peptide formation and its associated toxicities. To this end, inhibition of β-secretase activity and a corresponding reduction of Aβ peptide in the brain should provide a therapeutic method for treating AD and other Aβ peptide or plaque related disorders.

Consequently, the approach of regulating or reducing Aβ peptide formation and deposition as a potential treatment for AD has received tremendous attention, support and commitment from both researchers and investors alike. A small molecule γ-secretase inhibitor, LY450139 ("Semagacestat"), an Aβ peptide lowering agent, advanced to phase III clinical trials for the treatment of AD. The pharmacokinetics of semagacestat in plasma, as well as the plasma and cerebral spinal fluid (CSF) Aβ peptide levels as pharmacodynamic responses to semagacestat administration were evaluated in healthy human subjects in single and multiple doses, and pharmacokinetic and pharmacodynamic changes were also assessed in mild to moderate AD patients in two (2) clinical trials (Henley et al., *Expert Opin. Pharmacother.* 10(10): 1657-1664 (2009); Siemers et al., *Clin. Neuropharmacol.* 30(6): 317-325 (2007); and Siemers et al., *Neurology* 66(4): 602-604 (2006)). Additional approaches have been taken in attempts to treat AD and plaque-related disorders. See, for example, Yan et al., *Lancet Neurology* 13(3):319-329 (2014).

Furthermore, each of the following exemplary patent application publications describes inhibitors of BACE, useful for treating AD and other β-secretase mediated disorders: WO2014/098831, WO2014/099794, WO2014/099788, WO2014/097038, WO2014/093190, WO2014/066132, WO2014/065434, WO2014/062553, WO2014/062549, WO2014/045162, WO2014/013076, WO2013/182638, WO2013/164730, WO2013/030713, WO2013/028670, WO2013/004676, WO2012/162334, WO2012/162330, WO2012/147762, WO2012/139425, WO2012/138734, US2012/0245157, US2012/0245154, US2012/0238557, WO2011/029803, WO2011/005738, US2011/0152253, WO2010/013794, WO2010/013302, US2010/0160290, US2010/0075957, WO2009/151098, WO2009/134617, US2009/0209755, US2009/0082560, EP2703401 (equivalent of WO2012/146762) and EP1942105.

The lysosomal aspartic protease Cathepsin D (CatD) is ubiquitously expressed in eukaryotic organisms. CatD activity is essential to accomplish the acid-dependent extensive or partial proteolysis of protein substrates within endosomal and lysosomal compartments therein delivered via endocytosis, phagocytosis or autophagocytosis. CatD may also act at physiological pH on small-size substrates in the cytosol and in the extracellular milieu. Mouse and fruit fly CatD knock-out models have highlighted the multi-pathophysiological roles of CatD in tissue homeostasis and organ development.

Inhibition of protein CatD has been implicated in undesirable side effects. For instance, the inhibition of CatD is believed to be linked to adverse retinal development and retinal atrophy. Particularly, in mice it was found that CatD is essential for the metabolic maintenance of retinal photoreceptor cells and that its deficiency induces apoptosis of the cells, while the loss of inner nuclear layer (INL) neurons is mediated by nitric oxide release from microglial cells. However, in the very same mice, it was also found that no atrophic change was detected in the retina of mice deficient in Cathepsin B or L. Koike et al., *Mol. Cell Neurosci.* 22(2):146-161 (2003). Further, animal models of CatD deficiency are characterized by a progressive and relentless neurodegenerative phenotype similar to that observed in Neuronal Ceroid Lipofuscinoses (NCL), a group of pediatric neurodegenerative diseases known collectively as Batten Disease. It has been shown that the targeted deletion of the pro-apoptotic molecule Bax prevents apoptotic markers, but not neuronal cell death and neurodegeneration induced by CatD deficiency, which suggests that alterations in the macroautophagy-lysosomal degradation pathway can mediate neuronal cell death in NCL/Batten Disease in the absence of apoptosis. Shacka et al., *Autophagy* 3(5):474-476 (2007). Finally, an adverse effect of the inhibition of CatD is evident from the data presented in Folio et al., *PLoS One* 6(7):e21908 (2011). The authors of the PLoS One paper found that knock-down of CatD affects the retinal pigment epithelium, impairs swim-bladder ontogenesis and causes premature death in zebrafish. The main phenotypic alterations produced by CatD knock-down in zebrafish were: 1. abnormal development of the eye and of retinal pigment epithelium; 2. absence of the swim-bladder; 3. skin hyperpigmentation; 4. reduced growth and premature death. Rescue experiments confirmed the involvement of CatD in the developmental processes leading to these phenotypic alterations.

Moreover, such toxicity findings which, in view of the literature, may have played a role in the termination of a human BACE-mediated AD clinical trial. Eli Lilly terminated a phase I clinical trial of LY 2811376 after rat toxicology studies showed that a higher compound dose given for three months damaged the pigment epithelium of the rat's eye. The retinal layer had inclusions and extensive damage. The Phase I dosing trial was terminated and people brought in for eye assessments did not show any abnormalities. (Alzheimer's Research Forum News, Mar. 31, 2011 reporting on Martin Citron's presentation at the AD/PD Conference March 2011 in Barcelona, Spain).

Hence, it is desirable to provide compounds which modulate the activity of and are selective for BACE, while not suffering from undesirable side effects possibly due to intervention with or the reduction and/or direct or indirect inhibition of the expression and/or function of other proteins or biological pathways.

SUMMARY

The compounds disclosed herein are useful for the modulation of β-secretase activity, and as treatment of AD. Particularly, the compounds provided herein are useful for the regulation or reduction of the formation of Aβ peptide and, consequently, the regulation and/or reduction of formation of Aβ plaque both in the brain, as well as in the CNS. To this end, the compounds are useful for the treatment of AD and other β-secretase and/or plaque-related and/or mediated disorders. For example, the compounds are useful for the prophylaxis and/or treatment, acute and/or chronic, of AD and other diseases or conditions involving the deposition or accumulation of Aβ peptide, and formation of plaque, in the brain.

First, provided herein is a compound of Formula I

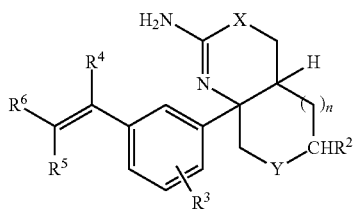

or a tautomer thereof, or a pharmaceutically acceptable salt of said compound or tautomer, wherein X is S or O;

Y is O or $NR^1$;

$R^1$ is —$C(O)C_{1-6}$alkyl, —$C(O)OC_{1-6}$alkyl, or 6-membered nitrogen-containing heteroaryl, wherein the $C_{1-6}$alkyl of —$C(O)C_{1-6}$alkyl and —$C(O)OC_{1-6}$alkyl is optionally substituted with 1 to 3 fluoro substituents, and wherein the heteroaryl is optionally substituted with 1 to 3 substituents independently selected from halogen, $C_{1-6}$alkyl, or $C_{1-6}$alkoxy;

$R^2$ is H or $C_{1-6}$alkyl, wherein the $C_{1-6}$alkyl is optionally substituted with 1 to 3 fluoro substituents;

$R^3$ is halogen;

$R^4$ is H or F;

one of $R^5$ and $R^6$ is F or H and the other of $R^5$ and $R^6$ is a 6-membered nitrogen-containing heteroaryl, which heteroaryl is optionally substituted with 1 to 3 substituents independently selected from halogen, —CN, $C_{1-6}$alkyl, $C_{1-6}$alkoxy, 2-propynyloxy, 2-butynyloxy, 3-butyn-2-yloxy, or (3-methyl-1,2,4-oxadiazol-5-yl)methoxy, wherein the $C_{1-6}$alkyl or $C_{1-6}$alkoxy is optionally substituted with 1 to 4 substituents independently selected from F or methoxy; and n is 0 or 1.

Second, provided herein are pharmaceutical compositions comprising a compound of Formula I and a pharmaceutically acceptable excipient.

Third, provided herein are compounds of Formula I or pharmaceutical compositions thereof for use as a medicament.

Fourth, provided herein are compounds of Formula I or pharmaceutical compositions thereof for use in reducing beta amyloid peptide levels in the cerebral spinal fluid of a subject.

Fifth, provided herein are compounds of Formula I or pharmaceutical compositions thereof for use in treating Alzheimer's disease, cognitive impairment, or a combination thereof in a subject. In addition, provided herein are compounds of Formula I or pharmaceutical compositions thereof for use in treating a neurological disorder selected from mild cognitive impairment, Down's syndrome, hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease, or a combination thereof in a subject.

Sixth, provided herein are compounds of Formula I or pharmaceutical compositions thereof for use in reducing formation of plaque in the brain of a subject.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

DETAILED DESCRIPTION

Provided herein as Embodiment 1 is a compound of Formula I

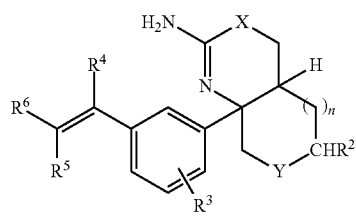

or a tautomer thereof, or a pharmaceutically acceptable salt of said compound or tautomer, wherein X is S or O;

Y is O or $NR^1$;

$R^1$ is —$C(O)C_{1-6}$alkyl, —$C(O)OC_{1-6}$alkyl, or 6-membered nitrogen-containing heteroaryl, wherein the $C_{1-6}$alkyl of —$C(O)C_{1-6}$alkyl and —$C(O)OC_{1-6}$alkyl is optionally substituted with 1 to 3 fluoro substituents, and wherein the heteroaryl is optionally substituted with 1 to 3 substituents independently selected from halogen, $C_{1-6}$alkyl, or $C_{1-6}$alkoxy;

$R^2$ is H or $C_{1-6}$alkyl, wherein the $C_{1-6}$alkyl is optionally substituted with 1 to 3 fluoro substituents;

$R^3$ is halogen;

$R^4$ is H or F;

one of $R^5$ and $R^6$ is F or H and the other of $R^5$ and $R^6$ is a 6-membered nitrogen-containing heteroaryl, which heteroaryl is optionally substituted with 1 to 3 substituents independently selected from halogen, —CN, $C_{1-6}$alkyl, $C_{1-6}$alkoxy, 2-propynyloxy, 2-butynyloxy, 3-butyn-2-yloxy, or (3-methyl-1,2,4-oxadiazol-5-yl)methoxy, wherein the $C_{1-6}$alkyl or $C_{1-6}$alkoxy is optionally substituted with 1 to 4 substituents independently selected from F or methoxy; and n is 0 or 1.

Provided herein as Embodiment 2 is the compound according to Embodiment 1, or a tautomer thereof, or a pharmaceutically acceptable salt of said compound or tautomer, wherein the compound of Formula I is a compound of Formula II

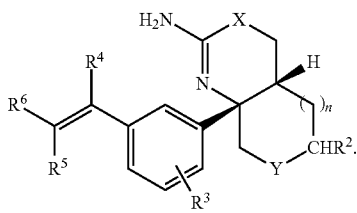

II

Provided herein as Embodiment 3 is the compound according to Embodiment 1, or a tautomer thereof, or a pharmaceutically acceptable salt of said compound or tautomer, wherein the compound of Formula I is a compound of Formula III

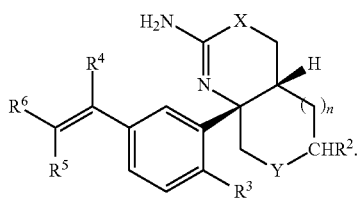

III

Provided herein as Embodiment 4 is the compound according to Embodiment 1, or a tautomer thereof, or a pharmaceutically acceptable salt of said compound or tautomer, wherein the compound of Formula I is a compound of Formula III

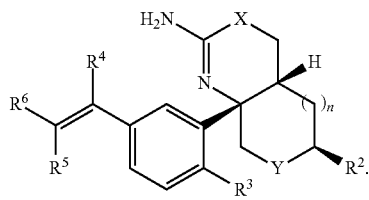

III'

Provided herein as Embodiment 5 is the compound according to any one of Embodiments 1 to 4, or a tautomer thereof, or a pharmaceutically acceptable salt of said compound or tautomer, wherein n is 0.

Provided herein as Embodiment 6 is the compound according to any one of Embodiments 1 to 4, or a tautomer thereof, or a pharmaceutically acceptable salt of said compound or tautomer, wherein n is 1.

Provided herein as Embodiment 7 is the compound according to any one of Embodiments 1 to 6, or a tautomer thereof, or a pharmaceutically acceptable salt of said compound or tautomer, wherein X is O.

Provided herein as Embodiment 8 is the compound according to any one of Embodiments 1 to 6, or a tautomer thereof, or a pharmaceutically acceptable salt of said compound or tautomer, wherein X is S.

Provided herein as Embodiment 9 is the compound according to any one of Embodiments 1 to 8, or a tautomer thereof, or a pharmaceutically acceptable salt of said compound or tautomer, wherein Y is O.

Provided herein as Embodiment 10 is the compound according to any one of Embodiments 1 to 8, or a tautomer thereof, or a pharmaceutically acceptable salt of said compound or tautomer, wherein Y is $NR^1$.

Provided herein as Embodiment 11 is the compound according to any one of Embodiments 1 to 8 and 10, or a tautomer thereof, or a pharmaceutically acceptable salt of said compound or tautomer, wherein
$R^1$ is

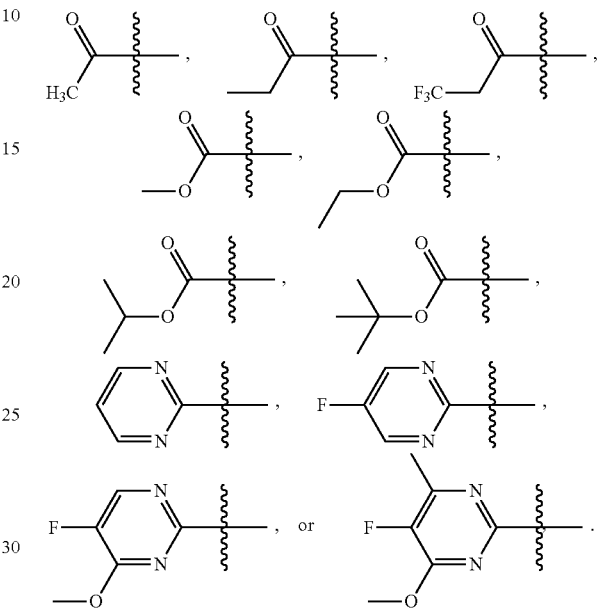

Provided herein as Embodiment 12 is the compound according to any one of Embodiments 1 to 8 and 10, or a tautomer thereof, or a pharmaceutically acceptable salt of said compound or tautomer, wherein
$R^1$ is a 6-membered nitrogen-containing heteroaryl, wherein the heteroaryl is optionally substituted with 1 to 3 substituents independently selected from halogen, $C_{1-6}$alkyl, or $C_{1-6}$alkoxy.

Provided herein as Embodiment 13 is the compound according to any one of Embodiments 1 to 8, 10, and 12, or a tautomer thereof, or a pharmaceutically acceptable salt of said compound or tautomer, wherein
$R^1$ is pyrimidinyl optionally substituted with 1 to 3 substituents independently selected from halogen, $C_{1-6}$alkyl, or $C_{1-6}$alkoxy.

Provided herein as Embodiment 14 is the compound according to any one of Embodiments 1 to 8 and 10 to 13, or a tautomer thereof, or a pharmaceutically acceptable salt of said compound or tautomer, wherein
$R^1$ is

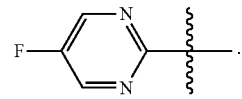

Provided herein as Embodiment 15 is the compound according to any one of Embodiments 1 to 9, or a tautomer thereof, or a pharmaceutically acceptable salt of said compound or tautomer, wherein
$R^2$ is H, methyl, monofluoromethyl, difluoromethyl, or trifluoromethyl.

Provided herein as Embodiment 16 is the compound according to any one of Embodiments 1 to 9, or a tautomer thereof, or a pharmaceutically acceptable salt of said compound or tautomer, wherein
R² is trifluoromethyl.

Provided herein as Embodiment 17 is the compound according to any one of Embodiments 1 to 17, or a tautomer thereof, or a pharmaceutically acceptable salt of said compound or tautomer, wherein R³ is F.

Provided herein as Embodiment 18 is the compound according to any one of Embodiments 1 to 17, or a tautomer thereof, or a pharmaceutically acceptable salt of said compound or tautomer, wherein R⁵ and R⁶ is F or H and the other of R⁵ and R⁶ is pyridyl or pyrazinyl, which pyridyl or pyrazinyl is optionally substituted with 1 to 3 substituents independently selected from halogen, —CN, C₁₋₆alkyl, C₁₋₆alkoxy, 2-propynyloxy, 2-butynyloxy, 3-butyn-2-yloxy, or (3-methyl-1,2,4-oxadiazol-5-yl)methoxy, wherein the C₁₋₆alkyl or C₁₋₆alkoxy is optionally substituted with 1 to 4 substituents independently selected from F or methoxy.

Provided herein as Embodiment 19 is the compound according to any one of Embodiments 1 to 17, or a tautomer thereof, or a pharmaceutically acceptable salt of said compound or tautomer, wherein R⁵ and R⁶ is F or H and the other of R⁵ and R⁶ is pyridyl or pyrazinyl, which pyridyl or pyrazinyl is optionally substituted with 1 to 3 substituents independently selected from —CN, C₁₋₆alkyl, C₁₋₆alkoxy, 2-propynyloxy, 2-butynyloxy, 3-butyn-2-yloxy, or (3-methyl-1,2,4-oxadiazol-5-yl)methoxy, wherein the C₁₋₆alkyl or C₁₋₆alkoxy is optionally substituted with 1 to 4 substituents independently selected from F or methoxy.

Provided herein as Embodiment 20 is the compound according to any one of Embodiments 1 to 18, or a tautomer thereof, or a pharmaceutically acceptable salt of said compound or tautomer, wherein one of R⁶ and R⁷ is

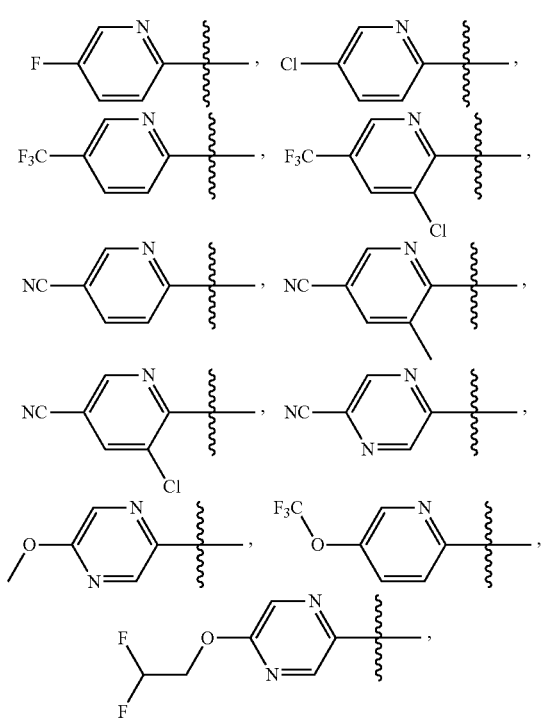

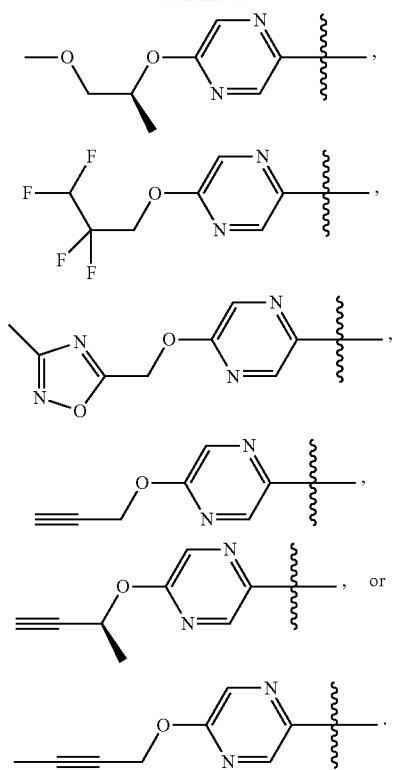

Provided herein as an alternative Embodiment 20 is the compound according to any one of Embodiments 1 to 18, or a tautomer thereof, or a pharmaceutically acceptable salt of said compound or tautomer, wherein one of R⁶ and R⁷ is

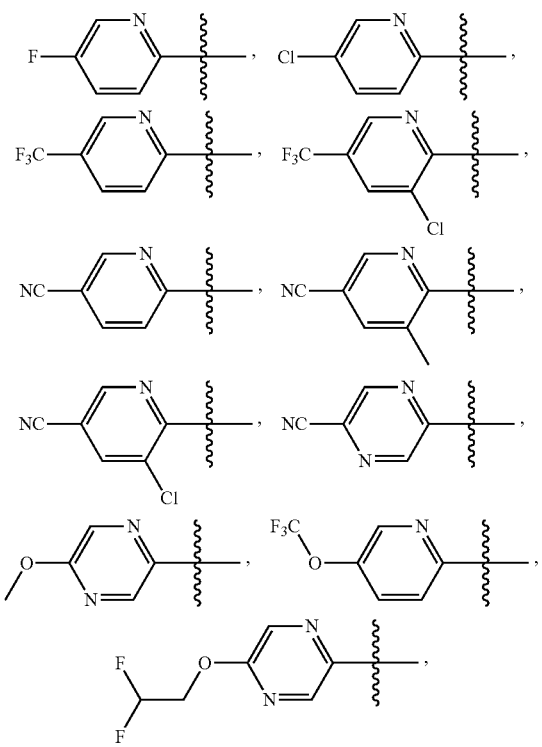

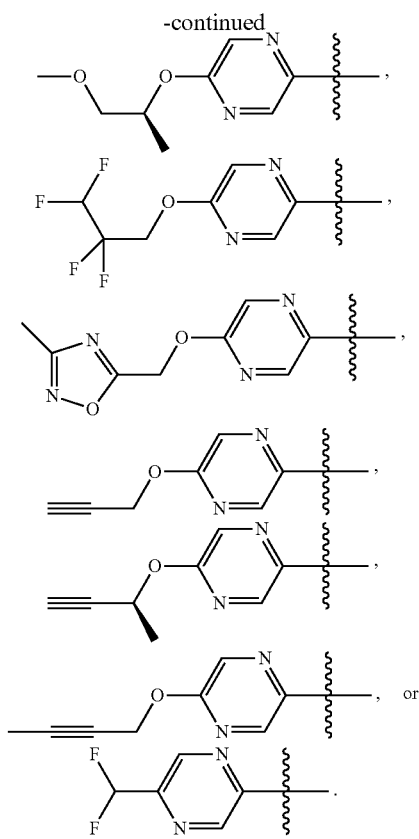

Provided herein as Embodiment 21 is the compound according to any one of Embodiments 1 to 19, or a tautomer thereof, or a pharmaceutically acceptable salt of said compound or tautomer, wherein one of $R^6$ and $R^7$ is

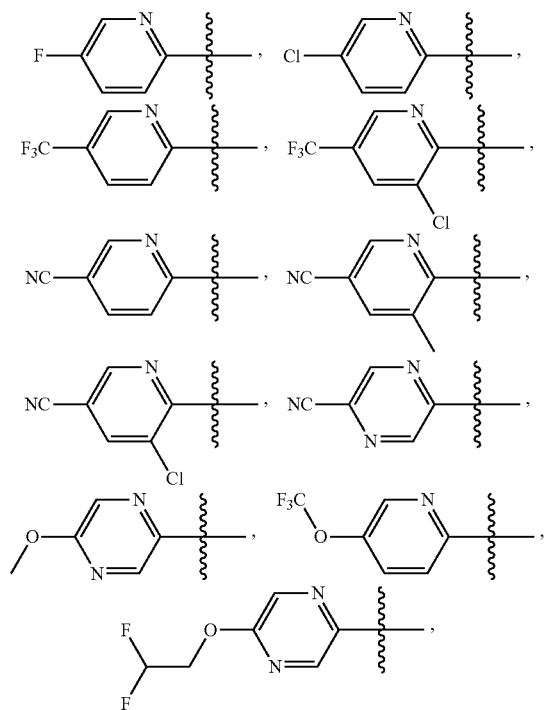

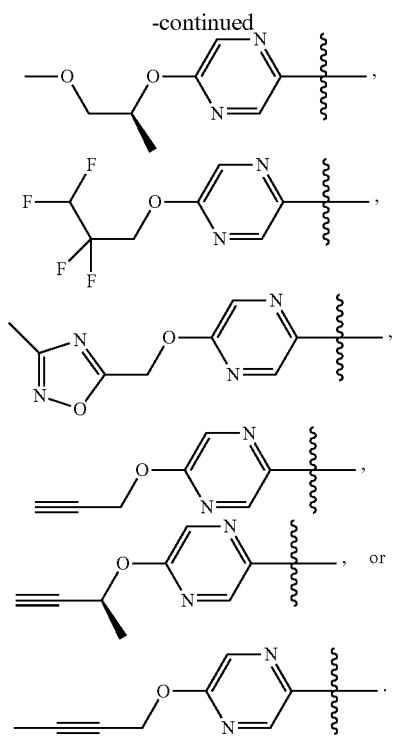

Provided herein as Embodiment 22 is the compound according to any one of Embodiments 1 to 21, or a tautomer thereof, or a pharmaceutically acceptable salt of said compound or tautomer, wherein
$R^4$ is H; and
$R^5$ is H.

Provided herein as Embodiment 23 is the compound according to any one of Embodiments 1 to 21, or a tautomer thereof, or a pharmaceutically acceptable salt of said compound or tautomer, wherein
$R^4$ is H; and
$R^6$ is H.

Provided herein as Embodiment 24 is the compound according to any one of Embodiments 1 to 21, or a tautomer thereof, or a pharmaceutically acceptable salt of said compound or tautomer, wherein
$R^4$ is F; and
$R^5$ is H.

Provided herein as Embodiment 25 is the compound according to any one of Embodiments 1 to 21, or a tautomer thereof, or a pharmaceutically acceptable salt of said compound or tautomer, wherein
$R^4$ is F; and
$R^6$ is H.

Provided herein as Embodiment 26 is the compound according to any one of Embodiments 1 to 21, or a tautomer thereof, or a pharmaceutically acceptable salt of said compound or tautomer, wherein
$R^4$ is H; and
$R^5$ is F.

Provided herein as Embodiment 27 is the compound according to any one of Embodiments 1 to 21 or a tautomer thereof, or a pharmaceutically acceptable salt of said compound or tautomer, wherein
$R^4$ is H; and
$R^6$ is F.

Provided herein as Embodiment 28 is the compound of Embodiment 1, or a tautomer thereof, or a pharmaceutically acceptable salt of said compound or tautomer, selected from (4aS,7aR)-7a-(5-((Z)-2-(5-chloropyridin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

(4aR,7aS)-7a-(5-((Z)-2-(5-chloropyridin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

6-((Z)-2-(3-((4aR,7aS)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aS,7aR)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

(4aR,7aR)-7a-(5-((Z)-2-(5-chloropyridin-2-yl)-2-fluorovinyl)-2-fluorophenyl)-4a,5,7,7a-tetrahydro-4H-furo[3,4-d][1,3]thiazin-2-amine;

(4aS,7aS)-7a-(5-((Z)-2-(5-chloropyridin-2-yl)-2-fluorovinyl)-2-fluorophenyl)-4a,5,7,7a-tetrahydro-4H-furo[3,4-d][1,3]thiazin-2-amine;

6-((Z)-2-(3-((4aR,7aR)-2-amino-4a,5,7,7a-tetrahydro-4H-furo[3,4-d][1,3]thiazin-7a-yl)-4-fluorophenyl)-1-fluorovinyl)nicotinonitrile;

6-((Z)-2-(3-((4aS,7aS)-2-amino-4a,5,7,7a-tetrahydro-4H-furo[3,4-d][1,3]thiazin-7a-yl)-4-fluorophenyl)-1-fluorovinyl)nicotinonitrile;

(4aR,7aS)-7a-(2-fluoro-5-((Z)-2-fluoro-2-(5-methoxypyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(2-fluoro-5-((Z)-2-fluoro-2-(5-(prop-2-yn-1-yloxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(2-fluoro-5-((Z)-2-fluoro-2-(5-((3-methyl-1,2,4-oxadiazol-5-yl)methoxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

5-((Z)-2-(3-((4aR,7aS)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)pyrazine-2-carbonitrile;

(4aR,7aS)-7a-(2-fluoro-5-((Z)-2-fluoro-2-(5-(2,2,3,3-tetrafluoropropoxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(5-((Z)-2-(5-(2,2-difluoroethoxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

(4aR,7aS)-7a-(2-fluoro-5-((Z)-2-fluoro-2-(5-(((S)-1-methoxypropan-2-yl)oxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(5-((Z)-2-(5-((S)-but-3-yn-2-yloxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

(4aR,7aS)-tert-butyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

(4aR,7aS)-7a-(5-((Z)-2-(5-(but-2-yn-1-yloxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)ethanone;

1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)-3,3,3-trifluoropropan-1-one;

(4aR,7aS)-7a-(2-fluoro-5-((Z)-2-fluoro-2-(5-(prop-2-yn-1-yloxy)pyrazin-2-yl)vinyl)phenyl)-6-(pyrimidin-2-yl)-4,4a,5,6,7,7a-hexahydropyrrolo[3,4-d][1,3]thiazin-2-amine;

(4aR,7aS)-methyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)propan-1-one;

(4aR,7aS)-ethyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

(4aR,7aS)-isopropyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

6-((Z)-2-(3-((4aR,5R,7aR)-2-amino-5-(trifluoromethyl)-4a,5,7,7a-tetrahydro-4H-furo[3,4-d][1,3]thiazin-7a-yl)-4-fluorophenyl)-1-fluorovinyl)nicotinonitrile;

6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)nicotinonitrile;

(4aS,5S,7aS)-7a-(2-fluoro-5-((Z)-2-fluoro-2-(5-(prop-2-ynyloxy)pyrazin-2-yl)vinyl)phenyl)-5-(trifluoromethyl)-4a,5,7,7a-tetrahydro-4H-furo[3,4-d][1,3]thiazin-2-amine;

5-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)pyrazine-2-carbonitrile;

(4aS,5S,7aS)-7a-(2-fluoro-5-((Z)-2-fluoro-2-(5-(trifluoromethoxy)pyridin-2-yl)vinyl)phenyl)-5-(trifluoromethyl)-4a,5,7,7a-tetrahydro-4H-furo[3,4-d][1,3]thiazin-2-amine;

6-((Z)-2-(3-((4aR,7aS)-2-amino-6-(5-fluoro-4-methoxy-6-methylpyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aS,5S,7aS)-2-amino-5-(fluoromethyl)-4a,5,7,7a-tetrahydro-4H-furo[3,4-d][1,3]thiazin-7a-yl)-4-fluorophenyl)-1-fluorovinyl)nicotinonitrile;

(4aS,5S,7aS)-7a-(2-fluoro-5-((Z)-2-fluoro-2-(5-fluoropyridin-2-yl)vinyl)phenyl)-5-(trifluoromethyl)-4a,5,7,7a-tetrahydro-4H-furo[3,4-d][1,3]thiazin-2-amine;

6-((Z)-2-(3-((4aR,5R,7aR)-2-amino-5-(fluoromethyl)-4a,5,7,7a-tetrahydro-4H-furo[3,4-d][1,3]thiazin-7a-yl)-4-fluorophenyl)-1-fluorovinyl)nicotinonitrile;

6-((Z)-2-(3-((4aR,7aS)-2-amino-6-(5-fluoro-4-methoxypyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aR,7aS)-2-amino-6-(pyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

(4aS,5S,7aS)-7a-(2-fluoro-5-((Z)-2-fluoro-2-(5-methoxypyrazin-2-yl)vinyl)phenyl)-5-(trifluoromethyl)-4a,5,7,7a-tetrahydro-4H-furo[3,4-d][1,3]thiazin-2-amine;

(4aS,5S,7aS)-7a-(5-((Z)-2-(3-chloro-5-(trifluoromethyl)pyridin-2-yl)-2-fluorovinyl)-2-fluorophenyl)-5-(trifluoromethyl)-4a,5,7,7a-tetrahydro-4H-furo[3,4-d][1,3]thiazin-2-amine;

6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)-5-methylnicotinonitrile;

(4aS,5S,7aS)-7a-(2-fluoro-5-((Z)-2-fluoro-2-(5-(trifluoromethyl)pyridin-2-yl)vinyl)phenyl)-5-(trifluoromethyl)-4a,5,7,7a-tetrahydro-4H-furo[3,4-d][1,3]thiazin-2-amine;

6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)-5-chloronicotinonitrile;

6-((Z)-2-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-1-fluorovinyl)nicotinonitrile; or 6-((Z)-2-(3-((4aS,5R,7aR)-2-amino-5-(trifluoromethyl)-4a,5,7,7a-tetrahydro-4H-furo[3,4-d][1,3]oxazin-7a-yl)-4-fluorophenyl)-1-fluorovinyl)nicotinonitrile.

Provided herein as an alternative Embodiment 28 is the compound of Embodiment 1, or a tautomer thereof, or a pharmaceutically acceptable salt of said compound or tautomer, selected from (4aS,7aR)-7a-(5-((Z)-2-(5-chloropyridin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

(4aR,7aS)-7a-(5-((Z)-2-(5-chloropyridin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

6-((Z)-2-(3-((4aR,7aS)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aS,7aR)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

(4aR,7aR)-7a-(5-((Z)-2-(5-chloropyridin-2-yl)-2-fluorovinyl)-2-fluorophenyl)-4a,5,7,7a-tetrahydro-4H-furo[3,4-d][1,3]thiazin-2-amine;

(4aS,7aS)-7a-(5-((Z)-2-(5-chloropyridin-2-yl)-2-fluorovinyl)-2-fluorophenyl)-4a,5,7,7a-tetrahydro-4H-furo[3,4-d][1,3]thiazin-2-amine;

6-((Z)-2-(3-((4aR,7aR)-2-amino-4a,5,7,7a-tetrahydro-4H-furo[3,4-d][1,3]thiazin-7a-yl)-4-fluorophenyl)-1-fluorovinyl)nicotinonitrile;

6-((Z)-2-(3-((4aS,7aS)-2-amino-4a,5,7,7a-tetrahydro-4H-furo[3,4-d][1,3]thiazin-7a-yl)-4-fluorophenyl)-1-fluorovinyl)nicotinonitrile;

(4aR,7aS)-7a-(2-fluoro-5-((Z)-2-fluoro-2-(5-methoxypyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(2-fluoro-5-((Z)-2-fluoro-2-(5-(prop-2-yn-1-yloxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(2-fluoro-5-((Z)-2-fluoro-2-(5-((3-methyl-1,2,4-oxadiazol-5-yl)methoxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

5-((Z)-2-(3-((4aR,7aS)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)pyrazine-2-carbonitrile;

(4aR,7aS)-7a-(2-fluoro-5-((Z)-2-fluoro-2-(5-(2,2,3,3-tetrafluoropropoxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(5-((Z)-2-(5-(2,2-difluoroethoxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

(4aR,7aS)-7a-(2-fluoro-5-((Z)-2-fluoro-2-(5-(((S)-1-methoxypropan-2-yl)oxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(5-((Z)-2-(5-((S)-but-3-yn-2-yloxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

(4aR,7aS)-tert-butyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

(4aR,7aS)-7a-(5-((Z)-2-(5-(but-2-yn-1-yloxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)ethanone;

1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)-3,3,3-trifluoropropan-1-one;

(4aR,7aS)-7a-(2-fluoro-5-((Z)-2-fluoro-2-(5-(prop-2-yn-1-yloxy)pyrazin-2-yl)vinyl)phenyl)-6-(pyrimidin-2-yl)-4,4a,5,6,7,7a-hexahydropyrrolo[3,4-d][1,3]thiazin-2-amine;

(4aR,7aS)-methyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)propan-1-one;

(4aR,7aS)-ethyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

(4aR,7aS)-isopropyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

6-((Z)-2-(3-((4aR,5R,7aR)-2-amino-5-(trifluoromethyl)-4a,5,7,7a-tetrahydro-4H-furo[3,4-d][1,3]thiazin-7a-yl)-4-fluorophenyl)-1-fluorovinyl)nicotinonitrile;

6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)nicotinonitrile;

(4aS,5S,7aS)-7a-(2-fluoro-5-((Z)-2-fluoro-2-(5-(prop-2-ynyloxy)pyrazin-2-yl)vinyl)phenyl)-5-(trifluoromethyl)-4a,5,7,7a-tetrahydro-4H-furo[3,4-d][1,3]thiazin-2-amine;

5-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)pyrazine-2-carbonitrile;

(4aS,5S,7aS)-7a-(2-fluoro-5-((Z)-2-fluoro-2-(5-(trifluoromethoxy)pyridin-2-yl)vinyl)phenyl)-5-(trifluoromethyl)-4a,5,7,7a-tetrahydro-4H-furo[3,4-d][1,3]thiazin-2-amine;

6-((Z)-2-(3-((4aR,7aS)-2-amino-6-(5-fluoro-4-methoxy-6-methylpyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aS,5S,7aS)-2-amino-5-(fluoromethyl)-4a,5,7,7a-tetrahydro-4H-furo[3,4-d][1,3]thiazin-7a-yl)-4-fluorophenyl)-1-fluorovinyl)nicotinonitrile;

(4aS,5S,7aS)-7a-(2-fluoro-5-((Z)-2-fluoro-2-(5-fluoropyridin-2-yl)vinyl)phenyl)-5-(trifluoromethyl)-4a,5,7,7a-tetrahydro-4H-furo[3,4-d][1,3]thiazin-2-amine;

6-((Z)-2-(3-((4aR,5R,7aR)-2-amino-5-(fluoromethyl)-4a,5,7,7a-tetrahydro-4H-furo[3,4-d][1,3]thiazin-7a-yl)-4-fluorophenyl)-1-fluorovinyl)nicotinonitrile;

6-((Z)-2-(3-((4aR,7aS)-2-amino-6-(5-fluoro-4-methoxypyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aR,7aS)-2-amino-6-(pyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

(4aS,5S,7aS)-7a-(2-fluoro-5-((Z)-2-fluoro-2-(5-methoxypyrazin-2-yl)vinyl)phenyl)-5-(trifluoromethyl)-4a,5,7,7a-tetrahydro-4H-furo[3,4-d][1,3]thiazin-2-amine;

(4aS,5S,7aS)-7a-(5-((Z)-2-(3-chloro-5-(trifluoromethyl)pyridin-2-yl)-2-fluorovinyl)-2-fluorophenyl)-5-(trifluoromethyl)-4a,5,7,7a-tetrahydro-4H-furo[3,4-d][1,3]thiazin-2-amine;

6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)-5-methylnicotinonitrile;

(4aS,5S,7aS)-7a-(2-fluoro-5-((Z)-2-fluoro-2-(5-(trifluoromethyl)pyridin-2-yl)vinyl)phenyl)-5-(trifluoromethyl)-4a,5,7,7a-tetrahydro-4H-furo[3,4-d][1,3]thiazin-2-amine;

6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)-5-chloronicotinonitrile;

6-((Z)-2-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-1-fluorovinyl)nicotinonitrile;

6-((Z)-2-(3-((4aS,5R,7aR)-2-amino-5-(trifluoromethyl)-4a,5,7,7a-tetrahydro-4H-furo[3,4-d][1,3]oxazin-7a-yl)-4-fluorophenyl)-1-fluorovinyl)nicotinonitrile;

6-((Z)-2-(3-((4aS,5S,7aS)-2-amino-5-(difluoromethyl)-4a,5,7,7a-tetrahydro-4H-furo[3,4-d][1,3]thiazin-7a-yl)-4-fluorophenyl)-1-fluorovinyl)nicotinonitrile;

6-((Z)-2-(3-((4aR,5R,7aR)-2-Amino-5-(difluoromethyl)-4a,5-dihydro-4H-furo[3,4-d][1,3]thiazin-7a(7H)-yl)-4-fluorophenyl)-1-fluorovinyl)nicotinonitrile; or (4aS,5S,7aS)-5-(difluoromethyl)-7a-(2-fluoro-5-((Z)-2-fluoro-2-(5-(trifluoromethyl)pyridin-2-yl)vinyl)phenyl)-4a,5,7,7a-tetrahydro-4H-furo[3,4-d][1,3]thiazin-2-amine.

Provided herein as yet another alternative Embodiment 28 is the compound of Embodiment 1, or a tautomer thereof, or a pharmaceutically acceptable salt of said compound or tautomer, selected from (4aS,5R,7aS)-7a-(5-((Z)-2-(5-(difluoromethyl)pyrazin-2-yl)-2-fluorovinyl)-2-fluorophenyl)-5-methyl-4a,5,7,7a-tetrahydro-4H-furo[3,4-d][1,3]thiazin-2-amine; or (4aR,5S,7aR)-7a-(5-((Z)-2-(5-(difluoromethyl)pyrazin-2-yl)-2-fluorovinyl)-2-fluorophenyl)-5-methyl-4a,5,7,7a-tetrahydro-4H-furo[3,4-d][1,3]thiazin-2-amine.

Provided herein as Embodiment 29 is the compound of Embodiment 1, or a tautomer thereof, or a pharmaceutically acceptable salt of said compound or tautomer, selected from 6-((Z)-2-(3-((4aR,7aS)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aS,7aR)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aR,7aR)-2-amino-4a,5,7,7a-tetrahydro-4H-furo[3,4-d][1,3]thiazin-7a-yl)-4-fluorophenyl)-1-fluorovinyl)nicotinonitrile;

6-((Z)-2-(3-((4aS,7aS)-2-amino-4a,5,7,7a-tetrahydro-4H-furo[3,4-d][1,3]thiazin-7a-yl)-4-fluorophenyl)-1-fluorovinyl)nicotinonitrile;

(4aR,7aS)-7a-(2-fluoro-5-((Z)-2-fluoro-2-(5-methoxypyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(2-fluoro-5-((Z)-2-fluoro-2-(5-(prop-2-yn-1-yloxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(2-fluoro-5-((Z)-2-fluoro-2-(5-((3-methyl-1,2,4-oxadiazol-5-yl)methoxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

5-((Z)-2-(3-((4aR,7aS)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)pyrazine-2-carbonitrile;

(4aR,7aS)-7a-(2-fluoro-5-((Z)-2-fluoro-2-(5-(2,2,3,3-tetrafluoropropoxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(5-((Z)-2-(5-(2,2-difluoroethoxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

(4aR,7aS)-7a-(2-fluoro-5-((Z)-2-fluoro-2-(5-(((S)-1-methoxypropan-2-yl)oxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(5-((Z)-2-(5-((S)-but-3-yn-2-yloxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

(4aR,7aS)-tert-butyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

(4aR,7aS)-7a-(5-((Z)-2-(5-(but-2-yn-1-yloxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)ethanone;

1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)-3,3,3-trifluoropropan-1-one;

(4aR,7aS)-7a-(2-fluoro-5-((Z)-2-fluoro-2-(5-(prop-2-yn-1-yloxy)pyrazin-2-yl)vinyl)phenyl)-6-(pyrimidin-2-yl)-4,4a,5,6,7,7a-hexahydropyrrolo[3,4-d][1,3]thiazin-2-amine;

(4aR,7aS)-methyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)propan-1-one;

(4aR,7aS)-ethyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

(4aR,7aS)-isopropyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

6-((Z)-2-(3-((4aR,5R,7aR)-2-amino-5-(trifluoromethyl)-4a,5,7,7a-tetrahydro-4H-furo[3,4-d][1,3]thiazin-7a-yl)-4-fluorophenyl)-1-fluorovinyl)nicotinonitrile;

6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)nicotinonitrile;

(4aS,5S,7aS)-7a-(2-fluoro-5-((Z)-2-fluoro-2-(5-(prop-2-ynyloxy)pyrazin-2-yl)vinyl)phenyl)-5-(trifluoromethyl)-4a,5,7,7a-tetrahydro-4H-furo[3,4-d][1,3]thiazin-2-amine;

5-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)pyrazine-2-carbonitrile;

(4aS,5S,7aS)-7a-(2-fluoro-5-((Z)-2-fluoro-2-(5-(trifluoromethoxy)pyridin-2-yl)vinyl)phenyl)-5-(trifluoromethyl)-4a,5,7,7a-tetrahydro-4H-furo[3,4-d][1,3]thiazin-2-amine;

6-((Z)-2-(3-((4aR,7aS)-2-amino-6-(5-fluoro-4-methoxy-6-methylpyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aS,5S,7aS)-2-amino-5-(fluoromethyl)-4a,5,7,7a-tetrahydro-4H-furo[3,4-d][1,3]thiazin-7a-yl)-4-fluorophenyl)-1-fluorovinyl)nicotinonitrile;

(4aS,5S,7aS)-7a-(2-fluoro-5-((Z)-2-fluoro-2-(5-fluoropyridin-2-yl)vinyl)phenyl)-5-(trifluoromethyl)-4a,5,7,7a-tetrahydro-4H-furo[3,4-d][1,3]thiazin-2-amine;

6-((Z)-2-(3-((4aR,5R,7aR)-2-amino-5-(fluoromethyl)-4a,5,7,7a-tetrahydro-4H-furo[3,4-d][1,3]thiazin-7a-yl)-4-fluorophenyl)-1-fluorovinyl)nicotinonitrile;

6-((Z)-2-(3-((4aR,7aS)-2-amino-6-(5-fluoro-4-methoxypyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aR,7aS)-2-amino-6-(pyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

(4aS,5S,7aS)-7a-(2-fluoro-5-((Z)-2-fluoro-2-(5-methoxypyrazin-2-yl)vinyl)phenyl)-5-(trifluoromethyl)-4a,5,7,7a-tetrahydro-4H-furo[3,4-d][1,3]thiazin-2-amine;

(4aS,5S,7aS)-7a-(5-((Z)-2-(3-chloro-5-(trifluoromethyl)pyridin-2-yl)-2-fluorovinyl)-2-fluorophenyl)-5-(trifluoromethyl)-4a,5,7,7a-tetrahydro-4H-furo[3,4-d][1,3]thiazin-2-amine;

6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)-5-methylnicotinonitrile;

(4aS,5S,7aS)-7a-(2-fluoro-5-((Z)-2-fluoro-2-(5-(trifluoromethyl)pyridin-2-yl)vinyl)phenyl)-5-(trifluoromethyl)-4a,5,7,7a-tetrahydro-4H-furo[3,4-d][1,3]thiazin-2-amine;

6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)-5-chloronicotinonitrile;

6-((Z)-2-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-1-fluorovinyl)nicotinonitrile; or 6-((Z)-2-(3-((4aS,5R,7aR)-2-amino-5-(trifluoromethyl)-4a,5,7,7a-tetrahydro-4H-furo[3,4-d][1,3]oxazin-7a-yl)-4-fluorophenyl)-1-fluorovinyl)nicotinonitrile.

Provided herein as an alternative Embodiment 29 is the compound of Embodiment 1, or a tautomer thereof, or a pharmaceutically acceptable salt of said compound or tautomer, selected from 6-((Z)-2-(3-((4aR,7aS)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aS,7aR)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aR,7aR)-2-amino-4a,5,7,7a-tetrahydro-4H-furo[3,4-d][1,3]thiazin-7a-yl)-4-fluorophenyl)-1-fluorovinyl)nicotinonitrile;

6-((Z)-2-(3-((4aS,7aS)-2-amino-4a,5,7,7a-tetrahydro-4H-furo[3,4-d][1,3]thiazin-7a-yl)-4-fluorophenyl)-1-fluorovinyl)nicotinonitrile;

(4aR,7aS)-7a-(2-fluoro-5-((Z)-2-fluoro-2-(5-methoxypyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(2-fluoro-5-((Z)-2-fluoro-2-(5-(prop-2-yn-1-yloxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(2-fluoro-5-((Z)-2-fluoro-2-(5-((3-methyl-1,2,4-oxadiazol-5-yl)methoxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

5-((Z)-2-(3-((4aR,7aS)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)pyrazine-2-carbonitrile;

(4aR,7aS)-7a-(2-fluoro-5-((Z)-2-fluoro-2-(5-(2,2,3,3-tetrafluoropropoxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(5-((Z)-2-(5-(2,2-difluoroethoxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

(4aR,7aS)-7a-(2-fluoro-5-((Z)-2-fluoro-2-(5-(((S)-1-methoxypropan-2-yl)oxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(5-((Z)-2-(5-((S)-but-3-yn-2-yloxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

(4aR,7aS)-tert-butyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

(4aR,7aS)-7a-(5-((Z)-2-(5-(but-2-yn-1-yloxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)ethanone;

1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)-3,3,3-trifluoropropan-1-one;

(4aR,7aS)-7a-(2-fluoro-5-((Z)-2-fluoro-2-(5-(prop-2-yn-1-yloxy)pyrazin-2-yl)vinyl)phenyl)-6-(pyrimidin-2-yl)-4,4a,5,6,7,7a-hexahydropyrrolo[3,4-d][1,3]thiazin-2-amine;

(4aR,7aS)-methyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)propan-1-one;

(4aR,7aS)-ethyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

(4aR,7aS)-isopropyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

6-((Z)-2-(3-((4aR,5R,7aR)-2-amino-5-(trifluoromethyl)-4a,5,7,7a-tetrahydro-4H-furo[3,4-d][1,3]thiazin-7a-yl)-4-fluorophenyl)-1-fluorovinyl)nicotinonitrile;

6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)nicotinonitrile;

(4aS,5S,7aS)-7a-(2-fluoro-5-((Z)-2-fluoro-2-(5-(prop-2-ynyloxy)pyrazin-2-yl)vinyl)phenyl)-5-(trifluoromethyl)-4a,5,7,7a-tetrahydro-4H-furo[3,4-d][1,3]thiazin-2-amine;

5-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)pyrazine-2-carbonitrile;

(4aS,5S,7aS)-7a-(2-fluoro-5-((Z)-2-fluoro-2-(5-(trifluoromethoxy)pyridin-2-yl)vinyl)phenyl)-5-(trifluoromethyl)-4a,5,7,7a-tetrahydro-4H-furo[3,4-d][1,3]thiazin-2-amine;

6-((Z)-2-(3-((4aR,7aS)-2-amino-6-(5-fluoro-4-methoxy-6-methylpyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aS,5S,7aS)-2-amino-5-(fluoromethyl)-4a,5,7,7a-tetrahydro-4H-furo[3,4-d][1,3]thiazin-7a-yl)-4-fluorophenyl)-1-fluorovinyl)nicotinonitrile;

(4aS,5S,7aS)-7a-(2-fluoro-5-((Z)-2-fluoro-2-(5-fluoropyridin-2-yl)vinyl)phenyl)-5-(trifluoromethyl)-4a,5,7,7a-tetrahydro-4H-furo[3,4-d][1,3]thiazin-2-amine;

6-((Z)-2-(3-((4aR,5R,7aR)-2-amino-5-(fluoromethyl)-4a,5,7,7a-tetrahydro-4H-furo[3,4-d][1,3]thiazin-7a-yl)-4-fluorophenyl)-1-fluorovinyl)nicotinonitrile;

6-((Z)-2-(3-((4aR,7aS)-2-amino-6-(5-fluoro-4-methoxy-pyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aR,7aS)-2-amino-6-(pyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

(4aS,5S,7aS)-7a-(2-fluoro-5-((Z)-2-fluoro-2-(5-methoxypyrazin-2-yl)vinyl)phenyl)-5-(trifluoromethyl)-4a,5,7,7a-tetrahydro-4H-furo[3,4-d][1,3]thiazin-2-amine;

(4aS,5S,7aS)-7a-(5-((Z)-2-(3-chloro-5-(trifluoromethyl)pyridin-2-yl)-2-fluorovinyl)-2-fluorophenyl)-5-(trifluoromethyl)-4a,5,7,7a-tetrahydro-4H-furo[3,4-d][1,3]thiazin-2-amine;

6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)-5-methylnicotinonitrile;

(4aS,5S,7aS)-7a-(2-fluoro-5-((Z)-2-fluoro-2-(5-(trifluoromethyl)pyridin-2-yl)vinyl)phenyl)-5-(trifluoromethyl)-4a,5,7,7a-tetrahydro-4H-furo[3,4-d][1,3]thiazin-2-amine;

6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)-5-chloronicotinonitrile;

6-((Z)-2-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-1-fluorovinyl)nicotinonitrile;

6-((Z)-2-(3-((4aS,5R,7aR)-2-amino-5-(trifluoromethyl)-4a,5,7,7a-tetrahydro-4H-furo[3,4-d][1,3]oxazin-7a-yl)-4-fluorophenyl)-1-fluorovinyl)nicotinonitrile;

6-((Z)-2-(3-((4aS,5S,7aS)-2-amino-5-(difluoromethyl)-4a,5,7,7a-tetrahydro-4H-furo[3,4-d][1,3]thiazin-7a-yl)-4-fluorophenyl)-1-fluorovinyl)nicotinonitrile; or 6-((Z)-2-(3-((4aR,5R,7aR)-2-Amino-5-(difluoromethyl)-4a,5-dihydro-4H-furo[3,4-d][1,3]thiazin-7a(7H)-yl)-4-fluorophenyl)-1-fluorovinyl)nicotinonitrile.

Provided herein as Embodiment 30 is the compound of Embodiment 1, or a tautomer thereof, or a pharmaceutically acceptable salt of said compound or tautomer, wherein the compound is

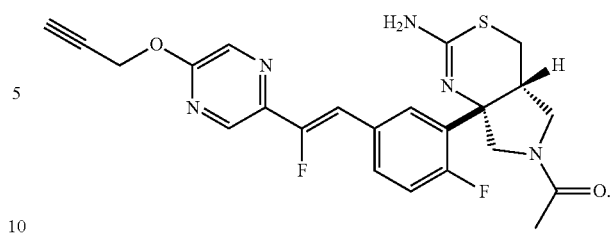

Provided herein as Embodiment 31 is the compound of Embodiment 1, or a tautomer thereof, or a pharmaceutically acceptable salt of said compound or tautomer, wherein the compound is

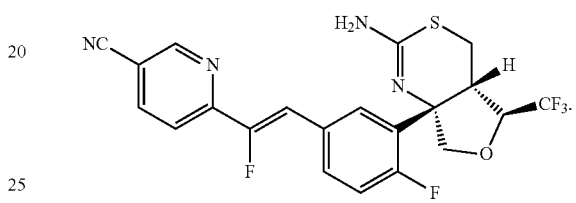

Provided herein as Embodiment 32 is the compound of Embodiment 1, or a tautomer thereof, or a pharmaceutically acceptable salt of said compound or tautomer, wherein the compound is

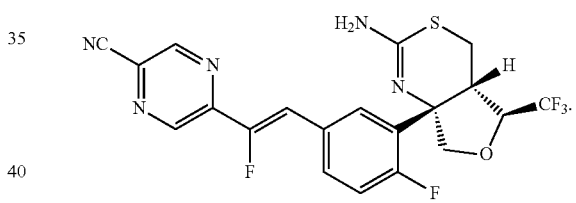

Provided herein as Embodiment 33 is the compound of Embodiment 1, or a tautomer thereof, or a pharmaceutically acceptable salt of said compound or tautomer, wherein the compound is

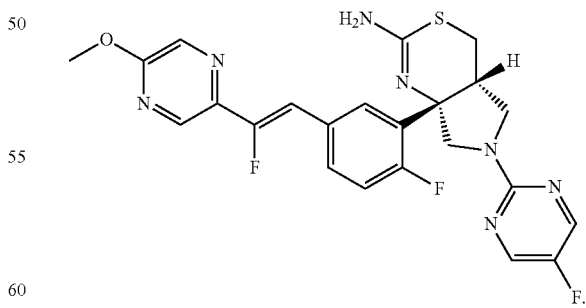

Provided herein as Embodiment 34 is the compound of Embodiment 1, or a tautomer thereof, or a pharmaceutically acceptable salt of said compound or tautomer, wherein the compound is

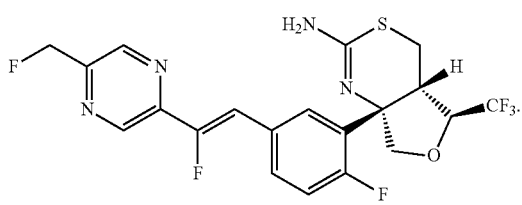 [SMILES: NC1=N[C@@]2(c3cc(/C=C(\F)c4cnc(CF)cn4)ccc3F)CO[C@H](C(F)(F)F)[C@H]2CS1]

Provided herein as Embodiment 35 is a pharmaceutical composition comprising the compound according to any one of Embodiments 1 to 34 and a pharmaceutically acceptable excipient.

Provided herein as Embodiment 36 is a compound according to any one of Embodiments 1 to 34, or a tautomer thereof, or a pharmaceutically acceptable salt of said compound or tautomer, or the pharmaceutical composition according to Embodiment 35 for use as a medicament.

Provided herein as Embodiment 37 is a compound according to any one of Embodiments 1 to 34, or a tautomer thereof, or a pharmaceutically acceptable salt of said compound or tautomer, or the pharmaceutical composition according to Embodiment 35 for use in reducing beta amyloid peptide levels in the cerebral spinal fluid of a subject.

Provided herein as Embodiment 38 is a compound according to any one of Embodiments 1 to 34, or a tautomer thereof, or a pharmaceutically acceptable salt of said compound or tautomer, or the pharmaceutical composition according to Embodiment 35 for use in treating Alzheimer's disease, cognitive impairment, or a combination thereof in a subject.

Provided herein as Embodiment 39 is a compound according to any one of Embodiments 1 to 34, or a tautomer thereof, or a pharmaceutically acceptable salt of said compound or tautomer, or the pharmaceutical composition according to Embodiment 35 for use in treating a neurological disorder selected from mild cognitive impairment, Down's syndrome, hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease, or a combination thereof in a subject.

Provided herein as Embodiment 40 is a compound according to any one of Embodiments 1 to 34, or a tautomer thereof, or a pharmaceutically acceptable salt of said compound or tautomer, or the pharmaceutical composition according to Embodiment 35 for use in reducing formation of plaque on the brain of a subject.

Provided herein as Embodiment 41 is a use of the compound according to any one of Embodiments 1 to 34, or a tautomer thereof, or a pharmaceutically acceptable salt of said compound or tautomer, or the pharmaceutical composition according to Embodiment 35 in the preparation of a medicament for reducing beta amyloid peptide levels in the cerebral spinal fluid of a subject.

Provided herein as Embodiment 42 is a use of the compound according to any one of Embodiments 1 to 34, or a tautomer thereof, or a pharmaceutically acceptable salt of said compound or tautomer, or the pharmaceutical composition according to Embodiment 35 in the preparation of a medicament for treating Alzheimer's disease, cognitive impairment, or a combination thereof in a subject.

Provided herein as Embodiment 43 is a use of the compound according to any one of Embodiments 1 to 34, or a tautomer thereof, or a pharmaceutically acceptable salt of said compound or tautomer, or the pharmaceutical composition according to Embodiment 35 in the preparation of a medicament for the treatment of a neurological disorder selected from mild cognitive impairment, Down's syndrome, hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease, or a combination thereof in a subject.

Provided herein as Embodiment 44 is a use of the compound according to any one of Embodiments 1 to 34, or a tautomer thereof, or a pharmaceutically acceptable salt of said compound or tautomer, or the pharmaceutical composition according to Embodiment 35 in the preparation of a medicament for the reduction of formation of plaque on the brain of a subject.

Provided herein as Embodiment 45 is a method of reducing beta amyloid peptide levels in the cerebral spinal fluid of a subject in need thereof, the method comprising administering to the subject a therapeutically effective amount of the compound according to any one of Embodiments 1 to 34, or a tautomer thereof, or a pharmaceutically acceptable salt of said compound or tautomer.

Provided herein as Embodiment 46 is a method of treating Alzheimer's disease, cognitive impairment or a combination thereof in a subject in need thereof, the method comprising administering to the subject a therapeutically effective amount of the compound according to any one of Embodiments 1 to 34, or a tautomer thereof, or a pharmaceutically acceptable salt of said compound or tautomer.

Provided herein as Embodiment 47 is a method of treating a neurological disorder selected from mild cognitive impairment, Down's syndrome, hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease, or a combination thereof in a subject in need thereof, the method comprising administering to the subject a therapeutically effective amount of the compound according to any one of Embodiments 1 to 34, or a tautomer thereof, or a pharmaceutically acceptable salt of said compound or tautomer.

Provided herein as Embodiment 48 is a method of reducing the formation of plaque on the brain of a subject in need thereof, the method comprising administering to the subject a therapeutically effective amount of the compound according to any one of Embodiments 1 to 34, or a tautomer thereof, or a pharmaceutically acceptable salt of said compound or tautomer.

If one or more alternative embodiments to a certain embodiment are provided, a reference to the certain embodiment is also considered to be a reference to any alternative embodiment provided. For example, the reference in Embodiment 35 to, inter alia, Embodiment 29 is meant to also include a reference to the alternative Embodiment 29 provided herein above.

The foregoing merely summarizes certain aspects of this disclosure and is not intended, nor should it be construed, as limiting the disclosure in any way.

Definitions

The following definitions are provided to assist in understanding the scope of this disclosure.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound.

Stereoisomers

The compounds of the present disclosure may contain, for example, double bonds, one or more asymmetric carbon atoms, and bonds with a hindered rotation, and therefore, may exist as stereoisomers, such as double-bond isomers (i.e., geometric isomers (E/Z)), enantiomers, diastereomers, or atropoisomers. Accordingly, the scope of the instant disclosure is to be understood to encompass all possible stereoisomers of the illustrated compounds including the stereoisomerically pure form (for example, geometrically pure, enantiomerically pure, diastereomerically pure, and atropoisomerically pure) and stereoisomeric mixtures (for example, mixtures of geometric isomers, enantiomers, diastereomers, and atropoisomers) of any chemical structures disclosed herein (in whole or in part). This disclosure also encompasses the pharmaceutical compositions comprising stereoisomerically pure forms and the use of stereoisomerically pure forms of any compounds disclosed herein. Further, this disclosure also encompasses pharmaceutical compositions comprising mixtures of stereoisomers of any compounds disclosed herein and the use of said pharmaceutical compositions or mixtures of stereoisomers. These stereoisomers or mixtures thereof may be synthesized in accordance with methods well known in the art and methods disclosed herein. Mixtures of stereoisomers may be resolved using standard techniques, such as chiral columns or chiral resolving agents. See, for example, Jacques et al., Enantiomers, Racemates and Resolutions (Wiley-Interscience, New York, 1981); Wilen et al., *Tetrahedron* 33:2725; Eliel, Stereochemistry of Carbon Compounds (McGraw-Hill, NY, 1962); and Wilen, Tables of Resolving Agents and Optical Resolutions, page 268 (Eliel, Ed., Univ. of Notre Dame Press, Notre Dame, Ind., 1972).

The term "stereoisomer" or "stereoisomerically pure" compound as used herein refers to one stereoisomer (for example, geometric isomer, enantiomer, diastereomer and atropoisomer) of a compound that is substantially free of other stereoisomers of that compound. For example, a stereoisomerically pure compound having one chiral center will be substantially free of the mirror image enantiomer of the compound and a stereoisomerically pure compound having two chiral centers will be substantially free of other enantiomers or diastereomers of the compound. A typical stereoisomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed. This is not to be confused with a wavy line drawn perpendicular to a bond which indicates the point of attachment of a group to the rest of the molecule.

Tautomers

As known by those skilled in the art, certain compounds disclosed herein may exist in one or more tautomeric forms. Because one chemical structure may only be used to represent one tautomeric form, it will be understood that for convenience, referral to a compound of a given structural formula includes other tautomers of said structural formula. For example, the following is illustrative of tautomers of the compounds of Formula I:

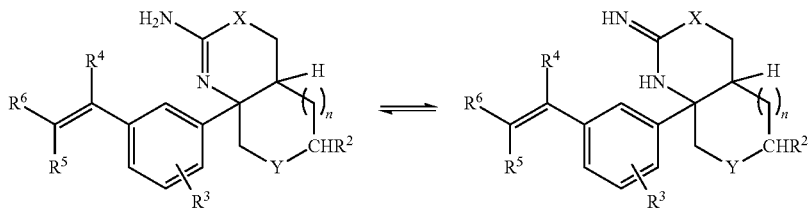

Accordingly, the scope of the instant disclosure is to be understood to encompass all tautomeric forms of the compounds disclosed herein.

Isotopically-Labelled Compounds

Further, the scope of present disclosure includes all pharmaceutically acceptable isotopically-labelled compounds of the compounds disclosed herein, such as the compounds of Formula I, wherein one or more atoms are replaced by atoms having the same atomic number, but an atomic mass or mass number different from the atomic mass or mass number usually found in nature. Examples of isotopes suitable for inclusion in the compounds disclosed herein include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$, and $^{18}O$, phosphorus, such as $^{32}P$, and sulphur, such as $^{35}S$. Certain isotopically-labelled compounds of Formula I, for example, those incorporating a radioactive isotope, are useful in drug and/or substrate tissue distribution studies. The radioactive isotopes tritium ($^{3}H$) and carbon-14 ($^{14}C$) are particularly useful for this purpose in view of their ease of incorporation and ready means of detection. Substitution with isotopes such as deuterium ($^{2}H$)

may afford certain therapeutic advantages resulting from greater metabolic stability, for example, increased in vivo half-life or reduced dosage requirements, and hence may be advantageous in some circumstances. Substitution with positron emitting isotopes, such as $^{11}C$, $^{18}F$, $^{15}O$ and $^{13}N$, can be useful in Positron Emission Topography (PET) studies, for example, for examining target occupancy. Isotopically-labelled compounds of the compounds disclosed herein can generally be prepared by conventional techniques known to those skilled in the art or by processes analogous to those described in the accompanying General Synthetic Schemes and Examples using an appropriate isotopically-labelled reagents in place of the non-labelled reagent previously employed.

Solvates

As discussed above, the compounds disclosed herein and the stereoisomers, tautomers and isotopically-labelled forms thereof or a pharmaceutically acceptable salt of any of the foregoing may exist in solvated or unsolvated forms.

The term "solvate" as used herein refers to a molecular complex comprising a compound or a pharmaceutically acceptable salt thereof as described herein and a stoichiometric or non-stoichiometric amount of one or more pharmaceutically acceptable solvent molecules. If the solvent is water, the solvate is referred to as a "hydrate."

Accordingly, the scope of the instant disclosure is to be understood to encompass all solvents of the compounds disclosed herein and the stereoisomers, tautomers and isotopically-labelled forms thereof or a pharmaceutically acceptable salt of any of the foregoing.

Amorphous and Crystalline Forms

In certain embodiments, the compounds described herein and the stereoisomers, tautomers, isotopically-labelled forms thereof or pharmaceutically acceptable salts of any of the foregoing or solvates of any of the foregoing may exist in different forms, such as amorphous forms and crystalline forms (polymorphs). Accordingly, the scope of the instant disclosure is to be understood to encompass all such forms.

Miscellaneous Definitions

This section will define additional terms used to describe the scope of the compounds, compositions and uses disclosed herein.

The term "$C_{1-6}$alkyl" as used herein means a straight or branched chain hydrocarbon containing from 1 to 6 carbon atoms. Representative examples of $C_{1-6}$alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "$C_{1-6}$alkoxy" as used herein refers to a radical —OR where R represents a $C_{1-6}$alkyl group as defined herein. Representative examples of $C_{1-6}$alkoxy include, but are not limited to, methoxy, ethoxy, propoxy, and butoxy.

The term "halogen" as used herein means —F, —Cl, —Br, or —I.

The term "6-membered nitrogen-containing heteroaryl" as used herein refers to a heteroaryl ring having 6 ring atoms in which at least one of the ring atoms is a nitrogen, with the remaining ring atoms being independently selected from the group consisting of carbon and nitrogen. Examples of 6-membered nitrogen-containing heteroaryls include, but are not limited to, pyridyl, pyrazinyl, pyrimidinyl, and pyridazinyl.

The term "pharmaceutically acceptable" as used herein refers to generally recognized for use in subjects, particularly in humans.

The term "pharmaceutically acceptable salt" as used herein refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, for example, an alkali metal ion, an alkaline earth ion, or an aluminum ion; or coordinates with an organic base such as ethanolamine, diethanolamine, triethanolamine, N-methylglucamine, dicyclohexylamine, and the like. Additional examples of such salts can be found in Berge et al., *J. Pharm. Sci.* 66(1):1-19 (1977). See also Stahl et al., Pharmaceutical Salts: Properties, Selection, and Use, $2^{nd}$ Revised Edition (2011).

The term "pharmaceutically acceptable excipient" as used herein refers to a broad range of ingredients that may be combined with a compound or salt disclosed herein to prepare a pharmaceutical composition or formulation. Typically, excipients include, but are not limited to, diluents, colorants, vehicles, anti-adherants, glidants, disintegrants, flavoring agents, coatings, binders, sweeteners, lubricants, sorbents, preservatives, and the like.

The term "subject" as used herein refers to humans and mammals, including, but not limited to, primates, cows, sheep, goats, horses, dogs, cats, rabbits, rats, and mice. In one embodiment the subject is a human.

The term "treating" as used herein refers not only to treating a subject to relieve the subject of one or more signs and symptoms of a disease or condition or to eliminate one or more such signs and symptoms, but also to prophylactically treating an asymptomatic subject to prevent the onset of the disease or condition or preventing, slowing or reversing the progression of the disease or condition.

The term "therapeutically effective amount" as used herein refers to that amount of a compound disclosed herein that will elicit the biological or medical response of a tissue, a system, or subject that is being sought by a researcher, veterinarian, medical doctor or other clinician. The term also encompasses the amount of compound disclosed herein that will prevent or reduce the risk of occurrence of the biological or medical event that is sought to be prevented in a tissue, a system, or subject by a researcher, veterinarian, medical doctor or other clinician.

General Synthetic Procedures

The compounds provided herein can be synthesized according to the procedures described in this and the following sections. The synthetic methods described herein are merely exemplary, and the compounds disclosed herein may also be synthesized by alternate routes utilizing alternative synthetic strategies, as appreciated by persons of ordinary skill in the art. It should be appreciated that the general synthetic procedures and specific examples provided herein are illustrative only and should not be construed as limiting the scope of the present disclosure in any manner.

Generally, the compounds of Formula I can be synthesized according to the following schemes. Any variables used in the following schemes are the variables as defined for Formula I, unless otherwise noted. All starting materials are either commercially available, for example, from Sigma-Aldrich Chemical Company, Inc., St. Louis, Mo., USA, or known in the art and may be synthesized by employing known procedures using ordinary skill. Starting material may also be synthesized via the procedures disclosed herein.

Scheme 1

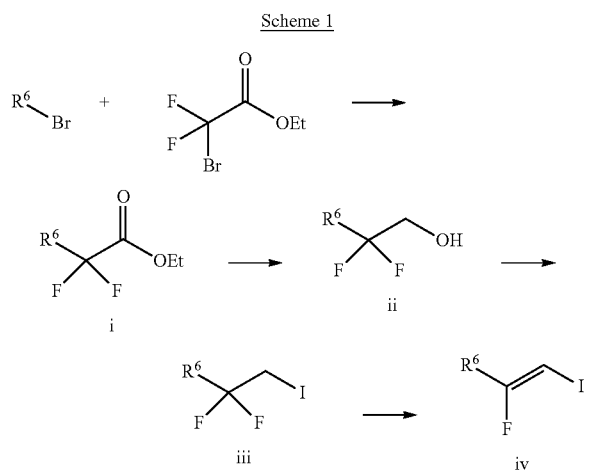

The alkene iv may be synthesized as shown in Scheme 1. The starting material $R^7$—Br is reacted with ethyl 2-bromo-2,2-difluoroacetate to give ester i. Ester i is then reduced, for example, with sodium borohydride, to give alcohol ii. The OH group of alcohol ii is then transformed into an iodo group yielding compound iii by transforming the OH group in a leaving group followed by a nucleophilic substitution, for example, by reacting alcohol ii with triflic anhydride in presence of a base, such as pyridine, followed by reaction with I⁻, sourced from, for example, sodium iodide. Alkene iv is then obtained by reacting compound iii with a base, such as potassium tert-butoxide.

Scheme 2

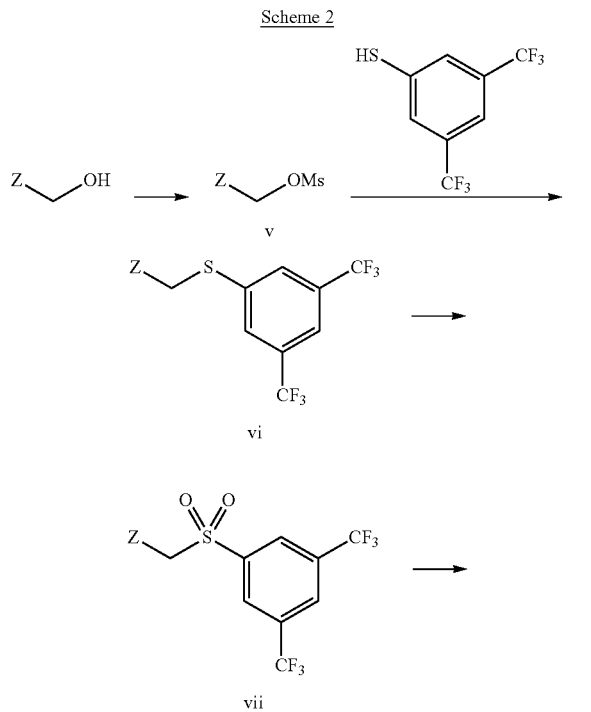

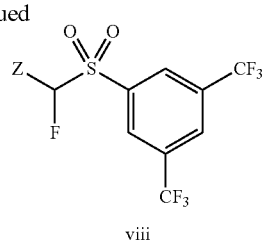

Sulfone viii, wherein Z is $R^5$ or $R^6$, may be synthesized as shown in Scheme 2. First, the OH group of $ZCH_2OH$ is transformed into a leaving group, for example by reacting $ZCH_2OH$ with methane sulfonyl chloride in presence of a base, such as trimethylamine, to give compound v. Then, compound v is reacted with 3,5-bis(trifluoromethyl)benzenethiol in presence of a base, such as sodium hydroxide, to give compound vi. Alternatively, $ZCH_2X$, wherein X is Cl, Br, or I, may be directly reacted with 3,5-bis(trifluoromethyl)benzenethiol in presence of a base, such as potassium carbonate, to give compound vi. The sulfone vii is obtained by reacting compound vi under oxidizing conditions using, for example, hydrogen peroxide. Sulfone viii was obtained reacting sulfone vii with an electrophilic fluorination agent, such as N-fluorodibenzenesulfonimide, in presence of a base, such as lithium diisopropylamide.

Scheme 3

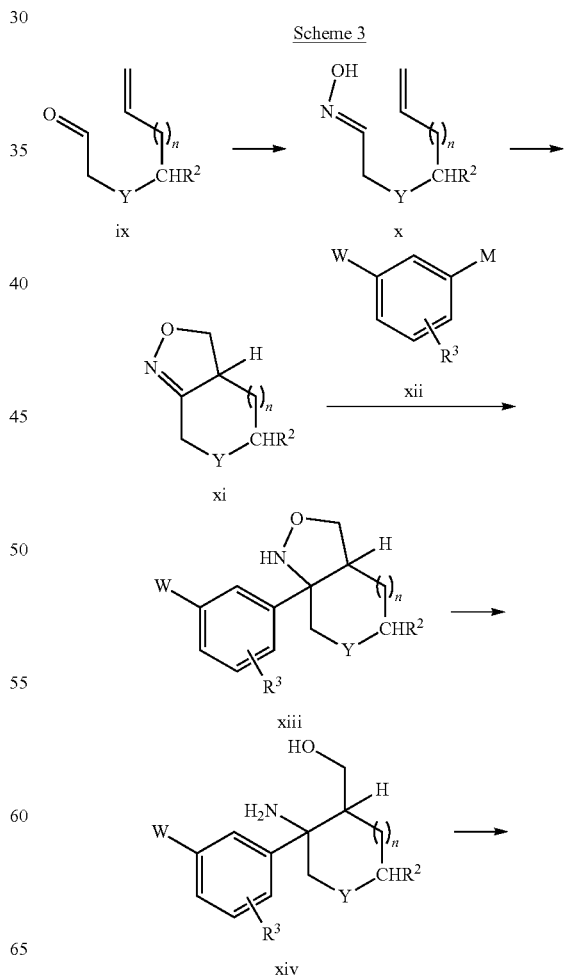

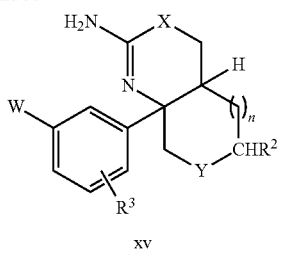

xv

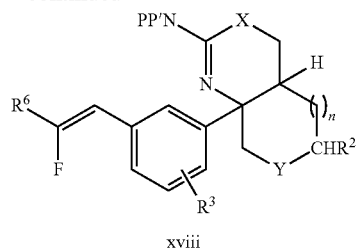

xviii

Compound xv, wherein W is Cl, Br, or I, may be synthesized as shown in Scheme 3. The aldehyde ix is reacted with hydroxylamine in form of, for example, hydroxylamine hydrochloride, in presence of a base, such as sodium acetate trihydrate, to give aldoxime x.

The bicyclic compound xi is formed by reacting the aldoxime x with, for example, an aqueous solution of sodium hypochlorite. Compound xiii is then obtained by reacting the bicyclic compound xi with the organometallic reagent xii, wherein M is, for example, Li or MgCl. Compound xiii is then reacted with, for example, powdered zinc in, for example, acetic acid, to give the hydroxyl compound xiv. The hydroxyl compound xiv is then reacted with, for example, BzNCS, followed by treatment with, for example, Tf$_2$O in presence of a base, such as pyridine, to give compound xv, wherein X is S, or followed by treatment with, for example, N,N'-carbonyldiimidazole and subsequently with acetic acid and trifluoroacetic acid, to give compound xv, wherein X is O.

The final compound xviii may be synthesized as shown in Scheme 4. First, the free amino group of compound xv, wherein W is Cl, Br, or I, is suitably protected, for example by reaction with di-tert-butyl dicarbonate in presence of a base, such as N,N-diisopropylethylamine (Hünig's base). The suitably protected compound xvi is then transformed into boronic acid xvii, for example by reacting bis(pinacolato)diboron in presence of a base, such as potassium acetate, and a suitable palladium catalyst, such [1,1'-bis(diphenylphosphino)ferrocene]-dichloropalladium(II). The final compound xviii is obtained by reacting boronic acid xvii with compound iv under Suzuki conditions, in presence of, for example, bis(di-tert-butyl(4-dimethylaminophenyl)phosphine)-dichloropalladium(II) and a base, such as potassium phosphate, followed by a deprotection of the amino group by reacting the Suzuki product with, for example, trifluoroacetic acid, if a di-BOC protecting strategy was employed.

Scheme 4

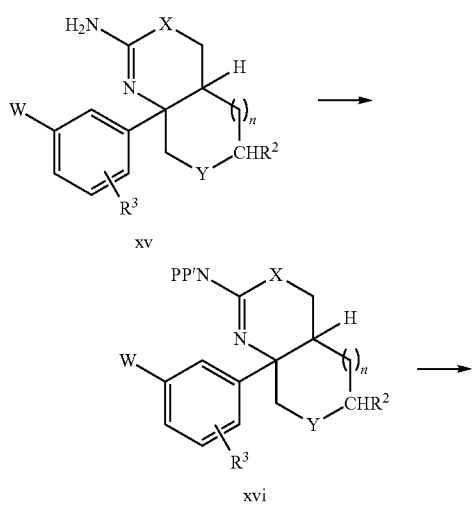

Scheme 5

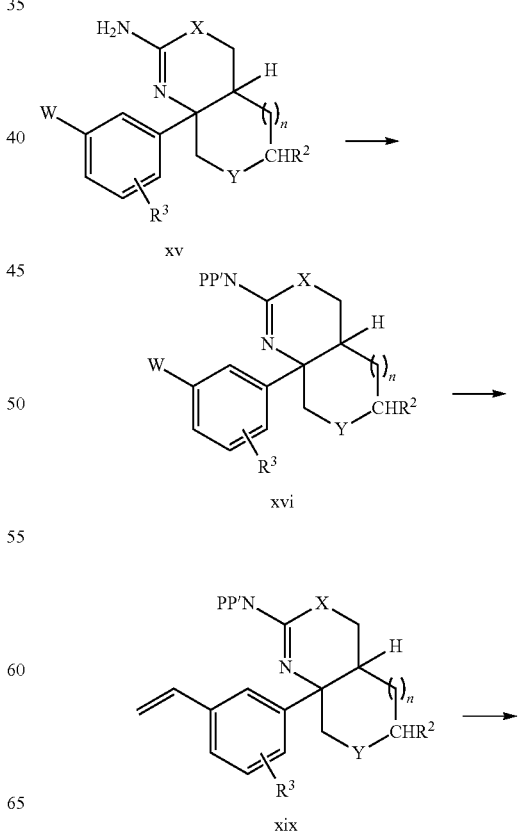

-continued

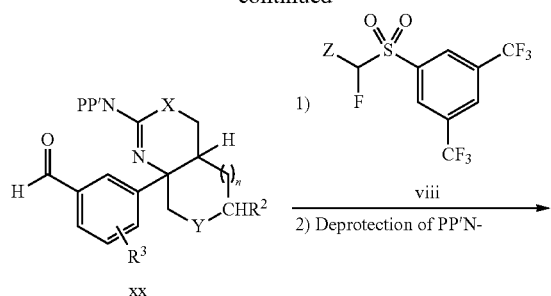

xx

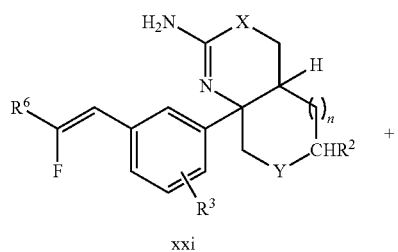

xxi

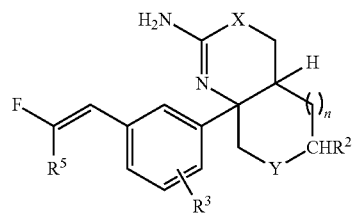

xxii

The final compounds xxi and xxii may be synthesized as shown in Scheme 5. First, the free amino group of compound xv is suitably protected, for example by reaction with benzoic anhydride in presence of a base, such as trimethylamine. The suitably protected compound xvi is then transformed into alkene xix by reacting compound xvi with, for example, potassium vinyltrifluoroborate in presence of a base, such as potassium acetate, and a suitable palladium catalyst, such as bis(di-tert-butyl(4-dimethylaminophenyl)phosphine)-dichloropalladium(II). Aldehyde xx is obtained by subjecting alkene xix to oxidizing conditions using, for example osmium tetroxide, 4-methylmorpholine-N-oxide, and potassium periodate. Aldehyde xx is then reacted with compound viii, wherein Z is $R^5$ or $R^6$, in presence of a base, such as lithium bis(trimethylsilyl)amide, followed by conditions removing the protecting group(s) from the amino group using, for example, 1,8-diazabicyclo[5.4.0]undec-7-ene (DBU), if a benzoyl protecting strategy was employed, to give final compound(s) xxi and/or xxii.

Scheme 6

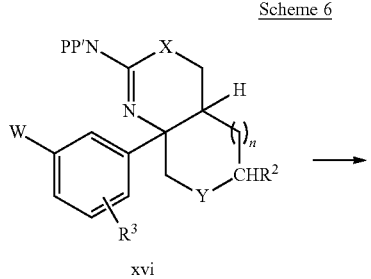

xvi

-continued

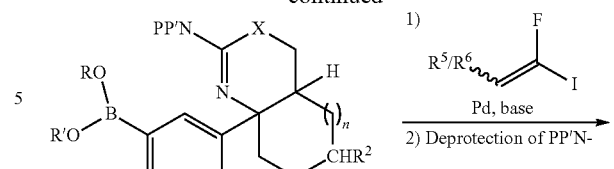

xvii

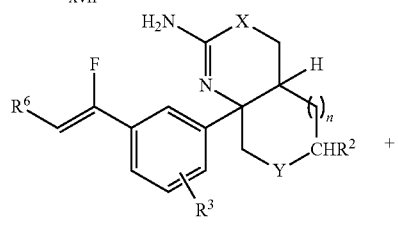

xxiii

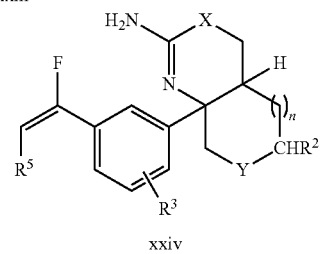

xxiv

The final compounds xxiii and xxiv may be synthesized as shown in Scheme 6. The suitably protected compound xvi is transformed into boronic ester xvii by reacting compound xvi with, for example, bispinacolatodioron in presence of a base, such as potassium acetate, and a suitable palladium catalyst, such as bis(di-tert-butyl(4-dimethylaminophenyl)phosphine)-dichloropalladium(II). Boronic ester xvii is then coupled to a suitable vinyl iodide, for example, in presence of a base, such as potassium acetate, and a suitable palladium catalyst, such as bis(di-tert-butyl(4-dimethylaminophenyl)phosphine)-dichloropalladium(II). The vinyl iodide may be synthesized by methods known in the art. Applying conditions removing the protecting group(s) from the amino group using, for example, 1,8-diazabicyclo[5.4.0]undec-7-ene (DBU), if a benzoyl protecting strategy was employed, gives final compound(s) xxiii and/or xxiv.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds disclosed herein, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3$^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, 2$^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, 2$^{nd}$ edition, Wiley-VCH, (1997); and L. Paquette, editor, Encyclopedia of Reagents for Organic Synthesis, John Wiley and Sons (1995).

All synthetic procedures described herein can be carried out under known reaction conditions, advantageously under those described herein, either in the absence or in the presence (usually) of solvents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H$^+$ form. The ability of the solvent to allow and/or influence the progress or rate of the reaction is generally dependent on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize the compounds provided herein include, but are not limited to, water; esters, including lower alkyl-lower alkanoates, for example, EtOAc; ethers including aliphatic ethers, for example, Et$_2$O and ethylene glycol dimethylether or cyclic ethers, for example, THF; liquid aromatic hydrocarbons, for example, benzene, toluene and xylene; alcohols, for example, MeOH, EtOH, 1-propanol, iPrOH, n- and t-butanol; nitriles, for example, CH$_3$CN; halogenated hydrocarbons, for example, CH$_2$Cl$_2$, CHCl$_3$ and CCl$_4$; acid amides, for example, DMF; sulfoxides, for example, DMSO; bases, including heterocyclic nitrogen bases, for example, pyridine; carboxylic acids, for example, lower alkanecarboxylic acids, for example, AcOH; inorganic acids, for example, HCl, HBr, HF, and H$_2$SO$_4$; carboxylic acid anhydrides, for example, lower alkane acid anhydrides, for example, acetic anhydride; cyclic, linear, or branched hydrocarbons, for example, cyclohexane, hexane, pentane, and isopentane; and mixtures of any of these solvents, such as purely organic solvent combinations, or water-containing solvent combinations, for example, aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (for example, liquid and gas phase), extraction, distillation, trituration, and reverse phase HPLC. Reactions conditions such as temperature, duration, pressure, and atmosphere (inert gas, ambient) are known in the art and may be adjusted as appropriate for the reaction.

The disclosure further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the scope of this disclosure.

Further, processes for making and further reacting these intermediates are also understood to be encompassed in the scope of this disclosure.

Also provided herein are new starting materials and/or intermediates, as well as processes for the preparation thereof. In select embodiments, such starting materials are used and reaction conditions so selected as to obtain the desired compound(s). Starting materials are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

EXAMPLES

This section provides specific examples of compounds of Formula I and methods of making the same.

List of Abbreviations

TABLE 1

| | |
|---|---|
| ACN | acetonitrile |
| Ac$_2$O | acetic anhydride |
| Boc | tert-butylcarboxy |
| Boc$_2$O | di-tert-butyldicarbonate |
| (BPin)$_2$ | bis(pinacolato)diboron |
| Bz | phenylcarbonyl |
| CDI | carbonyldiimidazole |
| DBU | 1,8-diazabicyclo[5.4.0]undec-7-ene |
| DCM | dichloromethane |
| DIPEA | diisopropylethylamine |
| DMA | dimethylacetamide |
| DMSO | dimethylsulfoxide |
| MsCl | methane sulfonylchloride |
| MTBE | methyl tert-butyl ether |
| NMP | N-methylpyrrolidinone |
| Pd(Amphos)Cl$_2$ | bis(di-tert-butyl(4-dimethylaminophenyl)-phosphine)dichloropalladium(II) |
| Pd$_2$(dba)$_3$ | tris(dibenzylideneacetone)dipalladium |
| Pd(dppf)Cl$_2$ | [1,1'-bis(diphenylphosphino)ferrocene]-dichloropalladium(II) |
| PdCl$_2$(dtbpf) | 1,1'-bis(di-tert-butylphosphino)ferrocene palladium |
| Pyr | pyridine |
| SFC | Supercritical fluid chromatography |
| s-Phos | 2-dicyclohexylphosphino-2',6'-dimethoxybiphenyl |
| TFA | trifluoroacetic acid |
| TFAA | trifluoroacetic anhydride |
| THF | tetrahydrofuran |
| Tf$_2$O | trifluormethanesulfonic anhydride |
| T3P | 1-propanephosphonic anhydride |

General Analytical and Purification Methods

Provided in this section are descriptions of the general analytical and purification methods used to prepare the specific compounds provided herein.

Chromatography:

Unless otherwise indicated, crude product-containing residues were purified by passing the crude material or concentrate through either a Biotage or Isco brand silica gel column (pre-packed or individually packed with $SiO_2$) and eluting the product off the column with a solvent gradient as indicated. For example a description of (330 g $SiO_2$, 0-40% EtOAc/hexane) means the product was obtained by elution from the column packed with 330 grams of silica, with a solvent gradient of 0% to 40% EtOAc in hexanes.

Preparative HPLC Method:

Where so indicated, the compounds described herein were purified via reverse phase HPLC using one of the following instruments: Shimadzu, Varian, Gilson; utilizing one of the following two HPLC columns: (a) a Phenomenex Luna or (b) a Gemini column (5 micron or 10 micron, C18, 150×50 mm)

A typical run through the instrument included: eluting at 45 mL/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1H$ NMR spectra were collected on a Bruker NMR Instrument at 300 MHz or 400 MHz. Where so characterized, all observed protons are reported as parts-per-million (ppm) downfield from tetramethylsilane (TMS) or other internal reference in the appropriate solvent indicated.

$^{19}F$ NMR Spectra:

Unless otherwise indicated, all $^{19}F$ NMR spectra were run on a Bruker NMR Instrument at 376 MHz. All observed protons are reported as parts-per-million (ppm) downfield.

Mass Spectra (MS)

Unless otherwise indicated, all mass spectral data for starting materials, intermediates and/or exemplary compounds are reported as mass/charge (m/z), having an $(M+H^+)$ molecular ion. The molecular ion reported was obtained by electrospray detection method (commonly referred to as an ESI MS) utilizing a PE SCIEX API 150EX MS instrument or an Agilent 1100 series LC/MSD system. Compounds having an isotopic atom, such as bromine and the like, are generally reported according to the detected isotopic pattern, as appreciated by those skilled in the art.

Compound Names

The compounds disclosed and described herein have been named using either (1) the naming convention provided with Chem-Draw Ultra 12.0.3. software, available in Chem Office, or (2) by the ISIS database software (Advanced Chemistry Design Labs or ACD software).

Specific Examples

Provided in this section are the procedures to synthesize specific examples of the compounds provided herein. All starting materials are either commercially available from Sigma-Aldrich Chemical Company, Inc., St. Louis, Mo., USA, unless otherwise noted, or known in the art and may be synthesized by employing known procedures using ordinary skill.

Intermediates

Intermediate 1:
(Z)-6-(1-fluoro-2-iodovinyl)nicotinonitrile

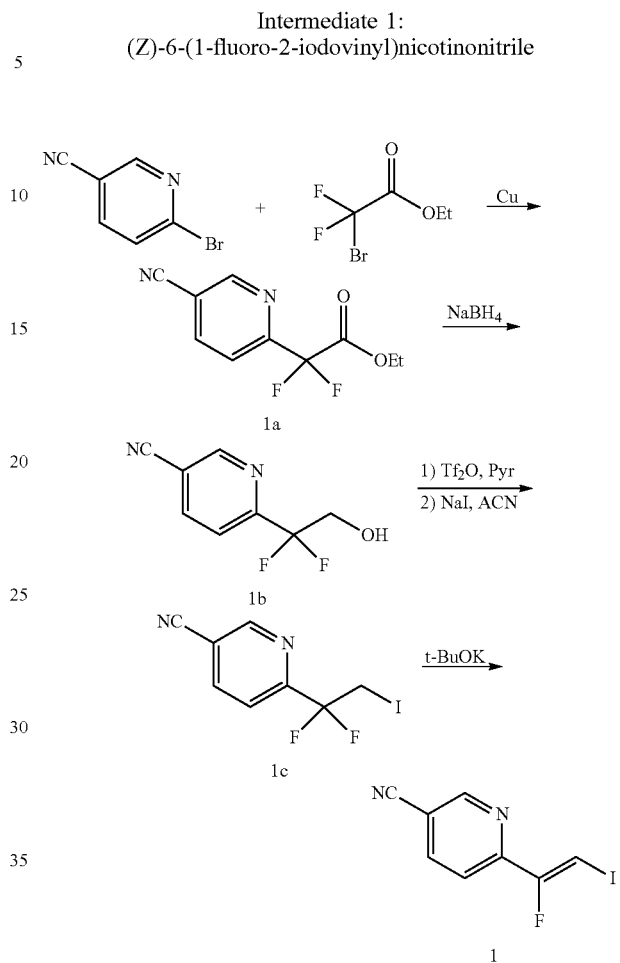

Preparation of ethyl
2-(5-cyanopyridin-2-yl)-2,2-difluoroacetate (1a)

To a suspension of copper(0) powder (Spectrochem PVT. LTD., Mumbai, India) (413 g, 6557 mmol) in dimethyl sulfoxide (6 L) was added ethyl 2-bromo-2,2-difluoroacetate (Matrix Scientific, Columbia, S.C., USA) (665 g, 3279 mmol) dropwise under nitrogen atmosphere at room temperature. The reaction mixture was stirred at room temperature for 1 hour and 2-bromo-5-cyanopyridine (Sigma-Aldrich, St. Louis, Mo., USA) (300 g, 1639 mmol) was added portion-wise. The reaction mixture was stirred at room temperature for 12 hours. It was filtered through a pad of celite and the filtrate was partitioned between EtOAc (3 L) and sat'd aqueous ammonium chloride (2.5 mL) solution. The organic layer was separated and the aqueous layer was extracted with EtOAc (2×2 L). The combined organic solution was washed with water (2×2 L), dried over $Na_2SO_4$ and concentrated under reduced pressure. The residue was purified by silica gel column chromatography (0-10% EtOAc in hexanes) to give 1a (320 g, 86% yield) as a colourless oil. MS (ESI+ve ion) m/z: [M+1]=227.1. $^1H$ NMR (400 MHz, Chloroform-d) δ 8.93 (d, J=2.0 Hz, 1H), 8.18 (dd, J=8.2, 2.1 Hz, 1H), 7.90 (dd, J=8.1, 1.0 Hz, 1H), 4.39 (q, J=7.1 Hz, 2H), 1.34 (t, J=7.1 Hz, 3H).

Preparation of 6-(1,1-difluoro-2-hydroxyethyl)nicotinonitrile (1b)

To a solution of 1a (105 g, 464 mmol) in THF (1.5 L) at −20° C. was added sodium borohydride (10.5 g, 279 mmol) in a portion-wise manner. The reaction mixture was stirred at −20° C. for 30 minutes and methanol (525 mL) was added dropwise. The reaction mixture was stirred at −20° C. for 1 hour then quenched with water (500 mL). The mixture was concentrated under reduced pressure. The residue was diluted with water (0.5 L) and extracted with EtOAc (2×1 L). The combined organic solution was dried over $Na_2SO_4$ and concentrated. The residue was purified by silica gel column chromatography (0-25% EtOAc in hexanes) to provide 1b (43.0 g, 50% yield) as a light-yellow solid. MS (ESI+ve ion) m/z: [M+1]=185.1. $^1$H NMR (400 MHz, Chloroform-d) δ 8.97-8.90 (m, 1H), 8.18 (dd, J=8.2, 2.1 Hz, 1H), 7.89 (dd, J=8.3, 0.9 Hz, 1H), 4.29 (t, J=12.4 Hz, 2H). Note: OH proton was not observed.

Preparation of 6-(1,1-difluoro-2-iodoethyl)nicotinonitrile (1c)

To a solution of 1b (87 g, 472 mmol) in acetonitrile (1.3 L) was added pyridine (74.7 g, 945 mmol) followed by dropwise addition of triflouoromethanesulfonic anhydride (Sigma-Aldrich, St. Louis, Mo., USA) (240 g, 850 mmol) at −10° C. under nitrogen atmosphere. The reaction mixture was stirred at room temperature for 5 hours then cooled to 0° C. Sodium iodide (354 g, 2362 mmol) was added in a portion-wise manner. The reaction mixture was heated at 60° C. for 2 hours then cooled to room temperature, diluted with water (2 L) and extracted with EtOAc (3×3 L). The combined organic solution was dried over $Na_2SO_4$ and concentrated under reduced pressure. The crude material was purified on a silica gel column (0-10% EtOAc in hexanes) to afford 1c (107 g, 77% yield) as a light-yellow solid. MS (ESI+ve ion) m/z: [M+1]=295.0. $^1$H NMR (400 MHz, Chloroform-d) δ 8.95 (s, 1H), 8.17-8.14 (m, 1H), 7.87-7.85 (d, J=8.0 Hz, 1H), 3.97 (t, J=14.4 Hz, 2H).

Preparation of 6-(1,1-difluoro-2-iodoethyl)nicotinonitrile (1)

To a solution of 1c (58 g, 197 mmol) in THF (580 mL) was added potassium tert-butoxide (26.6 g, 237 mmol) portion-wise at 0° C. The reaction mixture was stirred at 0° C. for 2 hours then quenched with sat'd aqueous $NH_4Cl$ (100 mL) and diluted with water (100 mL). The mixture was extracted with EtOAc (3×700 mL). The combined organic extracts were dried over $Na_2SO_4$ and concentrated. Purification of the residue by silica gel chromatography (1 to 5% EtOAc in hexanes) gave 6-(1,1-difluoro-2-iodoethyl)nicotinonitrile (1) (33 g, 61% yield) as a light yellow solid. MS (ESI+ve ion) m/z: [M+1]=274.9. $^1$H NMR (400 MHz, DMSO-$d_6$) δ 9.04 (dd, J=2.1, 1.0 Hz, 1H), 8.45 (dd, J=8.3, 2.1 Hz, 1H), 7.81 (dt, J=8.3, 1.1 Hz, 1H), 7.42 (d, J=36.4 Hz, 1H).

Intermediate 2: (Z)-5-fluoro-2-(1-fluoro-2-iodovinyl)pyridine

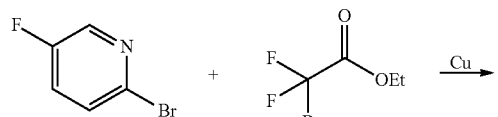

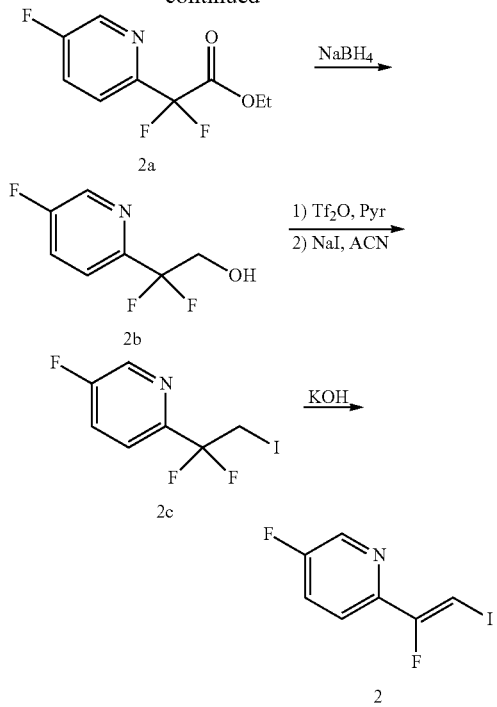

Preparation of ethyl 2,2-difluoro-2-(5-fluoropyridin-2-yl)acetate (2a)

Ethyl 2,2-difluoro-2-(5-fluoropyridin-2-yl)acetate (2a, 44.8 g, 80% yield) as a viscous colourless liquid was prepared in a fashion similar to that described for 1a, here starting from ethyl 2-bromo-2,2-difluoroacetate (104 g, 511 mmol) and 2-bromo-5-fluoropyridine (Shanghai Fchemicals Technology Co., Ltd., Shanghai, China) (45 g, 256 mmol). MS (ESI+ve ion) m/z: [M+1]=220.2. $^1$H NMR (400 MHz, DMSO-$d_6$) δ 8.73 (d, J=2.5 Hz, 1H), 8.05-7.95 (m, 2H), 4.34 (dd, J=7.2, 5.2 Hz, 2H), 1.23 (t, J=7.2 Hz, 3H).

Preparation of 2,2-difluoro-2-(5-fluoropyridin-2-yl)ethanol (2b)

2,2-Difluoro-2-(5-fluoropyridin-2-yl)ethanol (2b) (25 g, 69% yield) as a colourless liquid was prepared in a fashion similar to that described for 1b, here starting from 2a (45 g, 205 mmol). MS (ESI+ve ion) m/z: [M+1]=178.2. $^1$H NMR (400 MHz, DMSO-$d_6$) δ 8.69 (d, J=2.8 Hz, 1H), 7.90 (td, J=8.7, 2.8 Hz, 1H), 7.78 (dd, J=8.7, 4.3 Hz, 1H), 5.56 (td, J=6.4, 1.3 Hz, 1H), 4.03-3.96 (m, 2H).

Preparation of 2-(1,1-difluoro-2-iodoethyl)-5-fluoropyridine (2c)

2-(1,1-Difluoro-2-iodoethyl)-5-fluoropyridine (2c, 25 g, 62% yield) as a yellow solid was prepared in a fashion similar to that described for 1c, here starting from 2b (25 g, 141 mmol). MS (ESI+ve ion) m/z: [M+1]=288.0. $^1$H NMR (400 MHz, DMSO-$d_6$) δ 8.73 (d, J=2.7 Hz, 1H), 7.96 (td, J=8.7, 2.8 Hz, 1H), 7.88-7.82 (m, 1H), 4.08-3.98 (m, 2H).

Preparation of (Z)-5-fluoro-2-(1-fluoro-2-iodovinyl)pyridine (2)

To a solution of 2-(1,1-difluoro-2-iodoethyl)-5-fluoropyridine (2c, 25 g, 87 mmol) in DMSO (200 mL) was added 5.0 M aqueous NaOH solution (30 mL, 150 mmol) dropwise at 0° C. The reaction mixture was stirred at 0° C. for 2 hours then quenched with water (100 mL) and extracted with EtOAc (2×200 mL). The combined organic solution was washed with brine (200 mL), dried over $Na_2SO_4$ and concentrated. Purification of the residue by silica gel chromatography (0-5% EtOAc in hexanes) provided (Z)-5-fluoro-2-(1-fluoro-2-iodovinyl)pyridine (2) (18 g, 77% yield) as a clear oil. MS (ESI+ve ion) m/z: [M+1]=268.0. $^1$H NMR (400 MHz, DMSO-$d_6$) δ 8.64 (d, J=2.9 Hz, 1H), 7.86 (m, 1H), 7.72 (ddt, J=8.4, 3.8, 1.9 Hz, 1H), 7.02 (dd, J=36.7, 1.9 Hz, 1H).

Intermediate 3: (Z)-5-chloro-2-(1-fluoro-2-iodovinyl)pyridine

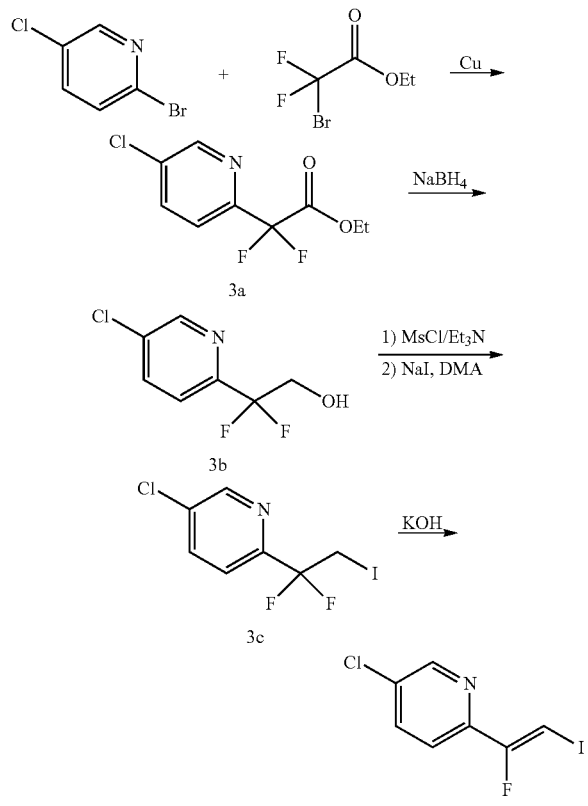

Preparation of ethyl 2-(5-chloropyridin-2-yl)-2,2-difluoroacetate (3a)

Ethyl 2-bromo-2,2-difluoroacetate (105 g, 520 mmol) was added slowly to a suspension of copper(0) powder (66.0 g, 1039 mmol) in DMSO (1.2 L) under nitrogen atmosphere at room temperature. The reaction mixture was stirred at room temperature for 1 hour and 2-bromo-5-chloropyridine (Shanghai Fchemicals Technology Co., Ltd., Shanghai, China) (50.0 g, 260 mmol) was added in one portion. The reaction mixture was stirred at room temperature for 12 hours then filtered through a pad of celite. The filter cake was rinsed with 400 mL of EtOAc. The filtrate was partitioned between EtOAc (1 L) and sat'd aqueous ammonium chloride (100 mL) and water (100 mL). The organic layer was separated and the aqueous layer was extracted with EtOAc (2×100 mL). The combined organic solution was washed with water (2×100 mL), dried over $Na_2SO_4$ and concentrated. Purification of the residue by silica gel chromatography (0-10% EtOAc in hexanes) gave 3a (60 g, 64% yield) as a clear liquid. MS (ESI+ve ion) m/z: [M+1]=236.0. $^1$H NMR (400 MHz, Chloroform-d) δ 8.63-8.59 (m, 1H), 7.85 (dt, J=8.4, 1.6 Hz, 1H), 7.70 (dt, J=8.4, 0.9 Hz, 1H), 4.11 (q, J=7.1, 1.0 Hz, 2H), 1.26 (t, J=7.1, 1.0 Hz, 3H).

Preparation of 2-(5-chloropyridin-2-yl)-2,2-difluoroethan-1-ol (3b)

To a solution of 3a (47.0 g, 199 mmol) in ethanol (600 mL) at 0° C. was added sodium borohydride (7.5 g, 199 mmol) portion-wise. The reaction mixture was stirred at room temperature for 1 hour then quenched with water (500 mL) and concentrated under reduced pressure. The crude material was diluted with water (500 mL) and extarcted with EtOAc (2×500 mL). The combined organic extracts were dried over $Na_2SO_4$ and concentrated. Purification of the residue by silica gel chromatography (0-10% EtOAc in hexanes) gave 3b (35 g, 91% yield) as a light yellow solid. MS (ESI+ve ion) m/z: [M+1]=194.2. $^1$H NMR (400 MHz, Chloroform-d) δ 8.64-8.58 (m, 1H), 7.86 (dd, J=8.4, 2.4 Hz, 1H), 7.70 (dt, J=8.5, 1.5 Hz, 1H), 4.24 (t, J=12.4 Hz, 2H). Note: OH proton not observed.

Preparation of 5-chloro-2-(1,1-difluoro-2-iodoethyl)pyridine (3c)

To a solution of 3b (31 g, 160 mmol) in DCM (500 mL) at 0° C. was added triethylamine (49.1 mL, 352 mmol) followed by dropwise addition of methanesulfonyl chloride (23.7 mL, 304 mmol). The reaction mixture was stirred at room temperature for 1 hour. The reaction mixture was diluted with water (500 mL) and extracted with DCM (2×500 mL). The combined organic extracts were washed with brine (250 mL), dried over $Na_2SO_4$ and concentrated under reduced pressure. The residue was dissolved in N,N-dimethyl acetamide (600 mL) and treated with sodium iodide (96 g, 641 mol) portion-wise. The reaction mixture was heated at 110° C. for 36 hours then cooled to room temperature, diluted with water (500 mL), and extracted with EtOAc (2×500 mL). The combined organic solution was washed with brine (500 mL), dried over $Na_2SO_4$ and concentrated. The residue was purified by silica gel chromatography (0-10% EtOAc in hexanes) to give 3c (30 g, 60% yield) as a brown solid. MS (ESI+ve ion) m/z: [M+1]=303.9. $^1$H NMR (400 MHz, Chloroform-d) δ 8.59 (s, 1H), 7.87-7.84 (m, 1H), 7.27 (d, J=2.0 Hz, 1H), 4.27 (t, J=12.4 Hz, 2H).

Preparation of (Z)-5-chloro-2-(1-fluoro-2-iodovinyl)pyridine (3)

To a solution of 3c (30 g, 99 mmol) in DMSO (50 mL, 1.66 mL/g) was added a solution of KOH (19.4 g, 346 mmol) in water (50 mL) dropwise at 0° C. The reaction mixture was stirred at room temperature for 10 hours then diluted with water (150 mL) and stirred for 15 minutes. The precipitated solids were collected by filtration, washed with water (2×100 mL), collected and dried to afford (Z)-5-chloro-2-(1-fluoro-2-iodovinyl)pyridine (3) (24.7 g, 87% yield) as a white crystalline solid. MS (ESI+ve ion) m/z: [M+1]=284.0. $^1$H NMR (400 MHz, Chloroform-d) δ 8.54-

8.51 (m, 1H), 7.74 (dd, J=8.5, 2.4 Hz, 1H), 7.50 (ddd, J=8.5, 1.8, 0.8 Hz, 1H), 6.94 (d, J=34.3 Hz, 1H).

Intermediate 4: (Z)-3-chloro-2-(1-fluoro-2-iodovinyl)-5-(trifluoromethyl)pyridine

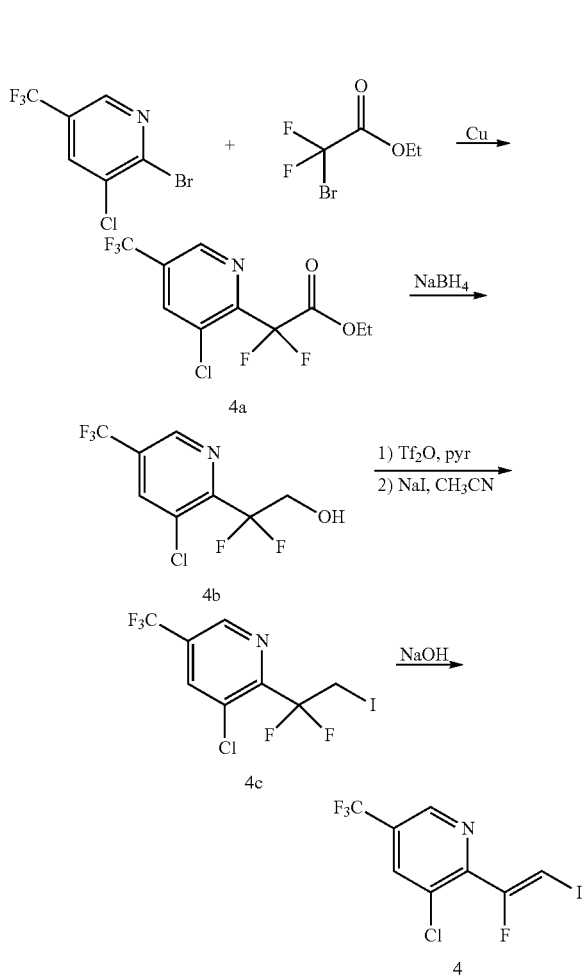

Ethyl 2-(3-chloro-5-(trifluoromethyl)pyridin-2-yl)-2,2-difluoroacetate (4a, 90 g, 86% yield) as a colorless oil was synthesized using a protocol similar to described for 5a, here starting from 2-bromo-3-chloro-5-(trifluoromethyl)pyridine (ChemPure Chemicals, Plymouth, Mich., USA) (90 g, 346 mmol) and ethyl bromodifluoroacetate (140 g, 691 mmol). MS (ESI+ve ion) m/z: [M+1]=304.1. $^1$H NMR (400 MHz, Chloroform-d) δ 8.80 (s, 1H), 8.09 (d, J=2.0 Hz, 1H), 4.47-4.41 (m, 2H), 1.39 (t, J=7.1 Hz, 3H).

Compounds 4b, 4c, and 4 were synthesized in a fashion similar to that described for 5b, 5c, and 5, respectively. 2-(3-chloro-5-(trifluoromethyl)pyridin-2-yl)-2,2-difluoroethanol (4b): MS (ESI+ve ion) m/z: [M+1]=262.3. $^1$H NMR (400 MHz, Chloroform-d) δ 8.77 (d, J=2.0 Hz, 1H), 8.13 (d, J=2.0 Hz, 1H), 4.34 (m, 2H), 2.97 (t, J=7.7 Hz, 1H). 3-Chloro-2-(1,1-difluoro-2-iodoethyl)-5-(trifluoromethyl) pyridine (4c): MS (ESI+ve ion) m/z: [M+1]=372.0. $^1$H NMR (400 MHz, Chloroform-d) δ 8.80 (d, J=6.1 Hz, 1H), 8.10 (s, 1H), 4.05 (tdd, J=15.1, 4.2, 2.6 Hz, 2H). (Z)-3-chloro-2-(1-fluoro-2-iodovinyl)-5-(trifluoromethyl)pyridine (4): MS (ESI+ve ion) m/z: [M+1]=352.2. $^1$H NMR (400 MHz, DMSO-d$_6$) δ 9.00 (d, J=2.0 Hz, 1H), 8.62 (d, J=2.1 Hz, 1H), 7.22-7.05 (m, 1H).

Intermediate 5: (Z)-2-(1-fluoro-2-iodovinyl)-5-(trifluoromethyl)pyridine

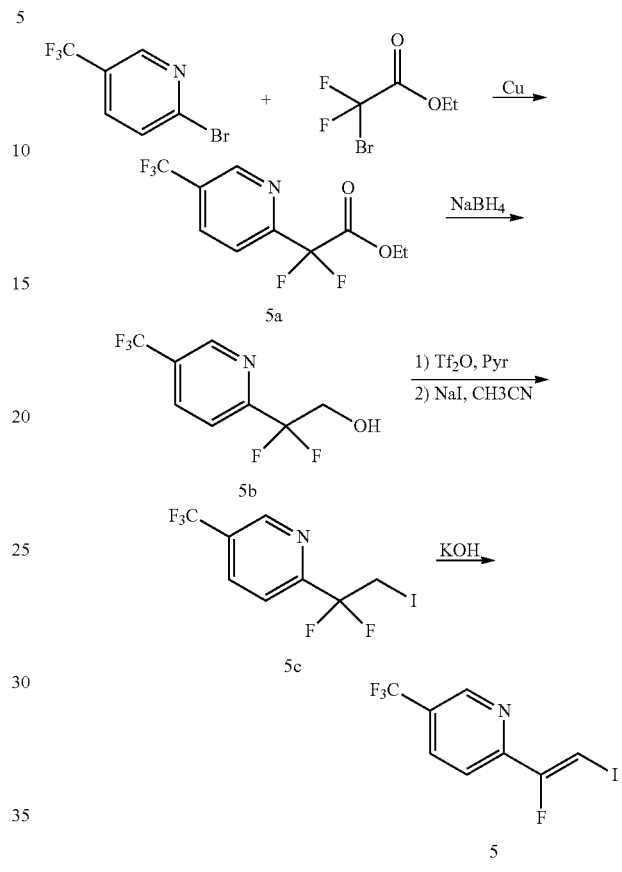

Preparation of ethyl 2,2-difluoro-2-(5-(trifluoromethyl)pyridin-2-yl)acetate (5a)

To a suspension of copper(0) powder (229 g, 1128 mmol) in DMSO (1.7 L) was added ethyl 2-bromo-2,2-difluoroacetate (47.9 g, 752 mmol) at room temperature. The reaction mixture was stirred for 1 hour and 2-bromo-5-(trifluoromethyl)pyridine (Arborchem, Mechanicsburg, Pa., USA) (85 g, 376 mmol) was added portion-wise. The reaction mixture was stirred at room temperature for 12 hours, then quenched with sat'd ammonia chloride (250 mL). The reaction mixture was filtered through a Celite pad and the filtrate was extracted with EtOAc (3×350 mL). The combined organic solution was dried over Na$_2$SO$_4$ and concentrated under reduced pressure. The crude residue was purified by silica gel chromatography (0-2% EtOAc in hexanes) to provide 5a (65 g, 64% yield). MS (ESI, positive ion) m/z: 270.1 (M+1). $^1$H NMR (400 MHz, Chloroform-d) δ 8.94 (d, J=1.7 Hz, 1H), 8.14 (dd, J=8.2, 2.2 Hz, 1H), 7.91 (d, J=8.3 Hz, 1H), 4.46-4.33 (m, 2H), 1.45-1.26 (m, 3H).

Preparation of 2,2-difluoro-2-(5-(trifluoromethyl)pyridin-2-yl)ethanol (5b)

To a solution of 5a (62 g, 230 mmol) in ethanol (620 mL) at 0° C. was added sodium borohydride (8.7 g, 230 mmol) portion-wise. The reaction mixture was stirred for 30 minutes at 0° C., then quenched with water (100 mL) and extracted with EtOAc (3×250 mL). The combined organic solution was dried over Na$_2$SO$_4$ and concentrated under reduced pressure. The crude residue was purified by silica gel chromatography (2-10% EtOAc in hexanes) to provide 5b (45 g, 86% yield) as a colourless liquid. MS (ESI, positive ion) m/z: 228.1 (M+1). $^1$H NMR (400 MHz, Chloroform-d) δ 9.01-8.88 (m, 1H), 8.15 (dd, J=8.3, 2.2 Hz, 1H), 7.90 (d, J=8.2 Hz, 1H), 4.30 (td, J=12.4, 7.2 Hz, 2H), 2.81 (t, J=7.2 Hz, 1H).

Preparation of 2-(1,1-difluoro-2-iodoethyl)-5-(trifluoromethyl)pyridine (5c)

To a solution of 5b (45 g, 198 mmol) in acetonitrile (450 mL) at 0° C. was added pyridine (32.0 mL, 396 mmol) followed by drop-wise addition of trifluoromethane sulfonic anhydride (50.2 mL, 297 mmol). The reaction mixture was stirred at 0° C. for 30 minutes. Sodium iodide (89 g, 594 mmol) was added portion-wise to the reaction mixture at room temperature. The reaction mixture was stirred at 70° C. for 2 hours. After the completion of the reaction (monitored by TLC), the reaction mixture was quenched with saturated sodium thiosulfate solution (250 mL) and extracted with EtOAc (3×250 mL). The combined organic layer was washed with brine, dried over Na$_2$SO$_4$ and concentrated under reduced pressure. The crude residue was purified by silica gel chromatography (0-2% EtOAc in hexanes) to afford 5c (45 g, 67% yield). MS (ESI, positive ion) m/z: 338.1 (M+1). $^1$H NMR (400 MHz, DMSO-d$_6$) δ 9.15 (s, 1H), 8.60-8.39 (m, 1H), 8.00 (d, J=8.2 Hz, 1H), 4.07 (t, J=16.2 Hz, 2H).

Preparation of (Z)-2-(1-fluoro-2-iodovinyl)-5-(trifluoromethyl)pyridine (5)

To a solution of 5c (50 g, 148 mmol) in DMSO (500 mL) was added dropwise a solution of sodium hydroxide (44.5 mL of 5 N solution, 223 mmol) at 0° C. The reaction mixture was stirred at 0° C. for 5 hours, then quenched with water (100 mL) and extracted with EtOAc (3×250 mL). The combined organic solution was washed with brine (150 mL), dried over Na$_2$SO$_4$ and concentrated under reduced pressure. The crude residue was purified by silica gel chromatography (2-10% EtOAc in hexanes) to afford Intermediate 5 (40 g, 85% yield) as an off-white solid. MS (ESI, positive ion) m/z: 318.1 (M+1). $^1$H NMR (400 MHz, DMSO-d$_6$) δ 9.07-8.91 (m, 1H), 8.34 (dd, J=8.5, 2.3 Hz, 1H), 7.83 (d, J=8.3 Hz, 1H), 7.36 (d, J=36.5 Hz, 1H).

Intermediate 6: (Z)-2-(1-fluoro-2-iodovinyl)-5-(trifluoromethyl)pyridine

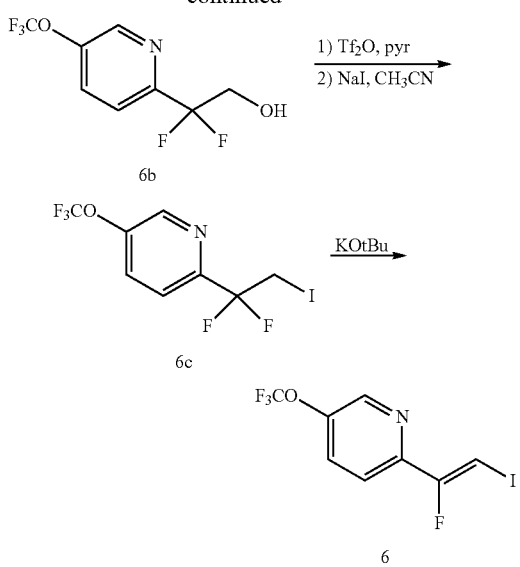

Ethyl 2,2-difluoro-2-(5-(trifluoromethoxy)pyridin-2-yl) acetate (6a, 2.61 g, 9.15 mmol, 87% yield) as a colorless oil was synthesized using a protocol similar to that described for 1a, here starting from 2-bromo-5-(trifluoromethoxy) pyridine (Shanghai Fchemicals Technology Co., Ltd., Shanghai, China) (2.54 mL, 10.50 mmol) and ethyl bromodifluoroacetate (1.48 mL, 11.55 mmol). MS (ESI+ve ion) m/z: [M+1]=286.2.

Compounds 6b, 6c, and 6 were synthesized in a fashion similar to that described for 1b, 1c, and 1, respectively. 2,2-Difluoro-2-(5-(trifluoromethoxy)pyridin-2-yl)ethanol (6b): MS (ESI+ve ion) m/z: [M+1]=244.1. 2-(1,1-Difluoro-2-iodoethyl)-5-(trifluoromethoxy)pyridine (6c): MS (ESI+ve ion) m/z: [M+1]=353.9. $^1$H NMR (400 MHz, DMSO-d$_6$) δ 8.82 (d, J=2.15 Hz, 1H), 8.13 (m, 1H), 7.92 (d, J=8.80 Hz, 1H), 4.04 (t, J=16.14 Hz, 2H). (Z)-2-(1-Fluoro-2-iodovinyl)-5-(trifluoromethoxy)pyridine (6): MS (ESI+ve ion) m/z: [M+1]=334.0. $^1$H NMR (400 MHz, DMSO-d$_6$) δ 8.71 (s, 1H), 8.02 (m, 1H), 7.78 (d, J=8.61 Hz, 1H), 7.16 (d, J=37.44 Hz, 1H). $^{19}$F NMR (376 MHz, DMSO-d$_6$) δ−57.16 (s, 3F), −99.23 (s, 1F).

Intermediate 7: (Z)-6-(1-fluoro-2-iodovinyl)-5-methylnicotinonitrile

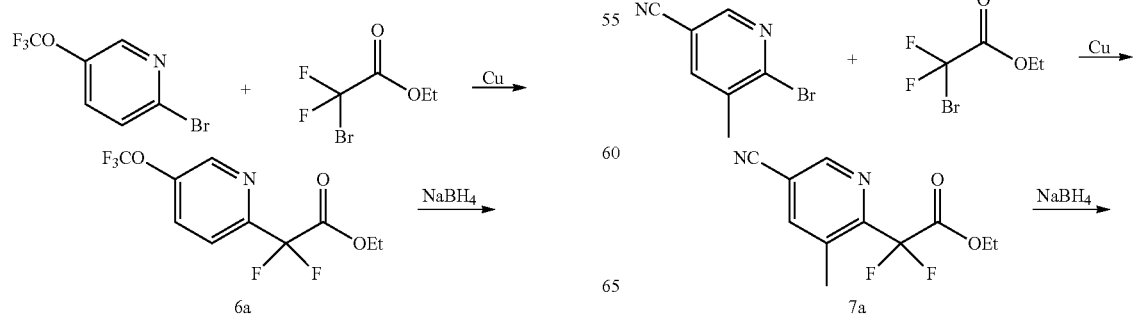

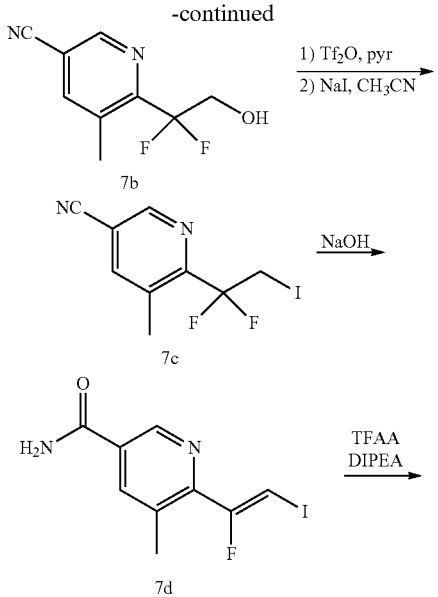

Ethyl 2-(5-cyano-3-methylpyridin-2-yl)-2,2-difluoroacetate (7a, 58 g, 59% yield) as a transparent oil was synthesized using a protocol similar to that described for 5a, starting from 6-bromo-5-methylnicotinonitrile (Shanghai Fchemicals Technology Co., Ltd., Shanghai, China) (80 g, 406 mmol) and ethyl bromodifluoroacetate (165 g, 812 mmol). MS (ESI+ve ion) m/z: [M+1]=241.0. $^1$H NMR (400 MHz, Chloroform-d) δ 8.68 (d, J=4.1 Hz, 1H), 7.93 (d, J=2.1 Hz, 1H), 4.46 (q, J=7.1 Hz, 2H), 2.63 (q, J=2.5 Hz, 3H), 1.41-1.34 (m, 3H).

Compounds 7b and 7c were synthesized in a fashion similar to that described for 5b and 5c, respectively. 6-(1,1-Difluoro-2-hydroxyethyl)-5-methylnicotinonitrile (7b): MS (ESI+ve ion) m/z: [M+1]=199.1. $^1$H NMR (400 MHz, Chloroform-d) δ 8.68 (dd, J=2.1, 1.0 Hz, 1H), 7.95 (dd, J=1.8, 0.9 Hz, 1H), 4.31 (td, J=12.4, 7.5 Hz, 2H), 3.24 (t, J=7.6 Hz, 1H), 2.64 (t, J=2.6 Hz, 3H). —OH proton was not observed. 6-(1,1-Difluoro-2-iodoethyl)-5-methylnicotinonitrile (7c): MS (ESI+ve ion) m/z: [M+1]=309.2. $^1$H NMR (400 MHz, Chloroform-d) δ 8.70 (dd, J=1.8, 1.0 Hz, 1H), 7.90 (dd, J=1.9, 0.9 Hz, 1H), 4.06 (t, J=15.3 Hz, 2H), 2.62 (t, J=3.2 Hz, 3H).

Preparation of (Z)-6-(1-fluoro-2-iodovinyl)-5-methylnicotinamide (7d)

To a solution of 7c (25 g, 81 mmol) in DMSO (250 mL) at 0° C. was added NaOH (32.5 mL of 5 N solution, 162 mmol). The reaction mixture was stirred at 0° C. for 10 hours, then quenched with water (250 mL) and extracted with EtOAc (2×500 mL). The combined organic solution was washed with brine (500 mL), dried over Na$_2$SO$_4$ and concentrated under reduced pressure. The crude residue was purified by silica gel chromatography (20-50% EtOAc in hexanes) to afford 7d (12 g, 48% yield) as an off-white solid. MS (ESI+ve ion) m/z: [M+1]=307.2. $^1$H NMR (300 MHz, DMSO-d$_6$) δ 8.85 (d, J=2.2 Hz, 1H), 8.22-8.13 (m, 2H), 7.67 (s, 1H), 6.87 (dd, J=36.4, 2.5 Hz, 1H), 2.43 (t, J=3.9 Hz, 3H).

Preparation of (Z)-6-(1-fluoro-2-iodovinyl)-5-methylnicotinonitrile (7)

To a solution of (Z)-6-(1-fluoro-2-iodovinyl)-5-methylnicotinonitrile (7) (12.0 g, 39.2 mmol) in THF (120 mL) at 0° C. was added DIPEA (34.2 mL, 196 mmol) followed by TFAA (27.7 mL, 196 mmol). The reaction mixture was stirred at 0° C. for 2 hours, then quenched with water (500 mL) and extracted with EtOAc (2×500 mL). The combined organic solution was washed with brine (20 mL), dried over Na$_2$SO$_4$ and concentrated under reduced pressure. The crude residue was purified by silica gel chromatography (10% EtOAc in hexanes) to afford Intermediate 7 (10.5 g, 93% yield) as an off-white solid. MS (ESI+ve ion) m/z: [M+1]=No ionization. $^1$H NMR (400 MHz, DMSO-d$_6$) δ 8.87 (d, J=2.0 Hz, 1H), 8.31 (d, J=2.2 Hz, 1H), 7.13-6.93 (m, 1H), 2.42 (d, J=5.2 Hz, 3H).

Intermediate 8: (Z)-5-chloro-6-(1-fluoro-2-iodovinyl)nicotinonitrile

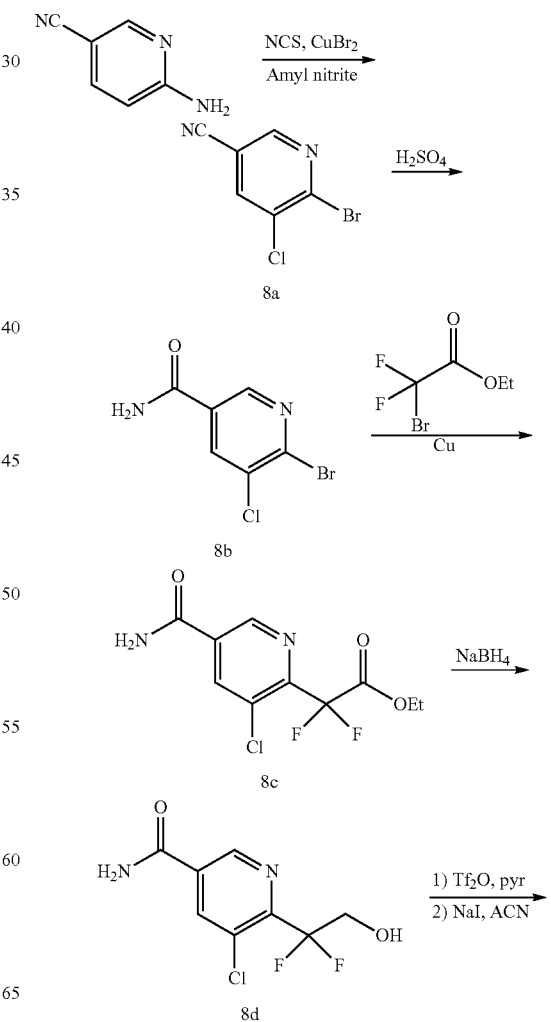

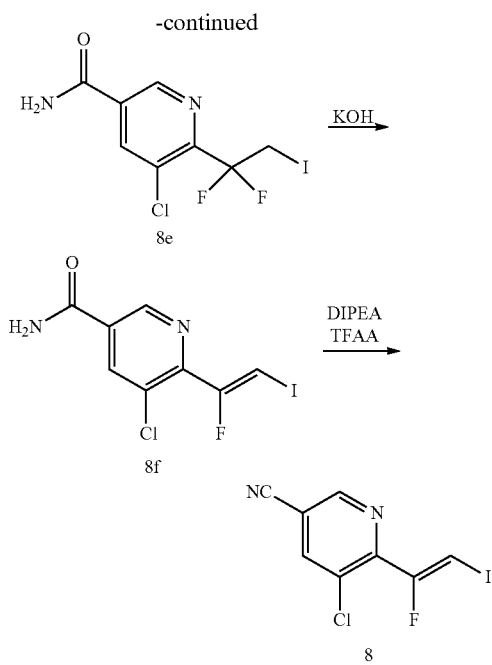

Preparation of 6-bromo-5-chloronicotinonitrile (8a)

A round bottom flask was charged with 6-aminonicotinonitrile (Arborchem, Mechanicsburg, Pa., USA) (100 g, 839 mmol), N-chlorosuccinimide (Sigma-Aldrich, St. Louis, Mo., USA) (123 g, 923 mmol), and acetonitrile (2 L). The reaction mixture was heated at 60° C. for 2 hours. After cooling to room temperature, copper (II) bromide (Sigma-Aldrich, St. Louis, Mo., USA) (375 g, 1678 mmol) and isoamyl nitrite (Arborchem, Mechanicsburg, Pa., USA) (230 mL, 1678 mmol) were added and the mixture was heated to 65° C. for 2 hours. After cooling to room temperature, the mixture was quenched with sat'd aqueous ammonium chloride solution (200 mL) and extracted with DCM (3×500 mL). The combined organic solution was dried over MgSO$_4$ and concentrated. The residue was purified by silica gel chromatography (10% EtOAc in hexanes) to provide 8a (63 g, 34% yield). MS (ESI, positive ion) m/z: no ionization. $^1$H NMR (400 MHz, Chloroform-d) δ 8.68-8.49 (m, 1H), 8.19-7.84 (m, 1H).

Preparation of 6-bromo-5-chloronicotinamide (8b)

A solution of 8a (63 g, 290 mmol) in sulfuric acid (154 mL) was stirred for 12 hours at 20° C. The reaction mixture was cooled to 0° C. and quenched by the addition of ice water (500 mL). The mixture was stirred for 10 minutes and the solid thus obtained was filtered and dried under reduced pressure to 8b (60 g, 88% yield). MS (ESI, positive ion) m/z: 235.2 (M+1).

Preparation of ethyl 2-(5-carbamoyl-3-chloropyridin-2-yl)-2,2-difluoroacetate (8c)

To a solution of copper (0) powder (27.0 g, 425 mmol) in DMSO (250 mL) at 20° C. was added ethyl 2-bromo-2,2-difluoroacetate (64.7 g, 319 mmol). The reaction mixture was stirred at 20° C. for 1 hour and treated with 8b (25 g, 106 mmol) was added portion-wise. The reaction mixture was stirred at 20° C. for 12 hours, and quenched with sat'd ammonia chloride (100 mL). The reaction mixture was filtered through a pad of celite. The filtrate was extracted with EtOAc (2×350 mL). The organic solution was dried over Na$_2$SO$_4$ and concentrated under reduced pressure. The crude residue was purified by silica gel chromatography (10-50% EtOAc in hexanes) to afford 8c (21 g, 71% yield). MS (ESI, positive ion) m/z: 279.4 (M+1). $^1$H NMR (400 MHz, Chloroform-d) δ 8.89 (d, J=1.9 Hz, 1H), 8.32 (d, J=1.9 Hz, 1H), 6.39 (d, J=72.1 Hz, 2H), 4.45 (q, J=7.1 Hz, 2H), 1.38 (t, J=7.2 Hz, 3H).

Preparation of 5-chloro-6-(1,1-difluoro-2-hydroxyethyl)nicotinamide (8d)

To a solution of 8c (21.00 g, 75 mmol) in THF (210 mL) at 0° C. was added sodium borohydride (2.85 g, 75 mmol) portion-wise followed by methanol (15.25 mL) dropwise. After completion of reaction (monitored by TLC), the reaction mixture was quenched with water (100 mL) and extracted with EtOAc. The combined organic extracts were dried over Na$_2$SO$_4$ and concentrated under reduced pressure. The crude residue was purified by silica gel chromatography (50% EtOAc in hexanes) to afford 8d (16 g, 90% yield). MS (ESI, positive ion) m/z: 237.0 (M+1). $^1$H NMR (300 MHz, DMSO-d$_6$) δ 8.99 (d, J=2.0 Hz, 1H), 8.43 (d, J=2.0 Hz, 1H), 8.35 (s, 1H), 7.89 (s, 1H), 5.62 (s, 1H), 4.12 (t, J=14.6 Hz, 2H).

Preparation of 5-chloro-6-(1,1-difluoro-2-iodoethyl)nicotinamide (8e)

To a solution of 8d (16.0 g, 67.6 mmol) in acetonitrile (160 mL) at −10° C. was added pyridine (10.9 mL, 135 mmol) followed by dropwise addition of trifluoromethane sulphonic anhydride (28.6 g, 101 mmol). The reaction mixture was stirred at 0° C. for 30 minutes then warmed to room temperature and treated with sodium iodide (30.4 g, 203 mmol) portion-wise. The reaction mixture was stirred at 70° C. for 2 hours. After cooling to room temperature, it was quenched with sat'd sodium thiosulfate solution (300 mL) and extracted with EtOAc (2×350 mL). The combined organic solution was washed with brine (250 mL), dried over Na$_2$SO$_4$ and concentrated under reduced pressure. The crude residue was purified by silica gel chromatography (20-50% EtOAc in hexanes) to afford 8e (12.0 g, 51% yield). MS (ESI, positive ion) m/z: 347.1 (M+1). $^1$H NMR (400 MHz, DMSO-d$_6$) δ 9.00 (d, J=1.8 Hz, 1H), 8.47 (d, J=1.8 Hz, 1H), 8.37 (s, 1H), 7.91 (s, 1H), 4.14 (t, J=16.4 Hz, 2H).

Preparation of (Z)-5-chloro-6-(1-fluoro-2-iodovinyl)nicotinamide (8f)

To the solution of 8e (12 g, 34.6 mmol) in DMSO (120 mL) at 0° C. was added potassium hydroxide (10.39 mL of 5 M solution, 51.9 mmol). The reaction mixture was stirred at 0° C. for 5 hours. The reaction mixture was quenched with water and extracted with EtOAc (3×250 mL). The combined organic solution was washed with brine (250 mL), dried over Na$_2$SO$_4$ and concentrated under reduced pressure. The crude residue was purified by silica gel chromatography (50% EtOAc in hexanes) to afford 8f (8.0 g, 71% yield). MS (ESI, positive ion) m/z: 327.2 (M+1). $^1$H NMR (300 MHz, DMSO-d$_6$) δ 8.97 (s, 1H), 8.41 (s, 1H), 8.32 (s, 1H), 7.85 (s, 1H), 7.05 (d, J=36.0 Hz, 1H).

Preparation of (Z)-5-chloro-6-(1-fluoro-2-iodovinyl) nicotinonitrile (8)

To a solution of 8f (8.0 g, 24.5 mmol) in THF (80 mL) at 0° C. was added drop N,N-diisopropylethylamine (15.8 g, 123 mmol) followed by trifluoroacetic anhydride (17.3 mL, 123 mmol). The reaction mixture was stirred at 0° C. for 2 hours, then quenched with water (250 mL) and extracted with EtOAc (3×250 mL). The combined organic solution was washed with brine (250 mL), dried over $Na_2SO_4$ and concentrated under reduced pressure. The crude residue was purified by silica gel chromatography (2-10% EtOAc in hexanes) to afford Intermediate 8 (6.0 g, 79% yield) as an off-white solid. MS (ESI, positive ion) m/z: no ionization. $^1$H NMR (400 MHz, Chloroform-d) δ 8.84-8.67 (m, 1H), 8.15-8.00 (m, 1H), 7.21-6.99 (m, 1H).

Intermediate 9: (Z)-2-chloro-5-(1-fluoro-2-iodovinyl)pyrazine

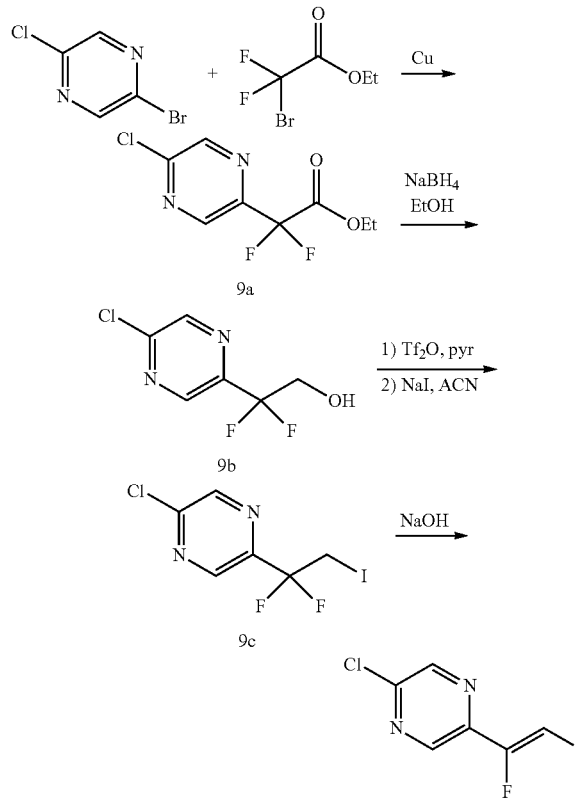

9

Preparation of ethyl 2-(5-chloropyrazin-2-yl)-2,2-difluoroacetate (9a)

To a suspension of copper(0) powder (244 g, 3877 mmol) in DMSO (5 L) was added ethyl 2-bromo-2,2-difluoroacetate (394 g, 1939 mmol) at room temperature. The reaction mixture was stirred at room temperature for 1 hour and 2-bromo-5-chloropyrazine (Shanghai Fchemicals Technology Co., Ltd., Shanghai, China) (250 g, 1292 mmol) was added in portion-wise. The reaction mixture was stirred at room temperature for 3 hours, and quenched with sat'd solution of ammonia chloride (2.0 L). The mixture was filtered through a celite pad and the filtrate was extracted with EtOAc (2×2 L). The combined solution was dried over $Na_2SO_4$ and concentrated under reduced pressure. The residue was purified by silica gel chromatography (0-2% EtOAc in hexanes) to afford 9a (215 g, 70% yield) as a viscous colorless liquid. $^1$H NMR (400 MHz, DMSO-$d_6$) δ 9.05 (d, J=1.4 Hz, 1H), 8.98 (dd, J=1.4, 0.7 Hz, 1H), 4.39-4.34 (m, 2H), 1.24 (t, J=7.1 Hz, 3H).

Preparation of 2-(5-chloropyrazin-2-yl)-2,2-difluoroethanol (9b)

To a solution of 9a (215 g, 909 mmol) in ethanol (400 mL) was added sodium borohydride (34.4 g, 909 mmol) portion-wise at 0° C. The reaction mixture was stirred for 30 minutes at 0° C. After completion of reaction (monitored by TLC), the reaction mixture was quenched with water (200 mL) and concentrated under reduced pressure to give the crude residue. The crude material was diluted with water (750 mL) and extracted with EtOAc (2×1.0 L). The combined organic solution was dried over $Na_2SO_4$ and concentrated under reduced pressure. The residue was purified by silica gel chromatography (0-10% EtOAc in hexanes) to afford 9b (130 g, 73% yield) as a colorless liquid. MS (ESI+ve ion) m/z: [M+1]=195.0. $^1$H NMR (300 MHz, DMSO-$d_6$) δ 8.97 (dt, J=1.4, 0.7 Hz, 1H), 8.82 (d, J=1.4 Hz, 1H), 5.70 (t, J=6.4 Hz, 1H), 4.01 (td, J=13.8, 6.4 Hz, 2H).

Preparation of 2-chloro-5-(1,1-difluoro-2-iodoethyl)pyrazine (9c)

To a solution of 9b (130 g, 668 mmol) in acetonitrile (1.3 L) at 0° C. was added pyridine (54.0 mL, 668 mmol) followed by the dropwise addition of triflic anhydride (147 mL, 869 mmol). The reaction mixture was stirred at 0° C. for 30 minutes then room temperature for 10 minutes. Sodium iodide (300 g, 2004 mmol) was then added in a portion-wise manner. The reaction mixture was stirred at 70° C. for 2 hours then cooled to room temperature and quenched with sat'd aqueous sodium thiosulfate solution (2.0 L). The mixture was extracted with EtOAc (2×2.0 L). The combined organic solution was washed with brine (2.0 L), dried over $Na_2SO_4$ and concentrated under reduced pressure. The residue was purified by silica gel chromatography (0-2% EtOAc in hexanes) to afford 9c (150.0 g, 71% yield) as a yellow solid. $^1$H NMR (300 MHz, DMSO-$d_6$) δ 8.96 (s, 1H), 8.89 (s, 1H), 4.07 (t, J=16.4 Hz, 2H).

Preparation of (Z)-2-chloro-5-(1-fluoro-2-iodovinyl) pyrazine (9)

To a solution of 9c (150 g, 493 mmol) in DMSO (900 mL) was added 5.0 M aqueous NaOH solution (148 mL, 740 mmol). The reaction mixture was stirred at 0° C. for 2 hours, and quenched with water (100 mL). It was extracted with EtOAc (2×200 mL). The combined organic solution was washed with brine (300 mL), dried over $Na_2SO_4$ and concentrated under reduced pressure. The residue was purified by silica gel chromatography (0-5% EtOAc in hexanes) to afford Intermediate 9 (78 g, 54% yield) as a white solid. $^1$H NMR (400 MHz, Chloroform-d) δ 8.59 (q, J=1.4 Hz, 1H), 8.54 (q, J=1.4 Hz, 1H), 7.05 (dd, J=34.1, 1.3 Hz, 1H).

Intermediate 10: (Z)-5-(1-fluoro-2-iodovinyl)pyrazine-2-carbonitrile

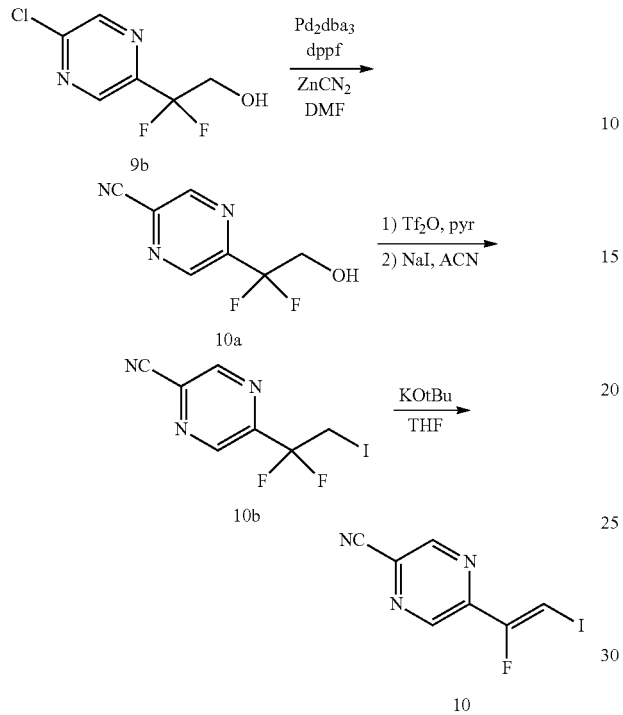

Preparation of 5-(1,1-difluoro-2-hydroxyethyl)pyrazine-2-carbonitrile (10a)

A solution of 2-(5-chloropyrazin-2-yl)-2,2-difluoroethanol (9b, 30.0 g, 154 mmol) in DMF (300 mL) was degassed with nitrogen for 10 minutes. To the solution was sequentially added dppf (Strem Chemicals, Inc., Newburyport, Mass., USA) (4.2 g, 7.7 mmol), Pd$_2$(dba)$_3$ (Strem Chemicals, Inc., Newburyport, Mass., USA) (7.1 g, 7.7 mmol), and Zn(CN)$_2$ (36.2 g, 308 mmol). The reaction mixture was heated at 80° C. for 5 hours. It was cooled to room temperature and partitioned between water (200 mL) and EtOAc (200 mL). The reaction mixture was filtered through a pad of celite. The filtrate was transferred to a separatory funnel. The solution was separated. The aqueous layer was extracted with EtOAc (2×500 mL). The combined organic solution was washed with brine (300 mL), dried over Na$_2$SO$_4$ and concentrated under reduced pressure. The residue was purified by silica gel chromatography (0-20% EtOAc in hexanes) to provide 10a (18 g, 62% yield) as a clear oil. MS (ESI+ve ion) m/z: [M+1]=no ionisation. $^1$H NMR (400 MHz, DMSO-d$_6$) δ 9.39 (d, J=1.5 Hz, 1H), 9.16 (d, J=1.5 Hz, 1H), 5.77 (t, J=6.4 Hz, 1H), 4.04 (td, J=13.8, 6.4 Hz, 2H).

Preparation of 5-(1,1-difluoro-2-iodoethyl)pyrazine-2-carbonitrile (10b)

To a solution of 5-(1,1-difluoro-2-hydroxyethyl)pyrazine-2-carbonitrile (10a, 18 g, 97 mmol) in acetonitrile (180 mL) at 0° C. was added pyridine (15.7 mL, 194 mmol) followed by dropwise addition of triflic anhydride (65.7 mL, 389 mmol). The reaction mixture was stirred at 0° C. for 30 min then treated with sodium iodide (72.9 g, 486 mmol) in a portion-wise manner. The mixture was stirred at 70° C. for 3 hours then cooled to room temperature and quenched with sat'd aqueous sodium thiosulfate solution (100 mL). The mixture was extracted with EtOAc (2×200 mL). The combined organic solution was washed with brine (200 mL), dried over Na$_2$SO$_4$ and concentrated under reduced pressure. Purification of the residue by silica gel chromatography (0-2% EtOAc in hexanes) afforded 10b (10.0 g, 35% yield) as a yellow solid. MS (ESI+ve ion) m/z: [M+1]=no ionisation. $^1$H NMR (400 MHz, Chloroform-d) δ 9.10 (t, J=1.2 Hz, 1H), 8.98 (dd, J=1.6, 0.8 Hz, 1H), 3.91 (td, J=14.3, 1.0 Hz, 2H).

Preparation of (Z)-5-(1-fluoro-2-iodovinyl)pyrazine-2-carbonitrile (10)

To a solution of 10b (1.00 g, 3.39 mmol) in THF (10 mL) was added potassium tert-butoxide (0.76 g, 6.78 mmol) at −75° C. The reaction mixture was stirred at −75° C. for 30 minutes. The reaction mixture was quenched with water (10 mL) and extracted with EtOAc (2×25 mL). The combined organic extracts were dried over Na$_2$SO$_4$ and concentrated under reduced pressure. Purification of the residue by silica gel chromatography (0-5% EtOAc in hexanes) afforded Intermediate 10 (0.34 g, 36% yield) as an off-white solid. MS (ESI+ve ion) m/z: no ionisation. $^1$H NMR (400 MHz, Chloroform-d) δ 8.92 (t, J=1.4 Hz, 1H), 8.84 (t, J=1.2 Hz, 1H), 7.38 (d, J=33.5 Hz, 1H).

Intermediate 11: (Z)-2-(1-fluoro-2-iodovinyl)-5-methoxypyrazine

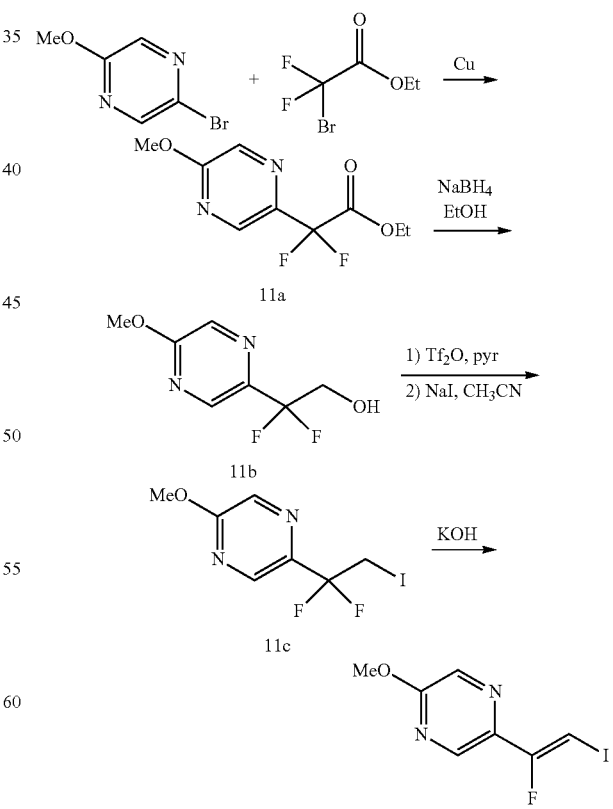

Ethyl 2-(3-chloro-5-(trifluoromethyl)pyridin-2-yl)-2,2-difluoroacetate (11a, 80 g, 65% yield) as a yellow liquid was synthesized using a protocol similar to that described for 9a, here starting from 2-bromo-5-methoxypyrazine (Shanghai Fchemicals Technology Co., Ltd., Shanghai, China) (100 g, 529 mmol) and ethyl bromodifluoroacetate (215 g, 1058 mmol). MS (ESI+ve ion) m/z: [M+1]=233.0. $^1$H NMR (400 MHz, Chloroform-d) δ 8.51 (s, 1H), 8.22 (s, 1H), 4.43-4.35 (m, 2H), 4.03 (m, 3H), 1.40-1.32 (m, 3H).

Compounds 11b, 11c, and 11 were synthesized in a fashion similar to that described for 9b, 9c, and 9, respectively. 2,2-Difluoro-2-(5-methoxypyrazin-2-yl)ethanol (11b): MS (ESI+ve ion) m/z: [M+1]=191.0. $^1$H NMR (400 MHz, Chloroform-d) δ 8.51 (d, J=2.0 Hz, 1H), 8.21 (d, J=2.0 Hz, 1H), 4.27-4.17 (m, 2H), 4.07-4.00 (m, 3H). 2-(1,1-Difluoro-2-iodoethyl)-5-methoxypyrazine (11c): MS (ESI+ve ion) m/z: [M+1]=301.0. $^1$H NMR (400 MHz, Chloroform-d) δ 8.46 (s, 1H), 8.22 (s, 1H), 4.03 (s, 3H), 3.93-3.86 (m, 2H). (Z)-2-(1-Fluoro-2-iodovinyl)-5-methoxypyrazine (11): MS (ESI+ve ion) m/z: [M+1]=281.0. $^1$H NMR (400 MHz, DMSO-$d_6$) δ 8.43 (t, J=1.3 Hz, 1H), 8.34 (t, J=1.2 Hz, 1H), 6.86 (d, J=37.2 Hz, 1H), 4.01 (s, 3H).

Intermediate 15: (4aR,7aS)-tert-butyl 2-benzamido-7a-(5-bromo-2-fluorophenyl)-4a,5,7,7a-tetrahydropyrrolo[3,4-d][1,3]thiazine-6(4H)-carboxylate; and Intermediate 16: (4aS,7aR)-tert-butyl 2-benzamido-7a-(5-bromo-2-fluorophenyl)-4a,5,7,7a-tetrahydropyrrolo[3,4-d][1,3]thiazine-6(4H)-carboxylate

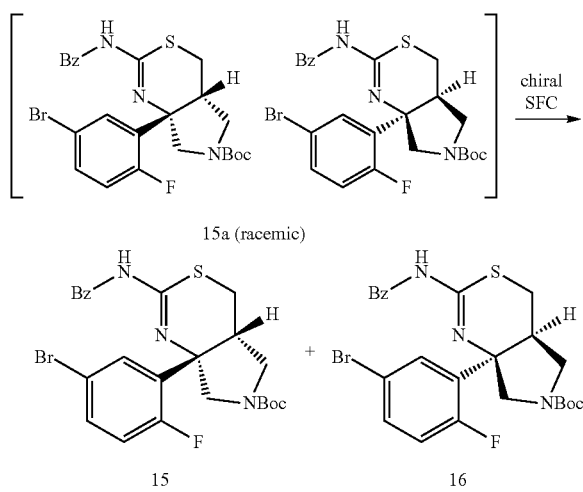

Racemic 15a (prepared according to the procedures reported in WO 2014143579) (41.0 g) was subjected to chiral SFC to provide two compounds: the 1$^{st}$ eluent was Intermediate 15 (16.0 g) and the 2$^{nd}$ eluent was Intermediate 16 (17.0 g). $^1$H NMR δ 8.11 (br. s., 2H), 7.61-7.40 (m, 5H), 7.12-6.93 (m, 1H), 4.21-3.99 (m, 1H), 3.84-3.61 (m, 3H), 3.33 (br. s., 1H), 3.07 (d, J=11.9 Hz, 1H), 2.99-2.82 (m, 1H), 1.48 (s, 9H). NH peak was not observed. The absolute stereochemistry was arbitrarily assigned. Preparative SFC conditions: Chiralpak AD, 300×50 mm I.D., 10 μm; Mobile phase: A for $CO_2$ and B for methanol; Gradient: B %=40%; Flow rate: 200 mL/min; Wavelength: 220 nm; Column temperature: 38° C.; System back pressure: 100 bar; Cycle time: 4.3 min; Injection amount: compound was dissolved in 500 mL of methanol, 7 mL per injection.

Intermediate 17: tert-butyl ((4aR,7aR)-7a-(5-bromo-2-fluorophenyl)-4a,5,7,7a-tetrahydro-4H-furo[3,4-d][1,3]thiazin-2-yl)carbamate; and Intermediate 18: tert-butyl ((4aS,7aS)-7a-(5-bromo-2-fluorophenyl)-4a,5,7,7a-tetrahydro-4H-furo[3,4-d][1,3]thiazin-2-yl)carbamate

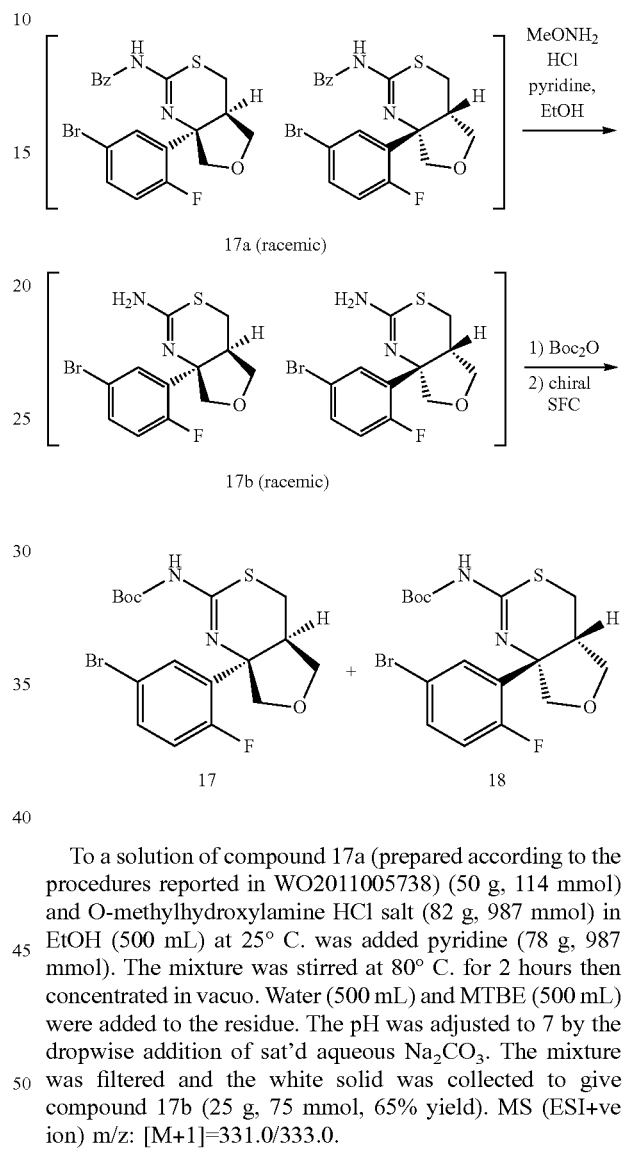

To a solution of compound 17a (prepared according to the procedures reported in WO2011005738) (50 g, 114 mmol) and O-methylhydroxylamine HCl salt (82 g, 987 mmol) in EtOH (500 mL) at 25° C. was added pyridine (78 g, 987 mmol). The mixture was stirred at 80° C. for 2 hours then concentrated in vacuo. Water (500 mL) and MTBE (500 mL) were added to the residue. The pH was adjusted to 7 by the dropwise addition of sat'd aqueous $Na_2CO_3$. The mixture was filtered and the white solid was collected to give compound 17b (25 g, 75 mmol, 65% yield). MS (ESI+ve ion) m/z: [M+1]=331.0/333.0.

To a solution of compound 17b (39 g, 117 mmol) in DCM (390 mL) and $H_2O$ (39 mL) was added $NaHCO_3$ (19.8 g, 235 mmol) and $(Boc)_2O$ (38 g, 176 mmol). After the mixture was stirred at 25° C. for 2 hours, it was treated with water (100 mL) and extracted with DCM (2×100 mL). The combined organic solution was concentrated and the residue was purified by chromatography on silica gel (petroleum ether: EtOAc=50:1 to 5:1) to give a racemic mixture of tert-butyl ((4aR,7aR)-7a-(5-bromo-2-fluorophenyl)-4a,5,7,7a-tetrahydro-4H-furo[3,4-d][1,3]thiazin-2-yl)carbamate and tert-butyl ((4aS,7aS)-7a-(5-bromo-2-fluorophenyl)-4a,5,7,7a-tetrahydro-4H-furo[3,4-d][1,3]thiazin-2-yl)carbamate (30 g, 69 mmol, 59% yield) as a white solid. MS (ESI+ve ion) m/z: 431.0/433.0. $^1$H NMR (400 MHz, CDCl3) δ 7.58-7.49 (m, 1H), 7.47-7.39 (m, 1H), 7.06-6.92 (m, 1H), 4.43-4.34 (m, 1H), 4.23-4.12 (m, 2H), 3.89-3.75 (m, 1H), 3.29-3.15 (m, 1H), 3.09-2.97 (m, 1H), 2.84-2.72 (m, 1H), 1.53 (s, 9H). NH peak was not observed.

The racemic mixture was subjected to chiral SFC to provide two compounds: the 1$^{st}$ eluent was 17 (11 g, yield 37%) and the 2$^{nd}$ eluent was 18 (11 g, yield 37%). The absolute stereochemistry was arbitrarily assigned. Preparative SFC conditions: Column was Chiralpak (AS-H 250*30 mm i.d. 5 μm); Mobile phase: A for $CO_2$ and B for 2-propanol (0.1% $NH_3H_2O$); Gradient: B %=25%; Flow rate: 60 g/min; Wavelength: 220 nm; Column temperature: 40° C.; System back pressure: 100 bar; Cycle time: 4 min; Injection amount: 70 mg per injection.

Intermediate 19: N-((4aR,5R,7aR)-7a-(5-bromo-2-fluorophenyl)-5-(trifluoromethyl)-4a,5,7,7a-tetrahydro-4H-furo[3,4-d][1,3]thiazin-2-yl)benzamide; and Intermediate 20: N-((4aS,5S,7aS)-7a-(5-bromo-2-fluorophenyl)-5-(trifluoromethyl)-4a,5,7,7a-tetrahydro-4H-furo[3,4-d][1,3]thiazin-2-yl)benzamide

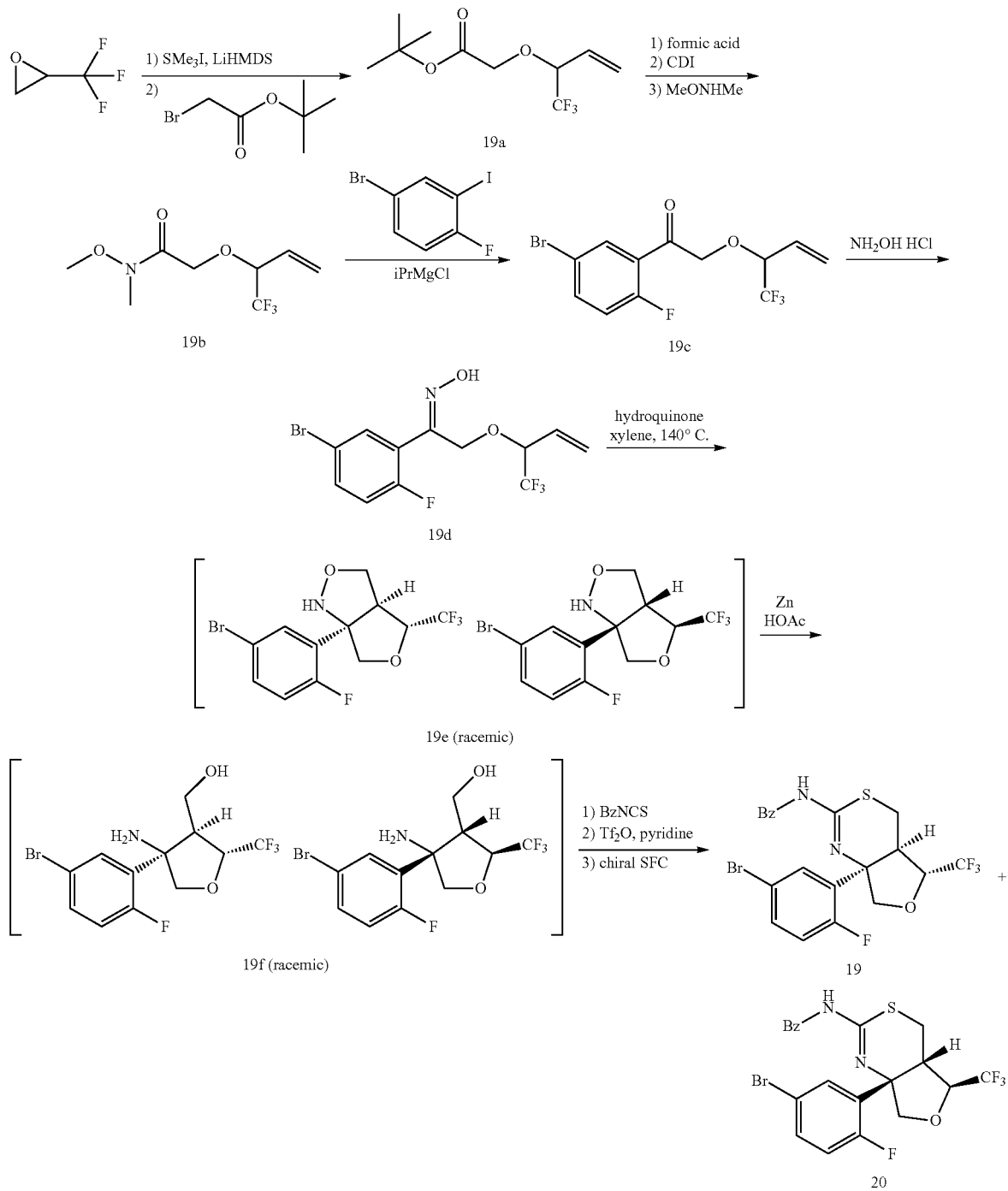

Preparation of tert-butyl 2-((1,1,1-trifluorobut-3-en-2-yl)oxy)acetate (19a)

To a solution of trimethyl sulphoxinium iodide (Avra Synthesis Pvt. Ltd., Habsiguda, Hyderabad, India) (410.0 g, 2.0 mol) in THF (3.0 L) at −78° C. was slowly added LHMDS (1.6 M in THF, 1.7 L, 2.7 mol). The reaction mixture was stirred for 2 hours at −30° C. then treated with 2-trifluoromethyl oxirane (Manchester Chemicals, Alderley Edge, UK) (150.0 g, 1.3 mol). The reaction mixture was allowed to warm to room temperature and stirred for 3 hours. t-Butyl-bromoacetate (Spectrochem Pvt. Ltd., Kalbadevi Road, Mumbai, India) (522.0 g, 2.6 mol) in NMP (750 mL) was added and the reaction mixture was stirred for 12 hours at room temperature then quenched with saturated ammonium chloride solution (3.0 L) and extracted with EtOAc (3×5.0 L). The combined organic solution was dried over sodium sulfate and concentrated under reduced pressure. The residue was passed through a short column of silica gel (eluted with 5% EtOAc in hexanes) to provide tert-butyl 2-((1,1,1-trifluorobut-3-en-2-yl)oxy)acetate (19a, 200.0 g, 62% yield). MS m/z: no ionization.

Preparation of N-methoxy-N-methyl-2-((1,1,1-trifluorobut-3-en-2-yl)oxy)acetamide (19b)

A solution of 19a (200.0 g, 830 mmol) in formic acid (400 mL) was heated to 55° C. for 3 hours then concentrated under reduced pressure. The residue was dissolved in DCM (2.0 L), cooled to at 0° C., and treated with CDI (162.0 g, 990 mmol). The reaction mixture was stirred at 0° C. for one hour and then N,O-dimethyl hydroxylamine hydrochloride (97.0 g, 990 mmol) was added. The reaction mixture was stirred at room temperature for 12 hours then quenched with water (2.0 L) and extracted by DCM (3×5.0 L). The combined organic solution was dried over sodium sulfate, filtered and concentrated under reduced pressure. The residue was purified by silica gel chromatography (20% EtOAc in hexanes) to afford 19b (90.0 g, 48% yield) as an oil. MS m/z=228.2 [M+H]$^+$. $^1$H NMR (400 MHz, Chloroform-d) δ 5.82 (ddd, J=17.4, 7.8, 2.2 Hz, 1H), 5.67-5.57 (m, 2H), 4.49-4.35 (m, 3H), 3.71 (d, J=1.7 Hz, 3H), 3.21 (d, J=1.7 Hz, 3H).

Preparation of 1-(5-bromo-2-fluorophenyl)-2-((1,1,1-trifluorobut-3-en-2-yl)oxy)ethanone (19c)

A solution of 4-bromo-1-fluoro-2-iodobenzene (177.0 g, 580 mmol) in THF (400 mL) at 0° C. was treated with isopropyl magnesium chloride (2.0 M in THF, 290 mL, 580 mmol) and stirred for 30 minutes at 0° C. The mixture was treated with a solution of 19b (112.5 g, 490 mmol) in THF (400 mL) and stirred for 2 hours at room temperature. The reaction was quenched with sat'd aqueous NH$_4$Cl and extracted with EtOAc (3×1.0 L). The combined organic solution was dried over sodium sulfate and concentrated under reduced pressure. The residue was purified by silica gel chromatography (10% EtOAc in hexanes) to give 19c (125.0 g, 74%). MS m/z=339.2 [M−H]$^+$. $^1$H NMR (400 MHz, Chloroform-d) δ 8.07 (dd, J=6.1, 2.7 Hz, 1H), 7.68 (ddd, J=8.8, 4.6, 2.6 Hz, 1H), 7.16-6.99 (m, 1H), 5.85 (ddd, J=17.4, 10.3, 7.2 Hz, 1H), 5.69-5.52 (m, 2H), 4.87-4.72 (m, 2H), 4.42-4.30 (m, 1H).

Preparation of (E)-1-(5-bromo-2-fluorophenyl)-2-((1,1,1-trifluorobut-3-en-2-yl)oxy) ethanone oxime (19d)

To a solution of 19c (250.0 g, 730 mmol) in methanol (5.0 L) at 0° C. was added sodium acetate (120.2 g, 1460 mmol) and hydroxylamine hydrochloride (76.0 g, 1090 mmol). The resulting mixture was heated to 55° C. for 3 hours. The reaction was quenched with water (1.0 L) and the mixture was concentrated under reduced pressure to remove most of the MeOH. The remaining mixture was extracted with EtOAc (3×3.0 L). The combined organic solution was dried over sodium sulfate and concentrated under reduced pressure. The crude material was purified by silica gel chromatography (15% EtOAc in hexanes) to provide 19d (250.0 g, 96% yield) as an off-white solid. MS m/z: 356.1 [M+H]$^+$. $^1$H NMR (300 MHz, DMSO-d$_6$) δ 12.02 (s, 1H), 7.69-7.59 (m, 2H), 7.25 (ddd, J=10.1, 8.8, 3.9 Hz, 1H), 5.74-5.60 (m, 1H), 5.51 (ddt, J=16.8, 11.1, 1.7 Hz, 2H), 4.73 (s, 2H), 4.54 (dd, J=8.9, 5.0 Hz, 1H).

Preparation of (3aS,4R,6aR)-6a-(5-bromo-2-fluorophenyl)-4-(trifluoromethyl)hexahydrofuro[3,4-c] isoxazole and (3aR,4S,6aS)-6a-(5-bromo-2-fluorophenyl)-4-(trifluoromethyl)hexahydrofuro[3,4-c] isoxazole (racemic) (19e)

To a solution of 19d (125.0 g, 351 mmol) in xylene (1.5 L) was added hydroquinone (9.7 g, 88 mmol) at room temperature. The resulting mixture was heated at 140° C. for 18 hours. The reaction mixture was cooled to room temperature then treated with water (3.0 L) and extracted with EtOAc (3×3.0 L). The combined organic solution was dried over Na$_2$SO$_4$ and concentrated under reduced pressure. The residue was purified by silica gel chromatography (5% EtOAc in hexanes) to give 19e (87.5 g, 70% yield) as an off-white solid. MS m/z=356.0 [M+H]$^+$. $^1$H NMR (300 MHz, DMSO-d$_6$) δ 7.84 (dd, J=6.9, 2.6 Hz, 1H), 7.60 (ddt, J=8.9, 4.5, 2.4 Hz, 1H), 7.25 (ddd, J=11.2, 8.7, 2.2 Hz, 1H), 6.72 (s, 1H), 4.66 (qd, J=7.9, 4.4 Hz, 1H), 4.16 (q, J=9.9 Hz, 3H), 3.99 (t, J=5.6 Hz, 1H), 3.83 (dt, J=6.9, 4.1 Hz, 1H).

Preparation of ((2R,3S,4R)-4-amino-4-(5-bromo-2-fluorophenyl)-2-(trifluoromethyl)tetrahydrofuran-3-yl)methanol and ((2S,3R,4S)-4-amino-4-(5-bromo-2-fluorophenyl)-2-(trifluoromethyl)tetrahydrofuran-3-yl)methanol (racemic) (19f)

Zinc(0) powder (88 g, 1.34 mol) was treated with acetic acid (400 mL) slowly while maintaining the internal temperature below 10° C. After 30 minutes of stirring, a solution of 19e (160 g, 0.449 mol) in THF (1.5 L) was added. The reaction mixture was stirred for 16 hours at room temperature then filtered through a pad of celite. The filter cake was washed with THF (2×200 mL). The filtrate was concentrated under reduced pressure. The residue was dissolved in EtOAc (3.0 L) and washed with sat'd aqueous sodium bicarbonate solution (3.0 L). The organic layer was concentrated under reduced pressure and the residue was purified by silica gel chromatography (40% EtOAc in hexanes) to give 19f (75.0 g, 47% yield). MS (ESI+ve ion) m/z=358.0 [M+1]. $^1$H NMR (400 MHz, DMSO-d$_6$) δ 7.90 (dt, J=7.3, 2.1 Hz, 1H), 7.52 (ddt, J=8.5, 4.0, 2.1 Hz, 1H), 7.16 (ddd, J=12.0, 8.6, 1.5 Hz, 1H), 4.38 (p, J=7.7 Hz, 1H), 4.18-4.12 (m, 1H), 3.90 (d, J=1.6 Hz, 1H), 3.81-3.75 (m, 1H), 3.71-3.65 (m, 1H), 3.55 (dd, J=11.5, 5.4 Hz, 1H), 3.01 (td, J=7.9, 5.3 Hz, 1H). NH$_2$ proton not observed.

Preparation of N-((4aR,5R,7aR)-7a-(5-bromo-2-fluorophenyl)-5-(trifluoromethyl)-4a,5,7,7a-tetrahydro-4H-furo[3,4-d][1,3]thiazin-2-yl)benzamide (Intermediate 19) and N-((4aS,5S,7aS)-7a-(5-bromo-2-fluorophenyl)-5-(trifluoromethyl)-4a,5,7,7a-tetrahydro-4H-furo[3,4-d][1,3]thiazin-2-yl)benzamide (Intermediate 20)

A solution of racemic 19f (20.0 g, 55.8 mmol) in THF (300 mL) at 0° C. was treated with benzoyl isothiocyanate (Shanghai Fchemicals Technology Co., Ltd., Shanghai, China) (10.9 g, 67.0 mmol). The resulting mixture was stirred for 12 hours at room temperature then concentrated under reduced pressure. The residue was dissolved in DCM (300 mL), cooled to −20° C., and then treated with pyridine (13.2 g, 168.0 mmol) followed by triflic anhydride (31.5 g, 112.2 mmol) dropwise. The reaction mixture was stirred for 2 hours at −20° C. then diluted with DCM (500 mL) and washed with sodium bicarbonate (3×500 mL). The organic layer was concentrated under reduced pressure. The residue was purified by silica gel chromatography (20% EtOAc in hexane) to give the racemic product (6.5 g, 23%) with MS (ESI+ve ion) m/z=503.1 [M+1]. $^1$H NMR (400 MHz, Chloroform-d) δ 7.99 (d, J=7.6 Hz, 2H), 7.60 (dd, J=8.6, 6.3 Hz, 1H), 7.50 (td, J=9.1, 8.1, 6.0 Hz, 4H), 7.10-6.98 (m, 1H), 4.80 (p, J=7.0 Hz, 1H), 4.60 (d, J=8.7 Hz, 1H), 3.95 (dd, J=8.0, 5.1 Hz, 1H), 3.57-3.48 (m, 1H), 3.15 (dd, J=14.1, 3.1 Hz, 1H), 2.83 (dd, J=14.0, 3.9 Hz, 1H). NH proton not observed.

Two more batches were performed on same scale and the combined racemic product (20 g) was purified by chiral SFC to give 2 compounds: the 1$^{st}$ eluent was Intermediate 19 (5.5 g, 99% ee) and the 2$^{nd}$ eluent was Intermediate 20 (6.5 g, 99% ee). The absolute stereochemistry of Intermediate 19 and 20 was arbitrarily assigned. Preparative SFC conditions: column=Lux-C3 (250×30 mm, 5 μm); mobile phase=55:45 (liquid CO$_2$: methanol); flow rate=150 mL/min; wave length=240 nm; cycle time=5 min; run time=7 min; pressure=100 bar; sample load=100 mg/injection; sample was dissolved in methanol 1 g/mL.

Alternative procedure for the preparation of N-((4aS,5S,7aS)-7a-(5-bromo-2-fluorophenyl)-5-(trifluoromethyl)-4a,5,7,7a-tetrahydro-4H-furo[3,4-d][1,3]thiazin-2-yl)benzamide (20)

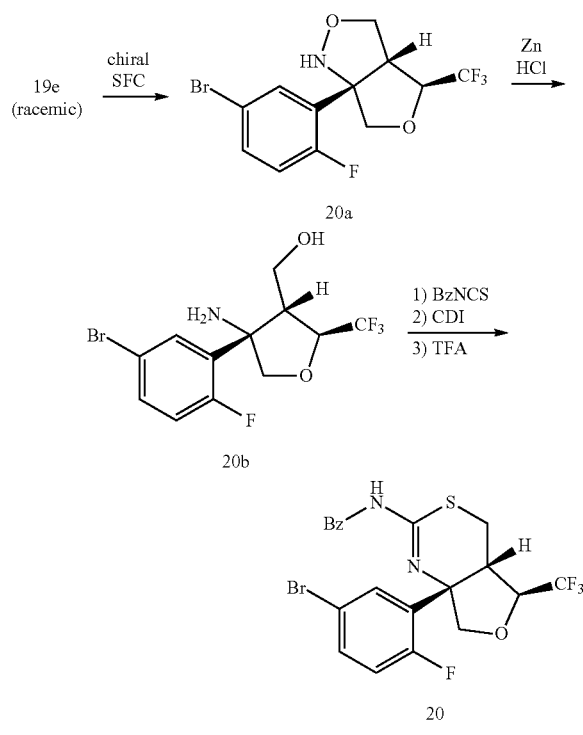

Preparation of (3aR,4S,6aS)-6a-(5-bromo-2-fluorophenyl)-4-(trifluoromethyl)hexahydrofuro[3,4-c]isoxazole (20a)

Racemic 19e (87.5 g) was subjected to chiral SFC to give 2 compounds: the 1$^{st}$ eluent was (3aR,4S,6aS)-6a-(5-bromo-2-fluorophenyl)-4-(trifluoromethyl)hexahydrofuro[3,4-c]isoxazole (20a, 34.2 g, 99% ee) and the 2$^{nd}$ eluent was (3aS,4R,6aR)-6a-(5-bromo-2-fluorophenyl)-4-(trifluoromethyl)hexahydrofuro[3,4-c]isoxazole (32.3 g, 99% ee). MS m/z=356.0 [M+H]$^+$. Preparative SFC conditions: column=Chiralpak ADH (250×30 mm, 5 μm); mobile phase=85:15 (liquid CO$_2$: 20 mM NH$_3$ in methanol); flow rate=100 mL/min; wave length=230 nm; cycle time=2 min; run time=5 min; pressure=100 bar; sample load=100 mg/injection; sample was dissolved in methanol 1 g/mL.

Preparation of ((2S,3R,4S)-4-amino-4-(5-bromo-2-fluorophenyl)-2-(trifluoromethyl)tetrahydrofuran-3-yl)methanol (20b)

Zinc(0) powder (13.8 g, 211.0 mmol) was added in a portion-wise manner to a solution of 20a (25 g, 70.2 mmol) in ethanol (375 mL) at room temperature. The mixture was cooled with an ice bath and treated with HCl (84.0 mL of 5.0 N aqueous solution, 421.0 mmol) dropwise over a period of 30 minutes. The reaction mixture was stirred for 45 minutes at room temperature then filtered through a sintered glass funnel. The filter cake was washed with EtOAc (2×500 mL). The filtrate was evaporated to dryness under reduced pressure. The residue was partitioned between sat'd aqueous NH$_4$Cl (500 mL) and extracted with EtOAc (500 mL). The aqueous layer was further extracted with EtOAc (2×500 mL). The combined organic solution was washed with brine (750 mL) and evaporated to dryness under reduced pressure to provide 20b (25.0 g, 99% yield) as an off-white solid which was used in next step without further purification. MS m/z=358.1 [M+H]$^+$. $^1$H NMR (400 MHz, DMSO-d$_6$) δ 7.90 (dd, J=7.3, 2.8 Hz, 1H), 7.51 (ddd, J=8.7, 4.2, 2.7 Hz, 1H), 7.16 (ddd, J=12.0, 8.6, 3.0 Hz, 1H), 4.61 (t, J=5.3 Hz, 1H), 4.37 (m, 1H), 4.15 (dd, J=8.5, 2.8 Hz, 1H), 3.77 (dd, J=8.3, 3.1 Hz, 1H), 3.68 (dt, J=12.3, 6.8 Hz, 1H), 3.54 (dt, J=11.1, 5.3 Hz, 1H), 3.01 (td, J=8.2, 5.4 Hz, 1H), 2.34 (d, J=3.1 Hz, 2H).

Preparation of N-((4aS,5S,7aS)-7a-(5-bromo-2-fluorophenyl)-5-(trifluoromethyl)-4a,5,7,7a-tetrahydro-4H-furo[3,4-d][1,3]thiazin-2-yl)benzamide (20)

To a solution of 20b (25.0 g, 69.8 mmol) in THF (250 mL) at 45° C. under a nitrogen atmosphere was added benzoyl isothiocyanate (11.5 g, 77.0 mmol) in THF (125 mL) dropwise over a period of 60 minutes. CDI (22.6 g, 139.6 mmol) was added and the resulting mixture was stirred at 65° C. for 8 hours. The reaction mixture was evaporated to dryness under reduced pressure. The residue was dissolved in DCM (375.0 mL) and treated with TFA (250.0 mL) dropwise. The mixture was stirred at ambient temperature for 3 hours then concentrated to dryness. The residue was diluted with EtOAc (1.0 L) and washed with 1.5 N aqueous HCl (500 mL) followed by brine (500 mL), dried over sodium sulfate and concentrated under reduced pressure. The residue was purified by silica gel chromatography (0 to 10% EtOAc in hexanes) to afford Intermediate 20 (26.5 g, 75% yield, 99% ee) as a white solid. MS m/z=503.0 [M+H]$^+$. $^1$H NMR (400 MHz, Chloroform-d) δ 8.03 (d, J=7.7 Hz, 2H), 7.67-7.59 (m, 1H), 7.57-7.47 (m, 4H), 7.11-7.01 (m, 1H), 4.80 (p, J=7.0

Hz, 1H), 4.62 (d, J=8.9 Hz, 1H), 4.06 (d, J=9.2 Hz, 1H), 3.58 (dt, J=7.7, 3.5 Hz, 1H), 3.18 (dd, J=14.0, 3.0 Hz, 1H), 2.86 (dd, J=14.1, 3.9 Hz, 1H). NH proton not observed.

Intermediate 21: N-((4aS,5S,7aS)-7a-(2-fluoro-5-(4,4,5,5-tetramethyl-1,3,2-dioxaborolan-2-yl)phenyl)-5-(trifluoromethyl)-4a,5,7,7a-tetrahydro-4H-furo[3,4-d][1,3]thiazin-2-yl)benzamide

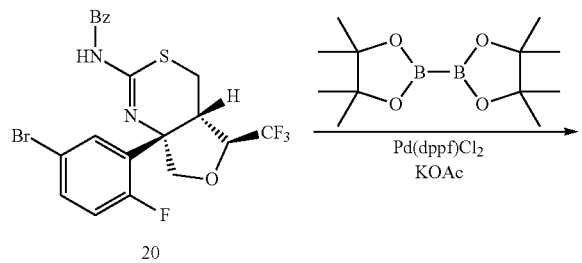

A suspension of 20 (3.5 g, 6.95 mmol), bis(pinacolato)diboron (Sigma-Aldrich Chemical Company, Inc., St. Louis, Mo., USA) (3.53 g, 13.91 mmol), 1,1'-bis(diphenylphosphino)ferrocene palladium(II)dichloride dichloromethane adduct (Sigma-Aldrich Chemical Company, Inc., St. Louis, Mo., USA) (0.284 g, 0.348 mmol), and potassium acetate (Sigma-Aldrich Chemical Company, Inc., St. Louis, Mo., USA, 2.047 g, 20.86 mmol) in 1,4-dioxane (30 mL) was sparged with argon for 5 minutes then heated to 100° C. for 45 minutes. The reaction was partitioned between EtOAc (150 mL) and 5% aqueous NaHCO$_3$ (50 mL). The organic solution was washed with brine (20 mL), dried over MgSO$_4$, and concentrated under reduced pressure. The residue was purified via silica gel chromatography (0 to 15% EtOAc/EtOH (3/1) in heptane) to afford boronic ester 21 (3.3 g, 86% yield) as a tan foam. MS (ESI+ve ion) m/z: [M+1]=551.1. $^1$H NMR (400 MHz, CHLOROFORM-d) δ ppm 8.06 (br s, 2H), 7.81-7.88 (m, 1H), 7.76 (d, J=8.41 Hz, 1H), 7.43-7.63 (m, 4H), 7.15 (dd, J=8.22, 4.50 Hz, 1H), 4.79-4.89 (m, 1H), 4.48-4.58 (m, 1H), 4.06-4.19 (m, 1H), 3.56-3.64 (m, 1H), 3.29-3.40 (m, 1H), 2.83-2.93 (m, 1H), 1.32-1.36 (s, 12H).

Intermediate 22: N-((4aR,5R,7aR)-7a-(5-bromo-2-fluorophenyl)-5-(hydroxymethyl)-4a,5,7,7a-tetrahydro-4H-furo[3,4-d][1,3]thiazin-2-yl)benzamide; and Intermediate 23: N-((4aS,5S,7aS)-7a-(5-bromo-2-fluorophenyl)-5-(hydroxymethyl)-4a,5,7,7a-tetrahydro-4H-furo[3,4-d][1,3]thiazin-2-yl)benzamide

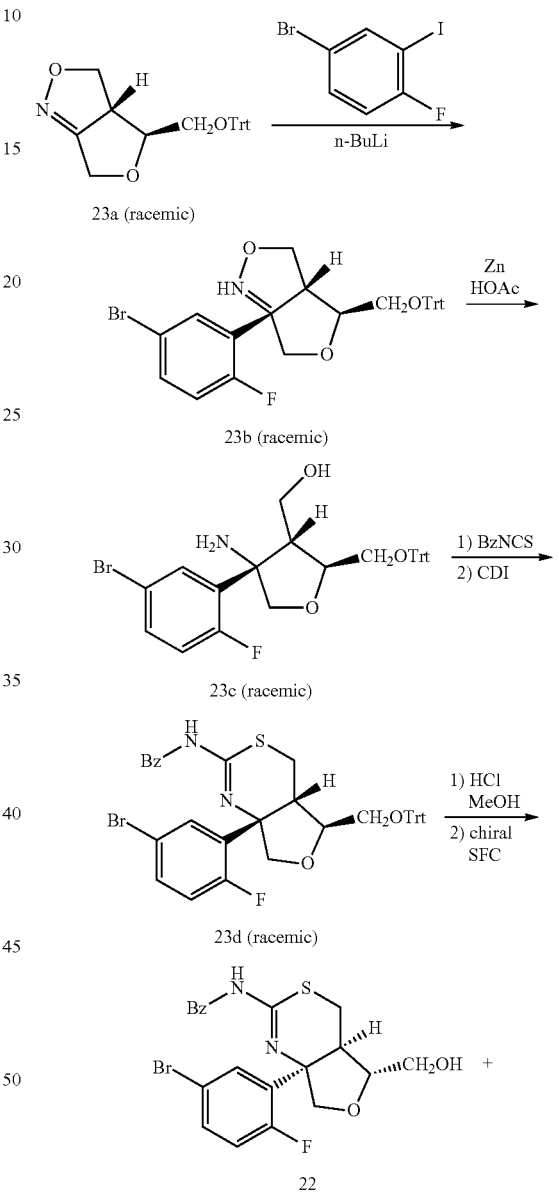

Preparation of racemic mixture of (3aS,4R)-4-((trityloxy)methyl)-3,3a,4,6-tetrahydrofuro[3,4-c]isoxazole and (3aR,4S)-4-((trityloxy)methyl)-3,3a,4,6-tetrahydrofuro[3,4-c]isoxazole (23b)

A solution of 4-bromo-1-fluoro-2-iodobenzene (Combi-Blocks, San Diego, Calif., USA) (60.0 g, 197 mmol) in THF (1.0 L) at −78° C. was treated with n-butyl lithium (1.6 M in THF, 123.0 mL, 197 mmol) dropwise followed by boron-trifluoride diethyl etherate (7.36 g, 52 mmol) dropwise. The resulting mixture was stirred for 10 minutes at −78° C. then treated with a solution of 23a (prepared according to the methods described in WO2012098461) (40.0 g, 104 mmol) in THF (200 mL) dropwise and stirred at −78° C. for 1.5 hours. The reaction was quenched with sat'd aqueous NH$_4$Cl (1.0 L) and extracted with ethyl acetate (3×1.0 L). The combined organic solution was dried over Na$_2$SO$_4$ and concentrated. The residue was purified by silica gel chromatography (20% ethyl acetate in hexanes) to give 23b (21.0 g, 36% yield). MS (ESI+ve ion) m/z: 560.2/562.2 [M+H]$^+$. $^1$H NMR (400 MHz, DMSO-d$_6$) δ 7.79-7.72 (m, 1H), 7.55 (dt, J=7.1, 3.1 Hz, 1H), 7.40-7.30 (m, 13H), 7.29-7.18 (m, 3H), 4.18-4.01 (m, 3H), 3.88 (d, J=10.0 Hz, 1H), 3.74-3.68 (m, 1H), 3.29-3.20 (m, 3H), 3.11-3.06 (m, 1H).

Preparation of racemic mixture of ((2R,3S,4R)-4-amino-4-(5-bromo-2-fluorophenyl)-2-((trityloxy)methyl)tetrahydrofuran-3-yl)methanol and ((2S,3R,4S)-4-amino-4-(5-bromo-2-fluorophenyl)-2-((trityloxy)methyl)tetrahydrofuran-3-yl)methanol (23c)

To a solution of 23b (20.0 g, 35.7 mmol) in acetic acid (70 mL) at 0° C. was added zinc(0) powder (5.9 g, 89.0 mmol) in portion-wise manner and the reaction mixture was stirred at room temperature for 6 hours. The mixture was diluted with ethyl acetate (100 mL) and filtered through a pad of celite. The celite bed was washed with ethyl acetate (2×50 mL). The filtrate was concentrated under reduced pressure. The residue was neutralized to pH ~7 with aqueous ammonia solution and extracted with ethyl acetate (5×100 mL). The combined organic solution was dried over Na$_2$SO$_4$ and concentrated to give 23c (18.0 g, 90% yield) which was used without further purification. MS (ESI+ve ion) m/z: 562.2/564.2 [M+H]$^+$.

Preparation of racemic mixture of N-((4aR,5R,7aR)-7a-(5-bromo-2-fluorophenyl)-5-((trityloxy)methyl)-4a,5,7,7a-tetrahydro-4H-furo[3,4-d][1,3]thiazin-2-yl)benzamide and N-((4aS,5S,7aS)-7a-(5-bromo-2-fluorophenyl)-5-((trityloxy)methyl)-4a,5,7,7a-tetrahydro-4H-furo[3,4-d][1,3]thiazin-2-yl)benzamide (23d)

A solution of 23c (18.0 g, 32.1 mmol) in THF (400 mL) at 0° C. was treated with benzoyl isothiocyanate (6.27 g, 38.4 mmol) stirred at room temperature for 6 hours. The reaction mixture was cooled to 0° C. and CDI (7.78 g, 48.0 mmol) was added in small portions. The mixture was stirred at room temperature for 24 hours then quenched with water (400 mL) and extracted with ethyl acetate (4×500 mL). The combined organic solution was dried over Na$_2$SO$_4$ and concentrated. The residue was purified by silica gel chromatography (50% ethyl acetate in hexanes) to afford 23d (13.5 g, 60% yield). MS (ESI+ve ion) m/z: 707.1/709.1 [M+H]$^+$. $^1$H NMR (400 MHz, Chloroform-d) δ 11.82 (s, 1H), 8.88 (s, 1H), 8.10 (s, 1H), 7.74-7.68 (m, 3H), 7.63 (t, J=7.3 Hz, 1H), 7.50 (t, J=7.8 Hz, 2H), 7.40-7.37 (m, 5H), 7.31-7.26 (m, 10H), 5.29 (d, J=10.3 Hz, 1H), 4.74 (dd, J=12.0, 8.2 Hz, 1H), 4.50 (dd, J=11.9, 4.6 Hz, 1H), 4.39 (d, J=10.1 Hz, 1H), 4.04 (dd, J=8.0, 4.0 Hz, 1H), 3.46 (dd, J=10.6, 3.8 Hz, 1H), 3.31-3.19 (m, 2H).

Preparation of N-((4aR,5R,7aR)-7a-(5-bromo-2-fluorophenyl)-5-(hydroxymethyl)-4a,5,7,7a-tetrahydro-4H-furo[3,4-d][1,3]thiazin-2-yl)benzamide (22) and N-((4aS,5S,7aS)-7a-(5-bromo-2-fluorophenyl)-5-(hydroxymethyl)-4a,5,7,7a-tetrahydro-4H-furo[3,4-d][1,3]thiazin-2-yl)benzamide (23)

To a solution of 23d (20.0 g, 28.3 mmol) in methanol (100 mL) at 0° C. was added HCl (35.0 mL of 4 N solution in methanol, 140 mmol) and the resulting mixture was stirred at room temperature for 2 hours. The mixture was concentrated under reduced pressure. The residue was diluted with water (250 mL) and extracted with ethyl acetate (3×500 mL). The combined organic solution was dried over Na$_2$SO$_4$ and concentrated under reduced pressure. The residue was purified by silica gel chromatography (25% ethyl acetate in hexanes) to afford a racemic mixture of 22 and 23 (4.6 g, 35%) as a white solid. MS (ESI+ve ion) m/z: 465.2/467.2 [M+H]$^+$. $^1$H NMR (400 MHz, Chloroform-d) δ 8.11 (s, 2H), 7.60-7.44 (m, 5H), 7.05 (dd, J=11.7, 8.6 Hz, 1H), 4.52 (dd, J=12.3, 9.0 Hz, 2H), 4.06 (s, 1H), 4.00-3.92 (m, 1H), 3.81-3.73 (m, 2H), 3.34 (s, 1H), 3.23 (d, J=14.1 Hz, 1H), 2.83 (d, J=13.6 Hz, 1H), 2.04 (s, 1H). The racemic mixture of 22 and 23 (4.6 g) was subjected to chiral SFC to provide 2 compounds: the 1$^{st}$ eluent was Intermediate 22 (1.45 g, 100% ee) as a white solid and the 2$^{nd}$ eluent was Intermediate 23 (1.45 g, 99.3% ee) as a white solid. Preparative SFC purification method: Chiralpak IA (250×30 mm, 5 μm); mobile phase (70:30)=(A:B), A=liquid CO$_2$, B=20 mM ammonia in MeOH; flow rate=100 mL/min; wave length=250 nm; inlet pressure=205 bar; 4.6 g of sample was dissolved in 92 mL of THF/MeOH (1/1), sample load=1.0 mL/injection; run time=10 minutes, cycle time=5 minutes. The absolute stereochemistry was arbitrarily assigned.

Intermediate 24: N-((4aR,5R,7aR)-7a-(2-fluoro-5-(4,4,5,5-tetramethyl-1,3,2-dioxaborolan-2-yl)phenyl)-5-(trifluoromethyl)-4a,5,7,7a-tetrahydro-4H-furo[3,4-d][1,3]thiazin-2-yl)benzamide

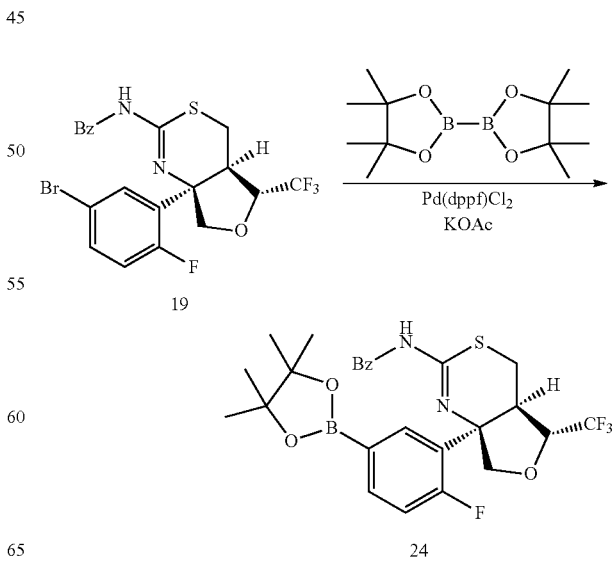

Boronic ester 24 (3.3 g, 86% yield) as a tan foam was prepared in a fashion similar to that described for boronic ester 21, here starting from N-((4aR,5R,7aR)-7a-(5-bromo-2-fluorophenyl)-5-(trifluoromethyl)-4a,5,7,7a-tetrahydro-4H-furo[3,4-d][1,3]thiazin-2-yl)benzamide (19) (3.5 g, 6.95 mmol). MS (ESI+ve ion) m/z: [M+1]=551.1.

Intermediate 25: (Z)-6-(1-fluoro-2-(4,4,5,5-tetramethyl-1,3,2-dioxaborolan-2-yl)vinyl)nicotinonitrile

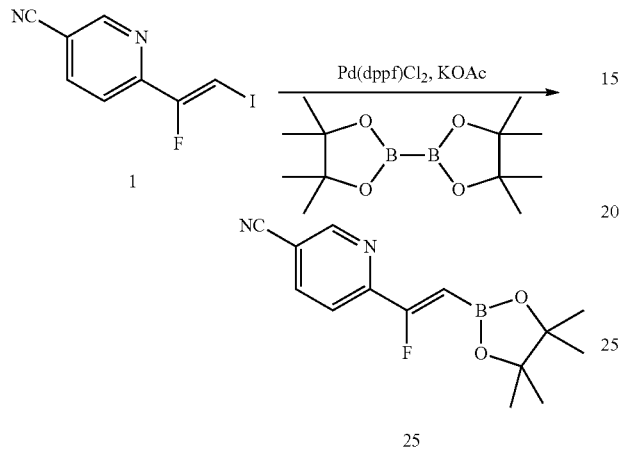

A mixture of (Z)-6-(1-fluoro-2-iodovinyl)nicotinonitrile (1) (1.00 g, 3.65 mmol), KOAc (0.71 g, 7.30 mmol) and bis(pinacolato)diboron (Sigma-Aldrich, St. Lois, Mo., USA) (1.39 g, 5.47 mmol) in 1,4-dioxane (20 mL) was purged with nitrogen for 10 min then treated with PdCl$_2$(dppf)-CH$_2$Cl$_2$ adduct (0.15 g, 0.18 mmol). The mixture was purged with nitrogen for 10 minutes then heated at 90° C. for 16 hours. After cooling to room temperature, the reaction mixture was filtered through a celite pad and washed with ethyl acetate (20 mL). The filtrate was evaporated under vacuum. The residue was purified by silica gel chromatography (20% to 30% EtOAc in hexanes) to provide (Z)-6-(1-fluoro-2-(4,4,5,5-tetramethyl-1,3,2-dioxaborolan-2-yl)vinyl)nicotinonitrile (1) (0.50 g, 1.82 mmol, 50% yield) as an off-white solid. MS (ESI positive ion) m/z: not ionized. $^1$H NMR (300 MHz, Chloroform-d) δ 8.99-8.63 (m, 1H), 8.20-7.84 (m, 1H), 7.73 (d, J=8.2 Hz, 1H), 6.26 (d, J=52.8 Hz, 1H), 1.37-1.27 (m, 12H). $^{19}$F NMR (376 MHz, Chloroform-d) δ −112.82 (s).

Intermediate 26: N-((4aR,5R,7aR)-7a-(5-bromo-2-fluorophenyl)-5-(hydroxymethyl)-4a,5,7,7a-tetrahydro-4H-furo[3,4-d][1,3]thiazin-2-yl)benzamide; and Intermediate 27: N-((4aS,5S,7aS)-7a-(5-bromo-2-fluorophenyl)-5-(hydroxymethyl)-4a,5,7,7a-tetrahydro-4H-furo[3,4-d][1,3]thiazin-2-yl)benzamide

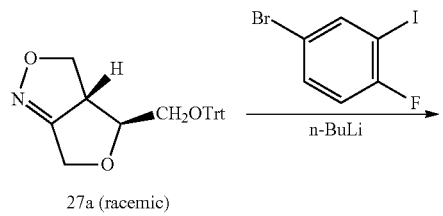

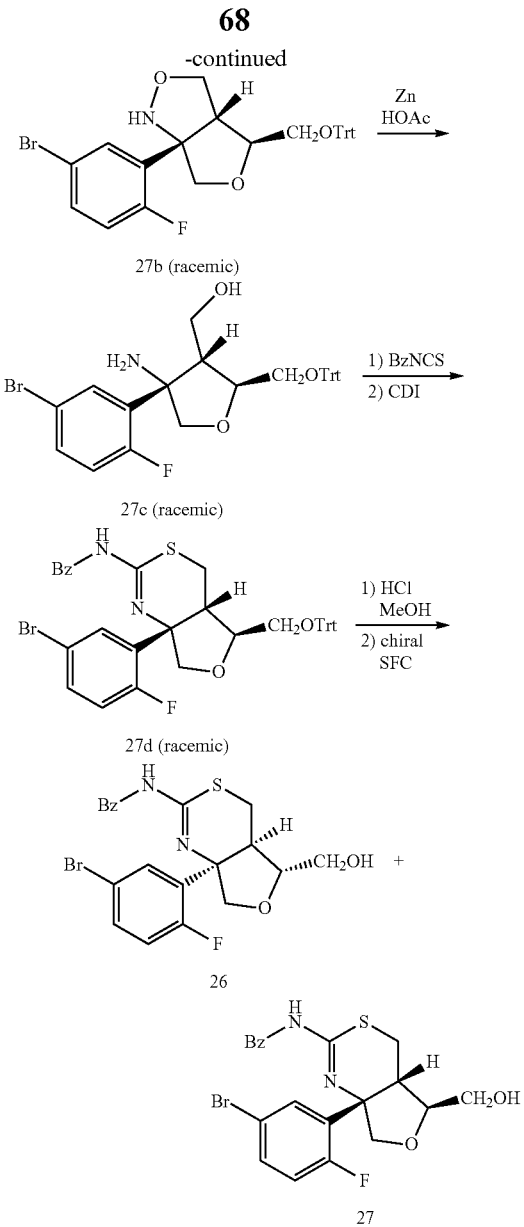

Preparation of racemic mixture of (3aS,4R)-4-((trityloxy)methyl)-3,3a,4,6-tetrahydrofuro[3,4-c]isoxazole and (3aR,4S)-4-((trityloxy)methyl)-3,3a,4,6-tetrahydrofuro[3,4-c]isoxazole (27b)

A solution of 4-bromo-1-fluoro-2-iodobenzene (CombiBlocks, San Diego, Calif., USA) (60.0 g, 197 mmol) in THF (1.0 L) at −78° C. was treated with n-butyl lithium (1.6 M in THF, 123.0 mL, 197 mmol) dropwise followed by borontrifluoride diethyl etherate (7.36 g, 52 mmol) dropwise. The resulting mixture was stirred for 10 minutes at −78° C. then treated with a solution of 27a (prepared according to the methods described in WO2012098461) (40.0 g, 104 mmol) in THF (200 mL) dropwise and stirred at −78° C. for 1.5 hours. The reaction was quenched with sat'd aqueous NH$_4$Cl (1.0 L) and extracted with ethyl acetate (3×1.0 L). The combined organic solution was dried over Na$_2$SO$_4$ and concentrated. The residue was purified by silica gel chromatography (20% ethyl acetate in hexanes) to give 27b (21.0 g, 36% yield). MS (ESI+ve ion) m/z: 560.2/562.2 [M+H]+. 1H NMR (400 MHz, DMSO-d6) δ 7.79-7.72 (m, 1H), 7.55 (dt, J=7.1, 3.1 Hz, 1H), 7.40-7.30 (m, 13H), 7.29-7.18 (m, 3H), 4.18-4.01 (m, 3H), 3.88 (d, J=10.0 Hz, 1H), 3.74-3.68 (m, 1H), 3.29-3.20 (m, 3H), 3.11-3.06 (m, 1H).

Preparation of racemic mixture of ((2R,3S,4R)-4-amino-4-(5-bromo-2-fluorophenyl)-2-((trityloxy)methyl)tetrahydrofuran-3-yl)methanol and ((2S,3R,4S)-4-amino-4-(5-bromo-2-fluorophenyl)-2-((trityloxy)methyl)tetrahydrofuran-3-yl)methanol (27c)

To a solution of 27b (20.0 g, 35.7 mmol) in acetic acid (70 mL) at 0° C. was added zinc(0) powder (5.9 g, 89.0 mmol) in a portion-wise manner and the reaction mixture was stirred at room temperature for 6 hours. The mixture was diluted with ethyl acetate (100 mL) and filtered through a pad of celite. The celite bed was washed with ethyl acetate (2×50 mL). The filtrate was concentrated under reduced pressure. The residue was neutralized to pH ~7 with aqueous ammonia solution and extracted with ethyl acetate (5×100 mL). The combined organic solution was dried over Na2SO4 and concentrated to give 27c (18.0 g, 90% yield) which was used without further purification. MS (ESI+ve ion) m/z: 562.2/564.2 [M+H]+.

Preparation of racemic mixture of N-((4aR,5R,7aR)-7a-(5-bromo-2-fluorophenyl)-5-((trityloxy)methyl)-4a,5,7,7a-tetrahydro-4H-furo[3,4-d][1,3]thiazin-2-yl)benzamide and N-((4aS,5S,7aS)-7a-(5-bromo-2-fluorophenyl)-5-((trityloxy)methyl)-4a,5,7,7a-tetrahydro-4H-furo[3,4-d][1,3]thiazin-2-yl)benzamide (27d)

A solution of 27c (18.0 g, 32.1 mmol) in THF (400 mL) at 0° C. was treated with benzoyl isothiocyanate (6.27 g, 38.4 mmol) then stirred at room temperature for 6 hours. The reaction mixture was cooled to 0° C. and CDI (7.78 g, 48.0 mmol) was added in small portions. The mixture was stirred at room temperature for 24 hours then quenched with water (400 mL) and extracted with ethyl acetate (4×500 mL). The combined organic solution was dried over Na2SO4 and concentrated. The residue was purified by silica gel chromatography (50% ethyl acetate in hexanes) to afford 27d (13.5 g, 60% yield). MS (ESI+ve ion) m/z: 707.1/709.1 [M+H]+. 1H NMR (400 MHz, Chloroform-d) δ 11.82 (s, 1H), 8.88 (s, 1H), 8.10 (s, 1H), 7.74-7.68 (m, 3H), 7.63 (t, J=7.3 Hz, 1H), 7.50 (t, J=7.8 Hz, 2H), 7.40-7.37 (m, 5H), 7.31-7.26 (m, 10H), 5.29 (d, J=10.3 Hz, 1H), 4.74 (dd, J=12.0, 8.2 Hz, 1H), 4.50 (dd, J=11.9, 4.6 Hz, 1H), 4.39 (d, J=10.1 Hz, 1H), 4.04 (dd, J=8.0, 4.0 Hz, 1H), 3.46 (dd, J=10.6, 3.8 Hz, 1H), 3.31-3.19 (m, 2H).

Preparation of N-((4aR,5R,7aR)-7a-(5-bromo-2-fluorophenyl)-5-(hydroxymethyl)-4a,5,7,7a-tetrahydro-4H-furo[3,4-d][1,3]thiazin-2-yl)benzamide (26) and N-((4aS,5S,7aS)-7a-(5-bromo-2-fluorophenyl)-5-(hydroxymethyl)-4a,5,7,7a-tetrahydro-4H-furo[3,4-d][1,3]thiazin-2-yl)benzamide (27)

To a solution of 27d (20.0 g, 28.3 mmol) in methanol (100 mL) at 0° C. was added HCl (35.0 mL of 4 N solution in methanol, 140 mmol) and the resulting mixture was stirred at room temperature for 2 hours. The mixture was concentrated under reduced pressure. The residue was diluted with water (250 mL) and extracted with ethyl acetate (3×500 mL). The combined organic solution was dried over Na2SO4 and concentrated under reduced pressure. The residue was purified by silica gel chromatography (25% ethyl acetate in hexanes) to afford a racemic mixture of compounds 26 and 27 (4.6 g, 35%) as a white solid. MS (ESI+ve ion) m/z: 465.2/467.2 [M+H]+. 1H NMR (400 MHz, Chloroform-d) δ 8.11 (s, 2H), 7.60-7.44 (m, 5H), 7.05 (dd, J=11.7, 8.6 Hz, 1H), 4.52 (dd, J=12.3, 9.0 Hz, 2H), 4.06 (s, 1H), 4.00-3.92 (m, 1H), 3.81-3.73 (m, 2H), 3.34 (s, 1H), 3.23 (d, J=14.1 Hz, 1H), 2.83 (d, J=13.6 Hz, 1H), 2.04 (s, 1H).

The racemic mixture of compounds 26 and 27 (4.6 g) was subjected to chiral SFC to provide 2 compounds: the 1st eluent was Intermediate 26 (1.45 g, 100% ee) afforded as a white solid and the 2nd eluent was Intermediate 27 (1.45 g, 99.3% ee) afforded as a white solid. Preparative SFC purification method: Chiralpak IA (250×30 mm, 5 μm); mobile phase (70:30)=(A:B), A=liquid CO2, B=20 mM ammonia in MeOH; flow rate=100 mL/min; wave length=250 nm; inlet pressure=205 bar; 4.6 g of sample was dissolved in 92 mL of THF/MeOH (1/1), sample load=1.0 mL/injection; run time=10 minutes, cycle time=5 minutes. The absolute stereochemistry was arbitrarily assigned.

Intermediate 28: N-((4aR,5R,7aR)-7a-(5-bromo-2-fluorophenyl)-5-(difluoromethyl)-4a,5,7,7a-tetrahydro-4H-furo[3,4-d][1,3]thiazin-2-yl)benzamide

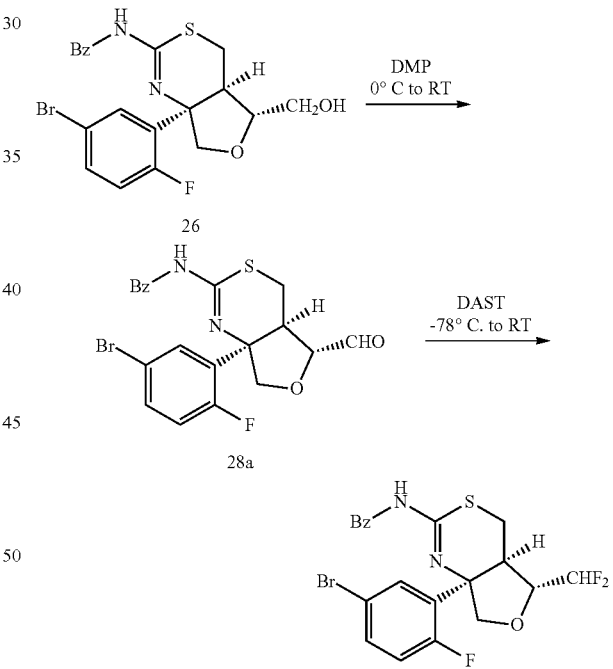

To a solution of N-((4aR,5R,7aR)-7a-(5-bromo-2-fluorophenyl)-5-(hydroxymethyl)-4a,5,7,7a-tetrahydro-4H-furo[3,4-d][1,3]thiazin-2-yl)benzamide (26) (1.00 g, 2.15 mmol) in DCM (15 mL) at 0° C. was added Dess-Martin periodinate (1.82 g, 4.30 mmol). After the reaction mixture was stirred at 0° C. for 2 h then at room temperature for 2 hours, it was quenched with sat'd sodium bicarbonate solution (20 mL) and extracted with DCM (2×20 mL). The organic solution was washed with brine (20 mL), dried over Na2SO4, filtered and concentrated in vacuo to give crude N-((4aR,5R,7aR)-7a-(5-bromo-2-fluorophenyl)-5-formyl-4a,5,7,7a-tetrahydro-4H-furo[3,4-d][1,3]thiazin-2-yl)benzamide (28a) (0.8 g, 79% yield) as a light yellow solid. This material was used without purification.

To a solution of crude N-((4aR,5R,7aR)-7a-(5-bromo-2-fluorophenyl)-5-formyl-4a,5,7,7a-tetrahydro-4H-furo[3,4-d][1,3]thiazin-2-yl)benzamide (28a) (0.8 g, 1.70 mmol) in DCM (10 mL) at −78° C. was added DAST (0.57 mL, 4.32 mmol) dropwise. After the reaction mixture was stirred for 3 hours at −78° C., it was quenched with sat'd sodium bicarbonate solution (10 mL) and extracted with DCM (2×50 mL). The organic solution was washed with brine (20 mL), dried over Na₂SO₄, filtered and concentrated in vacuo. The residue was purified on a silica gel column (15% to 20% EtOAc in petroleum ether) to provide N-((4aR,5R,7aR)-7a-(5-bromo-2-fluorophenyl)-5-(difluoromethyl)-4a,5,7,7a-tetrahydro-4H-furo[3,4-d][1,3]thiazin-2-yl)benzamide (28) (0.15 g, 0.31 mmol, 18% yield) as an off-white solid. MS (ESI positive ion) m/z: 485.0 (M+1). $^1$H NMR (400 MHz, Chloroform-d) δ 8.12 (s, 2H), 7.97-7.72 (m, 2H), 7.52 (dt, J=30.7, 8.5 Hz, 3H), 7.17 (dd, J=12.5, 8.2 Hz, 1H), 6.03 (ddd, J=57.6, 54.8, 3.6 Hz, 1H), 5.05-3.98 (m, 3H), 3.60 (d, J=6.9 Hz, 1H), 3.49-3.30 (m, 1H), 3.06-2.80 (m, 1H), 1.56-1.39 (m, 1H). $^{19}$F NMR (376 MHz, Chloroform-d) δ −111.05 (s, 1F), −132.12 (m, 2F).

Intermediate 29: N-((4aS,5S,7aS)-5-(difluoromethyl)-7a-(2-fluoro-5-(4,4,5,5-tetramethyl-1,3,2-dioxaborolan-2-yl)phenyl)-4a,5,7,7a-tetrahydro-4H-furo[3,4-d][1,3]thiazin-2-yl)benzamide

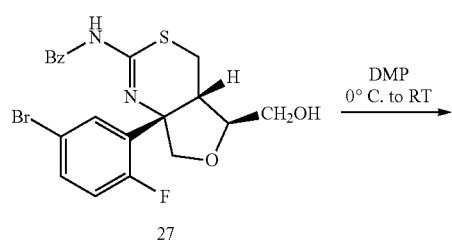

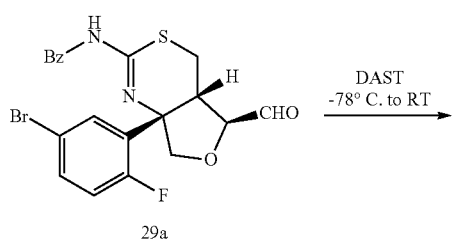

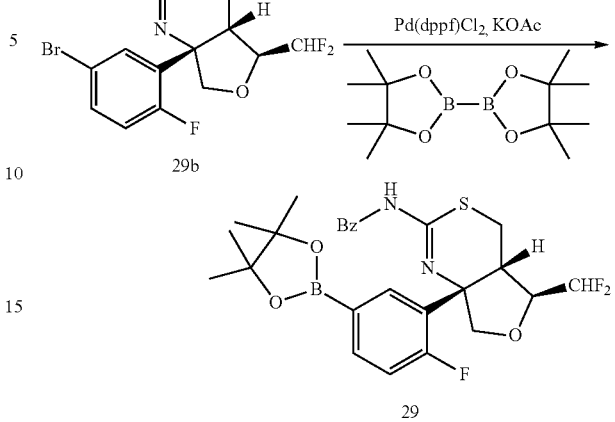

Preparation of N-((4aS,5S,7aS)-7a-(5-bBromo-2-fluorophenyl)-5-(difluoromethyl)-4a,5,7,7a-tetrahydro-4H-furo[3,4-d][1,3]thiazin-2-yl)benzamide (29b)

This 29b (0.15 g, 0.31 mmol) as an off-white solid was prepared from Intermediate 27 (1.00 g, 2.15 mmol) in a 2-step sequence similar to that described for Intermediate 28. MS (ESI positive ion) m/z: 485.0 (M+1). $^1$H NMR (400 MHz, Chloroform-d) δ 8.04 (d, J=7.3 Hz, 2H), 7.94-7.31 (m, 5H), 7.05 (dd, J=11.8, 8.6 Hz, 1H), 6.02 (s, 1H), 4.51 (d, J=8.9 Hz, 2H), 3.98 (s, 2H), 3.51 (s, 1H), 3.20 (d, J=13.9 Hz, 1H), 2.94-2.82 (m, 1H). $^{19}$F NMR (376 MHz, Chloroform-d) δ −111.05 (s, 1F), −132.12 (m, 2F).

Preparation of N-((4aS,5S,7aS)-5-(difluoromethyl)-7a-(2-fluoro-5-(4,4,5,5-tetramethyl-1,3,2-dioxaborolan-2-yl)phenyl)-4a,5,7,7a-tetrahydro-4H-furo[3,4-d][1,3]thiazin-2-yl)benzamide (29)

A mixture of N-((4aS,5S,7aS)-7a-(5-bromo-2-fluorophenyl)-5-(difluoromethyl)-4a,5,7,7a-tetrahydro-4H-furo[3,4-d][1,3]thiazin-2-yl)benzamide (29b) (0.10 g, 0.21 mmol), bis(pinacolato)diboron (65 mg, 0.25 mmol), and potassium acetate (42 mg, 0.43 mmol) in 1,4-dioxane (10 mL) was purged with nitrogen for 2 minutes then treated with PdCl₂(dppf)-CH₂Cl₂ adduct (9 mg). The mixture was purged with nitrogen for 2 minutes then heated at 90° C. for 16 hours. After cooling to room temperature, the reaction mixture was filtered through a celite pad and the filtered cake was washed with ethyl acetate (10 mL). The filtrate was evaporated under vacuum. The crude material was purified by silica gel chromatography (20% to 30% EtOAc in petroleum ether) to Intermediate 29 (65 mg, 59% yield) as an off-white solid. MS (ESI positive ion) m/z: 533.1 (M+1). $^1$H NMR (400 MHz, Chloroform-d) δ 8.12 (br s, 2H), 7.91-7.66 (m, 2H), 7.52-7.46 (m, 3H), 7.17 (dd, J=12.5, 8.2 Hz, 1H), 6.03 (ddd, J=57.6, 54.8, 3.6 Hz, 1H), 4.74-4.64 (m, 1H), 4.46-4.40 (m, 1H), 4.18-4.10 (m, 1H), 3.65-3.55 (m, 1H), 3.42-3.36 (m, 1H), 3.00-2.92 (m, 1H), 1.78-1.70 (m, 1H), 1.36 (s, 12H); $^{19}$F NMR (376 MHz, Chloroform-d) δ −112.82 (s, 1F), −132.12 (d, 2F).

EXAMPLES

Example 100: (4aS,7aR)-7a-(5-((Z)-2-(5-chloropyridin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine

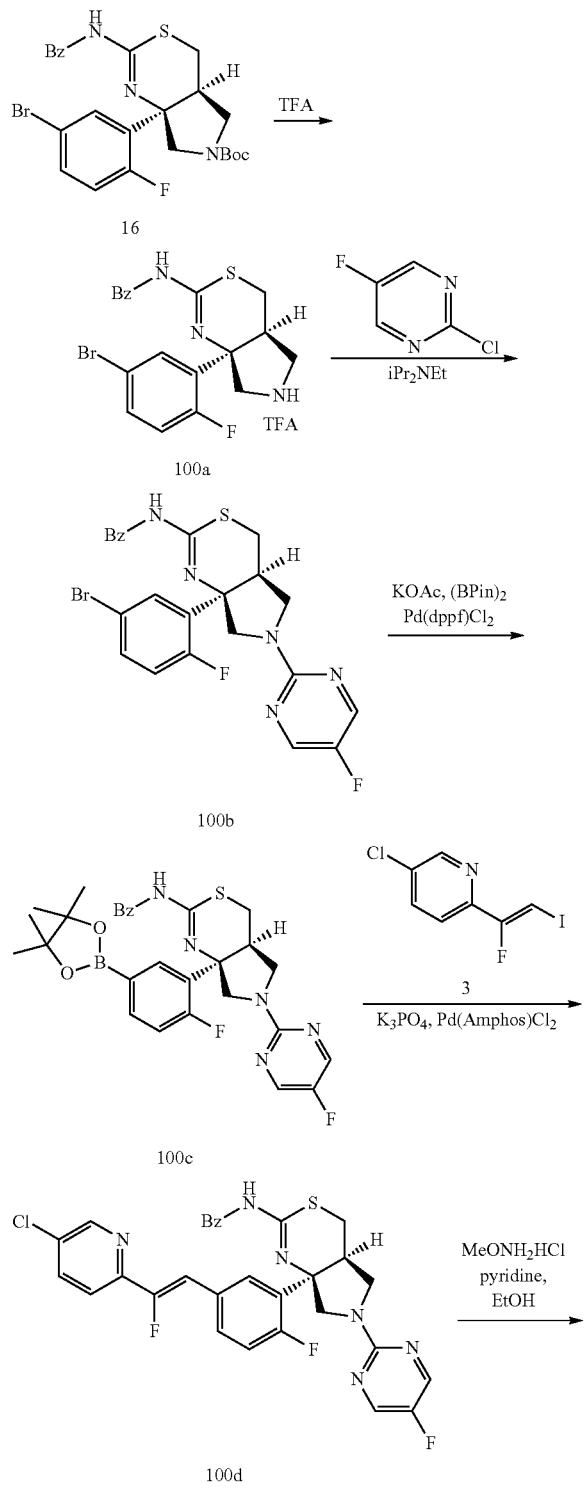

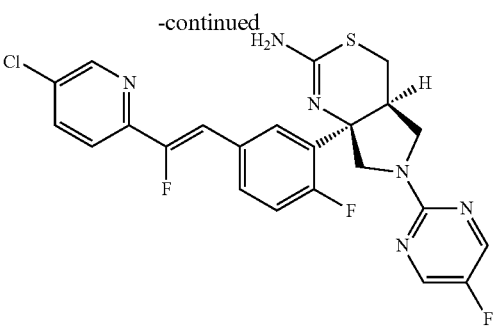

Preparation of N-((4aS,7aR)-7a-(5-bromo-2-fluorophenyl)-6-(5-fluoropyrimidin-2-yl)-4,4a,5,6,7,7a-hexahydropyrrolo[3,4-d][1,3]thiazin-2-yl)benzamide (100b)

To a solution of compound 16 (1.00 g, 1.87 mmol) in DCM (5 mL) at room temperature was added TFA (1.00 mL, 13.10 mmol) dropwise. The mixture was stirred for 18 hours then concentrated in vacuo to give N-((4aS,7aR)-7a-(5-bromo-2-fluorophenyl)-4,4a,5,6,7,7a-hexahydropyrrolo[3,4-d][1,3]thiazin-2-yl)benzamide 2,2,2-trifluoroacetate (100a) (813 mg) which was used without additional purification. MS (ESI, positive ion) m/z: 434/436 (M+1).

A mixture of 100a (813 mg, 1.87 mmol), N,N-diisopropylethylamine (2.28 mL, 13.10 mmol), and 2-chloro-5-fluoro-pyrimidine (Matrix Scientific) (1.15 mL, 9.36 mmol) in dioxane (6 mL) was heated to reflux for 2 hours. The mixture was diluted with water and extracted with EtOAc. The organic layer was dried over $Na_2SO_4$ and concentrated in vacuo. The residue was purified by silica gel chromatography (0 to 100% EtOAc in heptane) to provide N-((4aS,7aR)-7a-(5-bromo-2-fluorophenyl)-6-(5-fluoropyrimidin-2-yl)-4,4a,5,6,7,7a-hexahydropyrrolo[3,4-d][1,3]thiazin-2-yl)benzamide (100b) (0.88 g, 89% yield) as an off-white solid. MS (ESI, positive ion) m/z: 530/532 (M+1).

Preparation of N-((4aS,7aR)-7a-(2-fluoro-5-(4,4,5,5-tetramethyl-1,3,2-dioxaborolan-2-yl)phenyl)-6-(5-fluoropyrimidin-2-yl)-4,4a,5,6,7,7a-hexahydropyrrolo[3,4-d][1,3]thiazin-2-yl)benzamide (100c)

A mixture of N-((4aS,7aR)-7a-(5-bromo-2-fluorophenyl)-6-(5-fluoropyrimidin-2-yl)-4,4a,5,6,7,7a-hexahydropyrrolo[3,4-d][1,3]thiazin-2-yl)benzamide (100b) (0.88 g, 1.66 mmol), bis(pinacolato)diboron (0.55 g, 2.16 mmol), potassium acetate (0.49 g, 4.98 mmol) in dioxane (10 mL) was purged with argon, then treated with [1,1'-bis(diphenylphosphino)ferrocene]-dichloropalladium(II) complex with DCM (95 mg, 0.12 mmol). The mixture was heated to 90° C. for 1 hour, cooled to room temperature, and filtered through celite. The filter cake was washed with EtOAc. The filtrate was concentrated in vacuo. The residue was triturated with heptane. The mixture was filtered to provide N-((4aS,7aR)-7a-(2-fluoro-5-(4,4,5,5-tetramethyl-1,3,2-dioxaborolan-2-yl)phenyl)-6-(5-fluoropyrimidin-2-yl)-4,4a,5,6,7,7a-hexahydropyrrolo[3,4-d][1,3]thiazin-2-yl)benzamide (100c) (0.96 g, 100% yield) as a brown solid. MS (ESI, positive ion) m/z: 578 (M+1).

Preparation of N-((4aS,7aR)-7a-(5-((Z)-2-(5-chloro-pyridin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-yl)benzamide (100d)

A mixture of 100c (0.15 g, 0.26 mmol), (Z)-5-chloro-2-(1-fluoro-2-iodovinyl)pyridine (3) (0.08 g, 0.28 mmol), Pd(Amphos)Cl$_2$ (0.018 g, 0.026 mmol), and potassium phosphate (0.14 g, 0.64 mmol) in dioxane (1.5 mL) and water (0.25 mL) was purged with argon then heated to 80° C. for 30 minutes. The mixture was diluted with water and extracted with EtOAc. The organic solution was dried over Na$_2$SO$_4$ and concentrated in vacuo. The residue was purified by silica gel chromatography (0 to 100% EtOAc in heptane) to afford N-((4aS,7aR)-7a-(5-((Z)-2-(5-chloropyridin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-yl)benzamide (100d) (82 mg, 52% yield) as an off-white solid. MS (ESI, positive ion) m/z: 607 (M+1).

Preparation of (4aS,7aR)-7a-(5-((Z)-2-(5-chloro-pyridin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine (100)

A mixture of 100d (0.070 g, 0.115 mmol), O-methylhydroxylamine hydrochloride (TCI America) (0.193 g, 2.306 mmol) and pyridine (0.187 mL, 2.306 mmol) in ethanol (2 mL) was heated to 70° C. for 1 hour. The mixture was concentrated in vacuo; the residue was diluted with saturated Na$_2$CO$_3$ and extracted with EtOAc. The organic solution was dried over Na$_2$SO$_4$ and concentrated in vacuo. The residue was purified by silica gel chromatography (0 100% EtOAc:EtOH (3:1) in heptane) to give (4aS,7aR)-7a-(5-((Z)-2-(5-chloropyridin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine (Example 100, 57 mg, 98% yield) as a white solid. MS (ESI, positive ion) m/z: 503 (M+1). $^1$H NMR (400 MHz, CHLOROFORM-d) δ 8.54 (d, J=2.35 Hz, 1H), 8.23 (s, 2H), 7.67-7.75 (m, 2H), 7.67-7.75 (m, 2H), 7.61 (dd, J=1.96, 8.02 Hz, 1H), 7.55 (dd, J=1.37, 8.41 Hz, 1H), 6.95-7.15 (m, 2H), 4.37 (d, J=11.15 Hz, 1H), 3.86 (dd, J=2.64, 11.25 Hz, 1H), 3.81 (d, J=8.41 Hz, 2H), 3.24 (tt, J=4.23, 8.39 Hz, 1H), 3.02-3.11 (m, 1H), 2.91-2.99 (m, 1H).

Example 101: (4aR,7aS)-7a-(5-((Z)-2-(5-chloropyridin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine

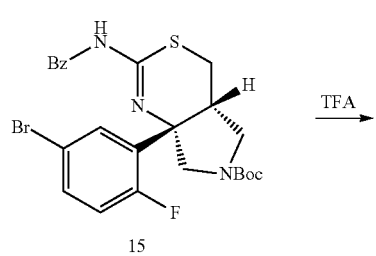

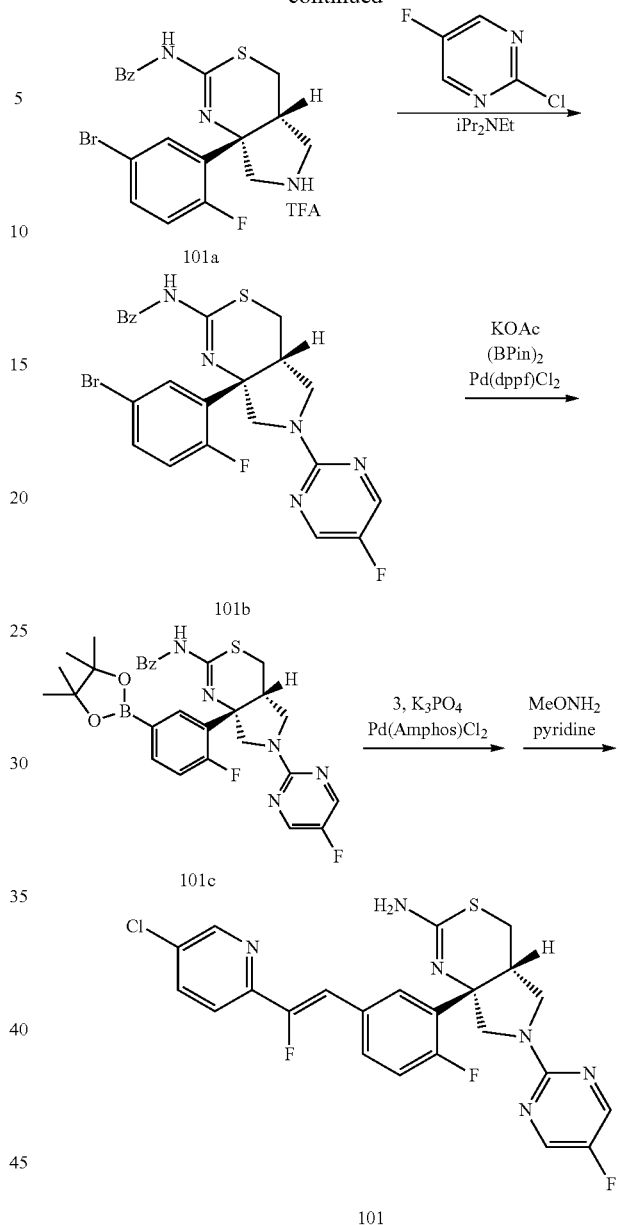

Preparation of N-((4aR,7aS)-7a-(2-fluoro-5-(4,4,5,5-tetramethyl-1,3,2-dioxaborolan-2-yl)phenyl)-6-(5-fluoropyrimidin-2-yl)-4,4a,5,6,7,7a-hexahydropyrrolo[3,4-d][1,3]thiazin-2-yl)benzamide (101c)

Boronic ester 101c was prepared in a sequence similar to that described for boronic ester 100c, here starting from (4aR,7aS)-tert-butyl 2-benzamido-7a-(5-bromo-2-fluorophenyl)-4a,5,7,7a-tetrahydropyrrolo[3,4-d][1,3]thiazine-6(4H)-carboxylate (15). MS (ESI, positive ion) m/z: 578 (M+1).

Preparation of (4aR,7aS)-7a-(5-((Z)-2-(5-chloro-pyridin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine (101)

This compound (86 mg, 52% overall yield) was prepared in a fashion similar to that described for Example 100, here starting from boronic ester 101c (200 mg, 0.34 mmol) and vinyl iodide 3 (108 mg, 0.38 mmol). MS (ESI, positive ion) m/z: 503 (M+1). $^1$H NMR (400 MHz, CHLOROFORM-d) δ 8.54 (d, J=2.15 Hz, 1H), 8.23 (s, 2H), 7.67-7.75 (m, 2H), 7.61 (dd, J=2.15, 8.02 Hz, 1H), 7.55 (d, J=7.24 Hz, 1H), 6.95-7.14 (m, 2H), 4.37 (d, J=11.15 Hz, 1H), 3.86 (dd, J=2.54, 11.15 Hz, 1H), 3.81 (d, J=8.22 Hz, 2H), 3.24 (tt, J=4.40, 8.41 Hz, 1H), 3.03-3.13 (m, 1H), 2.91-3.01 (m, 1H). NH$_2$ was not clear in NMR.

Example 102: 6-((Z)-2-(3-((4aR,7aS)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)nicotinonitrile

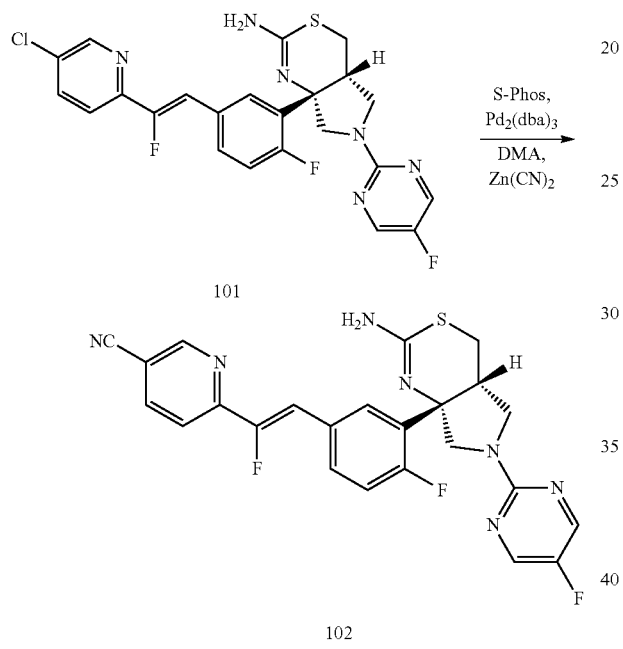

A 3-mL vial was charged with (4aR,7aS)-7a-(5-((Z)-2-(5-chloropyridin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine (101) (37.5 mg, 0.075 mmol), zinc cyanide (26 mg, 0.224 mmol), dicyclohexyl(2',6'-dimethoxy-[1,1'-biphenyl]-2-yl)phosphine (9.18 mg, 0.022 mmol), Pd$_2$(dba)$_3$ (10.2 mg, 0.011 mmol) and N, N-dimethylacetamide (0.8 mL). The vial was purged with argon and sealed. The mixture was heated at 120° C. for 2 hours, cooled to room temperature, and filtered through celite. The filter cake was washed with EtOAc. The filtrate was washed with water and brine, dried over Na$_2$SO$_4$ and concentrated in vacuo. The residue was purified by silica gel chromatography (0 to 100% EtOAc/EtOH (3/1) in heptane) to afford Example 102 (29 mg, 78% yield) as a yellow solid. MS (ESI, positive ion) m/z: 494 (M+1). $^1$H NMR (400 MHz, CHLOROFORM-d) δ ppm 8.83 (s, 1H), 8.23 (s, 2H), 8.02 (dd, J=8.31, 2.05 Hz, 1H), 7.62-7.79 (m, 3H), 7.24 (d, J=38.73 Hz, 1H), 7.12 (dd, J=11.93, 8.61 Hz, 1H), 4.37 (d, J=11.35 Hz, 1H), 3.75-3.93 (m, 3H), 3.25 (tt, J=8.31, 4.30 Hz, 1H), 2.88-3.13 (m, 4H). $^{19}$F NMR (376 MHz, CHLOROFORM-d) δ −109.21 (s, 1F), −125.17 (s, 1F), −158.01 (s, 1F).

Example 103: 6-((Z)-2-(3-((4aS,7aR)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)nicotinonitrile

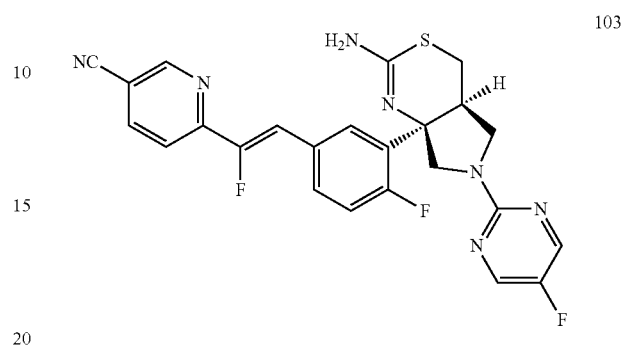

This compound (17 mg, 60% yield) as a yellow solid was prepared in a fashion similar to that described for Example 102, here starting from Example 100 (29 mg, 0.058 mmol). MS (ESI, positive ion) m/z: 494 (M+1). $^1$H NMR (400 MHz, CHLOROFORM-d) δ 8.82 (s, 1H), 8.23 (s, 2H), 7.96-8.09 (m, 1H), 7.61-7.78 (m, 3H), 7.03-7.27 (m, 2H), 4.36 (d, J=11.15 Hz, 1H), 3.72-3.93 (m, 3H), 3.25 (tt, J=4.23, 8.29 Hz, 1H), 2.88-3.12 (m, 2H), 2.88-3.12 (m, 2H). $^{19}$F NMR (376 MHz, CHLOROFORM-d) δ −109.20 (d, J=1.73 Hz, 1F), −125.18 (s, 1F), −158.03 (s, 1F).

Example 104: (4aR,7aR)-7a-(5-((Z)-2-(5-chloropyridin-2-yl)-2-fluorovinyl)-2-fluorophenyl)-4a,5,7,7a-tetrahydro-4H-furo[3,4-d][1,3]thiazin-2-amine

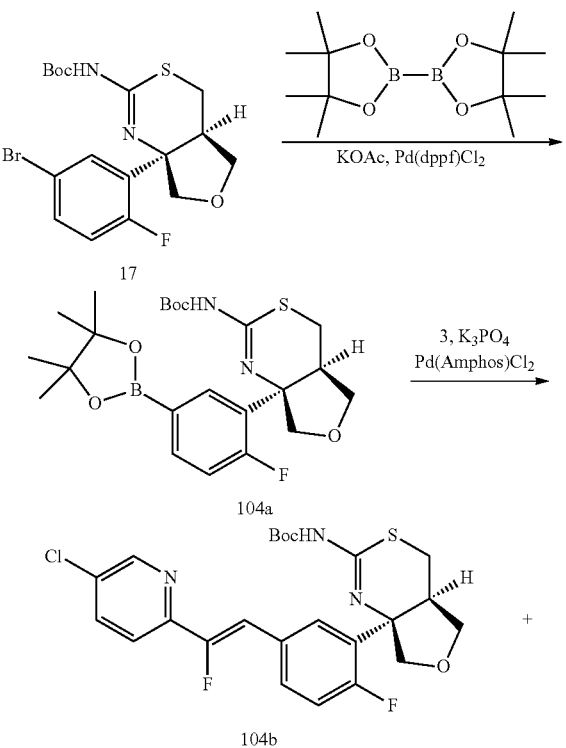

-continued

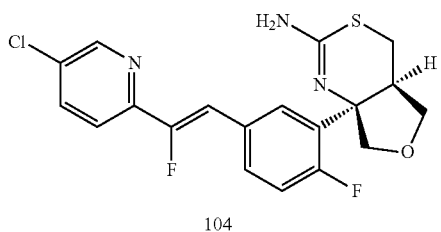

104

Tert-butyl ((4aR,7aR)-7a-(2-fluoro-5-(4,4,5,5-tetramethyl-1,3,2-dioxaborolan-2-yl)phenyl)-4a,5,7,7a-tetrahydro-4H-furo[3,4-d][1,3]thiazin-2-yl)carbamate (104a) was prepared in a fashion similar to that described for boronic ester 100c, here starting from tert-butyl ((4aR,7aR)-7a-(5-bromo-2-fluorophenyl)-4a,5,7,7a-tetrahydro-4H-furo[3,4-d][1,3]thiazin-2-yl)carbamate (17). MS (ESI, positive ion) m/z: 479.1 (M+1). 104a was used without additional purification.

Using boronic ester 104a (140 mg, 0.29 mmol) and vinyl iodide 3 (91 mg, 0.32 mmol) as the starting materials, the Suzuki coupling reaction was carried out in a fashion similar to that described for Example 100. LCMS showed the formation of two products, the Boc-protected 104b and the de-Boc 104. Purification of the crude mixture via silica gel chromatography (0 to 100% EtOAc in DCM) gave Example 104 (49 mg, 41% yield) as a light yellow solid. MS (ESI, positive ion) m/z: 408 (M+1). $^1$H NMR (400 MHz, CHLOROFORM-d) δ 8.55 (s, 1H), 7.64-7.78 (m, 3H), 7.57 (d, J=8.22 Hz, 1H), 6.97-7.13 (m, 2H), 4.49 (d, J=8.61 Hz, 1H), 4.04-4.19 (m, 2H), 3.80-3.87 (m, 1H), 2.98-3.12 (m, 2H), 2.84 (dd, J=5.18, 12.81 Hz, 1H). NH$_2$ was not clear. $^{19}$F NMR (376 MHz, CHLOROFORM-d) δ −110.61 (s, 1F), −123.80 (s, 1F).

Example 105: (4aS,7aS)-7a-(5-((Z)-2-(5-chloropyridin-2-yl)-2-fluorovinyl)-2-fluorophenyl)-4a,5,7,7a-tetrahydro-4H-furo[3,4-d][1,3]thiazin-2-amine

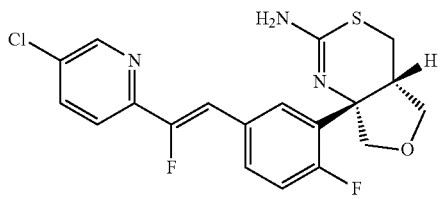

105

This compound was prepared in a sequence similar to that described for Example 104, here starting from tert-butyl ((4aS,7aS)-7a-(5-bromo-2-fluorophenyl)-4a,5,7,7a-tetrahydro-4H-furo[3,4-d][1,3]thiazin-2-yl)carbamate (18). MS (ESI, positive ion) m/z: 408 (M+1). $^1$H NMR (400 MHz, CHLOROFORM-d) δ 8.55 (s, 1H), 7.64-7.78 (m, 3H), 7.57 (d, J=8.41 Hz, 1H), 6.96-7.15 (m, 2H), 4.49 (d, J=8.80 Hz, 1H), 4.03-4.22 (m, 2H), 3.90 (d, J=8.80 Hz, 1H), 3.02-3.17 (m, 2H), 2.81-2.91 (m, 1H). NH$_2$ was not clear. $^{19}$F NMR (376 MHz, CHLOROFORM-d) δ −110.62 (s, 1F), −123.64 (br. s., 1F).

Example 106: 6-((Z)-2-(3-((4aR,7aR)-2-amino-4a,5,7,7a-tetrahydro-4H-furo[3,4-d][1,3]thiazin-7a-yl)-4-fluorophenyl)-1-fluorovinyl)nicotinonitrile

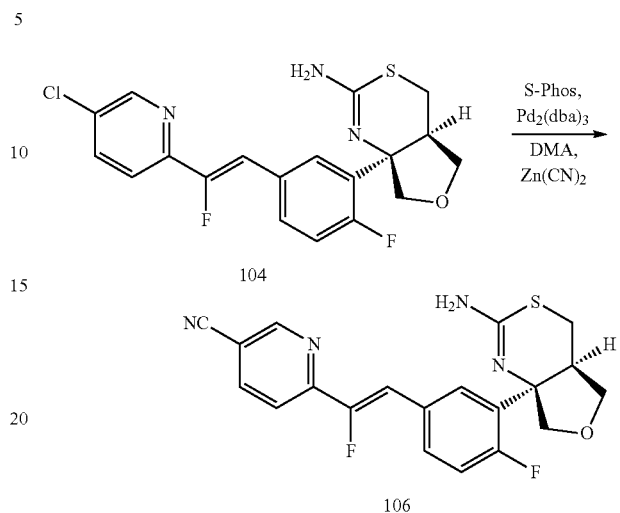

This compound (11 mg, 33% yield) was prepared in a fashion similar to that described for Example 102, here starting from Example 104 (35 mg, 0.086 mmol). MS (ESI, positive ion) m/z: 399 (M+1). $^1$H NMR (400 MHz, CHLOROFORM-d) δ 8.83 (s, 1H), 8.02 (dd, J=2.05, 8.31 Hz, 1H), 7.78 (dd, J=1.86, 7.92 Hz, 1H), 7.68-7.75 (m, 2H), 7.26 (d, J=22.30 Hz, 1H), 7.11 (dd, J=8.51, 11.84 Hz, 1H), 4.49 (d, J=8.80 Hz, 1H), 4.03-4.22 (m, 2H), 3.86 (dd, J=1.96, 8.80 Hz, 1H), 3.02-3.14 (m, 2H), 2.80-2.92 (m, 1H). NH$_2$ was not clear. $^{19}$F NMR (376 MHz, CHLOROFORM-d) δ −109.12 (d, J=1.73 Hz, 1F), −125.22 (d, J=0.87 Hz, 1F).

Example 107: 6-((Z)-2-(3-((4aS,7aS)-2-amino-4a,5,7,7a-tetrahydro-4H-furo[3,4-d][1,3]thiazin-7a-yl)-4-fluorophenyl)-1-fluorovinyl)nicotinonitrile

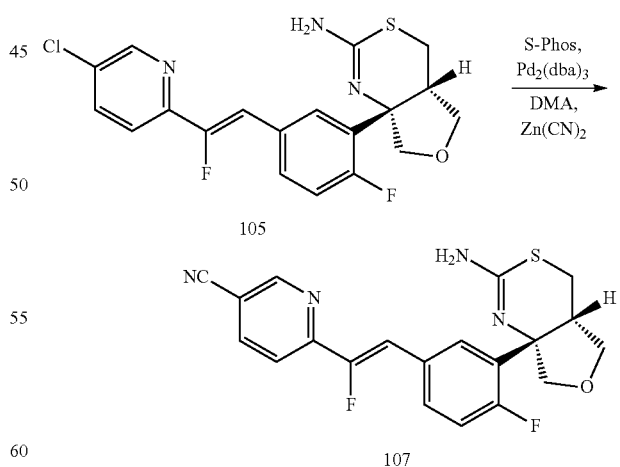

This compound (15 mg, 32% yield) was prepared in a fashion similar to that described for Example 102, here starting from Example 105 (30 mg, 0.074 mmol). MS (ESI, positive ion) m/z: 399 (M+1). $^1$H NMR (400 MHz, CHLOROFORM-d) δ 8.83 (s, 1H), 8.02 (dd, J=2.05, 8.31 Hz, 1H), 7.78 (dd, J=2.05, 7.92 Hz, 1H), 7.68-7.75 (m, 2H), 7.26 (d, J=37.95 Hz, 1H), 7.11 (dd, J=8.51, 11.83 Hz, 1H), 4.49 (dd, J=0.88, 8.71 Hz, 1H), 4.03-4.26 (m, 2H), 3.85 (dd, J=2.15, 8.80 Hz, 1H), 3.02-3.12 (m, 2H), 2.82-2.90 (m, 1H). NH$_2$ was not clear. $^{19}$F NMR (376 MHz, CHLOROFORM-d) δ −109.11 (d, J=1.73 Hz, 1F), −125.24 (d, J=1.73 Hz, 1F).

Example 108: (4aR,7aS)-7a-(2-fluoro-5-((Z)-2-fluoro-2-(5-methoxypyrazin-2-yl)vinyl)phenyl)-6-(5-fluoropyrimidin-2-yl)-4,4a,5,6,7,7a-hexahydropyrrolo[3,4-d][1,3]thiazin-2-amine

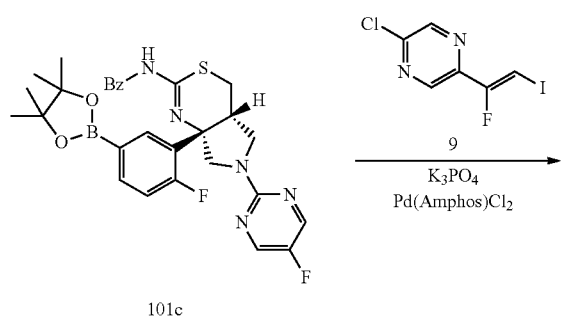

101c

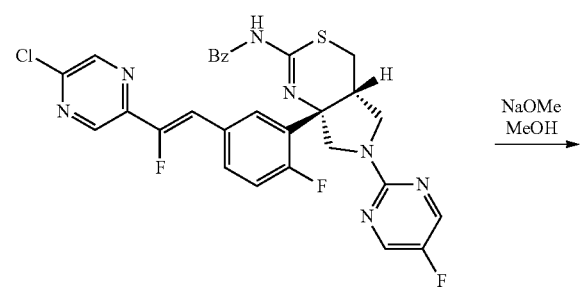

108a

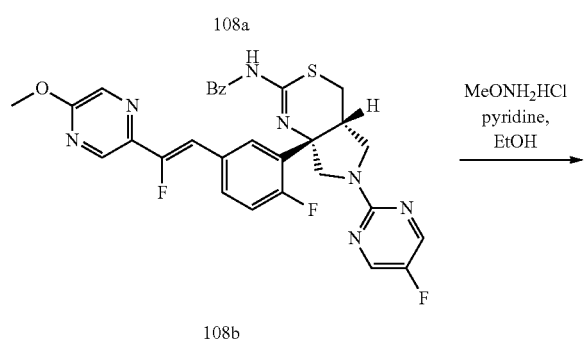

108b

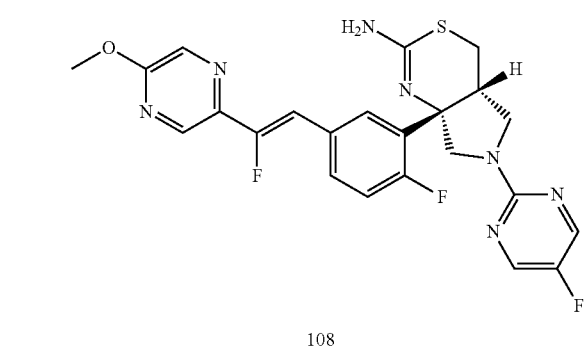

108

Preparation of N-((4aR,7aS)-7a-(5-((Z)-2-(5-chloropyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-yl)benzamide (108a)

A mixture of N-((4aR,7aS)-7a-(2-fluoro-5-(4,4,5,5-tetramethyl-1,3,2-dioxaborolan-2-yl)phenyl)-6-(5-fluoropyrimidin-2-yl)-4,4a,5,6,7,7a-hexahydropyrrolo[3,4-d][1,3]thiazin-2-yl)benzamide (101c) (0.200 g, 0.346 mmol), vinyl iodide 9 (0.207 g, 0.727 mmol), potassium phosphate (0.184 g, 0.866 mmol), and Pd(Amphos)Cl$_2$ (0.025 g, 0.035 mmol) in dioxane (3 mL) and water (0.50 mL) was purged with argon, then the vial was sealed and heated to 80° C. for 30 minutes. The mixture was diluted with water and extracted with EtOAc. The organic solution was dried over Na$_2$SO$_4$ and concentrated in vacuo. The residue was purified by silica gel chromatography (0 to 100% EtOAc in heptane) to provide 108a as an off-white solid (0.15 g, 71% yield). MS (ESI, positive ion) m/z: 608 (M+1).

Preparation of N-((4aR,7aS)-7a-(2-fluoro-5-((Z)-2-fluoro-2-(5-methoxypyrazin-2-yl)vinyl)phenyl)-6-(5-fluoropyrimidin-2-yl)-4,4a,5,6,7,7a-hexahydropyrrolo[3,4-d][1,3]thiazin-2-yl)benzamide (108b)

A mixture of N-((4aR,7aS)-7a-(5-((Z)-2-(5-chloropyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-yl)benzamide (108a) (0.040 g, 0.064 mmol) and sodium methoxide solution (25 wt. % in methanol, 1.50 mL, 6.58 mmol) was heated to 70° C. for 2 hours. The mixture was diluted with water and extracted with EtOAc. The organic solution was dried over Na$_2$SO$_4$ and concentrated in vacuo to afford 108b which was use as crude (theoretical yield was 40 mg). MS (ESI, positive ion) m/z: 604 (M+1).

Preparation of (4aR,7aS)-7a-(2-fluoro-5-((Z)-2-fluoro-2-(5-methoxypyrazin-2-yl)vinyl)phenyl)-6-(5-fluoropyrimidin-2-yl)-4,4a,5,6,7,7a-hexahydropyrrolo[3,4-d][1,3]thiazin-2-amine (108)

A mixture of 108b (0.040 g, 0.066 mmol), O-methylhydroxylamine hydrochloride (0.138 g, 1.657 mmol), and pyridine (0.134 mL, 1.657 mmol) in ethanol (2 mL) was heated to 70° C. for 1 hour. The mixture was concentrated in vacuo; the residue was diluted with EtOAc and water. The organic solution was washed sequentially with sat'd aqueous NH$_4$Cl, 1.0 M aqueous NaOH, and brine, dried over Na$_2$SO$_4$, and concentrated in vacuo. The residue was purified by silica gel chromatography (0 to 100% EtOAc in DCM) to afford Example 108 as a white solid (12 mg, 36% yield over two steps). MS (ESI, positive ion) m/z: 500 (M+1). $^1$H NMR (400 MHz, CHLOROFORM-d) δ 8.35 (s, 1H), 8.22 (s, 2H), 8.20 (s, 1H), 7.67 (ddd, J=2.35, 4.70, 8.41 Hz, 1H), 7.59 (dd, J=2.15, 8.02 Hz, 1H), 7.08 (dd, J=8.61, 12.13 Hz, 1H), 6.71-6.88 (m, 1H), 4.37 (d, J=11.35 Hz, 1H), 4.01 (s, 3H), 3.88 (dd, J=2.54, 11.15 Hz, 1H), 3.81 (d, J=8.22 Hz, 2H), 3.26 (tt, J=4.28, 8.34 Hz, 1H), 3.03-3.12 (m, 1H), 2.92-3.00 (m, 1H). NH$_2$ was not clear. $^{19}$F NMR (376 MHz, CHLOROFORM-d) δ -111.29 (s, 1F), -125.19 (s, 1F), -158.09 (s, 1F).

Example 109: (4aR,7aS)-7a-(2-fluoro-5-((Z)-2-fluoro-2-(5-(prop-2-yn-1-yloxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine

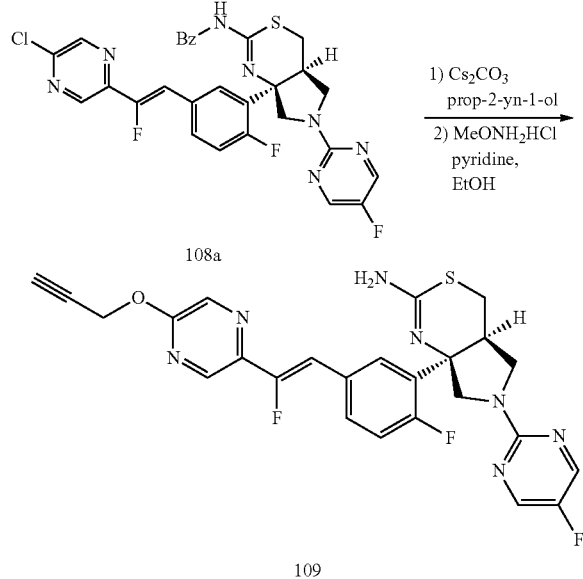

108a

109

This compound (22 mg, 56% overall yield) as a white solid was prepared in a manner similar to that described for Example 108, here starting from 108a (0.046 g, 0.077 mmol) and prop-2-yn-1-ol (Sigma-Aldrich) (0.045 mL, 0.768 mmol). MS (ESI, positive ion) m/z: 524 (M+1). $^1$H NMR (400 MHz, CHLOROFORM-d) δ 8.38 (s, 1H), 8.15-8.30 (m, 3H), 7.62-7.72 (m, 1H), 7.58 (dd, J=1.96, 8.02 Hz, 1H), 7.08 (dd, J=8.61, 12.13 Hz, 1H), 6.75-6.91 (m, 1H), 5.04 (d, J=2.35 Hz, 2H), 4.37 (d, J=11.15 Hz, 1H), 3.86 (dd, J=2.45, 11.05 Hz, 1H), 3.81 (d, J=8.22 Hz, 2H), 3.24 (tt, J=4.35, 8.26 Hz, 1H), 3.03-3.11 (m, 1H), 2.89-3.01 (m, 1H), 2.53 (t, J=2.35 Hz, 1H). NH$_2$ was not clear. $^{19}$F NMR (376 MHz, CHLOROFORM-d) δ −111.02 (d, J=1.73 Hz, 1F), −125.44 (d, J=1.73 Hz, 1F), −158.16 (s, 1F).

Example 110: (4aR,7aS)-7a-(2-fluoro-5-((Z)-2-fluoro-2-(54(3-methyl-1,2,4-oxadiazol-5-yl)methoxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine

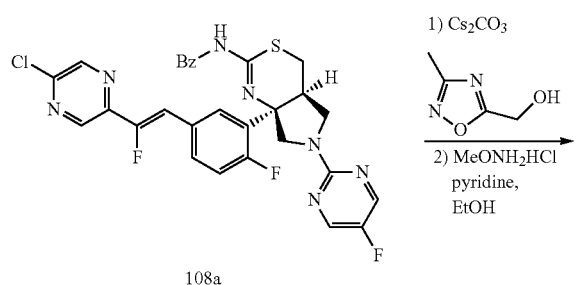

108a

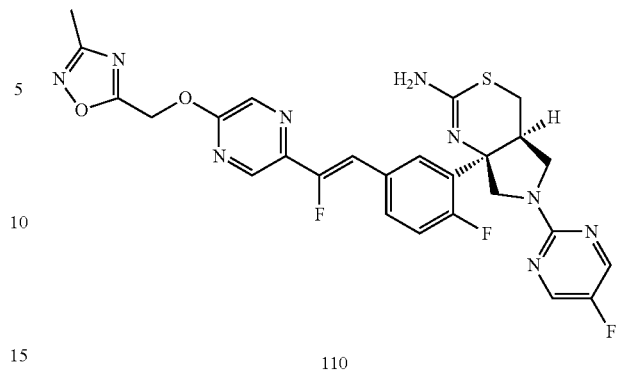

110

This compound (33 mg, 50% yield) was prepared in a fashion similar to that described for Example 109, here starting from 108a (70 mg, 0.115 mmol) and (3-methyl-1,2,4-oxadiazol-5-yl)methanol (Enamine LLC., Monmouth Jct., N.J., USA) (66 mg, 0.576 mmol). MS (ESI, positive ion) m/z: 582 (M+1). $^1$H NMR (400 MHz, CHLOROFORM-d) δ 8.34 (d, J=18.19 Hz, 2H), 8.22 (s, 2H), 7.62-7.68 (m, 1H), 7.60 (dd, J=1.96, 8.02 Hz, 1H), 7.08 (dd, J=8.51, 12.03 Hz, 1H), 6.76-6.92 (m, 1H), 5.63 (s, 2H), 4.36 (d, J=11.15 Hz, 1H), 3.87 (dd, J=2.45, 11.05 Hz, 1H), 3.81 (d, J=8.41 Hz, 2H), 3.24 (tt, J=4.25, 8.36 Hz, 1H), 2.90-3.12 (m, 2H), 2.43 (s, 3H). NH$_2$ was not clear. $^{19}$F NMR (376 MHz, CHLOROFORM-d) δ −110.83 (d, J=1.73 Hz, 1F), −125.59 (s, 1F), −158.15 (s, 1F).

Example 111: 5-((Z)-2-(3-((4aR,7aS)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)pyrazine-2-carbonitrile

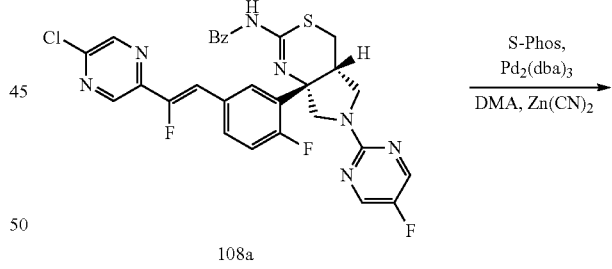

108a

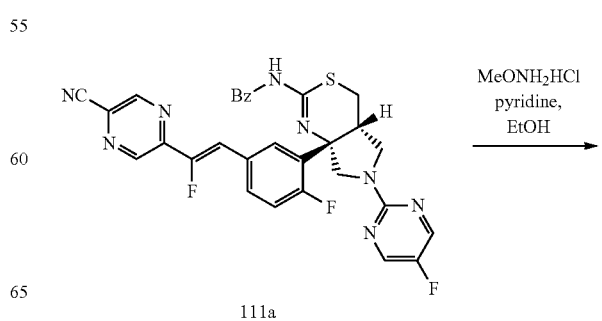

111a

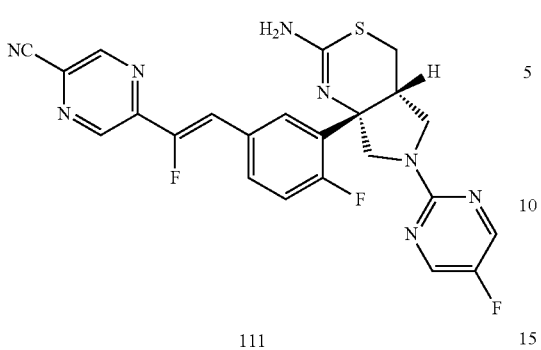

111

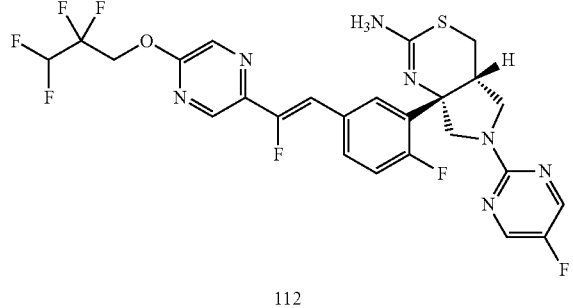

112

N-((4aR,7aS)-7a-(5-((Z)-2-(5-Cyanopyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-yl)benzamide (111a) (35 mg, 36% yield) as a yellow solid was prepared in a fashion similar to that described for Example 102, here starting from N-((4aR,7aS)-7a-(5-((Z)-2-(5-chloropyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-yl)benzamide (108a) (100 mg, 0.164 mmol). MS (ESI, positive ion) m/z: 599 (M+1).

5-((Z)-2-(3-((4aR,7aS)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)pyrazine-2-carbonitrile (Example 111) (16 mg, 55% yield) as a yellow solid was prepared in a fashion similar to that described for Example 109, here starting from 111a (35 mg, 0.058 mmol). MS (ESI, positive ion) m/z: 495 (M+1). $^1$H NMR (400 MHz, CHLOROFORM-d) δ 8.94 (s, 1H), 8.83 (s, 1H), 8.23 (s, 2H), 7.63-7.80 (m, 2H), 7.24 (d, J=37.17 Hz, 1H), 7.14 (dd, J=8.61, 11.93 Hz, 1H), 4.36 (d, J=11.15 Hz, 1H), 3.77-3.93 (m, 3H), 3.27 (br. s., 1H), 2.92-3.12 (m, 2H). NH$_2$ was not clear.

Example 112: (4aR,7aS)-7a-(2-fluoro-5-((Z)-2-fluoro-2-(5-(2,2,3,3-tetrafluoropropoxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine This compound (31 mg, 62% overall yield) was prepared in a fashion similar to that described for Example 109, here starting from 108a (50 mg, 0.082 mmol) and 2,2,3,3-tetrafluoropropan-1-ol (Sigma-Aldrich) (54 mg, 0.411 mmol). MS (ESI, positive ion) m/z: 600 (M+1). $^1$H NMR (400 MHz, CHLOROFORM-d) δ 8.36 (s, 1H), 8.31 (s, 1H), 8.23 (s, 2H), 7.64-7.72 (m, 1H), 7.60 (dd, J=1.96, 8.02 Hz, 1H), 7.09 (dd, J=8.51, 12.03 Hz, 1H), 6.78-6.95 (m, 1H), 5.85-6.19 (m, 1H), 4.81 (t, J=12.62 Hz, 2H), 4.37 (d, J=11.15 Hz, 1H), 3.73-3.94 (m, 3H), 3.25 (tt, J=4.28, 8.34 Hz, 1H), 2.86-3.13 (m, 2H). NH$_2$ was not clear. $^{19}$F NMR (376 MHz, CHLOROFORM-d) δ −110.75 (s, 1F), −123.88 (t, J=3.04 Hz, 2F), −125.61 (s, 1F), −137.85 (t, J=3.47 Hz, 2F), −158.14 (s, 1F).

Example 113: (4aR,7aS)-7a-(5-((Z)-2-(5-(2,2-difluoroethoxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine

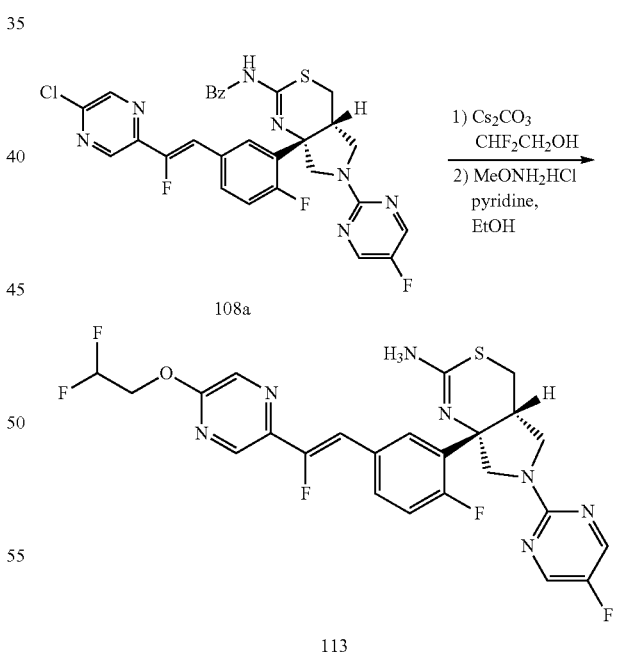

108a

113

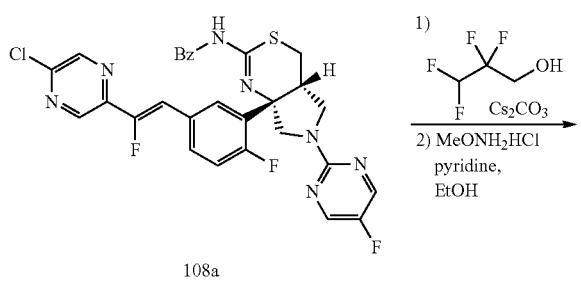

108a

This compound (12 mg, 46% overall yield) as a white solid was prepared in a fashion similar to that described for Example 109, here starting from 2,2-difluoroethanol (Accela Chembio Inc., San Diego, Calif., USA) (22 mg, 0.271 mmol) and 108a (27 mg, 0.045 mmol). MS (ESI, positive ion) m/z: 550 (M+1). $^1$H NMR (400 MHz, CHLOROFORM-d) δ 8.33 (s, 1H), 8.28 (s, 1H), 8.23 (s, 2H), 7.63-7.69 (m, 1H), 7.60 (d, J 7.82 Hz, 1H), 7.08 (dd, J=8.51, 12.03 Hz, 1H), 6.75-6.93 (m, 1H), 5.96-6.35 (m, 1H), 4.60 (dt, J=4.11, 13.40 Hz, 2H), 4.36 (d, J=11.15 Hz, 1H), 3.88 (d, J=11.15 Hz, 1H), 3.81 (d, J=8.41 Hz, 2H), 3.26 (tt, J=4.13, 8.19 Hz, 1H), 2.90-3.14 (m, 2H). NH₂ was not clear. ¹⁹F NMR (376 MHz, CHLOROFORM-d) δ −110.89 (s, 1F), −125.52 (br. s., 1F), −125.66 (s, 2F), −158.09 (br. s., 1F).

Example 114: (4aR,7aS)-7a-(2-fluoro-5-((Z)-2-fluoro-2-(5-(((S)-1-methoxypropan-2-yl)oxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine

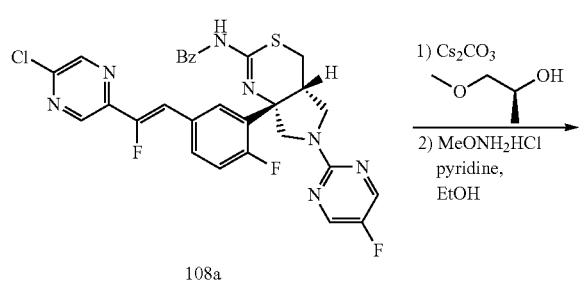

108a

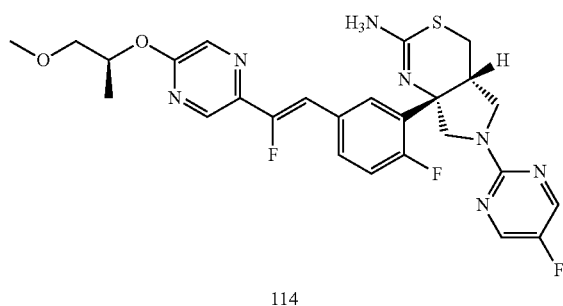

114

This compound (10 mg, 39% overall yield) as a white solid was prepared in a fashion similar to that described for Example 109, here starting from (S)-1-methoxy-2-propanol (Sigma-Aldrich) (24 mg, 0.271 mmol) and 108a (27 mg, 0.045 mmol). MS (ESI, positive ion) m/z: 558 (M+1). ¹H NMR (400 MHz, CHLOROFORM-d) δ 8.32 (s, 1H), 8.22 (s, 2H), 8.19 (s, 1H), 7.66 (dd, J=3.03, 5.58 Hz, 1H), 7.58 (d, J=7.82 Hz, 1H), 7.07 (dd, J=8.51, 12.03 Hz, 1H), 6.69-6.88 (m, 1H), 5.37-5.51 (m, 1H), 4.49 (br. s., 2H), 4.36 (d, J=11.15 Hz, 1H), 3.86 (dd, J=1.86, 11.25 Hz, 1H), 3.81 (d, J=8.41 Hz, 2H), 3.53-3.66 (m, 2H), 3.41 (s, 3H), 3.24 (tt, J=4.25, 8.26 Hz, 1H), 3.03-3.12 (m, 1H), 2.91-2.99 (m, 1H), 1.38 (d, J=6.26 Hz, 3H). ¹⁹F NMR (376 MHz, CHLOROFORM-d) δ −111.32 (s, 1F), −125.21 (s, 1F), −158.20 (s, 1F).

Example 115: (4aR,7aS)-7a-(5-((Z)-2-(5-((S)-but-3-yn-2-yloxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine

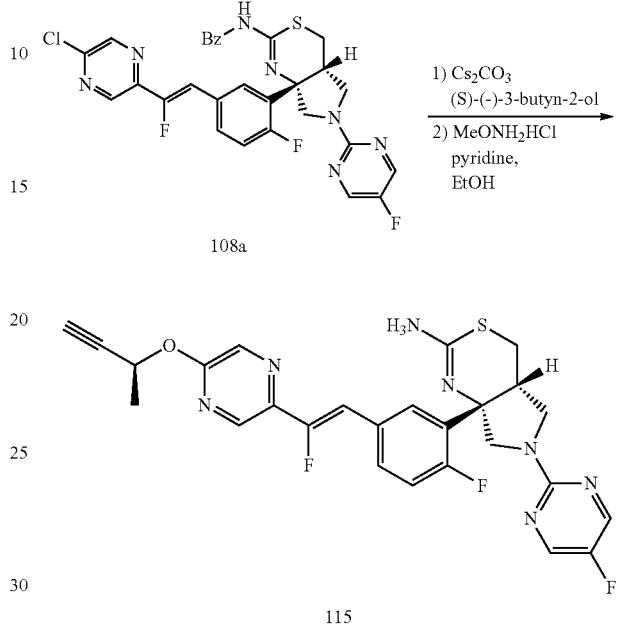

108a

115

This compound (4.3 mg, 18% overall yield) as a white solid was prepared in a fashion similar to that described for Example 109, here starting from (S)-(−)-3-butyn-2-ol (Alfa Aesar) (18 mg, 0.257 mmol) and 108a (26 mg, 0.043 mmol). MS (ESI, positive ion) m/z: 538 (M+1). ¹H NMR (400 MHz, CHLOROFORM-d) δ 8.38 (s, 1H), 8.15-8.27 (m, 3H), 7.68 (dd, J=2.54, 6.06 Hz, 1H), 7.58 (d, J=7.43 Hz, 1H), 7.08 (dd, J=8.61, 12.13 Hz, 1H), 6.71-6.90 (m, 1H), 5.76 (q, J=6.52 Hz, 1H), 4.37 (d, J=11.15 Hz, 1H), 3.88 (d, J=11.15 Hz, 1H), 3.81 (d, J=8.41 Hz, 2H), 3.25 (td, J=3.89, 8.07 Hz, 1H), 3.03-3.13 (m, 1H), 2.90-3.01 (m, 1H), 2.48 (d, J=1.76 Hz, 1H), 1.69 (d, J=6.65 Hz, 3H). NH₂ was not clear. ¹⁹F NMR (376 MHz, CHLOROFORM-d) δ −111.13 (s, 1F), −125.31 (br. s., 1F), −158.10 (br. s., 1F).

Example 116: (4aR,7aS)-tert-butyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate

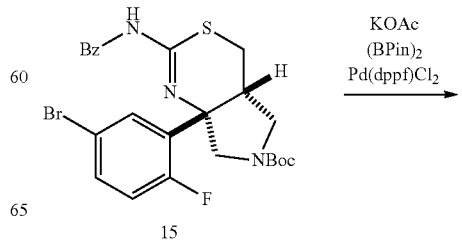

15

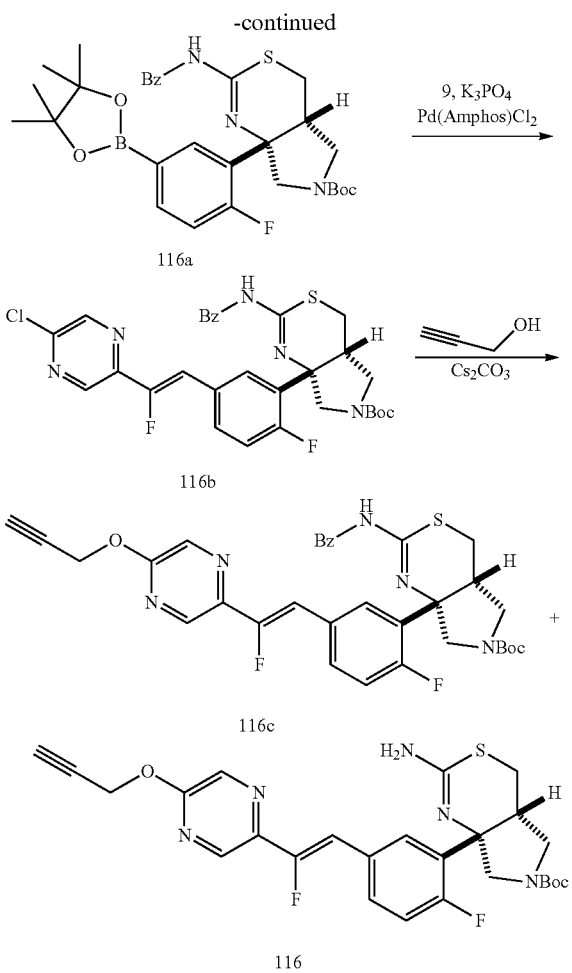

Preparation of (4aR,7aS)-tert-butyl 2-benzamido-7a-(2-fluoro-5-(4,4,5,5-tetramethyl-1,3,2-dioxaborolan-2-yl)phenyl)-4a,5,7,7a-tetrahydropyrrolo[3,4-d][1,3]thiazine-6(4H)-carboxylate (116a)

A mixture of (4aR,7aS)-tert-butyl 2-benzamido-7a-(5-bromo-2-fluorophenyl)-4a,5,7,7a-tetrahydropyrrolo[3,4-d][1,3]thiazine-6(4H)-carboxylate (15) (2.05 g, 3.84 mmol), bis(pinacolato)diboron (1.28 g, 5.06 mmol), potassium acetate (1.13 g, 11.51 mmol) in 1,4-dioxane (20.0 mL) was purged with argon, then [1,1'-bis(diphenylphosphino)ferrocene]-dichloropalladium(II) complex with DCM (0.19 g, 0.23 mmol) was added. The mixture was heated to 90° C. for 1 hour then cooled to room temperature and filtered through celite. The filter cake was washed with EtOAc. The filtrate was concentrated in vacuo to provide boronic ester 116a as a beige solid which was used without additional purification. MS (ESI, positive ion) m/z: 582 (M+1).

Preparation of (4aR,7aS)-tert-butyl 2-benzamido-7a-(5-((Z)-2-(5-chloropyrazin-2-yl)-2-fluorovinyl)-2-fluorophenyl)-4a,5,7,7a-tetrahydropyrrolo[3,4-d][1,3]thiazine-6(4H)-carboxylate (116b)

This compound (0.75 g, 46% yield) as a beige solid was prepared via a Suzuki coupling reaction similar to that described for compound 100d, here starting from boronic ester 116a (1.54 g, 2.65 mmol) and vinyl iodide 9 (0.78 g, 2.75 mmol). MS (ESI, positive ion) m/z: 612 (M+1).

Preparation of (4aR,7aS)-tert-butyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate (116)

A mixture of (4aR,7aS)-tert-butyl 2-benzamido-7a-(5-((Z)-2-(5-chloropyrazin-2-yl)-2-fluorovinyl)-2-fluorophenyl)-4a,5,7,7a-tetrahydropyrrolo[3,4-d][1,3]thiazine-6(4H)-carboxylate (116b, 0.74 g, 1.22 mmol), propargyl alcohol (0.36 mL, 6.11 mmol), and cesium carbonate (1.194 g, 3.66 mmol) in THF (10 mL) was heated to 55° C. for 8 hours then cooled to room temperature. LCMS showed the presence of two products (116c and 116). The mixture was diluted with water and extracted with EtOAc. The organic layer was dried over $Na_2SO_4$ and concentrated in vacuo. The residue was purified by silica gel chromatography (0 to 100% EtOAc in heptane) to give 2 compounds. The $1S^t$ eluent was (4aR,7aS)-tert-butyl 2-benzamido-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate (116c, 0.23 g, 30% yield) as a yellow solid. MS (ESI, positive ion) m/z: 612 (M+1). The $2^{nd}$ eluent was (4aR,7aS)-tert-butyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate (Example 116, 0.308 g, 48% yield) as a yellow solid. MS (ESI, positive ion) m/z: 528 (M+1). $^1$H NMR (400 MHz, CHLOROFORM-d) δ 8.39 (s, 1H), 8.26 (s, 1H), 7.62-7.69 (m, 1H), 7.54-7.61 (m, 1H), 7.07 (dd, J=8.51, 12.03 Hz, 1H), 6.75-6.92 (m, 1H), 5.04 (d, J=2.35 Hz, 2H), 4.44 (br. s., 2H), 4.09-4.21 (m, 1H), 3.51-3.65 (m, 3H), 2.81-3.16 (m, 3H), 2.53 (t, J=2.35 Hz, 1H), 1.44-1.50 (m, 9H). $^{19}$F NMR (376 MHz, CHLOROFORM-d) δ −111.64-110.37 (m, 1F), −125.85-124.75 (m, 1F).

Example 117: (4aR,7aS)-7a-(5-((Z)-2-(5-(but-2-yn-1-yloxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine

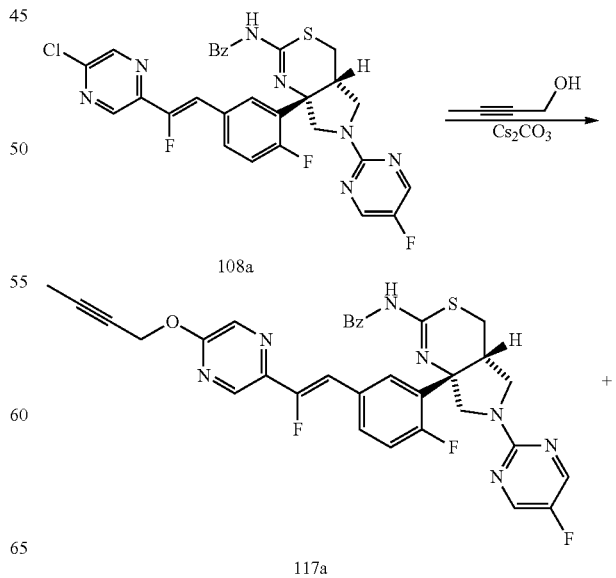

-continued

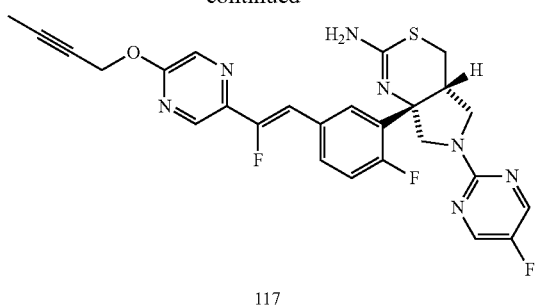

117

A mixture of N-((4aR,7aS)-7a-(5-((Z)-2-(5-chloropyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-yl)benzamide (108a, 28 mg, 0.047 mmol), but-2-yn-1-ol (130 mg, 1.862 mmol), and cesium carbonate (45 mg, 0.140 mmol) in THF (0.2 mL) was heated to 60° C. for 3.5 hours. LCMS indicated the formation of 2 products, with MS (ESI, positive ion) m/z: 642.2 (M+1) and 538.2 (M+1) for 117a and 117, respectively. Heating was continued until the conversion to product 117 was complete. The mixture was diluted with water and extracted with EtOAc. The organic layer was dried over $Na_2SO_4$ and concentrated in vacuo. The residue was purified by silica gel chromatography (0 to 100% EtOAc in DCM) to afford Example 117 (18 mg, 73% yield) as an off-white solid. MS (ESI, positive ion) m/z: 538.2 (M+1). $^1$H NMR (400 MHz, CHLOROFORM-d) δ 8.37 (s, 1H), 8.19-8.28 (m, 3H), 7.67 (br. s., 1H), 7.58 (d, J=8.22 Hz, 1H), 7.08 (dd, J=8.61, 11.93 Hz, 1H), 6.72-6.92 (m, 1H), 4.99 (br. s., 2H), 4.37 (d, J=11.15 Hz, 1H), 3.76-3.92 (m, 3H), 3.19-3.31 (m, 1H), 3.03-3.12 (m, 1H), 2.89-3.01 (m, 1H), 1.89 (s, 3H). $NH_2$ was not clear. $^{19}$F NMR (376 MHz, CHLOROFORM-d) δ -111.12 (s, 1F), -125.35 (s, 1F), -158.17 (s, 1F).

Example 118: 1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)ethanone

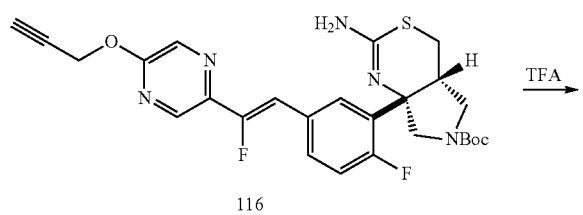

116

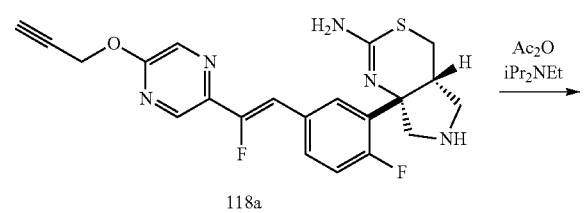

118a

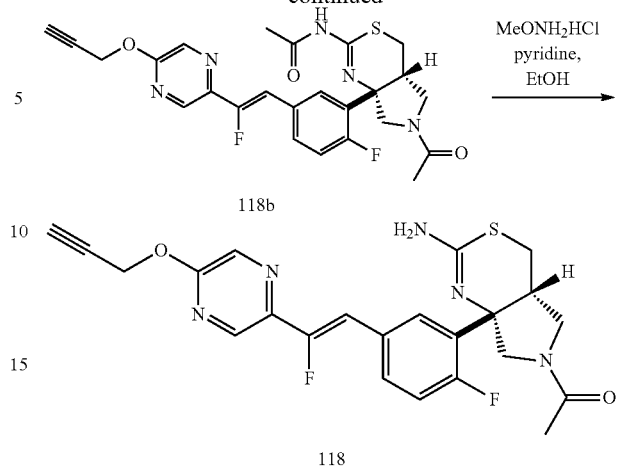

118b

118

Preparation of (4aR,7aS)-7a-(2-fluoro-5-((Z)-2-fluoro-2-(5-(prop-2-yn-1-yloxy)pyrazin-2-yl)vinyl)phenyl)-4,4a,5,6,7,7a-hexahydropyrrolo[3,4-d][1,3]thiazin-2-amine (118a)

A mixture of Example 116 (0.161 g, 0.306 mmol) in TFA (0.341 mL, 4.43 mmol) and DCM (1 mL) was stirred at room temperature for 30 minutes, then cooled to 0° C. and basified by the dropwise addition of 1 M aqueous NaOH. The mixture was extracted with DCM followed by EtOAc. The combined organic solution was dried over $Na_2SO_4$ and concentrated in vacuo to provide 118a (0.131 g, 100% yield) as a yellow solid which was used without additional purification. MS (ESI, positive ion) m/z: 428 (M+1).

Preparation of N-((4aR,7aS)-6-acetyl-7a-(2-fluoro-5-((Z)-2-fluoro-2-(5-(prop-2-yn-1-yloxy)pyrazin-2-yl)vinyl)phenyl)-4,4a,5,6,7,7a-hexahydropyrrolo[3,4-d][1,3]thiazin-2-yl)acetamide (118b)

To a mixture of (4aR,7aS)-7a-(2-fluoro-5-((Z)-2-fluoro-2-(5-(prop-2-yn-1-yloxy)pyrazin-2-yl)vinyl)phenyl)-4,4a,5,6,7,7a-hexahydropyrrolo[3,4-d][1,3]thiazin-2-amine (118a) (0.020 g, 0.047 mmol) and N,N-diisopropylethylamine (0.024 mL, 0.140 mmol) in DCM (1 mL) was added acetic anhydride (4.86 μL, 0.051 mmol). The mixture was stirred at room temperature for 5 hours, then diluted with sat'd aqueous $Na_2CO_3$ and extracted with EtOAc. The organic layer was dried over $Na_2SO_4$ and concentrated in vacuo. The residue was purified by silica gel chromatography (0 to 100% EtOAc in DCM) to give 118b (13 mg, 54% yield) as an off-white solid. MS (ESI, positive ion) m/z: 512 (M+1).

Preparation of 1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)ethanone (118)

A mixture of N-((4aR,7aS)-6-acetyl-7a-(2-fluoro-5-((Z)-2-fluoro-2-(5-(prop-2-yn-1-yloxy)pyrazin-2-yl)vinyl)phenyl)-4,4a,5,6,7,7a-hexahydropyrrolo[3,4-d][1,3]thiazin-2-yl)acetamide (118b, 13.0 mg, 0.025 mmol), methoxylamine hydrochloride (10.61 mg, 0.127 mmol), and pyridine (10.364, 0.127 mmol) in ethanol (1 mL) was stirred at 60° C. for 2 hours, then diluted with sat'd aqueous $Na_2CO_3$ and extracted with EtOAc. The organic layer was dried over Na$_2$SO$_4$ and concentrated in vacuo. The residue was purified by silica gel chromatography (0 to 100% EtOAc/EtOH (3/1) in heptane) to give Example 118 (11 mg, 92% yield) as an off-white solid. MS (ESI, positive ion) m/z: 470 (M+1). $^1$H NMR (400 MHz, CHLOROFORM-d) δ 8.35-8.46 (m, 1H), 8.27 (s, 1H), 7.69 (br. s., 1H), 7.51-7.61 (m, 1H), 7.03-7.14 (m, 1H), 6.77-6.92 (m, 1H), 5.04 (s, 2H), 4.17-4.30 (m, 1H), 3.62-3.88 (m, 3H), 3.13-3.32 (m, 1H), 3.04 (d, J=13.30 Hz, 1H), 2.82-2.94 (m, 1H), 2.53 (br. s., 1H), 1.99-2.12 (m, 3H). NH$_2$ was not clear. $^{19}$F NMR (376 MHz, CHLOROFORM-d) δ −111.33 (m, 1F), −125.21 (m, 1F).

Example 119: 1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)-3,3,3-trifluoropropan-1-one

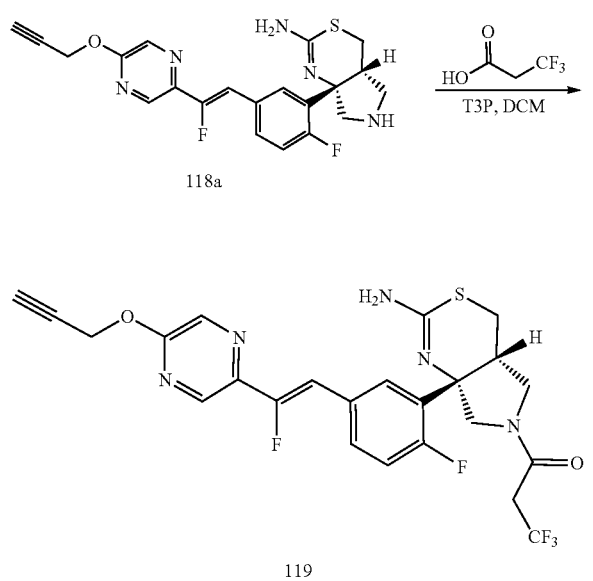

A mixture of (4aR,7aS)-7a-(2-fluoro-5-((Z)-2-fluoro-2-(5-(prop-2-yn-1-yloxy)pyrazin-2-yl)vinyl)phenyl)-4,4a,5,6,7,7a-hexahydropyrrolo[3,4-d][1,3]thiazin-2-amine (118a) (19.5 mg, 0.046 mmol), 3,3,3-trifluoropropanoic acid (Sigma-Aldrich) (23 mg, 0.182 mmol) in DCM (0.5 mL) at room temperature was treated with propylphosphonic anhydride solution (Sigma-Aldrich) (50 wt. % in EtOAc, 0.109 mL, 0.182 mmol) and stirred for 18 hours. The mixture was diluted with sat'd aqueous Na$_2$CO$_3$ and extracted with EtOAc. The organic layer was dried over Na$_2$SO$_4$ and concentrated in vacuo. The residue was purified by silica gel chromatography (0 to 100% EtOAc/EtOH (3:1) in heptane) to afford the title compound (Example 119) (10 mg, 41% yield) as a yellow solid. MS (ESI, positive ion) m/z: 538 (M+1). $^1$H NMR (400 MHz, CHLOROFORM-d) δ ppm 8.36-8.43 (m, 1H), 8.22-8.29 (m, 1H), 7.63-7.74 (m, 1H), 7.52-7.61 (m, 1H), 7.03-7.15 (m, 1H), 6.76-6.93 (m, 1H), 5.04 (d, J=2.35 Hz, 2H), 4.18-4.35 (m, 1H), 3.62-3.94 (m, 3H), 3.10-3.33 (m, 3H), 2.98-3.10 (m, 1H), 2.81-2.93 (m, 1H), 2.53 (t, J=2.35 Hz, 1H). NH$_2$ was not clear. $^{19}$F NMR (376 MHz, CHLOROFORM-d) δ −62.34 (m, 3F), −111.59 (m, 1F), −125.45 (m, 1F).

Example 120: (4aR,7aS)-7a-(2-fluoro-5-((Z)-2-fluoro-2-(5-(prop-2-yn-1-yloxy)pyrazin-2-yl)vinyl)phenyl)-6-(pyrimidin-2-yl)-4,4a,5,6,7,7a-hexahydropyrrolo[3,4-d][1,3]thiazin-2-amine

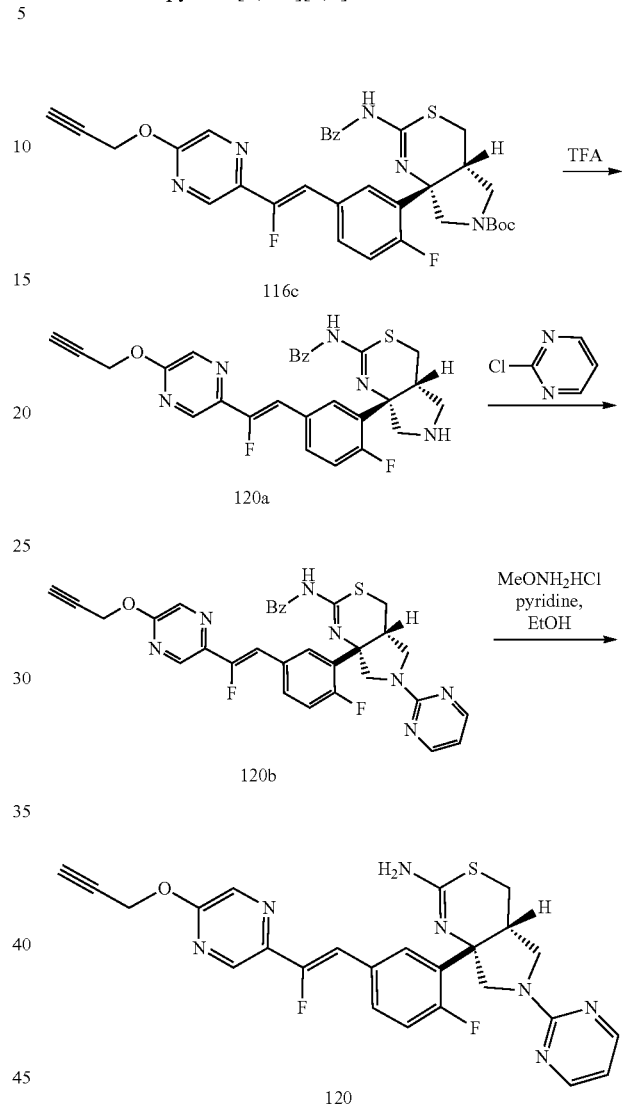

Preparation of N-((4aR,7aS)-7a-(2-fluoro-5-((Z)-2-fluoro-2-(5-(prop-2-yn-1-yloxy)pyrazin-2-yl)vinyl)phenyl)-4,4a,5,6,7,7a-hexahydropyrrolo[3,4-d][1,3]thiazin-2-yl)benzamide (120a)

A mixture of (4aR,7aS)-tert-butyl 2-benzamido-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate (116c) (0.205 g, 0.325 mmol) in TFA (0.36 mL, 4.71 mmol) and DCM (1 mL) was stirred at room temperature for 30 minutes then concentrated in vacuo. The residue was diluted with DCM, neutralized with 1 M aqueous NaOH, and extracted with DCM. The organic layer was dried over Na$_2$SO$_4$ and concentrated in vacuo to afford 120a (0.160 g, 93% yield) as a yellow solid which was used without additional purification. MS (ESI, positive ion) m/z: 532 (M+1).

Preparation of N-((4aR,7aS)-7a-(2-fluoro-5-((Z)-2-fluoro-2-(5-(prop-2-yn-1-yloxy)pyrazin-2-yl)vinyl)phenyl)-6-(pyrimidin-2-yl)-4,4a,5,6,7,7a-hexahydropyrrolo[3,4-d][1,3]thiazin-2-yl)benzamide (120b)

A mixture of N-((4aR,7aS)-7a-(2-fluoro-5-((Z)-2-fluoro-2-(5-(prop-2-yn-1-yloxy)pyrazin-2-yl)vinyl)phenyl)-4,4a,5,6,7,7a-hexahydropyrrolo[3,4-d][1,3]thiazin-2-yl)benzamide (120a) (0.040 g, 0.075 mmol), 2-chloropyrimidine (Acros Organics) (0.043 g, 0.376 mmol) and N,N-diisopropylethylamine (0.105 mL, 0.602 mmol) in dimethyl sulfoxide (1 mL) was heated in a sealed vial at 110° C. for 2 hours. After cooling to room temperature, the mixture was diluted with sat'd aqueous Na₂CO₃ and extracted with EtOAc. The organic layer was dried over Na₂SO₄ and concentrated in vacuo. The residue was purified by silica gel chromatography (0 to 100% EtOAc in heptane) to give 120b (36.8 mg, 80% yield) as an off-white solid. MS (ESI, positive ion) m/z: 610 (M+1).

Preparation of (4aR,7aS)-7a-(2-fluoro-5-((Z)-2-fluoro-2-(5-(prop-2-yn-1-yloxy)pyrazin-2-yl)vinyl)phenyl)-6-(pyrimidin-2-yl)-4,4a,5,6,7,7a-hexahydropyrrolo[3,4-d][1,3]thiazin-2-amine (120)

A mixture of N-((4aR,7aS)-7a-(2-fluoro-5-((Z)-2-fluoro-2-(5-(prop-2-yn-1-yloxy)pyrazin-2-yl)vinyl)phenyl)-6-(pyrimidin-2-yl)-4,4a,5,6,7,7a-hexahydropyrrolo[3,4-d][1,3]thiazin-2-yl)benzamide (120b) (36.8 mg, 0.060 mmol), methoxylamine hydrochloride (55 mg, 0.664 mmol) and pyridine (0.054 mL, 0.664 mmol) in ethanol (2 mL) was stirred at 70° C. for 2 hours. The mixture was concentrated in vacuo. The residue was diluted with EtOAc then sequentially washed with NH₄Cl, 1.0 M aqueous NaOH, and brine, dried over Na₂SO₄, and concentrated in vacuo. The residue was purified by silica gel chromatography (0 to 100% EtOAc in DCM) to give Example 120 (22.2 mg, 73% yield) as a white solid. MS (ESI, positive ion) m/z: 506 (M+1). ¹H NMR (400 MHz, CHLOROFORM-d) δ 8.36 (s, 1H), 8.33 (d, J=4.69 Hz, 2H), 8.25 (s, 1H), 7.65 (ddd, J=2.25, 4.60, 8.41 Hz, 1H), 7.60 (dd, J=2.05, 7.92 Hz, 1H), 7.07 (dd, J=8.61, 12.13 Hz, 1H), 6.73-6.90 (m, 1H), 6.50 (t, J=4.79 Hz, 1H), 5.03 (d, J=2.35 Hz, 2H), 4.40 (d, J=11.15 Hz, 1H), 3.74-3.98 (m, 3H), 3.24 (tt, J=4.35, 8.26 Hz, 1H), 2.89-3.12 (m, 2H), 2.53 (t, J=2.45 Hz, 1H). NH₂ was not clear. ¹⁹F NMR (376 MHz, CHLOROFORM-d) δ −110.99 (d, J=1.73 Hz, 1F), −125.44 (d, J=1.73 Hz, 1F).

Example 121: (4aR,7aS)-methyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate

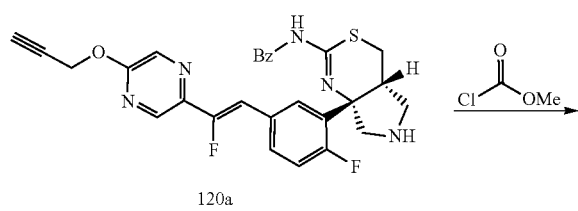

120a

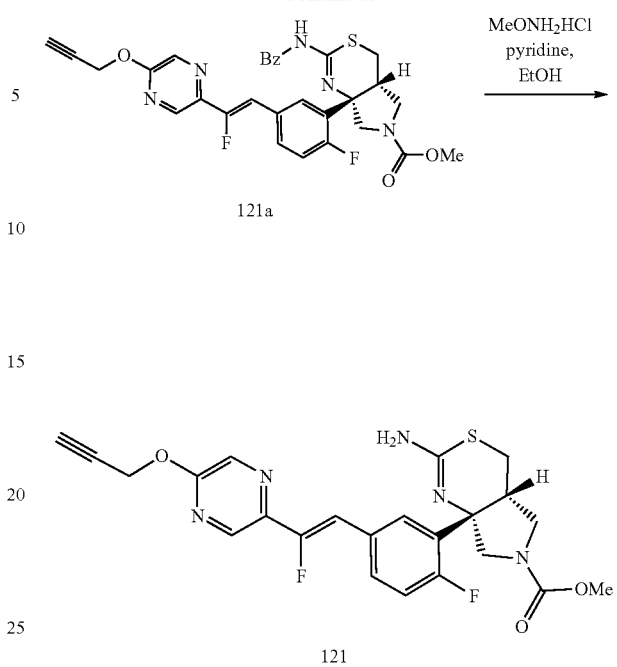

121a

121

Preparation of (4aR,7aS)-methyl 2-benzamido-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate (121a)

A mixture of N-((4aR,7aS)-7a-(2-fluoro-5-((Z)-2-fluoro-2-(5-(prop-2-yn-1-yloxy)pyrazin-2-yl)vinyl)phenyl)-4,4a,5,6,7,7a-hexahydropyrrolo[3,4-d][1,3]thiazin-2-yl)benzamide (120a) (33.5 mg, 0.063 mmol) and methyl chloroformate (0.024 mL, 0.315 mmol, Aldrich) in DCM (1 mL) at room temperature was treated with N,N-diisopropylethylamine (0.077 mL, 0.441 mmol) and stirred for 2.5 hours. The mixture was concentrated in vacuo and the residue was purified by silica gel chromatography (0 to 100% EtOAc in heptane) to give 121a (34.8 mg, 94% yield) as an off-white solid. MS (ESI, positive ion) m/z: 590 (M+1).

Preparation of (4aR,7aS)-methyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate (121)

This compound (22.3 mg, 78%) as a white solid was prepared in a fashion similar to that described for Example 120, here starting from 121a (34.8 mg, 0.059 mmol) and methoxylamine hydrochloride (0.054 g, 0.649 mmol). MS (ESI, positive ion) m/z: 486 (M+1). ¹H NMR (400 MHz, CHLOROFORM-d) δ 8.39 (s, 1H), 8.27 (s, 1H), 7.62-7.72 (m, 1H), 7.56 (dd, J=2.05, 7.92 Hz, 1H), 7.07 (dd, J=8.51, 12.03 Hz, 1H), 6.74-6.91 (m, 1H), 5.04 (d, J=2.54 Hz, 2H), 4.44 (d, J=7.63 Hz, 2H), 4.13-4.23 (m, 1H), 3.58-3.75 (m, 6H), 3.11 (td, J=4.25, 8.31 Hz, 1H), 2.97-3.04 (m, 1H), 2.80-2.92 (m, 1H), 2.53 (t, J=2.45 Hz, 1H). ¹⁹F NMR (376 MHz, CHLOROFORM-d) δ −111.23 (d, J=18.21 Hz, 1F), −125.32 (d, J=13.01 Hz, 1F).

Example 122: 1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)propan-1-one

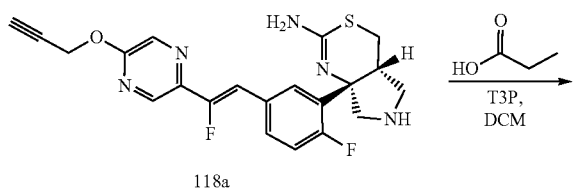

118a

This compound (7 mg, 27% yield) as an off-white solid was prepared in a fashion similar to that described for Example 119, here starting from 118a (22 mg, 0.05 mmol) and propionic acid (19 mg, 0.25 mmol). MS (ESI, positive ion) m/z: 484 (M+1). $^1$H NMR (400 MHz, CHLOROFORM-d) δ 8.36-8.46 (m, 1H), 8.27 (br. s., 1H), 7.67 (br. s., 1H), 7.58 (d, J=7.63 Hz, 1H), 7.02-7.15 (m, 1H), 6.74-6.94 (m, 1H), 4.99-5.08 (m, 2H), 5.04 (s, 2H), 4.17-4.29 (m, 1H), 3.59-3.89 (m, 3H), 3.08-3.28 (m, 1H), 3.03 (d, J=13.30 Hz, 1H), 2.80-2.94 (m, 1H), 2.53 (s, 1H), 2.21-2.38 (m, 2H), 1.18 (q, J=6.98 Hz, 3H). $^{19}$F NMR (376 MHz, CHLOROFORM-d) δ −111.27 (d, J=34.68 Hz, 1F), −125.22 (d, J=76.29 Hz, 1F).

Example 123: (4aR,7aS)-ethyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate

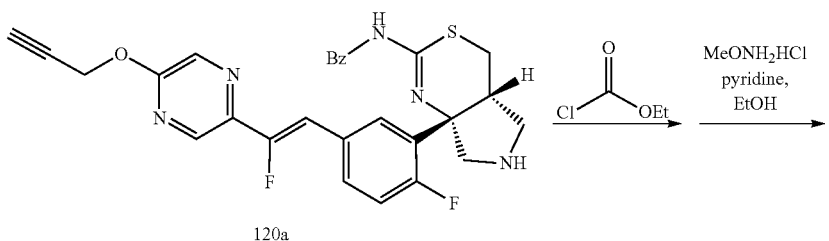

120a

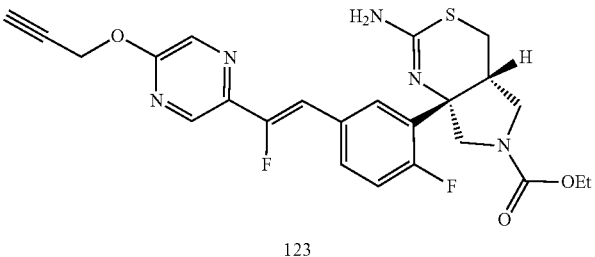

123

-continued

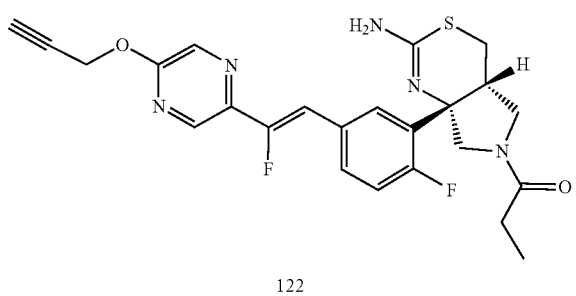

122

This compound (18 mg, 91% yield) as a white solid was prepared in a fashion similar to that described for Example 121, here starting from 120a (21 mg, 0.04 mmol) and ethyl chloroformate (21 mg, 0.20 mmol). MS (ESI, positive ion) m/z: 500 (M+1). $^1$H NMR (400 MHz, CHLOROFORM-d) δ 8.39 (s, 1H), 8.26 (s, 1H), 7.62-7.70 (m, 1H), 7.57 (d, J=7.82 Hz, 1H), 7.07 (dd, J=8.71, 12.03 Hz, 1H), 6.75-6.92 (m, 1H), 5.04 (d, J=2.35 Hz, 2H), 4.46 (br. s., 2H), 4.13-4.23 (m, 3H), 3.56-3.73 (m, 3H), 3.11 (tt, J=4.28, 8.44 Hz, 1H), 2.97-3.05 (m, 1H), 2.80-2.93 (m, 1H), 2.53 (t, J=2.45 Hz, 1H), 1.26-1.29 (m, 3H). $^{19}$F NMR (376 MHz, CHLOROFORM-d) δ −111.11 (m, 1F), −125.35 (m, 1F).

Example 124: (4aR,7aS)-isopropyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate

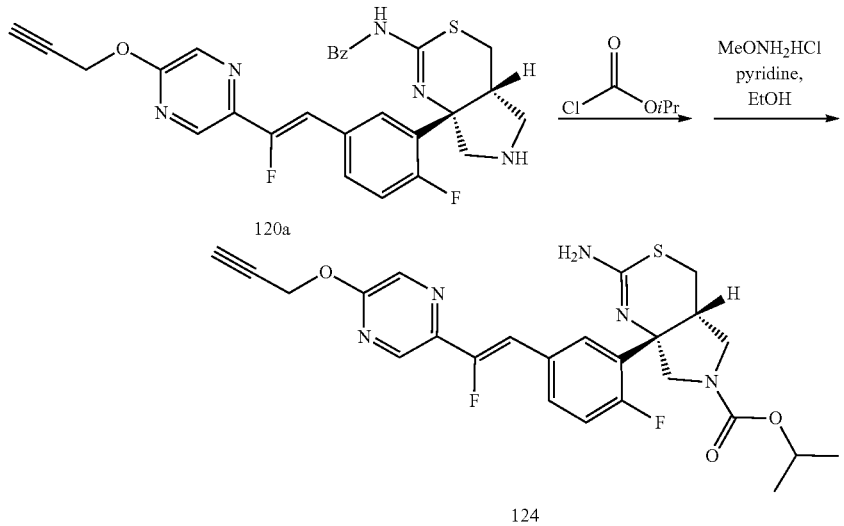

This compound (16 mg, 76% yield) as a white solid was prepared in a fashion similar to that described for Example 121, here starting from 120a (21 mg, 0.04 mmol) and isopropyl chloroformate (Sigma-Aldrich) (0.20 mL of 1.0 M solution in toluene, 0.20 mmol). MS (ESI, positive ion) m/z: 514 (M+1). $^1$H NMR (400 MHz, CHLOROFORM-d) δ 8.39 (s, 1H), 8.27 (s, 1H), 7.67 (br. s., 1H), 7.57 (d, J=7.82 Hz, 1H), 7.08 (dd, J=8.51, 12.03 Hz, 1H), 6.75-6.93 (m, 1H), 5.04 (d, J=2.35 Hz, 2H), 4.88-5.01 (m, 1H), 4.08-4.23 (m, 1H), 3.55-3.77 (m, 3H), 3.16 (dd, J=4.40, 8.12 Hz, 1H), 2.96-3.06 (m, 1H), 2.82-2.95 (m, 1H), 2.53 (t, J=2.35 Hz, 1H), 1.23-1.29 (m, 6H). NH$_2$ was not clear. $^{19}$F NMR (376 MHz, CHLOROFORM-d) δ −111.20 (m, 1F), −125.67 (m, 1F).

Example 125: 6-((Z)-2-(3-((4aR,5R,7aR)-2-amino-5-(trifluoromethyl)-4a,5,7,7a-tetrahydro-4H-furo[3,4-d][1,3]thiazin-7a-yl)-4-fluorophenyl)-1-fluorovinyl)nicotinonitrile

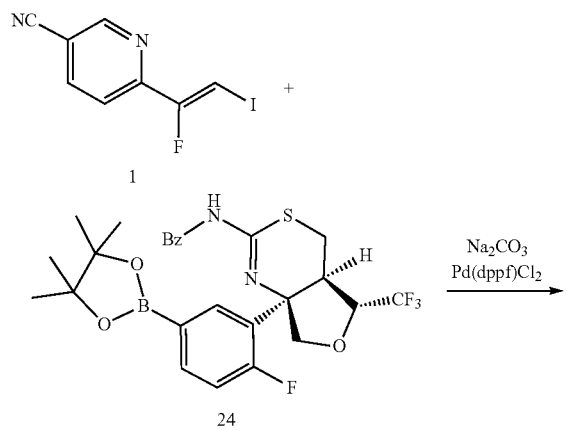

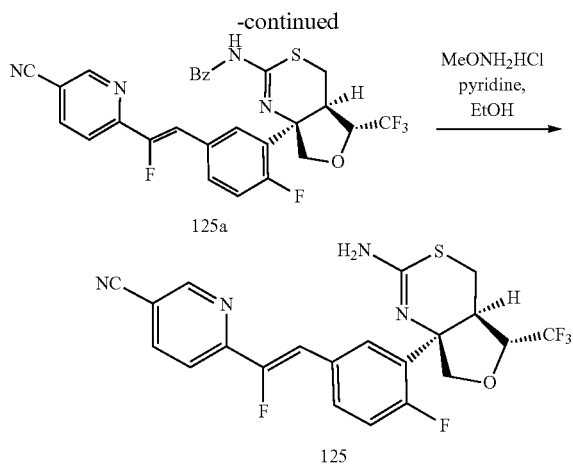

Preparation of N-((4aR,5R,7aR)-7a-(5-((Z)-2-(5-cyanopyridin-2-yl)-2-fluorovinyl)-2-fluorophenyl)-5-(trifluoromethyl)-4a,5,7,7a-tetrahydro-4H-furo[3,4-d][1,3]thiazin-2-yl)benzamide (125a)

A suspension of boronic ester 24 (1.30 g, 2.36 mmol), vinyl iodide 1 (0.97 g, 3.54 mmol), 1,1'-bis(diphenylphosphino)ferrocene palladium(II)dichloride dichloromethane adduct (Sigma-Aldrich Chemical Company, Inc., St. Louis, Mo., USA) (58 mg, 0.07 mmol), sodium carbonate (0.75 g, 7.09 mmol) in 1,4-dioxane (10 mL) and water (5 mL) was sparged with argon for 5 minutes. The suspension was heated to 70° C. with rapid stirring for 45 minutes. The reaction mixture was partitioned between EtOAc (60 mL) and 5% aqueous NaHCO$_3$ (30 mL). The organic solution was washed with brine (10 mL), dried over MgSO$_4$, then purified via silica gel chromatography (0 to 15% EtOAc/EtOH (3:1) in heptane) to afford N-((4aR,5R,7aR)-7a-(5-

((Z)-2-(5-cyanopyridin-2-yl)-2-fluorovinyl)-2-fluorophenyl)-5-(trifluoromethyl)-4a,5,7,7a-tetrahydro-4H-furo[3,4-d][1,3]thiazin-2-yl)benzamide (125a, 0.95 g, 70% yield) as a tan foam. MS (ESI+ve ion) m/z: [M+1]=571.1. $^1$H NMR (400 MHz, CHLOROFORM-d) δ ppm 8.83 (s, 1H), 7.98-8.10 (m, 3H), 7.77-7.86 (m, 1H), 7.65-7.73 (m, 2H), 7.55-7.63 (m, 1H), 7.46-7.54 (m, 2H), 7.16-7.33 (m, 3H), 4.77-4.89 (m, 1H), 4.66 (d, J=8.80 Hz, 1H), 4.04 (br d, J=8.02 Hz, 1H), 3.52-3.64 (m, 1H), 3.23 (br d, J=14.09 Hz, 1H), 2.87 (br dd, J=13.89, 3.52 Hz, 1H).

Preparation of Example 125

A suspension of N-((4aR,5R,7aR)-7a-(5-((Z)-2-(5-cyanopyridin-2-yl)-2-fluorovinyl)-2-fluorophenyl)-5-(trifluoromethyl)-4a,5,7,7a-tetrahydro-4H-furo[3,4-d][1,3]thiazin-2-yl)benzamide (125a) (900 mg, 1.57 mmol), methoxylamine hydrochloride (Sigma-Aldrich Chemical Company, Inc., St. Louis, Mo., USA, 659 mg, 7.89 mmol), and pyridine (643 μL, 7.89 mmol) in EtOH (6 mL) was heated to 50° C. for 4 hours. The reaction mixture was partitioned between EtOAc (60 mL) and sat'd aqueous NaHCO$_3$ (40 mL). The organic solution was washed with brine (5 mL), dried over MgSO$_4$, filtered, and then concentrated under reduced pressure to afford a white solid. The solid was then suspended in boiling EtOH (5 mL), and after cooling the liquid was discarded. The resulting white solid was dried overnight at 50° C. with a gentle stream of argon to afford 6-((Z)-2-(3-((4aR,5R,7aR)-2-amino-5-(trifluoromethyl)-4a,5,7,7a-tetrahydro-4H-furo[3,4-d][1,3]thiazin-7a-yl)-4-fluorophenyl)-1-fluorovinyl)nicotinonitrile (Example 125) (375 mg, 51% yield) as a white solid. MS (ESI+ve ion) m/z: [M+1]=467.0. $^1$H NMR (400 MHz, DMSO-d$_6$) δ ppm 9.08 (s, 1H), 8.44 (dd, J=8.41, 1.96 Hz, 1H), 7.87 (br d, J=8.02 Hz, 2H), 7.74-7.80 (m, 1H), 7.24-7.40 (m, 2H), 6.33 (s, 2H), 4.68 (quin, J=7.38 Hz, 1H), 4.40 (d, J=8.02 Hz, 1H), 3.84 (br d, J=6.26 Hz, 1H), 3.21-3.28 (m, 1H), 3.08 (dd, J=13.99, 2.84 Hz, 1H), 2.88 (dd, J=13.99, 3.81 Hz, 1H).

Example 126: 6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)nicotinonitrile

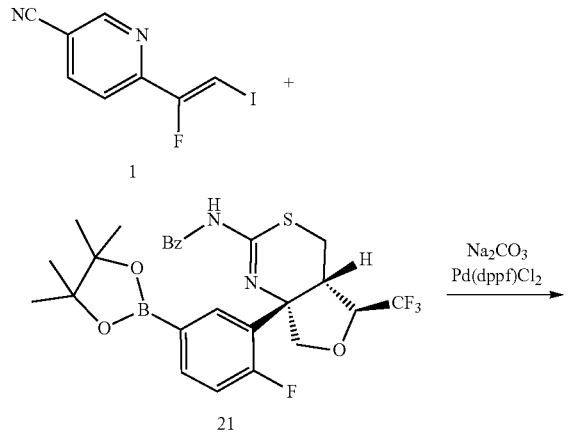

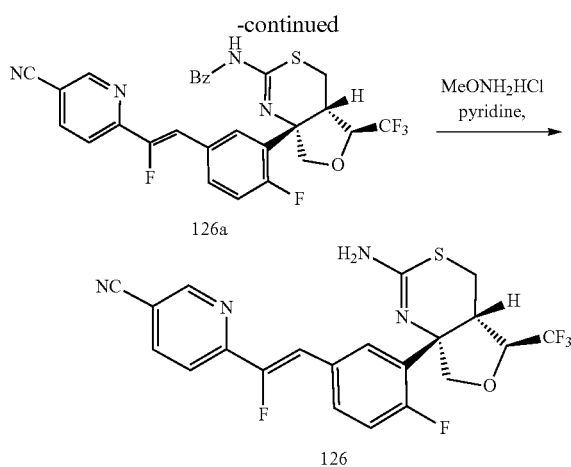

Preparation of N-((4aS,5S,7aS)-7a-(5-((Z)-2-(5-cyanopyridin-2-yl)-2-fluorovinyl)-2-fluorophenyl)-5-(trifluoromethyl)-4a,5,7,7a-tetrahydro-4H-furo[3,4-d][1,3]thiazin-2-yl)benzamide (126a)

This compound (2.0 g, 69% yield) as a tan foam was prepared in a fashion similar to that described for compound 125a, here using boronic ester 21 (2.80 g, 5.09 mmol) and (Z)-6-(1-fluoro-2-iodovinyl)nicotinonitrile (1) (1.81 g, 6.61 mmol) as starting materials. MS (ESI+ve ion) m/z: [M+1]=571.1. $^1$H NMR (400 MHz, CHLOROFORM-d) δ 8.77-8.80 (m, 1H), 7.95-8.06 (m, 3H), 7.74-7.81 (m, 1H), 7.62-7.69 (m, 2H), 7.56 (t, J=14.90 Hz, 1H), 7.47 (t, J=15.10 Hz, 2H), 7.12-7.29 (m, 3H), 4.74-4.84 (m, 1H), 4.62 (d, J=8.80 Hz, 1H), 4.00 (d, J=6.85 Hz, 1H), 3.50-3.58 (m, 1H), 3.19 (d, J=13.69 Hz, 1H), 2.82 (dd, J=2.74, 13.69 Hz, 1H).

Preparation of Example 126

A suspension of N-((4aS,5S,7aS)-7a-(5-((Z)-2-(5-cyanopyridin-2-yl)-2-fluorovinyl)-2-fluorophenyl)-5-(trifluoromethyl)-4a,5,7,7a-tetrahydro-4H-furo[3,4-d][1,3]thiazin-2-yl)benzamide (126a) (2.00 g, 3.51 mmol) and methoxylamine hydrochloride (1.46 g, 17.53 mmol) in pyridine (11.93 mL, 140 mmol) was heated to 60° C. for 90 minutes. After cooling to room temperature, the reaction mixture was partitioned between DCM (75 mL) and sat'd aqueous NaHCO$_3$ (50 mL). The aqueous was further extracted with DCM (25 mL). The combined organic solution was concentrated under reduced pressure and the residue was purified by silica gel chromatography (10 to 25% EtOH/EtOAc (1:3) in DCM) to give the desired product (MS (ESI+ve ion) m/z: [M+1]=467.0) as a brown solid containing a small amount of impurity. The material was dissolved in DCM/MeOH then adsorbed onto silica gel (20 g) after removal of solvent under reduced pressure. The material was further purified by silica gel chromatography (0 to 100% EtOAc (0.3% AcOH) in heptane (0.3% AcOH)) to give the desired product as a white solid. The resulting white solid was then partitioned between EtOAc (75 mL) and 1 M aqueous NaOH (50 mL). The separated aqueous was extracted once with EtOAc (20 mL). The combined organic solution was washed with brine (20 mL), dried over MgSO$_4$, filtered, then concentrated under reduced pressure to afford 6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)nicotinonitrile (Example 126) (0.75 g, 46% yield) as a white solid. MS (ESI+ve ion) m/z: [M+1]=467.0. $^1$H NMR (400 MHz, DMSO-d$_6$) δ ppm 9.08 (s, 1H), 8.45 (dd, J=8.31, 1.66 Hz, 1H), 8.22 Hz, 2H), 7.79 (br d, J=3.52 Hz, 1H), 7.25-7.41 (m, 2H), 6.33 (s, 2H), 4.68 (quin, J=7.48 Hz, 1H), 4.40 (d, J=7.82 Hz, 1H), 3.85 (br d, J=7.04 Hz, 1H), 3.21-3.29 (m, 1H), 3.04-3.14 (m, 1H), 2.89 (dd, J=13.79, 3.42 Hz, 1H).

Example 127: (4aS,5S,7aS)-7a-(2-fluoro-5-((Z)-2-fluoro-2-(5-(prop-2-ynyloxy)pyrazin-2-yl)vinyl)phenyl)-5-(trifluoromethyl)-4a,5,7,7a-tetrahydro-4H-furo[3,4-d][1,3]thiazin-2-amine

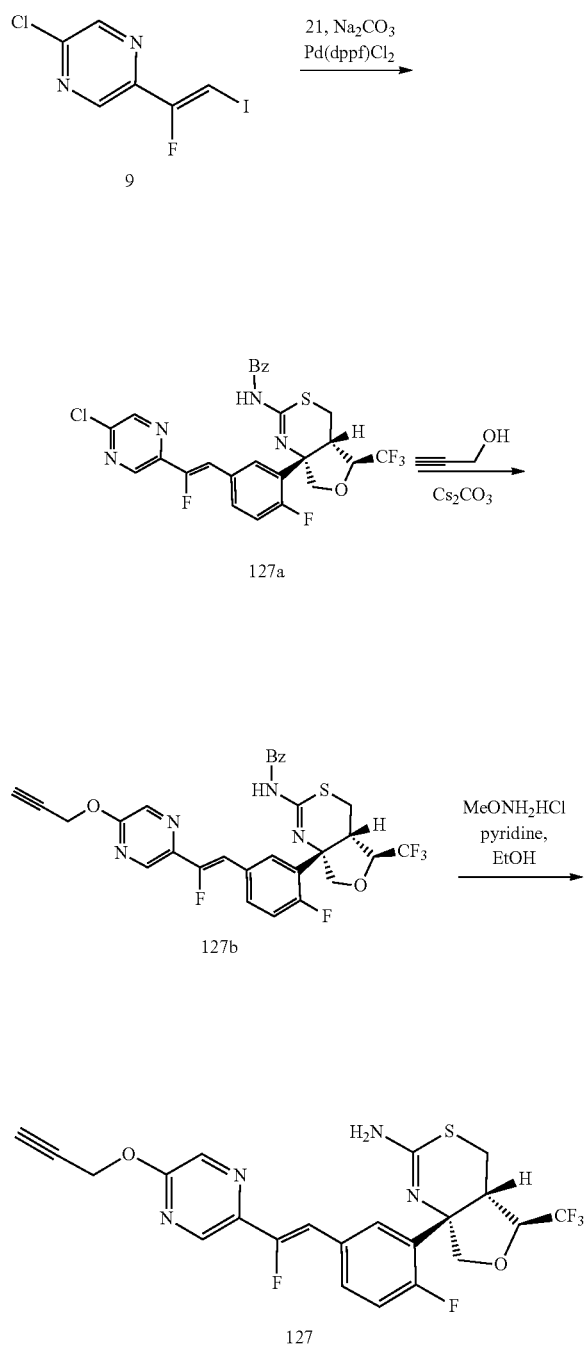

Preparation of 127a: N-((4aS,5S,7aS)-7a-(5-((Z)-2-(5-chloropyrazin-2-yl)-2-fluorovinyl)-2-fluorophenyl)-5-(trifluoromethyl)-4a,5,7,7a-tetrahydro-4H-furo[3,4-d][1,3]thiazin-2-yl)benzamide This compound (1.3 g, 77% yield) as a white solid was prepared in a fashion similar to that described for compound 125a, here starting from boronic ester 21 (1.60 g, 2.91 mmol) and vinyl iodide 9 (1.24 g, 4.36 mmol). MS (ESI+ve ion) m/z: [M+1]=581.0.

Preparation of 127b: N-((4aS,5S,7aS)-7a-(2-fluoro-5-((Z)-2-fluoro-2-(5-(prop-2-ynyloxy)pyrazin-2-yl)vinyl)phenyl)-5-(trifluoromethyl)-4a,5,7,7a-tetrahydro-4H-furo[3,4-d][1,3]thiazin-2-yl)benzamide A suspension of N-((4aS,5S,7aS)-7a-(5-((Z)-2-(5-chloropyrazin-2-yl)-2-fluorovinyl)-2-fluorophenyl)-5-(trifluoromethyl)-4a,5,7,7a-tetrahydro-4H-furo[3,4-d][1,3]thiazin-2-yl)benzamide (127a) (1.30 g, 2.24 mmol), propargyl alcohol (Sigma-Aldrich Chemical Company, Inc., St. Louis, Mo., USA) (0.66 mL, 11.19 mmol), cesium carbonate (Sigma-Aldrich Chemical Company, Inc., St. Louis, Mo., USA) (2.18 g, 6.71 mmol) in THF (10 mL) was stirred for 18 hours at 20° C. The reaction was partitioned between EtOAc (40 mL) and sat'd aqueous NaHCO$_3$ (20 mL). The organic solution was washed with brine (5 mL), dried over MgSO$_4$, and concentrated under reduced pressure. The residue was purified by silica gel chromatography (0 to 20% EtOAc/EtOH (3:1) in heptane) to afford N-((4aS,5S,7aS)-7a-(2-fluoro-5-((Z)-2-fluoro-2-(5-(prop-2-ynyloxy)pyrazin-2-yl)vinyl)phenyl)-5-(trifluoromethyl)-4a,5,7,7a-tetrahydro-4H-furo[3,4-d][1,3]thiazin-2-yl)benzamide (127b) (780 mg, 58% yield) as a white foam. MS (ESI+ve ion) m/z: [M+1]=601.1.

Preparation of (4aS,5S,7aS)-7a-(2-fluoro-5-((Z)-2-fluoro-2-(5-(prop-2-yn-1-yloxy)pyrazin-2-yl)vinyl)phenyl)-5-(trifluoromethyl)-4a,5,7,7a-tetrahydro-4H-furo[3,4-d][1,3]thiazin-2-amine acetate (127)

A suspension of 127b (780 mg, 1.30 mmol), methoxylamine hydrochloride (1085 mg, 12.99 mmol) and pyridine (1.06 mL, 12.99 mmol) in EtOH (5 mL) was heated to 70° C. for 1 hour. The reaction was then partitioned between EtOAc (40 mL) and sat'd aqueous NaHCO$_3$ (25 mL). The organic solution was washed with brine (5 mL), dried over MgSO$_4$, filtered, and then concentrated under reduced pressure. Purification of the residue via silica gel chromatography (0 to 100% EtOAc (0.3% AcOH) in heptane (0.3% AcOH)) afforded (4aS,5S,7aS)-7a-(2-fluoro-5-((Z)-2-fluoro-2-(5-(prop-2-yn-1-yloxy)pyrazin-2-yl)vinyl)phenyl)-5-(trifluoromethyl)-4a,5,7,7a-tetrahydro-4H-furo[3,4-d][1,3]thiazin-2-amine acetate (Example 127) (425 mg, 59% yield) as a white solid. MS (ESI+ve ion) m/z: [M+1]=497.0. $^1$H NMR (400 MHz, DMSO-d$_6$) δ ppm 11.96 (br s, 1H), 8.53 (s, 1H), 8.46 (s, 1H), 7.81 (br d, J=8.02 Hz, 1H), 7.66-7.74 (m, 1H), 7.29 (dd, J=12.23, 8.51 Hz, 1H), 6.95 (d, J=41.28 Hz, 1H), 6.33 (br s, 2H), 5.09 (d, J=2.15 Hz, 2H), 4.68 (quin, J=7.43 Hz, 1H), 4.41 (d, J=8.02 Hz, 1H), 3.84 (br d, J=6.65 Hz, 1H), 3.62 (t, J=2.25 Hz, 1H), 3.21-3.29 (m, 1H), 3.09 (dd, J=13.79, 2.84 Hz, 1H), 2.89 (dd, J=13.99, 3.81 Hz, 1H), 1.91 (s, 3H).

Example 128: 5-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)pyrazine-2-carbonitrile

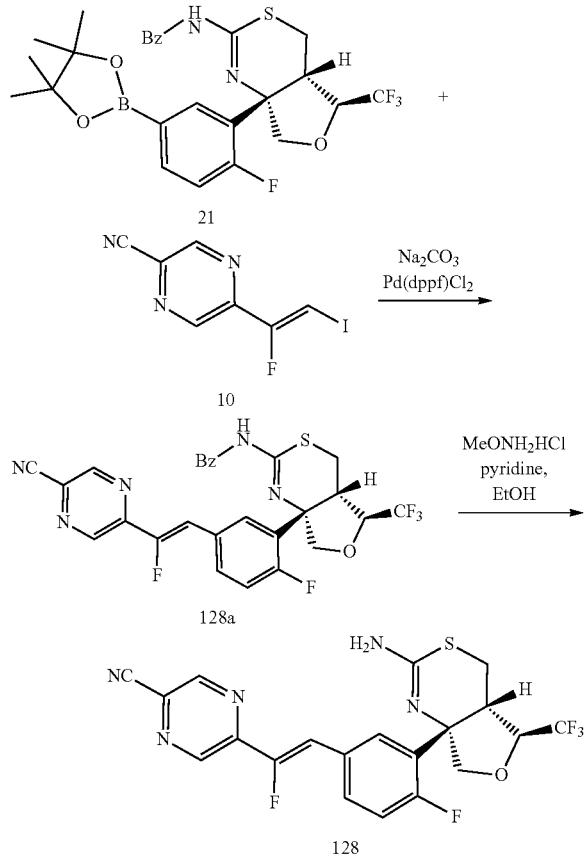

N-((4aS,5S,7aS)-7a-(5-((Z)-2-(5-Cyanopyrazin-2-yl)-2-fluorovinyl)-2-fluorophenyl)-5-(trifluoromethyl)-4a,5,7,7a-tetrahydro-4H-furo[3,4-d][1,3]thiazin-2-yl)benzamide (128a) (320 mg, 62% yield) as a white solid was prepared in a fashion similar to that described for compound 125a, here starting from boronic ester 21 (500 mg, 0.91 mmol) and (Z)-5-(1-fluoro-2-iodovinyl)pyrazine-2-carbonitrile (10) (375 mg, 1.36 mmol). MS (ESI+ve ion) m/z: [M+1]=572.0. $^1$H NMR (400 MHz, CHLOROFORM-d) δ 8.96 (s, 1H), 8.84 (s, 1H), 8.06 (br s, 2H), 7.81-7.89 (m, 1H), 7.71 (d, J=7.24 Hz, 1H), 7.62 (t, J=14.70 Hz, 1H), 7.53 (t, J=15.30 Hz, 2H), 7.20-7.35 (m, 3H), 4.78-4.88 (m, 1H), 4.67 (d, J=8.80 Hz, 1H), 4.00-4.08 (m, 1H), 3.54-3.64 (m, 1H), 3.22 (d, J=14.67 Hz, 1H), 2.83-2.94 (m, 1H).

5-((Z)-2-(3-((4aS,5S,7aS)-2-Amino-5-(trifluoromethyl)-4a,5,7,7a-tetrahydro-4H-furo[3,4-d][1,3]thiazin-7a-yl)-4-fluorophenyl)-1-fluorovinyl)pyrazine-2-carbonitrile (Example 128) (70 mg, 26% yield) as a white solid was prepared in a fashion similar to that described for Example 125 here starting from N-((4aS,5S,7aS)-7a-(5-((Z)-2-(5-cyanopyrazin-2-yl)-2-fluorovinyl)-2-fluorophenyl)-5-(trifluoromethyl)-4a,5,7,7a-tetrahydro-4H-furo[3,4-d][1,3]thiazin-2-yl)benzamide (128a) (320 mg, 0.56 mmol) and methoxylamine hydrochloride (187 mg, 2.24 mmol). MS (ESI+ve ion) m/z: [M+1]=480.0. $^1$H NMR (400 MHz, DMSO-d$_6$) δ 9.25 (s, 1H), 9.16 (s, 1H), 7.92 (d, J=8.22 Hz, 1H), 7.77-7.84 (m, 1H), 7.30-7.48 (m, 2H), 6.33 (br s, 2H), 4.63-4.73 (m, 1H), 4.41 (d, J=8.22 Hz, 1H), 3.84 (d, J=7.43 Hz, 1H), 3.21-3.28 (m, 1H), 3.08 (d, J=13.89 Hz, 1H), 2.89 (dd, J=13.50, 14.28 Hz, 1H). $^{19}$F NMR (376 MHz, DMSO-d$_6$) δ ppm −125.87 (s, 1 F), −108.23 (s, 1F), −76.24 (s, 3F).

Example 129: (4aS,5S,7aS)-7a-(2-fluoro-5-((Z)-2-fluoro-2-(5-(trifluoromethoxy)pyridin-2-yl)vinyl)phenyl)-5-(trifluoromethyl)-4a,5,7,7a-tetrahydro-4H-furo[3,4-d][1,3]thiazin-2-amine

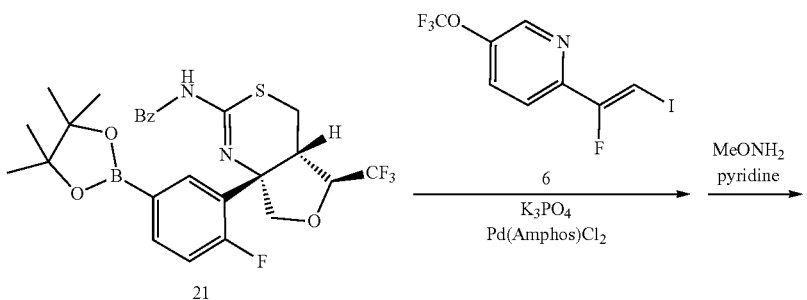

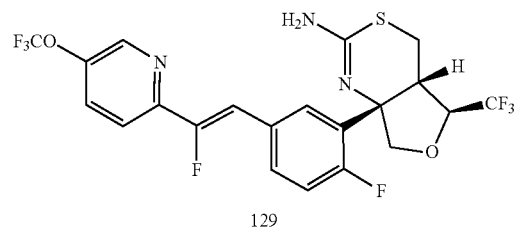

A suspension of boronic ester 21 (247 mg, 0.45 mmol), (Z)-2-(1-fluoro-2-iodovinyl)-5-(trifluoromethoxy)pyridine (6) (115 mg, 0.345 mmol), bis-(di-tert-butyl(4-dimethylaminophenyl)phosphine)dichloropalladium(II) (20 mg, 0.03 mmol), potassium phosphate tribasic monohydrate (239 mg, 1.04 mmol) in 1,4-dioxane (3 mL) and water (1.5 mL) was sparged with argon for 2 minutes. The reaction was then heated to 90° C. for 45 minutes, then cooled to room temperature and partitioned between EtOAc (10 mL) and sat'd aqueous NaHCO₃ (2 mL). The EtOAc layer was concentrated under reduced pressure. The residue was purified by silica gel chromatography (15 to 35% EtOAc in heptane) to afford a brown amorphous solid that contained N-((4aS,5S,7aS)-7a-(2-fluoro-5-(((Z)-2-fluoro-2-(5-(trifluoromethoxy)pyridin-2-yl)vinyl)phenyl)-5-(trifluoromethyl)-4a,5,7,7a-tetrahydro-4H-furo[3,4-d][1,3]thiazin-2-yl)benzamide (160 mg) as an off-white amorphous solid. MS m/z=630.1 [M+H]⁺.

A suspension of N-((4aS,5S,7aS)-7a-(2-fluoro-5-(((Z)-2-fluoro-2-(5-(trifluoromethoxy)pyridin-2-yl)vinyl)phenyl)-5-(trifluoromethyl)-4a,5,7,7a-tetrahydro-4H-furo[3,4-d][1,3]thiazin-2-yl)benzamide (160 mg) and methoxylamine hydrochloride (115 mg, 1.38 mmol) in pyridine (0.88 mL, 10.36 mmol) was heated to 60° C. for 90 minutes. The reaction mixture was partitioned between EtOAc (35 mL) and water (5 mL). The aqueous was discarded. The EtOAc layer was concentrated and the residue was purified silica gel chromatography twice (20 to 35% EtOAc in heptane) to give (4aS,5S,7aS)-7a-(2-fluoro-5-(((Z)-2-fluoro-2-(5-(trifluoromethoxy)pyridin-2-yl)vinyl)phenyl)-5-(trifluoromethyl)-4a,5,7,7a-tetrahydro-4H-furo[3,4-d][1,3]thiazin-2-amine (Example 129) (24 mg, 13% yield) as a brown crystalline solid. MS m/z=526.0 [M+H]⁺. ¹H NMR (400 MHz, DMSO-d₆) δ 8.75 (d, J=2.35 Hz, 1H), 8.04 (d, J=8.88 Hz, 1H), 7.83 (m, 2H), 7.74 (m, 1H), 7.30 (dd, J=8.61, 12.32 Hz, 1H), 7.15 (d, J=39.55 Hz, 1H), 6.32 (br., 2H), 4.67 (m, 1H), 4.40 (d, J=8.02 Hz, 1H), 3.83 (m, 1H), 3.26 (m, 1H), 3.08 (dd, J=2.93, 13.89 Hz, 1H), 2.88 (dd, J=3.81, 13.99 Hz, 1H). ¹⁹F NMR (376 MHz, DMSO-d₆) δ −57.14 (s, 3F), −76.21 (s, 3F), −109.96 (s, 1F), −122.79 (s, 1F).

Example 130: 6-((Z)-2-(3-((4aR,7aS)-2-amino-6-(5-fluoro-4-methoxy-6-methylpyrimidin-2-yl)-4,4a,5,6,7,7a-hexahydropyrrolo[3,4-d][1,3]thiazin-7a-yl)-4-fluorophenyl)-1-fluorovinyl)nicotinonitrile

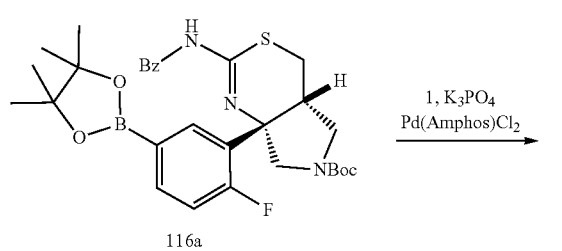

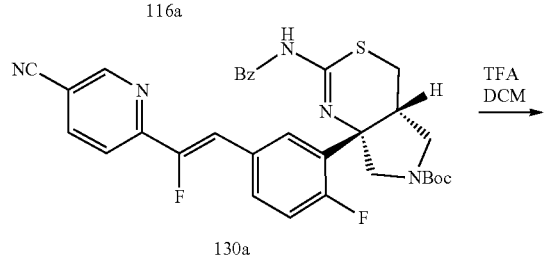

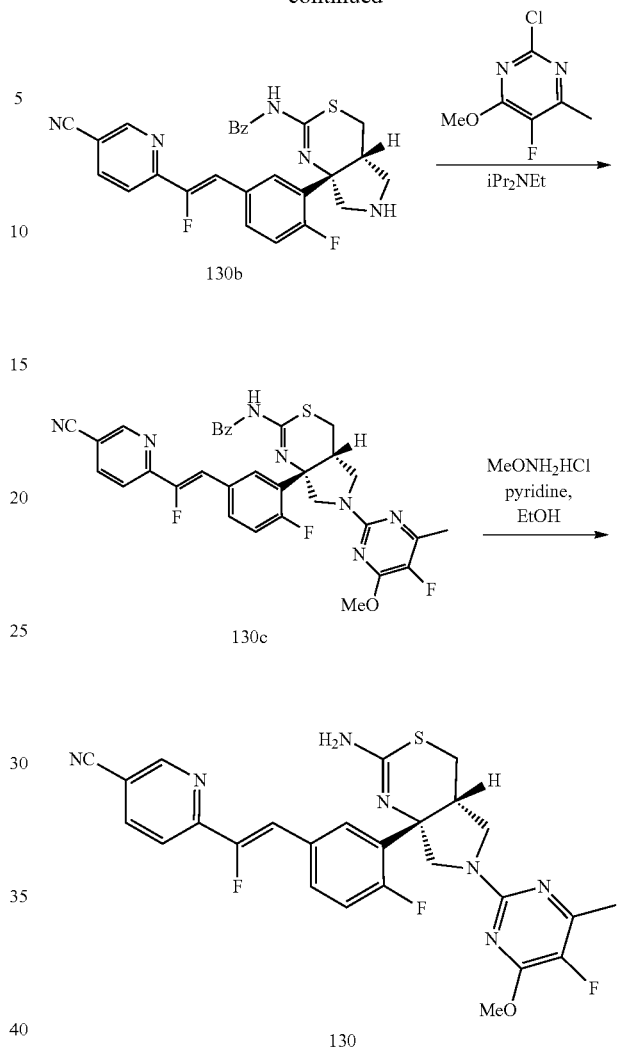

Preparation of (4aR,7aS)-tert-butyl 2-benzamido-7a-(5-((Z)-2-(5-cyanopyridin-2-yl)-2-fluorovinyl)-2-fluorophenyl)-4a,5,7,7a-tetrahydropyrrolo[3,4-d][1,3]thiazine-6(4H)-carboxylate (130a)

A mixture of (4aR,7aS)-tert-butyl 2-benzamido-7a-(2-fluoro-5-(4,4,5,5-tetramethyl-1,3,2-dioxaborolan-2-yl)phenyl)-4a,5,7,7a-tetrahydropyrrolo[3,4-d][1,3]thiazine-6(4H)-carboxylate (116a) (1.00 g, 1.72 mmol), vinyl iodide 1 (0.56 g, 2.06 mmol), Pd(Amphos)Cl₂ (0.12 g, 0.17 mmol)) and potassium phosphate tribasic monohydrate (919 mg, 4.00 mmol) in 1,4-dioxane (7.8 mL) and water (1.3 mL) was purged with argon, then the flask was sealed and heated to 80° C. for 1.5 hours. The mixture was diluted with water and extracted with EtOAc (3×). The organic solution was dried over Na₂SO₄ and concentrated in vacuo. The crude was purified by silica gel chromatography (0 to 50% EtOAc in heptane) to give (4aR,7aS)-tert-butyl 2-benzamido-7a-(5-((Z)-2-(5-cyanopyridin-2-yl)-2-fluorovinyl)-2-fluorophenyl)-4a,5,7,7a-tetrahydropyrrolo[3,4-d][1,3]thiazine-6(4H)-carboxylate (130a) (0.79 g, 76% yield) as a beige solid. MS (ESI+ve ion) m/z: [M+1]=602.2.

Preparation of N-((4aR,7aS)-7a-(5-((Z)-2-(5-cyano-pyridin-2-yl)-2-fluorovinyl)-2-fluorophenyl)-4,4a,5, 6,7,7a-hexahydropyrrolo[3,4-d][1,3]thiazin-2-yl) benzamide (130b)

To a solution of 130a (0.78 g, 1.3 mmol) in DCM (6.5 mL) was added trifluoroacetic acid (2.1 ml, 27 mmol) dropwise. The reaction mixture was stirred for 2 hours. The mixture was evaporated in vacuo and the residue was added DCM and evaporated again in vacuo. The residue was partitioned between DCM and sat'd aqueous $NaHCO_3$. The aqueous layer was extracted with DCM (2×) and the combined DCM extracts were dried over $Na_2SO_4$ and concentrated to give 130b as a light yellow solid which was used without additional purification, assuming theoretical yield. MS (ESI+ve ion) m/z: [M+1]=502.1.

Preparation of N-((4aR,7aS)-7a-(5-((Z)-2-(5-cyano-pyridin-2-yl)-2-fluorovinyl)-2-fluorophenyl)-6-(5-fluoro-4-methoxy-6-methylpyrimidin-2-yl)-4,4a,5,6, 7,7a-hexahydropyrrolo[3,4-d][1,3]thiazin-2-yl) benzamide (130c)

A mixture of N-((4aR,7aS)-7a-(5-((Z)-2-(5-cyanopyridin-2-yl)-2-fluorovinyl)-2-fluorophenyl)-4,4a,5,6,7,7a-hexahydropyrrolo[3,4-d][1,3]thiazin-2-yl)benzamide (130b) (0.19 g, 0.38 mmol), N,N-diisopropylethylamine (0.46 mL, 2.65 mmol), and 2-chloro-5-fluoro-4-methoxy-6-methylpyrimidine (Enamine) (0.33 g, 1.89 mmol) in dioxane (1.2 ml) was heated to reflux for 2 hours. The mixture was diluted with water and extracted with EtOAc. The organic layer was concentrated in vacuo. The crude was purified by silica gel chromatography (0 to 40% EtOAc in heptane) to give N-((4aR,7aS)-7a-(5-((Z)-2-(5-cyanopyridin-2-yl)-2-fluorovinyl)-2-fluorophenyl)-6-(5-fluoro-4-methoxy-6-methylpyrimidin-2-yl)-4,4a,5,6,7,7a-hexahydropyrrolo[3,4-d][1,3]thiazin-2-yl)benzamide (130c) (90 mg, 37% yield) as an off-white solid. MS (ESI+ve ion) m/z: [M+1]=642.2.

Preparation of 6-((Z)-2-(3-((4aR,7aS)-2-amino-6-(5-fluoro-4-methoxy-6-methylpyrimidin-2-yl)-4,4a,5,6, 7,7a-hexahydropyrrolo[3,4-d][1,3]thiazin-7a-yl)-4-fluorophenyl)-1-fluorovinyl)nicotinonitrile (130)

A mixture of N-((4aR,7aS)-7a-(5-((Z)-2-(5-cyanopyridin-2-yl)-2-fluorovinyl)-2-fluorophenyl)-6-(5-fluoro-4-methoxy-6-methylpyrimidin-2-yl)-4,4a,5,6,7,7a-hexahydropyrrolo[3,4-d][1,3]thiazin-2-yl)benzamide (130c) (90 mg, 0.14 mmol), O-methylhydroxylamine hydrochloride (117 mg, 1.40 mmol), pyridine (113 4, 1.4 mmol) and EtOH (1.8 mL) was heated to 70° C. for 1 hour. The mixture was diluted with EtOAc and water. The organic solution was washed with $NH_4Cl$, and brine, and concentrated in vacuo. The residue was purified by silica gel chromatography (0 to 40% (3:1) EtOAc/EtOH in heptane) followed by reverse phase HPLC (Phenomenex Gemini column, 10 micron, C18, 110 Å, 150×30 mm, 0.1% TFA in $CH_3CN/H_2O$, gradient 10 to 70% over 15 minutes, then neutralized with aqueous $NaHCO_3$ and extracted with DCM) to provide 6-((Z)-2-(3-((4aR,7aS)-2-amino-6-(5-fluoro-4-methoxy-6-methylpyrimidin-2-yl)-4,4a,5,6,7,7a-hexahydropyrrolo[3,4-d][1,3] thiazin-7a-yl)-4-fluorophenyl)-1-fluorovinyl)nicotinonitrile (Example 130) (20 mg, 26% yield) as a white solid. MS (ESI+ve ion) m/z: [M+1]=538.1. $^1$H NMR (CHLOROFORM-d) δ: 8.92 (br s, 1H), 8.12 (br d, J=7.4 Hz, 1H), 7.78 (br d, J=6.8 Hz, 3H), 7.14-7.30 (m, 2H), 4.44 (br d, J=11.7 Hz, 1H), 4.05 (br s, 3H), 3.79-3.99 (m, 3H), 3.30 (br s, 1H), 2.96-3.19 (m, 2H), 2.40 (br s, 3H). $NH_2$ peak was not observed. $^{19}$F NMR (CHLOROFORM-d) δ: −109.05 (br s, 1F), −125.23 (br s, 1F), −176.34 (m, 1F).

Example 131: 6-((Z)-2-(3-((4aS,5S,7aS)-2-amino-5-(fluoromethyl)-4a,5,7,7a-tetrahydro-4H-furo[3,4-d] [1,3]thiazin-7a-yl)-4-fluorophenyl)-1-fluorovinyl) nicotinonitrile

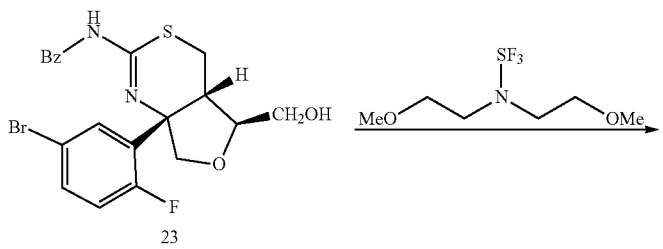

23

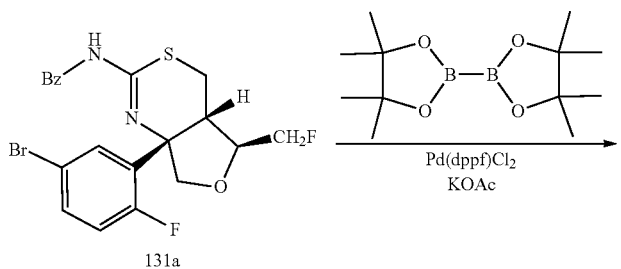

131a

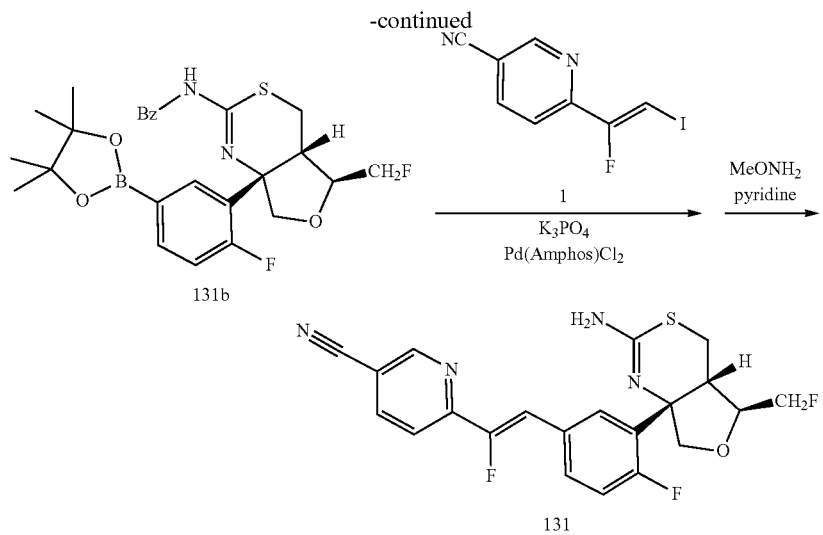

Preparation of N-((4aS,5S,7aS)-7a-(5-bromo-2-fluorophenyl)-5-(fluoromethyl)-4a,5,7,7a-tetrahydro-4H-furo[3,4-d][1,3]thiazin-2-yl)benzamide (131a)

A solution of bis(2-methoxyethyl)aminosulfur trifluoride (123 µL, 0.55 mmol) in 1 mL of DCM was added to a solution of N-((4aS,5S,7aS)-7a-(5-bromo-2-fluorophenyl)-5-(hydroxymethyl)-4a,5,7,7a-tetrahydro-4H-furo[3,4-d][1,3]thiazin-2-yl)benzamide (23) (225 mg, 0.48 mmol) in 2 mL of DCM at 0° C. The mixture was stirred at 0° C. for 45 minutes then room temperature for 18 hours. It was cooled with an ice bath and treated with 10 mL of sat'd aqueous NaHCO$_3$ followed by 35 mL of DCM. The mixture was stirred for 15 minutes. The solution was separated. The DCM layer was concentrated and the residue was purified on a silica gel column (30 to 65% EtOAc in heptane) to give 2 compounds: 85 mg (0.18 mmol, 37% yield) of N-((4aS,5S,7aS)-7a-(5-bromo-2-fluorophenyl)-5-(fluoromethyl)-4a,5,7,7a-tetrahydro-4H-furo[3,4-d][1,3]thiazin-2-yl)benzamide (131a) (MS m/z=467/469 [M+H]$^+$) and 100 mg of N-((4aS,5S,7aS)-7a-(5-bromo-2-fluorophenyl)-5-(hydroxymethyl)-4a,5,7,7a-tetrahydro-4H-furo[3,4-d][1,3]thiazin-2-yl)benzamide (23) (MS m/z=465/467 [M+H]$^+$).

Preparation of N-((4aS,5S,7aS)-7a-(2-fluoro-5-(4,4,5,5-tetramethyl-1,3,2-dioxaborolan-2-yl)phenyl)-5-(fluoromethyl)-4a,5,7,7a-tetrahydro-4H-furo[3,4-d][1,3]thiazin-2-yl)benzamide (131b)

A suspension of N-((4aS,5S,7aS)-7a-(5-bromo-2-fluorophenyl)-5-(fluoromethyl)-4a,5,7,7a-tetrahydro-4H-furo[3,4-d][1,3]thiazin-2-yl)benzamide (131a) (125 mg, 0.27 mmol), bis(pinacolato)diboron (88 mg, 0.35 mmol), [1,1'-bis(diphenylphosphino)ferrocene]-dichloropalladium(ii) complex with dichloromethane (9 mg, 10.7 µmop, potassium acetate (79 mg, 0.82 mmol) in 1,4-dioxane (3 mL) was sparged with argon for 10 minutes then heated to 100° C. for 1 hour. Additional bis(pinacolato)diboron (25 mg) and [1,1'-bis(diphenylphosphino)ferrocene]-dichloropalladium(II) complex with dichloromethane (3 mg) were added to the reaction mixture which was heated again at 100° C. for 20 minutes. After cooling to room temperature, the reaction mixture was filtered through a pad of celite and the filter cake was rinsed with (2×3 mL) of EtOAc. The filtrate was concentrated under reduced pressure to give N-((4aS,5S,7aS)-7a-(2-fluoro-5-(4,4,5,5-tetramethyl-1,3,2-dioxaborolan-2-yl)phenyl)-5-(fluoromethyl)-4a,5,7,7a-tetrahydro-4H-furo[3,4-d][1,3]thiazin-2-yl)benzamide (131b) as a brown solid which was used without additional purification. MS m/z=515.0 [M+H]$^+$.

Preparation of 6-((Z)-2-(3-((4aS,5S,7aS)-2-amino-5-(fluoromethyl)-4a,5,7,7a-tetrahydro-4H-furo[3,4-d][1,3]thiazin-7a-yl)-4-fluorophenyl)-1-fluorovinyl)nicotinonitrile (131)

A mixture of the above obtained crude boronic ester 131b, potassium phosphate tribasic (170 mg, 0.80 mmol), (Z)-6-(1-fluoro-2-iodovinyl)nicotinonitrile (1) (70 mg, 0.25 mmol), and bis(di-tert-butyl(4-dimethylaminophenyl)phosphine)dichloropalladium(II) (15 mg, 0.02 mmol) in 2 mL of dioxane and 1 mL of water was purged with argon for 2 minutes and then heated in an oil bath at 90° C. for 90 minutes. The mixture was partitioned between EtOAc (10 mL) and sat'd aqueous NaHCO$_3$ (2 mL). The organic layer was concentrated under reduced pressure. The residue was purified by silica gel chromatography (25 to 55% EtOAc in heptane) to afford N-((4aS,5S,7aS)-7a-(5-((Z)-2-(5-cyanopyridin-2-yl)-2-fluorovinyl)-2-fluorophenyl)-5-(fluoromethyl)-4a,5,7,7a-tetrahydro-4H-furo[3,4-d][1,3]thiazin-2-yl)benzamide (56 mg) as a brown amorphous solid. MS m/z=535.1 [M+H]$^+$.

A suspension of N-((4aS,5S,7aS)-7a-(5-((Z)-2-(5-cyanopyridin-2-yl)-2-fluorovinyl)-2-fluorophenyl)-5-(fluoromethyl)-4a,5,7,7a-tetrahydro-4H-furo[3,4-d][1,3]thiazin-2-yl)benzamide (56 mg, 0.10 mmol) and methoxylamine hydrochloride (34 mg, 0.41 mmol) in pyridine (0.5 mL) was heated to 60° C. for 90 minutes. The mixture was partitioned between EtOAc (35 mL) and water (5 mL). The aqueous portion was discarded. The EtOAc layer was concentrated and the residue purified via silica gel chromatography twice (35 to 85% EtOAc in heptane) to give 6-((Z)-2-(3-((4aS,5S,7aS)-2-amino-5-(fluoromethyl)-4a,5,7,7a-tetrahydro-4H-furo[3,4-d][1,3]thiazin-7a-yl)-4-fluorophenyl)-1-fluorovinyl)nicotinonitrile (Example 131) (20 mg, 17% overall yield) an off-white crystalline solid. MS m/z=431.9 [M+H]$^+$.
$^1$H NMR (400 MHz, DMSO-d$_6$) δ 9.08 (s, 1H), 8.44 (dd, J=2.15, 8.22 Hz, 1H), 7.82-7.89 (m, 2H), 7.74 (m, 1H), 7.24-7.37 (m, 2H), 6.14 (br., 2H), 4.45-4.69 (m, 2H), 4.28-4.41 (m, 2H), 3.75 (dd, J=2.74, 8.22 Hz, 1H), 3.01 (m, 2H), 2.80 (m, 1H). $^{19}$F NMR (376 MHz, DMSO-$d_6$) δ −108.74 (s, 1F), −124.33 (s, 1F), −225.47 (s, 1F).

Example 132: (4aS,5S,7aS)-7a-(2-fluoro-5-((Z)-2-fluoro-2-(5-fluoropyridin-2-yl)vinyl)phenyl)-5-(trifluoromethyl)-4a,5,7,7a-tetrahydro-4H-furo[3,4-d][1,3]thiazin-2-amine

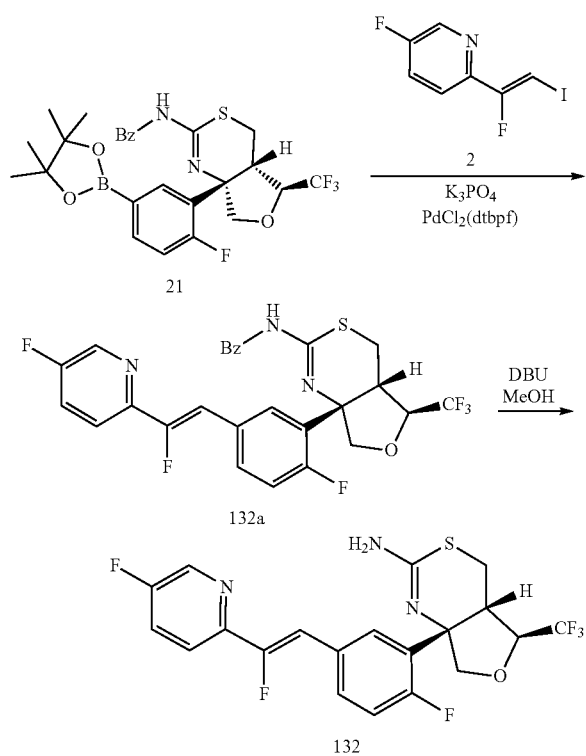

A solution of boronic ester 21 (200 mg, 0.36 mmol), vinyl iodide 2 (97 mg, 0.36 mmol) and potassium phosphate tribasic (193 mg, 0.91 mmol) in 1,4-dioxane:water (5:1, 6 mL) was degassed with nitrogen for 10 minutes then treated with 1,1'-bis(di-tert-butylphosphino)ferrocene palladium dichloride (25.7 mg, 0.036 mmol). The reaction mixture was degassed with nitrogen for 10 minutes then heated at 80° C. for 1.5 hours. After cooling to room temperature, the mixture was partitioned between water (50 mL) and EtOAc (150 mL). The organic layer was washed with brine (50 mL) and concentrated under reduced pressure. The residue was purified by silica gel chromatography (0 to 15% EtOAc in hexanes) to afford N-((4aS,5S,7aS)-7a-(2-fluoro-5-((Z)-2-fluoro-2-(5-fluoropyridin-2-yl)vinyl)phenyl)-5-(trifluoromethyl)-4a,5,7,7a-tetrahydro-4H-furo[3,4-d][1,3]thiazin-2-yl)benzamide (132a) 150 mg, 73% yield) as an off-white solid. MS m/z=564.2 [M+H]$^+$.

A mixture of 132a (150 mg, 0.27 mmol) and DBU (60 μL, 0.40 mmol) in methanol (3 mL) was stirred at 70° C. for 3 hours. The reaction mixture was cooled to room temperature and concentrated under reduced pressure. The residue was diluted with water (20 mL) and extracted with EtOAc (3×20 mL). The combined organic solution was washed with brine (20 mL), dried over Na$_2$SO$_4$ and concentrated under reduced pressure. The residue was purified by silica gel chromatography (0 to 30% EtOAc in hexanes) to provide (4aS,5S,7aS)-7a-(2-fluoro-5-((Z)-2-fluoro-2-(5-fluoropyridin-2-yl)vinyl)phenyl)-5-(trifluoromethyl)-4a,5,7,7a-tetrahydro-4H-furo[3,4-d][1,3]thiazin-2-amine (Example 132) (50 mg, 41%) as a white solid. MS m/z=460.2 [M+H]$^+$. $^1$H NMR (400 MHz, DMSO-$d_6$) δ 8.67 (d, J=2.8 Hz, 1H), 7.89-7.84 (m, 1H), 7.80 (td, J=9.6, 8.7, 3.4 Hz, 2H), 7.71 (ddd, J=7.2, 4.7, 2.3 Hz, 1H), 7.28 (dd, J=12.3, 8.5 Hz, 1H), 7.06 (d, J=40.3 Hz, 1H), 6.33 (s, 2H), 4.66 (m, 1H), 4.40 (d, J=8.1 Hz, 1H), 3.83 (dd, J=8.5, 2.6 Hz, 1H), 3.24 (dd, J=7.9, 4.1 Hz, 1H), 3.08 (dd, J=13.8, 3.1 Hz, 1H), 2.88 (dd, J=13.8, 3.9 Hz, 1H). $^{19}$F NMR (400 MHz, DMSO-$d_6$) δ −76.213 (s, 3F), −110.498 (s, 1F), −122.269 (s, 1F), −126.210 (s, 1F).

Example 133: 6-((Z)-2-(3-((4aR,5R,7aR)-2-amino-5-(fluoromethyl)-4a,5,7,7a-tetrahydro-4H-furo[3,4-d][1,3]thiazin-7a-yl)-4-fluorophenyl)-1-fluorovinyl)nicotinonitrile

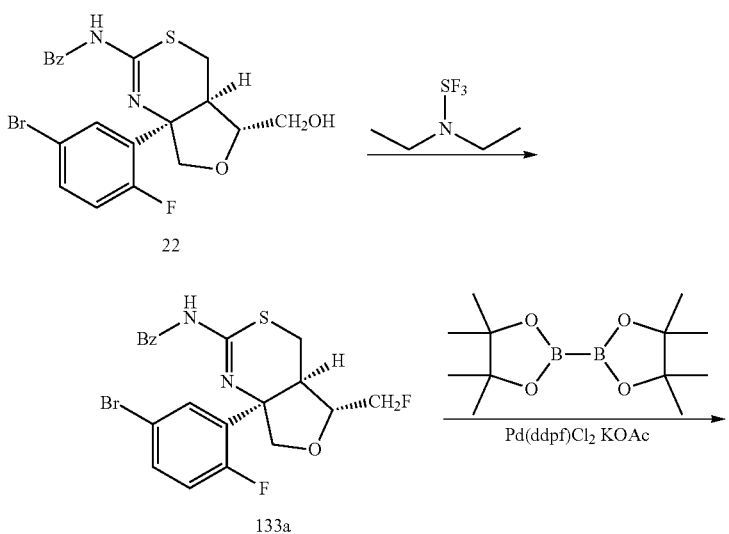

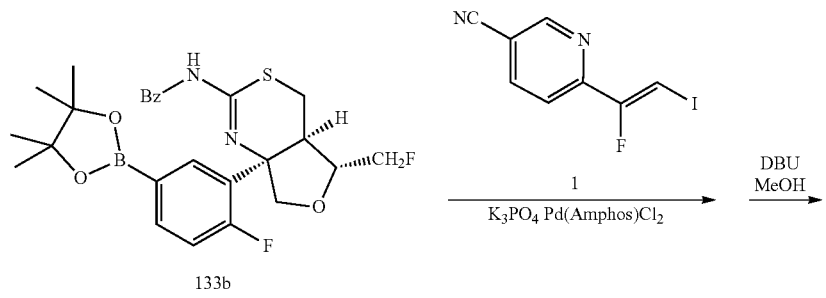

133b

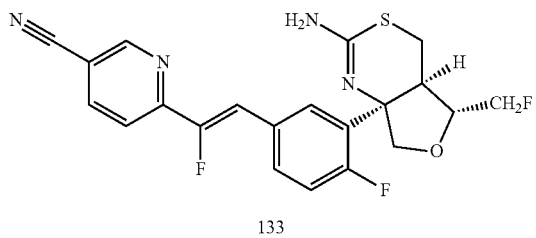

133

Preparation of N-((4aR,5R,7aR)-7a-(5-bromo-2-fluorophenyl)-5-(fluoromethyl)-4a,5,7,7a-tetrahydro-4H-furo[3,4-d][1,3]thiazin-2-yl)benzamide (133a)

A solution of (diethylamino)trifluorosulfur (76 mg, 0.47 mmol) in 1 mL of DCM was added to a solution of N-((4aR,5R,7aR)-7a-(5-bromo-2-fluorophenyl)-5-(hydroxymethyl)-4a,5,7,7a-tetrahydro-4H-furo[3,4-d][1,3]thiazin-2-yl)benzamide (22) (176 mg, 0.38 mmol) in 2 mL of DCM at −30° C. The mixture was slowly warmed to room temperature and stirred 18 hours. It was cooled with an ice bath and treated with 10 mL of sat'd aqueous $NaHCO_3$ followed by 35 mL of DCM. The mixture was stirred for 15 minutes. The solution was separated. The DCM layer was concentrated and the residue was purified on a silica gel column (30 to 65% EtOAc in heptane) to give N-((4aR,5R,7aR)-7a-(5-bromo-2-fluorophenyl)-5-(fluoromethyl)-4a,5,7,7a-tetrahydro-4H-furo[3,4-d][1,3]thiazin-2-yl)benzamide (133a) (65 mg, 36% yield). MS m/z=467/469 [M+H]+.

Preparation of N-((4aR,5R,7aR)-7a-(2-fluoro-5-(4,4,5,5-tetramethyl-1,3,2-dioxaborolan-2-yl)phenyl)-5-(fluoromethyl)-4a,5,7,7a-tetrahydro-4H-furo[3,4-d][1,3]thiazin-2-yl)benzamide (133b)

A suspension of 133a (122 mg, 0.26 mmol), bis(pinacolato)diboron (86 mg, 0.34 mmol), [1,1'-bis(diphenylphosphino)ferrocene]-dichloropalladium(ii) complex with dichloromethane (9 mg, 10.7 umol), potassium acetate (77 mg, 0.78 mmol) in 1,4-dioxane (3 mL) was sparged with argon for 10 minutes then heated to 100° C. for 1 hour. After cooling to room temperature, the reaction mixture was filtered through a pad of celite and the filter cake was rinsed with (2×3 mL) of EtOAc. The filtrate was concentrated under reduced pressure to give N-((4aR,5R,7aR)-7a-(2-fluoro-5-(4,4,5,5-tetramethyl-1,3,2-dioxaborolan-2-yl)phenyl)-5-(fluoromethyl)-4a,5,7,7a-tetrahydro-4H-furo[3,4-d][1,3]thiazin-2-yl)benzamide (133b) as a brown solid which was used without additional purification, assuming theoretical yield. MS m/z=515.0 [M+H]+.

Preparation of 6-((Z)-2-(3-((4aR,5R,7aR)-2-amino-5-(fluoromethyl)-4a,5,7,7a-tetrahydro-4H-furo[3,4-d][1,3]thiazin-7a-yl)-4-fluorophenyl)-1-fluorovinyl)nicotinonitrile (133)

This compound (20 mg, 18% overall yield) as a white solid was prepared via a 2-step protocol similar to that described for Example 132, here starting from boronic ester 133b (133 mg, 0.26 mmol) and vinyl iodide 1 (68 mg, 0.25 mmol). MS m/z=431.9 [M+H]+. $^1$H NMR (400 MHz, DMSO-$d_6$) δ 9.08 (s, 1H), 8.44 (dd, J=2.15, 8.22 Hz, 1H), 7.82-7.89 (m, 2H), 7.74 (m, 1H), 7.24-7.37 (m, 2H), 6.14 (br., 2H), 4.45-4.69 (m, 2H), 4.28-4.41 (m, 2H), 3.75 (dd, J=2.74, 8.22 Hz, 1H), 3.01 (m, 2H), 2.80 (m, 1H). $^{19}$F NMR (376 MHz, DMSO-$d_6$) δ −108.74 (s, 1F), −124.33 (s, 1F), −225.47 (s, 1F).

Example 134: 6-((Z)-2-(3-((4aR,7aS)-2-amino-6-(5-fluoro-4-methoxypyrimidin-2-yl)-4,4a,5,6,7,7a-hexahydropyrrolo[3,4-d][1,3]thiazin-7a-yl)-4-fluorophenyl)-1-fluorovinyl)nicotinonitrile

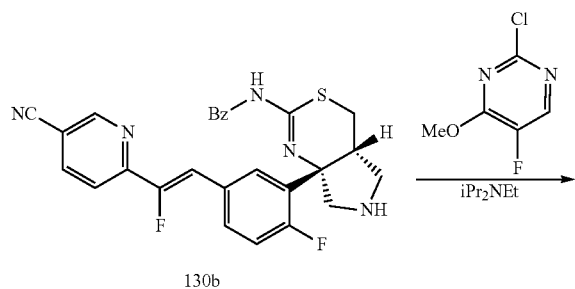

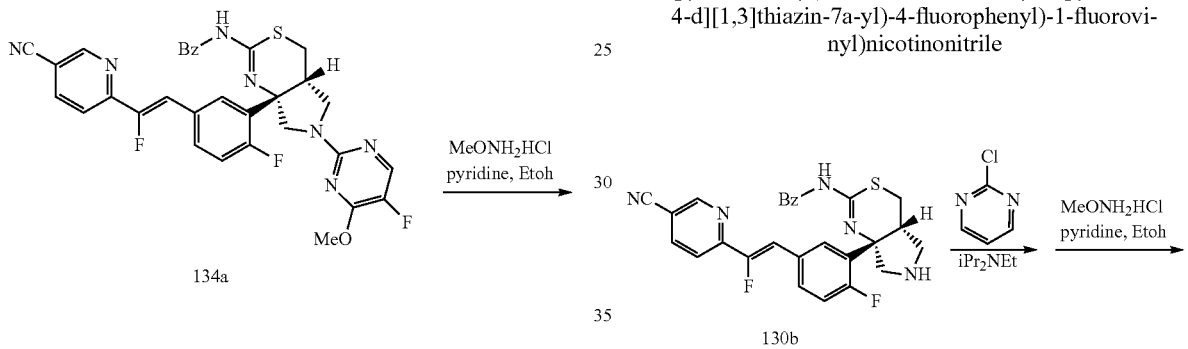

Preparation of 6-((Z)-2-(3-((4aR,7aS)-2-amino-6-(5-fluoro-4-methoxypyrimidin-2-yl)-4,4a,5,6,7,7a-hexahydropyrrolo[3,4-d][1,3]thiazin-7a-yl)-4-fluorophenyl)-1-fluorovinyl)nicotinonitrile (134)

A mixture of 134a (97 mg, 0.16 mmol), O-methylhydroxylamine hydrochloride (129 mg, 1.55 mmol), pyridine (125 μL, 1.55 mmol) and EtOH (2 mL) was heated to 70° C. for 1 hour. The mixture was diluted with EtOAc and water. The organic layer was washed with sat'd aqueous NH$_4$Cl followed by brine, and concentrated in vacuo. The residue was purified by HPLC using 5-95% gradient of 0.1% NH$_4$OH in acetonitrile and water as mobile phase to give 6-((Z)-2-(3-((4aR,7aS)-2-amino-6-(5-fluoro-4-methoxypyrimidin-2-yl)-4,4a,5,6,7,7a-hexahydropyrrolo[3,4-d][1,3]thiazin-7a-yl)-4-fluorophenyl)-1-fluorovinyl)nicotinonitrile (Example 134) (6 mg, 7% yield) as an off-white solid. MS (ESI+ve ion) m/z: [M+1]=524.0.

Example 135: 6-((Z)-2-(3-((4aR,7aS)-2-amino-6-(pyrimidin-2-yl)-4,4a,5,6,7,7a-hexahydropyrrolo[3,4-d][1,3]thiazin-7a-yl)-4-fluorophenyl)-1-fluorovinyl)nicotinonitrile

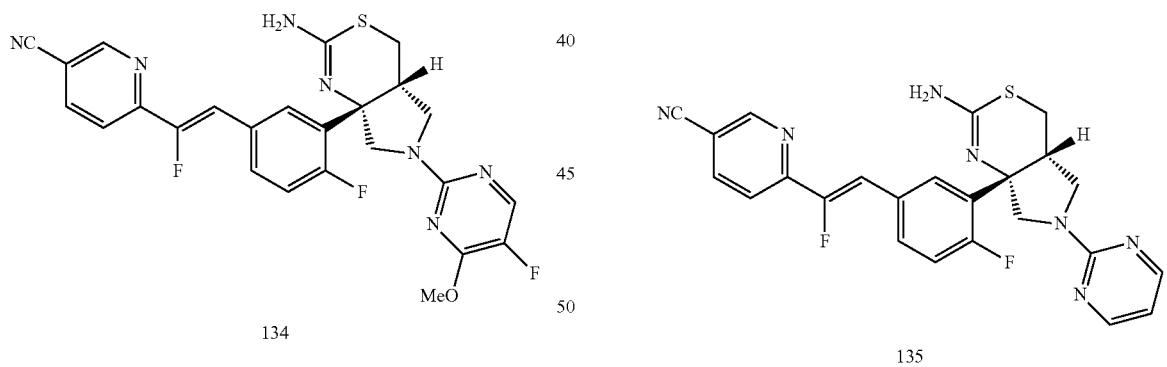

Preparation of N-((4aR,7aS)-7a-(5-((Z)-2-(5-cyanopyridin-2-yl)-2-fluorovinyl)-2-fluorophenyl)-6-(5-fluoro-4-methoxypyrimidin-2-yl)-4,4a,5,6,7,7a-hexahydropyrrolo[3,4-d][1,3]thiazin-2-yl)benzamide (134a)

This compound (97 mg, 57% yield) as an off-white solid was prepared in a manner similar to that described for compound 130c, here starting from 130b (0.13 g, 0.27 mmol) and 2-chloro-5-fluoro-4-methoxypyrimidine (SynQuest Laboratories, Inc., Alachua, Fla., USA) (0.22 g, 1.36 mmol). MS (ESI+ve ion) m/z: [M+1]=628.1.

This compound (32 mg, 27% overall yield) as an off-white solid was prepared in a 2-step protocol similar to that described for Example 134, here starting from 130b (0.13 g, 0.26 mmol) and 2-chloropyrimidine (Acros Organics) (0.15 g, 1.28 mmol). MS (ESI+ve ion) m/z: [M+1]=476.0. $^1$H NMR (DMSO-d$_6$) δ: 9.07 (d, J=2.1 Hz, 1H), 8.40-8.46 (m, 1H), 8.34 (d, J=4.7 Hz, 2H), 7.83 (d, J=8.2 Hz, 1H), 7.71-7.78 (m, 2H), 7.26-7.35 (m, 1H), 7.28 (d, J=32 Hz, 1H), 6.62 (t, J=4.8 Hz, 1H), 6.18 (s, 2H), 4.13 (d, J=11.2 Hz, 1H), 3.68-3.81 (m, 2H), 3.54-3.65 (m, 1H), 3.01-3.12 (m, 2H), 2.90-2.98 (m, 1H).

Example 136: (4aS,5S,7aS)-7a-(2-fluoro-5-((Z)-2-fluoro-2-(5-methoxypyrazin-2-yl)vinyl)phenyl)-5-(trifluoromethyl)-4a,5,7,7a-tetrahydro-4H-furo[3,4-d][1,3]thiazin-2-amine

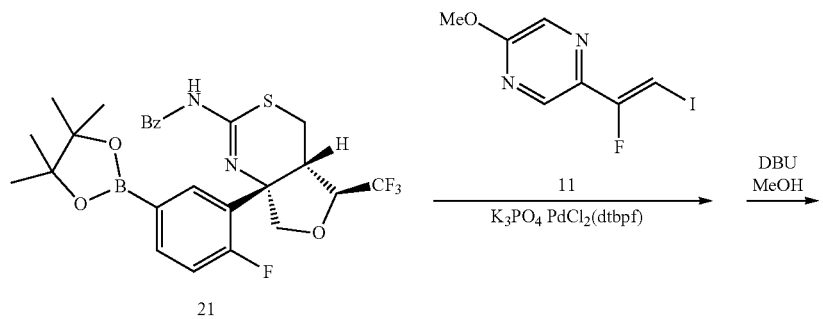

This compound (45 mg, 25% overall yield) as a white solid was prepared via a 2-step protocol similar to that described for Example 132, here starting from boronic ester 21 (200 mg, 0.36 mmol) and vinyl iodide 11 (102 mg, 0.36 mmol). MS m/z=473.2 [M+H]$^+$. $^1$H NMR (300 MHz, DMSO-d$_6$) δ 8.50 (s, 1H), 8.40 (d, J=1.3 Hz, 1H), 7.80 (dd, J=8.1, 2.4 Hz, 1H), 7.75-7.65 (m, 1H), 7.28 (dd, J=12.3, 8.5 Hz, 1H), 6.93 (d, J=40.9 Hz, 1H), 6.34 (s, 2H), 4.67 (q, J=7.5 Hz, 1H), 4.41 (d, J=8.0 Hz, 1H), 3.98 (s, 3H), 3.83 (dd, J=8.4, 2.8 Hz, 1H), 3.27-3.23 (m, 1H), 3.08 (dd, J=13.9, 3.2 Hz, 1H), 2.88 (dd, J=14.0, 3.9 Hz, 1H). $^{19}$F NMR (400 MHz, DMSO-d$_6$) δ −76.213 (s, 3F), −110.700 (s, 1F), −124.383 (s, 1F).

Example 137: (4aS,5S,7aS)-7a-(5-((Z)-2-(3-chloro-5-(trifluoromethyl)pyridin-2-yl)-2-fluorovinyl)-2-fluorophenyl)-5-(trifluoromethyl)-4a,5,7,7a-tetrahydro-4H-furo[3,4-d][1,3]thiazin-2-amine

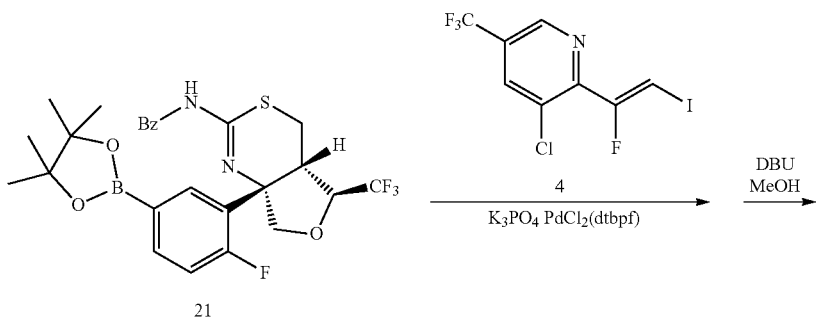

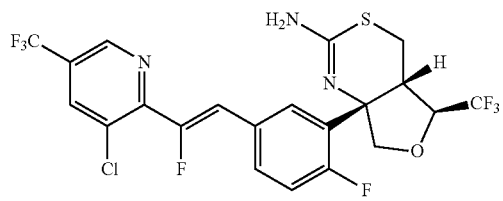

This compound (45 mg, 23% overall yield) as a white solid was prepared via a 2-step protocol similar to that described for Example 132, here starting from boronic ester 21 (200 mg, 0.36 mmol) and vinyl iodide 4 (128 mg, 0.36 mmol). MS m/z=544.1 [M+H]+. 1H NMR (400 MHz, DMSO-d6) δ 9.03 (d, J=1.8 Hz, 1H), 8.61 (d, J=1.8 Hz, 1H), 7.86-7.81 (m, 1H), 7.74 (ddd, J=7.0, 4.5, 2.3 Hz, 1H), 7.32 (dd, J=12.3, 8.5 Hz, 1H), 7.00 (d, J=38.3 Hz, 1H), 6.33 (s, 2H), 4.67 (q, J=7.5 Hz, 1H), 4.41 (d, J=8.1 Hz, 1H), 3.86-3.79 (m, 1H), 3.25 (dd, J=7.7, 3.9 Hz, 1H), 3.07 (dd, J=14.2, 3.1 Hz, 1H), 2.88 (dd, J=14.0, 3.9 Hz, 1H). 19F NMR (400 MHz, DMSO-d6) δ −60.759 (s, 3F), −76.206 (s, 3F), −109.315 (s, 1F), −113.235 (s, 1F).

Example 138: 6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)-5-methylnicotinonitrile

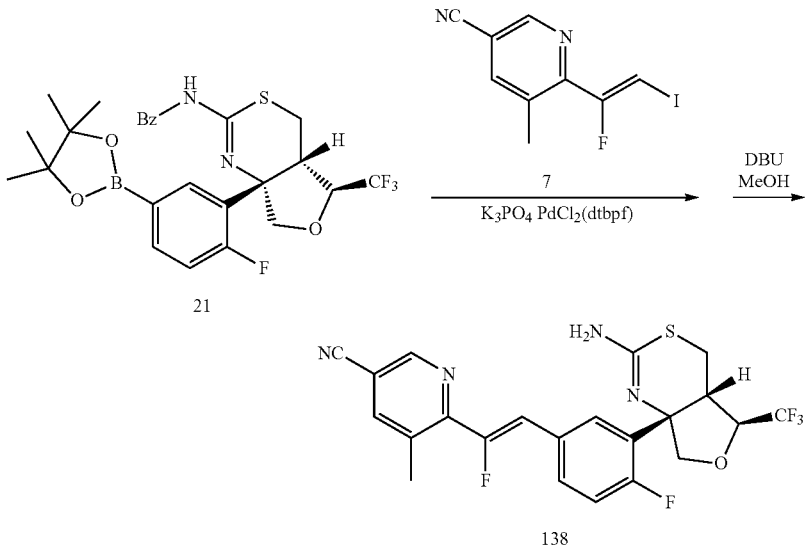

This compound (55 mg, 34% overall yield) as a white solid was prepared via a 2-step protocol similar to that described for Example 132, here starting from boronic ester 21 (188 mg, 0.33 mmol) and vinyl iodide 7 (98 mg, 0.33 mmol). MS m/z=481.2 [M+H]+. 1H NMR (400 MHz, DMSO-d6) δ 8.94-8.87 (m, 1H), 8.31 (d, J=2.1 Hz, 1H), 7.81 (dd, J=8.0, 2.4 Hz, 1H), 7.75 (ddd, J=8.7, 4.7, 2.4 Hz, 1H), 7.31 (dd, J=12.3, 8.6 Hz, 1H), 7.03 (d, J=39.2 Hz, 1H), 6.33 (s, 2H), 4.68 (m, 1H), 4.40 (d, J=8.1 Hz, 1H), 3.84 (dd, J=8.1, 2.8 Hz, 1H), 3.26 (dt, J=7.9, 3.7 Hz, 1H), 3.09 (dd, J=13.9, 3.2 Hz, 1H), 2.89 (dd, J=13.9, 4.0 Hz, 1H), 2.54 (d, J=6.3 Hz, 3H). 19F NMR (400 MHz, DMSO-d6) δ −76.220 (s, 3F), −109.740 (s, 1F), −113.575 (s, 1F).

Example 139: (4aS,5S,7aS)-7a-(2-fluoro-5-((Z)-2-fluoro-2-(5-(trifluoromethyl)pyridin-2-yl)vinyl)phenyl)-5-(trifluoromethyl)-4a,5,7,7a-tetrahydro-4H-furo[3,4-d][1,3]thiazin-2-amine

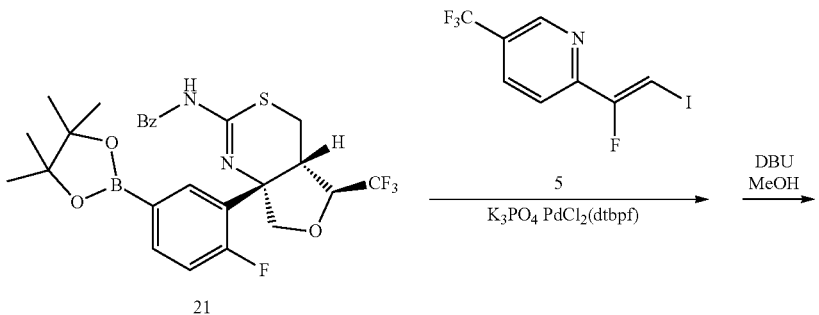

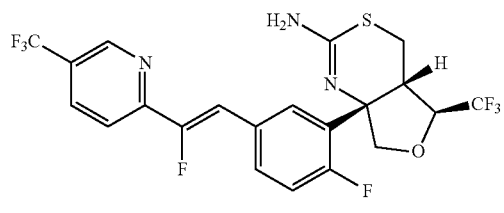

139

This compound (55 mg, 28% overall yield) as a white solid was prepared via a 2-step protocol similar to that described for Example 132, here starting from boronic ester 21 (214 mg, 0.39 mmol) and vinyl iodide 5 (124 mg, 0.39 mmol). MS m/z=510.2 [M+H]$^+$. $^1$H NMR (400 MHz, DMSO-d$_6$) δ 9.04 (s, 1H), 8.39-8.32 (m, 1H), 7.95-7.84 (m, 2H), 7.82-7.74 (m, 1H), 7.38-7.24 (m, 2H), 6.35 (s, 2H), 4.68 (m, 1H), 4.41 (d, J=8.1 Hz, 1H), 3.84 (dd, J=8.0, 2.7 Hz, 1H), 3.26 (dd, J=7.7, 3.9 Hz, 1H), 3.09 (dd, J=14.2, 3.1 Hz, 1H), 2.89 (dd, J=14.0, 3.9 Hz, 1H). $^{19}$F NMR (400 MHz, DMSO-d$_6$) δ −60.825 (s, 3F), −76.217 (s, 3F), −109.449 (s, 1F), −123.777 (s, 1F).

Example 140: 6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)-5-chloronicotinonitrile

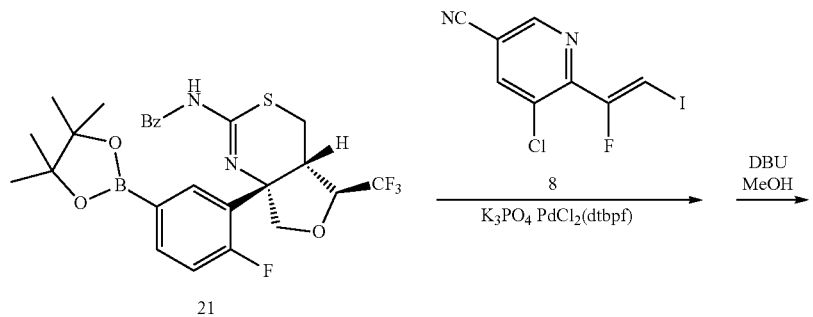

140

This compound (60 mg, 11% overall yield) as a white solid was prepared via a 2-step protocol similar to that described for Example 132, here starting from boronic ester 21 (600 mg, 1.09 mmol) and vinyl iodide 8 (335 mg, 1.09 mmol). MS m/z=501.2 [M+H]$^+$. $^1$H NMR (400 MHz, DMSO-d$_6$) δ 9.06 (d, J=3.2 Hz, 1H), 8.74 (d, J=1.8 Hz, 1H), 7.87-7.81 (m, 1H), 7.75 (q, J=4.8, 3.2 Hz, 1H), 7.33 (dd, J=12.3, 8.5 Hz, 1H), 7.08 (dd, J=38.1, 2.7 Hz, 1H), 6.33 (s, 2H), 4.68 (m, 1H), 4.41 (d, J=8.1 Hz, 1H), 3.88-3.80 (m, 1H), 3.25 (dd, J=8.0, 4.0 Hz, 1H), 3.09 (dd, J=14.0, 3.2 Hz, 1H), 2.89 (dd, J=13.9, 3.9 Hz, 1H). $^{19}$F NMR (400 MHz, DMSO-d$_6$) δ −76.214 (s, 3F), −108.987 (s, 1F), −114.129 (s, 1F).

Example 141: 6-((Z)-2-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-1-fluorovinyl)nicotinonitrile and 6-((Z)-2-(3-((4aS,5R,7aR)-2-amino-5-(trifluoromethyl)-4a,5,7,7a-tetrahydro-4H-furo[3,4-d][1,3]oxazin-7a-yl)-4-fluorophenyl)-1-fluorovinyl)nicotinonitrile; and Example 142: 6-((Z)-2-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-1-fluorovinyl)nicotinonitrile; and Example 143: 6-((Z)-2-(3-((4aS,5R,7aR)-2-amino-5-(trifluoromethyl)-4a,5,7,7a-tetrahydro-4H-furo[3,4-d][1,3]oxazin-7a-yl)-4-fluorophenyl)-1-fluorovinyl)nicotinonitrile Preparation of 141a To a solution of racemic 19f (2.46 g, 6.87 mmol) in THF (25 mL) under a nitrogen atmosphere at 45° C. was added a solution of benzoyl isothiocyanate (Sigma-Aldrich, St. Louis, Mo., USA) (0.92 mL, 6.88 mmol) in THF (12 mL) dropwise in a period of 45 minutes. Once the addition was complete, the mixture was stirred for another 10 minutes. CDI (Sigma-Aldrich, St. Louis, Mo., USA) (1.25 g, 7.71 mmol) was added in one portion and the reaction stirred for another 90 minutes. The mixture was evaporated to dryness under reduced pressure and the crude was suspended in DCM (50 mL). It was stirred for 5 minutes after which a thick white precipitate formed. Heptane (30 mL) was added slowly and the mixture stirred for another 20 minutes. The

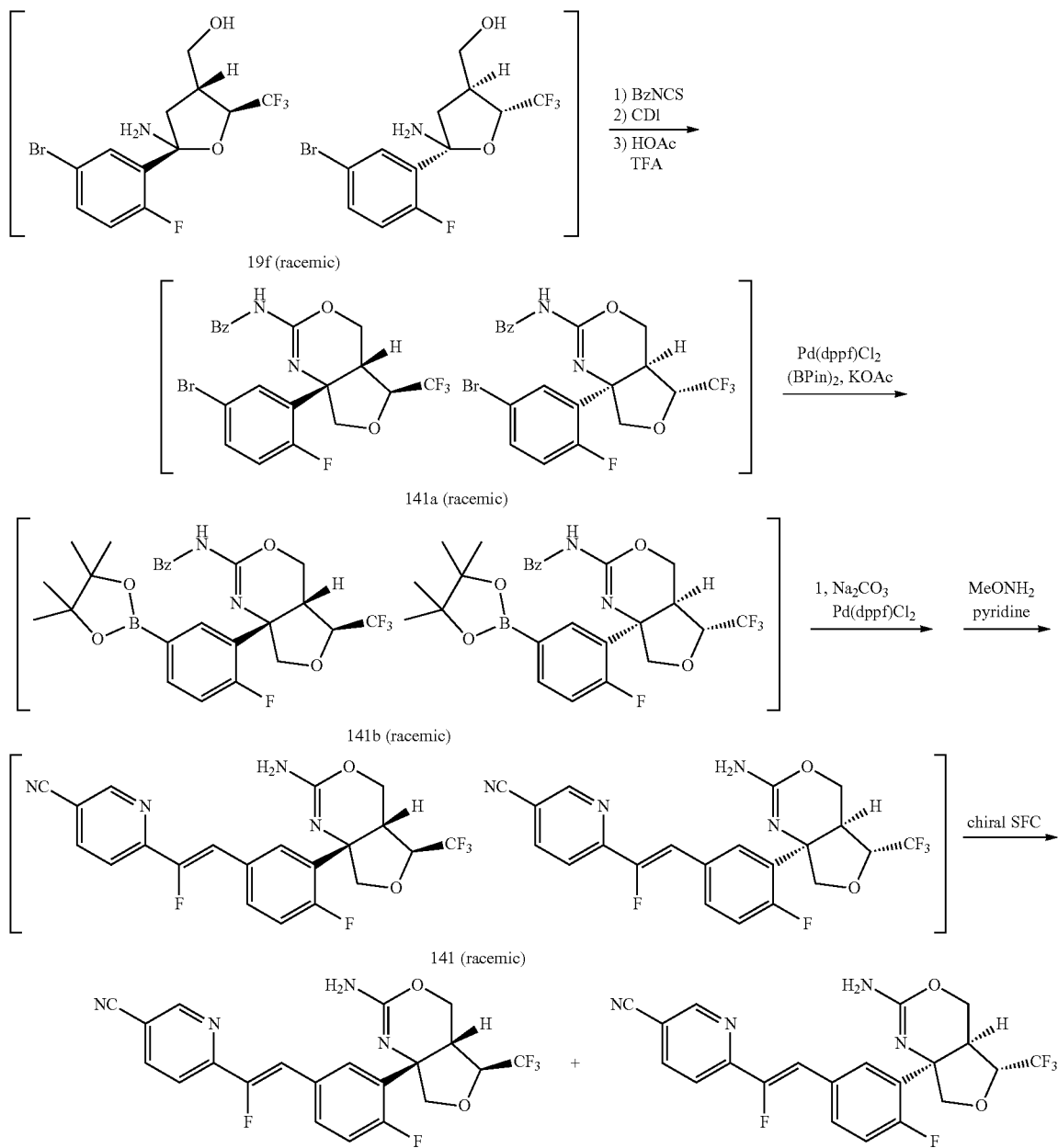

slurry was filtered through a sintered glass frit and the solid was washed with DCM/heptane (1/1, 10 mL). The solid was collected and dried to give a racemic mixture of ((2S,3R,4S)-4-(3-benzoylthioureido)-4-(5-bromo-2-fluorophenyl)-2-(trifluoromethyl)tetrahydrofuran-3-yl)methyl 1H-imidazole-1-carboxylate and ((2R,3S,4R)-4-(3-benzoylthioureido)-4-(5-bromo-2-fluorophenyl)-2-(trifluoromethyl)tetrahydrofuran-3-yl)methyl 1H-imidazole-1-carboxylate (2.83 g, 4.60 mmol, 67% yield) which was used without further purification. MS m/z=637.4/639.4 [M+Na]+.

The above obtained racemic mixture of ((2S,3R,4S)- and ((2R,3S,4R)-(4-(3-benzoylthioureido)-4-(5-bromo-2-fluorophenyl)-2-(trifluoromethyl)tetrahydrofuran-3-yl)methyl 1H-imidazole-1-carboxylate (2.40 g, 3.90 mmol) was dissolved in acetic acid (50 mL) and heated to reflux for 2 hours. The mixture was then evaporated to dryness under reduced pressure. The residue was dissolved in TFA (50 mL) and heated at 80° C. bath for 2 hours. The mixture was evaporated to dryness under reduced pressure. The residue was dissolved in EtOAc (150 mL) then washed with 0.5 N aqueous NaOH (75 mL) followed by brine (50 mL) and concentrated in vacuo. Purification of the residue using silica gel chromatography (25 to 75% EtOAc in heptane) gave 141a (0.39 g, 21% yield). MS m/z=487.2/489.2 [M+H]+.

Preparation of 141b

A solution of 141a (200 mg, 0.41 mmol) in 1,4-dioxane (3 mL) was sparged with argon for 5 minutes then treated with bis(pinacolato)diboron (136 mg, 0.53 mmol), [1,1'-bis(diphenylphosphino)ferrocene]-dichloropalladium(II) complex with dichloromethane (17 mg, 0.02 mmol), potassium acetate (121 mg, 1.23 mmol) and heated at 100° C. for 1 hour. Additional bis(pinacolato)diboron (136 mg, 0.53 mmol), [1,1'-bis(diphenylphosphino)ferrocene]dichloropalladium(II) complex with dichloromethane (17 mg) and potassium acetate (121 mg) were added in and heating was continued at 100° C. for an additional 2 hours. After cooling to room temperature, the reaction mixture was partitioned between EtOAc (20 mL) and sat'd aqueous NaHCO$_3$ (10 mL). The organic solution was dried over MgSO$_4$, concentrated under reduced pressure, then purified by silica gel chromatography (0 to 20% EtOAc in heptane) to afford boronic ester 141b (150 mg, 0.28 mmol, 68% yield) as a colorless film. MS (ESI+ve ion) m/z: [M+1]=535.0

Preparation of Example 141

A suspension of boronic ester 141b (150 mg, 0.42 mmol), vinyl iodide 1 (115 mg, 0.42 mmol), [1,1'-bis(diphenylphosphino)ferrocene]-dichloropalladium(II) complex with dichloromethane (Sigma-Aldrich Chemical Company, Inc., St. Louis, Mo., USA, 12 mg, 0.014 mmol), sodium carbonate (89 mg, 0.84 mmol) in 1,4-dioxane (2 mL) and water (1 mL) was sparged with argon for 3 minutes then heated to 70° C. for 1 hour. The reaction mixture was partitioned between EtOAc (15 mL) and sat'd aqueous NaHCO$_3$ (7 mL). The organic was concentrated under reduced pressure then purified by silica gel chromatography (0 to 20% EtOAc in heptane) to afford a racemic mixture of N-((4aR,5S,7aS)-7a-(5-((Z)-2-(5-cyanopyridin-2-yl)-2-fluorovinyl)-2-fluorophenyl)-5-(trifluoromethyl)-4a,5,7,7a-tetrahydro-4H-furo[3,4-d][1,3]oxazin-2-yl)benzamide and N-((4aS,5R,7aR)-7a-(5-((Z)-2-(5-cyanopyridin-2-yl)-2-fluorovinyl)-2-fluorophenyl)-5-(trifluoromethyl)-4a,5,7,7a-tetrahydro-4H-furo[3,4-d][1,3]oxazin-2-yl)benzamide (75 mg, 48% yield) as a brown solid. MS (ESI+ve ion) m/z: [M+1]=555.0.

To the above obtained brown solid (75 mg, 0.13 mmol) was added methoxylamine hydrochloride (40 mg, 0.41 mmol) and pyridine (460 µL, 5.41 mmol) and the resulting mixture was heated to 70° C. for 45 minutes. The reaction was partitioned between EtOAc (15 mL) and sat'd aqueous NaHCO$_3$ (10 mL). The organic solution was concentrated in vacuo. The residue was purified by silica gel chromatography (0 to 80% EtOAc (0.3% AcOH) in heptane (0.3% AcOH)) to afford Example 141 as an AcOH salt (30 mg, 0.06 mmol, 44% yield) as a white solid. MS (ESI+ve ion) m/z: [M+1]=451.1. $^1$H NMR (400 MHz, DMSO-d$_6$) δ 11.99 (br s, 1H), 9.07 (d, J=1.17 Hz, 1H), 8.45 (dd, J=1.96, 8.22 Hz, 1H), 8.10 (dd, J=1.96, 7.82 Hz, 1H), 7.88 (d, J=8.22 Hz, 1H), 7.73-7.80 (m, 1H), 7.26-7.40 (m, 2H), 5.85 (br s, 2H), 4.50-4.59 (m, 1H), 4.31 (d, J=8.02 Hz, 1H), 3.99-4.05 (m, 1H), 3.86-3.92 (m, 1H), 3.75-3.81 (m, 1H), 3.18-3.23 (m, 1H), 1.89-1.91 (s, 3H). $^{19}$F NMR (376 MHz, DMSO-d$_6$) δ ppm −76.63 (s, 3F), −109.73 (s, 1F), −124.23 (s, 1F).

Preparation of Examples 142 and 143

Example 141 as an AcOH salt (20 mg) was subjected to chiral SFC to provide two compounds: the 1$^{st}$ eluent was Example 142 (8 mg) as a white solid and the 2$^{nd}$ eluent was Example 143 (8 mg) as a white solid. Preparative SFC purification method: (OD-H (250×30 mm, 5 µm)); mobile phase (65:35 (A:B), A=liquid CO$_2$, B=20 mM ammonia in MeOH); flow rate 75 mL/min; wave length 210 nm; BPI (Bar) 102; Sample conc. 10 mg/mL; Inj. Vol. 2.0 mL; run time 5 minutes. The absolute stereochemistry was arbitrarily assigned.

6-((Z)-2-(3-((4aR,5S,7aS)-2-Amino-5-(trifluoromethyl)-4a,5,7,7a-tetrahydro-4H-furo[3,4-d][1,3]oxazin-7a-yl)-4-fluorophenyl)-1-fluorovinyl)nicotinonitrile (142): MS (ESI+ve ion) m/z: [M+1]=451.1. $^1$H NMR (400 MHz, DMSO-d$_6$) δ 9.07 (s, 1H), 8.44 (dd, J=1.96, 8.22 Hz, 1H), 8.10 (dd, J=1.96, 7.63 Hz, 1H), 7.87 (d, J=8.22 Hz, 1H), 7.73-7.80 (m, 1H), 7.26-7.40 (m, 2H), 5.84 (s, 2H), 4.49-4.60 (m, 1H), 4.31 (d, J=8.41 Hz, 1H), 4.01 (d, J=11.54 Hz, 1H), 3.89 (d, J=11.35 Hz, 1H), 3.78 (d, J=8.02 Hz, 1H), 3.20 (d, J=7.24 Hz, 1H).

6-((Z)-2-(3-((4aS,5R,7aR)-2-Amino-5-(trifluoromethyl)-4a,5,7,7a-tetrahydro-4H-furo[3,4-d][1,3]oxazin-7a-yl)-4-fluorophenyl)-1-fluorovinyl)nicotinonitrile (143): MS (ESI+ve ion) m/z: [M+1]=451.1. $^1$H NMR (400 MHz, DMSO-d$_6$) δ 9.07 (s, 1H), 8.44 (dd, J=1.96, 8.22 Hz, 1H), 8.10 (dd, J=1.96, 7.63 Hz, 1H), 7.87 (d, J=8.22 Hz, 1H), 7.73-7.80 (m, 1H), 7.26-7.40 (m, 2H), 5.84 (s, 2H), 4.49-4.60 (m, 1H), 4.31 (d, J=8.41 Hz, 1H), 4.01 (d, J=11.54 Hz, 1H), 3.89 (d, J=11.35 Hz, 1H), 3.78 (d, J=8.02 Hz, 1H), 3.20 (d, J=7.24 Hz, 1H).

Example 144: 6-((Z)-2-(3-((4aS,5S,7aS)-2-amino-5-(difluoromethyl)-4a,5,7,7a-tetrahydro-4H-furo[3,4-d][1,3]thiazin-7a-yl)-4-fluorophenyl)-1-fluorovinyl)nicotinonitrile

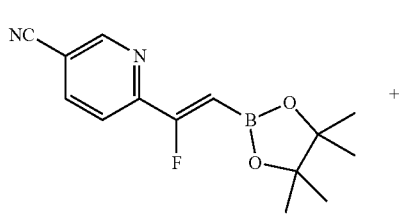

25

-continued

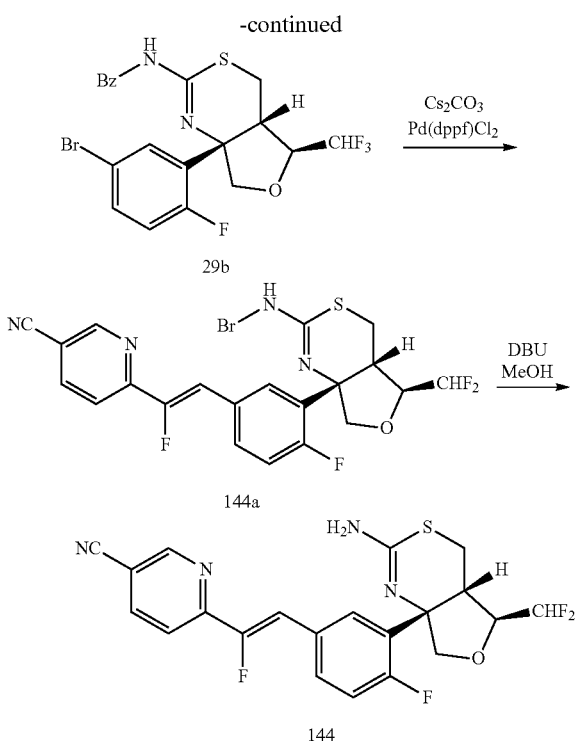

Preparation of N-((4aS,5S,7aS)-7a-(5-((Z)-2-(5-cyanopyridin-2-yl)-2-fluorovinyl)-2-fluorophenyl)-5-(difluoromethyl)-4a,5,7,7a-tetrahydro-4H-furo[3,4-d][1,3]thiazin-2-yl)benzamide (144a)

A mixture of N-((4aS,5S,7aS)-7a-(5-bromo-2-fluorophenyl)-5-(difluoromethyl)-4a,5,7,7a-tetrahydro-4H-furo[3,4-d][1,3]thiazin-2-yl)benzamide (29b) (0.10 g, 0.21 mmol), boronic ester 25 (0.17 g, 0.62 mmol) and cesium carbonate (0.20 g, 0.62 mmol) in 1,4-dioxane (9 mL) and water (3 mL) was purged with nitrogen for 2 minutes then treated with Pd(dppf)Cl$_2$—CH$_2$Cl$_2$ adduct (9 mg). The mixture was heated at 80° C. for 5 hours. After cooling to room temperature, the reaction mixture was diluted with water (5 mL) and extracted with EtOAc (2×20 mL). The organic solution was washed with brine (10 mL), dried over Na$_2$SO$_4$, filtered and concentrated in vacuo. The residue was purified via silica gel chromatography (10% to 20% EtOAc in petroleum ether) to afford 144a (0.08 g, 70% yield) as an off-white solid. MS (ESI positive ion) m/z: 553.1 (M+1). $^1$H NMR (400 MHz, CHLOROFORM-d) δ 8.84 (s, 1H), 8.11 (d, J=7.5 Hz, 2H), 8.04 (dd, J=8.2, 2.2 Hz, 1H), 7.86-7.78 (m, 1H), 7.77-7.68 (m, 2H), 7.59 (t, J=7.2 Hz, 1H), 7.54-7.48 (m, 2H), 7.32 (s, 1H), 7.26-7.20 (m, 1H), 6.03 (td, J=55.6, 3.2 Hz, 1H), 4.70-4.56 (m, 1H), 4.61-4.52 (m, 1H), 4.08-4.06 (m, 1H), 3.58 (s, 1H), 3.31-3.22 (m, 1H), 2.91 (dd, J=13.8, 3.8 Hz, 1H), 2.00-1.90 (m, 1H); $^{19}$F NMR (376 MHz, CHLOROFORM-d) δ −109.09 (s, 1F), −120.96 (s, 1F), −132.12 (d, 2F).

Preparation of 6-((Z)-2-(3-((4aS,5S,7aS)-2-amino-5-(difluoromethyl)-4a,5,7,7a-tetrahydro-4H-furo[3,4-d][1,3]thiazin-7a-yl)-4-fluorophenyl)-1-fluorovinyl)nicotinonitrile (144)

A solution of N-((4aS,5S,7aS)-7a-(5-((Z)-2-(5-cyanopyridin-2-yl)-2-fluorovinyl)-2-fluorophenyl)-5-(difluoromethyl)-4a,5,7,7a-tetrahydro-4H-furo[3,4-d][1,3]thiazin-2-yl)benzamide (144a) (0.08 g, 0.14 mmol) and DBU (0.07 mL, 0.44 mmol) in methanol (2 mL) was stirred at 70° C. for 3 hours. The reaction mixture was cooled to room temperature and concentrated under reduced pressure. The residue was diluted with water (20 mL) and extracted with EtOAc (3×20 mL). The combined organic solution was washed with brine (20 mL), dried over Na$_2$SO$_4$ and concentrated under reduced pressure. The residue was purified by reverse-phase preparative HPLC [Phenomenex Luna C8(2), (150×21.2 mm, 5 micron); mobile phase: 0.1% TFA in CH$_3$CN/H$_2$O, gradient 2% to 5%; flow rate: 15 mL/min; run time: 30 min] to provide 6-((Z)-2-(3-((4aS,5S,7aS)-2-amino-5-(difluoromethyl)-4a,5,7,7a-tetrahydro-4H-furo[3,4-d][1,3]thiazin-7a-yl)-4-fluorophenyl)-1-fluorovinyl)nicotinonitrile (144) as a TFA salt (25 mg, 39% yield) as an off-white solid. MS (ESI positive ion) m/z: 449.1 (M+1). $^1$H NMR (400 MHz, DMSO-d$_6$) δ 10.75 (s, 1H), 9.45-8.27 (m, 3H), 8.33-7.68 (m, 3H), 7.65-7.22 (m, 2H), 6.27 (td, J=54.8, 3.6 Hz, 1H), 5.32-3.79 (m, 4H), 3.71-3.39 (m, 3H). $^{19}$F NMR (376 MHz, DMSO-d$_6$) δ −73.57 (s, 3F), −109.60 (s, 1F), −123.57 (s, 1F), −126.71 (dd, 1F), −130.19 (dd, 1F).

Example 145: 6-((Z)-2-(3-((4aR,5R,7aR)-2-Amino-5-(difluoromethyl)-4a,5-dihydro-4H-furo[3,4-d][1,3]thiazin-7a(7H)-yl)-4-fluorophenyl)-1-fluorovinyl)nicotinonitrile

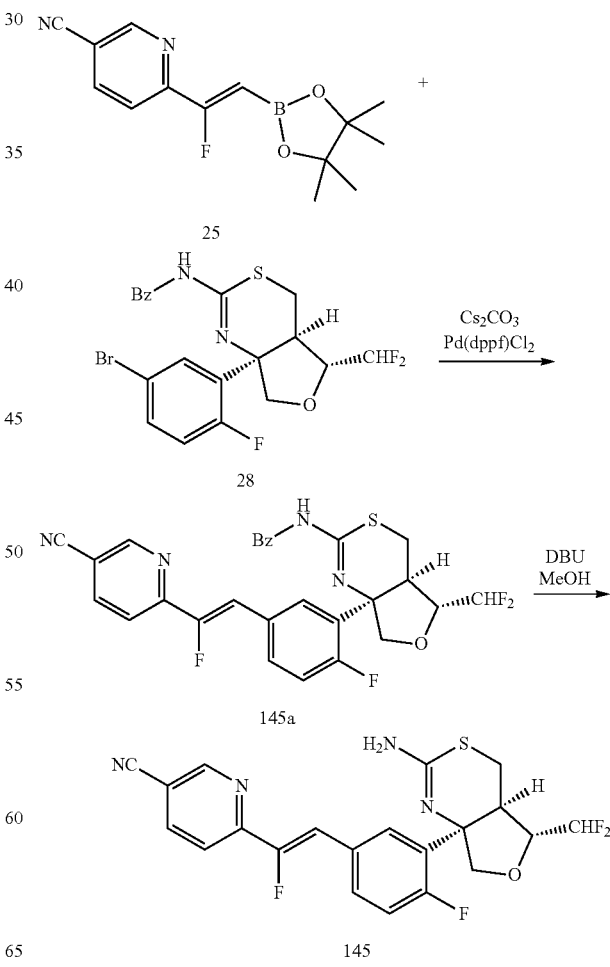

N-((4aR,5R,7aR)-7a-(5-((Z)-2-(5-Cyanopyridin-2-yl)-2-fluorovinyl)-2-fluorophenyl)-5-(difluoromethyl)-4a,5,7,7a-tetrahydro-4H-furo[3,4-d][1,3]thiazin-2-yl)benzamide (145a, 120 mg, 70% yield) as a light-yellow solid was prepared in a fashion similar to that described for compound 144a, here starting from N-((4aR,5R,7aR)-7a-(5-bromo-2-fluorophenyl)-5-(difluoromethyl)-4a,5,7,7a-tetrahydro-4H-furo[3,4-d][1,3]thiazin-2-yl)benzamide (28) (150 mg, 0.31 mmol) and boronic ester 25 (169 mg, 0.62 mmol). MS (ESI positive ion) m/z: 553.10 (M+1). $^{1}$H NMR (400 MHz, CHLOROFORM-d) δ 8.84 (s, 1H), 8.12-8.02 (m, 3H), 7.86-7.80 (m, 1H), 7.74-7.68 (m, 2H), 7.62-7.56 (m, 1H), 7.54-7.48 (m, 2H), 7.28 (s, 1H), 7.25-7.20 (m, 1H), 6.04 (td, J=55.6, 3.2 Hz, 1H), 4.72-4.64 (m, 1H), 4.60-4.56 (m, 1H), 4.08-4.04 (m, 1H), 3.58-3.54 (m, 1H), 3.30-3.24 (m, 1H), 2.92 (d, J=13.6 Hz, 1H), 2.01-1.92 (m, 1H); $^{19}$F NMR (376 MHz, CHLOROFORM-d) δ −112.12 (s, 1F), −121.06 (s, 1F), −132.12 (d, 2F).

Preparation of 6-((Z)-2-(3-((4aR,5R,7aR)-2-Amino-5-(difluoromethyl)-4a,5-dihydro-4H-furo[3,4-d][1,3]thiazin-7a(7H)-yl)-4-fluorophenyl)-1-fluorovinyl)nicotinonitrile (145)

6-((Z)-2-(3-((4aR,5R,7aR)-2-Amino-5-(difluoromethyl)-4a,5-dihydro-4H-furo[3,4-d][1,3]thiazin-7a(7H)-yl)-4-fluorophenyl)-1-fluorovinyl)nicotinonitrile as a TFA salt (145) (12 mg, 12% yield) as an off-white solid was prepared in a fashion similar to that described for compound 144, here starting from 145a (120 mg, 0.22 mmol) and DBU (66 mg, 0.43 mmol) in methanol (5 mL). MS (ESI positive ion) m/z: 449.1 (M+1). $^{1}$H NMR (400 MHz, DMSO-d$_6$) δ 10.75 (s, 1H), 9.45-8.27 (m, 3H), 8.33-7.68 (m, 3H), 7.65-7.22 (m, 2H), 6.27 (td, J=54.8, 3.6 Hz, 1H), 5.32-3.79 (m, 4H), 3.71-3.39 (m, 3H). $^{19}$F NMR (376 MHz, DMSO-d6) −73.57 (s, 3F), −110.99 (s, 1F), −125.87 (s, 1F), −127.87 (dd, 1F), −132.97 (dd, 1F).

Example 146: (4aS,5S,7aS)-5-(difluoromethyl)-7a-(2-fluoro-5-((Z)-2-fluoro-2-(5-(trifluoromethyl)pyridin-2-yl)vinyl)phenyl)-4a,5,7,7a-tetrahydro-4H-furo[3,4-d][1,3]thiazin-2-amine

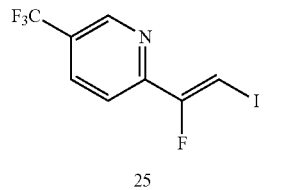

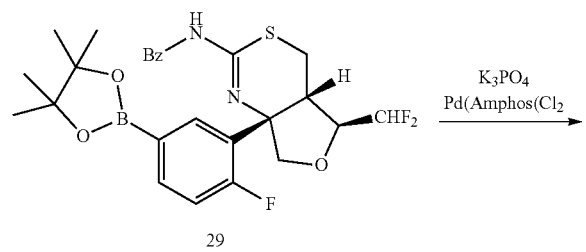

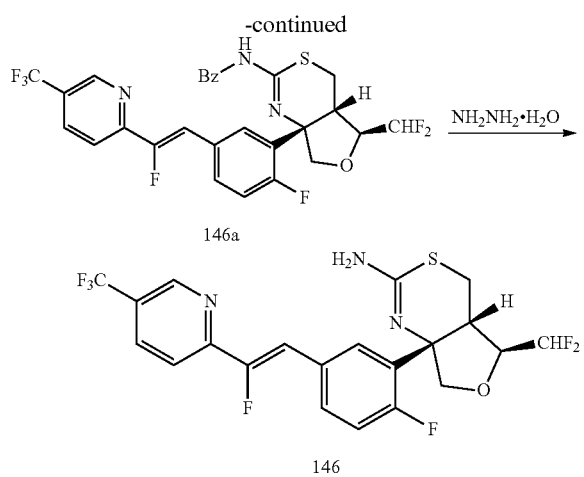

Preparation of N-((4aS,5S,7aS)-5-(difluoromethyl)-7a-(2-fluoro-5-((Z)-2-fluoro-2-(5-(trifluoromethyl)pyridin-2-yl)vinyl)phenyl)-4a,5,7,7a-tetrahydro-4H-furo[3,4-d][1,3]thiazin-2-yl)benzamide (146a)

A mixture of N-((4aS,5S,7aS)-5-(difluoromethyl)-7a-(2-fluoro-5-(4,4,5,5-tetramethyl-1,3,2-dioxaborolan-2-yl)phenyl)-4a,5,7,7a-tetrahydro-4H-furo[3,4-d][1,3]thiazin-2-yl)benzamide (29) (65 mg, 0.12 mmol), potassium phosphate tribasic (52 mg, 0.24 mmol) and (Z)-2-(1-fluoro-2-iodovinyl)-5-(trifluoromethyl)pyridine (5) (47 mg, 0.14 mmol) in 1,4-dioxane (6 mL) and water (2 mL) was degassed for 5 minutes then treated with Pd(Amphos)Cl$_2$ (5 mg). The mixture was degassed for 2 minutes and heated at 90° C. for 4 hours. The reaction mixture was allowed to cool to room temperature, diluted with water (5 mL) and extracted with EtOAc (2×20 mL). The organic solution was washed with brine (20 mL), dried over Na$_2$SO$_4$, filtered and concentrated in vacuo. The resulting yellow oil was purified on silica gel column (20% to 30% EtOAc in hexanes) to provide 145a (35 mg, 48% yield) as an off-white solid. MS (ESI positive ion) m/z: 596.1 (M+1).

Preparation of (4aS,5S,7aS)-5-(difluoromethyl)-7a-(2-fluoro-5-((Z)-2-fluoro-2-(5-(trifluoromethyl)pyridin-2-yl)vinyl)phenyl)-4a,5,7,7a-tetrahydro-4H-furo[3,4-d][1,3]thiazin-2-amine (146)

A solution of N-((4aS,5S,7aR)-5-(difluoromethyl)-7a-(3-((Z)-2-fluoro-2-(5-(trifluoromethyl)pyridin-2-yl)vinyl)phenyl)-4a-methyl-4a,5,7,7a-tetrahydro-4H-furo[3,4-d][1,3]thiazin-2-yl)benzamide (146a) (35 mg, 0.06 mmol) and hydrazine hydrate (10 μL, 0.30 mmol) in ethanol (2 mL) was stirred for 4 hours at ambient temperature. The reaction mixture was diluted with water (10 mL) and extracted with EtOAc (2×20 mL). The organic extracts were washed with brine (10 mL), dried over Na$_2$SO$_4$, filtered and concentrated in vacuo. The resulting yellow oil was purified by reverse-phase preparative HPLC [Phenomenex Luna C8(2), (150× 21.2 mm, 5 micron); mobile phase: 0.1% TFA in CH$_3$CN/ H$_2$O, gradient 80% to 100%; flow rate: 15 mL/min; run time: 30 min] to give (4aS,5S,7aS)-5-(difluoromethyl)-7a-(2-fluoro-5-((Z)-2-fluoro-2-(5-(trifluoromethyl)pyridin-2-yl)vinyl)phenyl)-4a,5,7,7a-tetrahydro-4H-furo[3,4-d][1,3]thiazin-2-amine as a TFA salt (146) (12 mg, 42% yield) as an off-white solid. MS (ESI positive ion) m/z: 492.1 (M+1).

$^1$H NMR (400 MHz, METHANOL-d$_4$) δ 8.92 (s, 1H), 8.26-8.14 (m, 1H), 7.92-7.67 (m, 3H), 7.26-7.15 (m, 1H), 6.10 (dd, J=55.7, 4.0 Hz, 1H), 4.60 (d, J=8.3 Hz, 1H), 4.46 (qd, J=8.9, 4.5 Hz, 1H), 3.87 (dd, J=8.3, 2.6 Hz, 1H), 3.26 (dd, J=8.1, 3.9 Hz, 1H), 3.19-3.08 (m, 2H), 2.94 (dd, J=13.5, 4.1 Hz, 1H). $^{19}$F NMR (376 MHz, METHANOL-d$_4$) δ −63.94 (s, 3F), −111.06 (s, 1F), −125.82 (s, 2F), −126.91 (d, 2F), −132.10 (d, 2F).

Example 147: (4aS,5R,7aS)-7a-(5-((Z)-2-(5-(difluoromethyl)pyrazin-2-yl)-2-fluorovinyl)-2-fluorophenyl)-5-methyl-4a,5,7,7a-tetrahydro-4H-furo[3,4-d][1,3]thiazin-2-amine

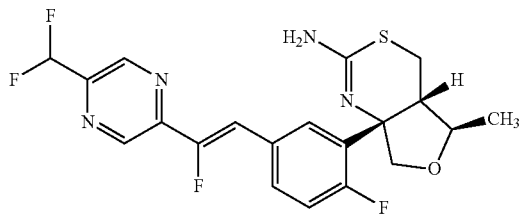

147

(4aS,5R,7aS)-7a-(5-((Z)-2-(5-(difluoromethyl)pyrazin-2-yl)-2-fluorovinyl)-2-fluorophenyl)-5-methyl-4a,5,7,7a-tetrahydro-4H-furo[3,4-d][1,3]thiazin-2-amine (146) is synthesized by methods disclosed herein or methods known to the person of ordinary skill in the art.

Example 148: (4aR,5S,7aR)-7a-(5-((Z)-2-(5-(difluoromethyl)pyrazin-2-yl)-2-fluorovinyl)-2-fluorophenyl)-5-methyl-4a,5,7,7a-tetrahydro-4H-furo[3,4-d][1,3]thiazin-2-amine

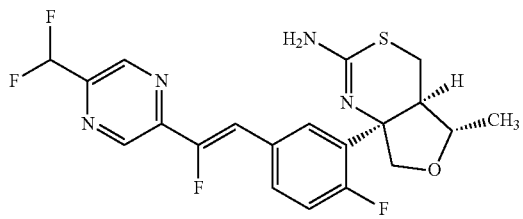

148

(4aR,5S,7aR)-7a-(5-((Z)-2-(5-(difluoromethyl)pyrazin-2-yl)-2-fluorovinyl)-2-fluorophenyl)-5-methyl-4a,5,7,7a-tetrahydro-4H-furo[3,4-d][1,3]thiazin-2-amine (147) is synthesized by methods disclosed herein or methods known to the person of ordinary skill in the art.

Biological Evaluation

Provided in this section is the biological evaluation of the specific examples provided herein. In particular, Table 2 contains biological activity data. The data presented in Table 2 provides the IC$_{50}$ (μM) for the specific examples obtained in a BACE1 enzyme assay, BACE1 cell assay, BACE2 enzyme assay and CatD assay.

TABLE 2

| Ex. No. | BACE1 Enzyme IC$_{50}$ (μM) | BACE1 Cell IC$_{50}$ (μM) | BACE2 Enzyme IC$_{50}$ (μM) | Cat D Enzyme IC$_{50}$ (μM) |
|---|---|---|---|---|
| 100 | 0.84667 | 1.245 | 0.495 | 544.3 |
| 101 | 0.0018417 | 0.00194 | 0.001033 | 49.1 |
| 102 | 0.00024133 | 0.00068175 | 0.00308 | 117.5 |
| 103 | 0.00186 | 0.005445 | 0.02715 | 246 |
| 104 | 0.804 | 2.26 | 7.48 | 654.4 |
| 105 | 0.0644 | 0.129 | 0.0569 | 181 |
| 106 | 0.5025 | 0.9845 | 6.39 | 815 |
| 107 | 0.011685 | 0.041 | 0.279 | >400.0 |
| 108 | 0.00271 | 0.016 | 0.034 | 14.8 |
| 109 | 0.0001495 | 0.0003115 | 0.00549 | 7.6 |
| 110 | 0.001565 | 0.004105 | 0.0855 | 4.5 |
| 111 | 0.00032 | 0.000807 | 0.00518 | 19.6 |
| 112 | 0.108 | 0.02005 | 0.136 | 1.32 |
| 113 | 0.0226 | 0.00935 | 0.0381 | 26.6 |
| 114 | 0.00896 | 0.00257 | 0.0306 | 38.7 |
| 115 | 0.0010065 | 0.000542 | 0.0153 | 18.9 |
| 116 | 0.00253 | 0.00188 | 0.052 | 28.6 |
| 117 | 0.0002865 | 0.00038 | 0.00279 | 13.2 |
| 118 | 0.0074525 | 0.019775 | 0.39433 | 125 |
| 119 | 0.009445 | 0.0265 | 0.51 | 105 |
| 120 | 0.0001865 | 0.0007605 | 0.034 | 6.3 |
| 121 | 0.00159 | 0.006795 | 0.258 | 47.9 |
| 122 | 0.00236 | 0.0086 | 0.353 | 87.9 |
| 123 | 0.004495 | 0.00478 | 0.214 | 36.5 |
| 124 | 0.002615 | 0.00269 | 0.0922 | 23.8 |
| 125 | 2.54 | 1.385 | 18 | 30.6 |
| 126 | 0.020067 | 0.0057417 | 0.33383 | 292.4 |
| 127 | 0.1029 | 0.0243 | 2.9 | 160 |
| 128 | 0.015333 | 0.0036367 | 0.34133 | 417.9 |
| 129 | 0.1075 | 0.0151 | 2.215 | >44.4 |
| 130 | 0.000405 | 0.000906 | 0.00178 | 25.8 |
| 131 | 0.003835 | 0.01145 | 0.427 | >400.0 |
| 132 | 0.4265 | 0.112 | 0.427 | >400.0 |
| 133 | 1.215 | 1.995 | 28 | 139 |
| 134 | 0.0014 | 0.0009 | 0.0043 | 59.3 |
| 135 | 0.0043 | 0.0018 | 0.0223 | 106 |
| 136 | 0.622 | 2.03 | 6.63 | >400.0 |
| 137 | 0.015 | 0.2 | 0.605 | 382 |
| 138 | 0.0272 | 0.116 | 1.14 | >400.0 |
| 139 | 0.0158 | 0.117 | 1.5 | >400.0 |
| 140 | 0.0087 | 0.0482 | 0.22 | 333 |
| 141 | 0.08625 | 0.1605 | 9.725 | 237 |
| 142 | 0.03715 | 0.05885 | 3.54 | >400.0 |
| 143 | 9.01 | 53.5 | 139.5 | 95.6 |
| 144 | 0.0216 | 0.01805 | 0.74133 | >400.0 |
| 145 | 0.04845 | 0.041 | 1.4 | >400.0 |

The results presented in Table 2 have been generated with the in vitro assays described below. These assays may be used to test any of the compounds described herein to assess and characterize a compound's ability to modulate BACE activity and to regulate the cleavage of Aβ precursor protein, thereby reducing or inhibiting the production of Aβ protein.

In Vitro Enzymatic BACE1 and BACE2 FRET (Fluorescence Resonance Energy Transfer) Assays The cDNAs for both human recombinant BACE1 and 2 with C-terminal 6-His Tags were cloned into transient protein expression vectors, which were subsequently transfected into mammalian cell lines. These recombinant proteins were further purified using Ni-NTA affinity chromatography (Qiagen). The assay buffer used in these screens was 0.05 M acetate, pH 4.5, 8% DMSO final, 100 μM genapol (which is a nonionic detergent, below its Critical Micelle Concentration). The β-secretase enzyme (0.02 nM for BACE1 and 0.64 nM for BACE2), which was pre-incubated for one hour with the test compound, typically in about luL of DMSO according to a serial dilution, was added thereto. The assay was effectively started by the addition of FRET substrate (50 nM) and the combination was incubated for one hour. The FRET assay was terminated by the addition of tris buffer, which raised the pH to neutrality, and the fluorescence was determined. The FRET substrate was a peptide with commercially available fluorophore and quencher, on opposite sides of the BACE cleavage site. The specific FRET substrate used in this assay was made by Amgen in-house. Commercially available FRET substrates, for example, the FRET substrate offered with the BACE1 FRET Assay Kit sold by ThermoFisher Scientific (Catalog Number P2985), may be used in this assay with the appropriate modifications, which are within the purview of the ability of a person with ordinary skill in the art. Proteolytic cleavage of the FRET substrate released quenching of fluorescence (excitation 488 nm and emission 590 nm).

The in vitro BACE FRET enzyme data for each of the Examples is provided in Table 2.

In Vitro BACE1 Cell-Based Assay

The cell-based assay measures inhibition or reduction of Aβ40 in conditioned medium of test compound treated cells expressing amyloid precursor protein. Cells stably expressing Amyloid Precursor Protein (APP) were plated at a density of 45K cells/well in 384 well plates (Corning/BioCoat 354663). The test compounds were then added to cells in 22-point dose response concentrations with the starting concentration being 62.5 µM. The compounds were diluted from stock solutions in DMSO and the final DMSO concentration of the test compounds on cells was 0.625%. The cells were cultivated overnight at 37° C. and 5% $CO_2$ in DMEM supplemented with 10% FBS. After 24 h of incubation with the test compounds, the conditioned media was collected and the Aβ40 levels were determined using HTRF (Homogeneous Time Resolved Fluorescence). The $IC_{50}$ of the compound was calculated from the percent of control or percent inhibition of Aβ 40 as a function of the concentration of the test compound.

The HTRF to detect Aβ40 was performed in 384 well plates (Costar 3658). The antibody pair that were used to detect Aβ 40 from cell supernatants were ConfAb40 antibody (Amgen in-house) and biotinylated 6E10 (BIOLEGEND). As an alternative to ConfAb40, a commercially available antibody, Anti-beta Amyloid 1-40 antibody [BDI350] from Abcam, Cambridge, Mass. 02139-1517 (Product code: ab20068), may be used in this assay. The concentrations were 0.35 µg/mL of ConfAb40 antibody and 1.33 µg/mL of 6E10-biotinylated antibody, as well as 4.5 µg/mL of Streptavidin Allophycocyanin Conjugate (ThermoFisher Scientific) in HTRF Buffer (1M Hepes pH 7.5, 1M NaCl, 1% BSA, 0.5% Tween 20).

The conditioned media was incubated with above antibodies and Streptavidin Allophycocyanin Conjugate for 30-60 minutes at 23° C. The final readout was performed on Envision from PerkinElmer.

The in vitro BACE cell-based data for each of the Examples is provided in Table 2.

In Vitro Enzymatic Cathepsin D (CatD) FRET Assay

Recombinant CatD was expressed in CHO cells. The assay buffer for CatD was 0.05 M citrate pH 3.5, 10% DMSO final, 5 mM CHAPS. The CatD enzyme (9 nM) was pre-incubated for one hour with inhibitors, typically in about 1 uL of DMSO according to a serial dilution, is added thereto. The assays was effectively started by the addition of different FRET substrates (20 nM for CatD) and the combination was incubated for one hour. The FRET assay was terminated with by addition of tris buffer, which raises the pH to neutrality, and the fluorescence was determined. The FRET substrate was a peptide with commercially available fluorophore and quencher, on opposite sides of the CatD cleavage site. The CatD substrate peptide sequence was based on sequence #1 of Table 1 from Gulnik et al., *FEBS Lett.* 413(2):379-384 (1997). Proteolytic cleavage of the FRET substrate released quenching of fluorescence (CatD excitation 500 nm and emission 580 nm).

Alternatively, a CatD assay may also be run according to the procedure described in Yasuda et al., *J. Biochem.* 125 (6):1137-1143 (1999). In addition, the CatD and Cathepsin E assays are described in International Patent Application Publication No. WO2011069934.

The in vitro CatD FRET assay data for each of the Examples is provided in Table 2, conducted by the first procedure described above. As shown by the high micromolar CatD data (very poorly active or inactive against CatD), the compounds disclosed herein possess the unexpected property of little to no ability to inhibit the activity of CatD. Thus, with this surprising selectivity profile, the compounds provided herein are believed to minimize, reduce or completely eliminate any risk of retinal atrophy and abnormal development of the eye and of the retinal pigmented epithelium as it relates to the normal function and activity of CatD.

In vivo Inhibition of β-Secretase

Several animal models, including mouse, rat, dog, and monkey, may be used to screen for inhibition of β-secretase activity in vivo following administration of a test compound. This procedure may be used to show that the compounds provided herein reduce the formation and/or deposition of Aβ peptide in the cerebrospinal fluid (CSF) as well as in the brain. Animals to be used in this experiment can be wild type, transgenic, or gene knockout animals. For example, the Tg2576 mouse model, prepared and conducted as described in Hsiao et al., *Science* 274:99-102 (1996), and other non-transgenic or gene knockout animals are useful to analyze in vivo inhibition of Aβ peptide production in the presence of test compounds.

Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of Aβ levels and test compound concentrations (Dovey et al., *J. Neurochem.,* 76(1):173-181 (2001)) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., *J. Pharmacol. Exp. Ther.* 313(2):902-908 (2005)), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of Aβ by specific sandwich ELISA assays based on ECL (Electrochemiluminescence) technology. For example, rat Aβ40 is measured using biotinylated-4G8 (Signet) as a capture antibody and Fab40 (an in-house antibody specific to the C-terminal of Aβ40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, Aβ peptide levels are measured for reduction by X % and Y % in cerebrospinal fluid and brain, respectively, when compared to the levels measured in the vehicle-treated or control mice. Alternatively, the antibody sold with the V-PLEX abeta40 Peptide (4G8) Kit, commercially available from Meso Scale Diagnostics (MSD), Rockville, Md. 20850-3173 (Catalog NO. K150SJE-1) may be used in this assay.

This procedure may be used to show that the compounds provided herein reduce the formation and/or deposition of Aβ peptide in the cerebrospinal fluid (CSF) as well as in the brain of a mouse or rat at either 3 mpk, 10 mpk or 30 mpk (mpk=mg compound per kg weight of the animal) dosing concentrations after 4 hrs.

The results presented in Table 3 were obtained using certain compounds described herein in the in vivo protocol described above.

TABLE 3

| Ex. No. | % Aβ reduction in rat CSF at 10 mpk | % Aβ reduction in rat brain at 10 mpk |
|---|---|---|
| 118 | 43 | 43 |
| 126 | 83 | 80 |
| 128 | 79 | 77 |

Methods of Use

According to the amyloid cascade hypothesis, cerebral deposition of amyloid-beta (Aβ) peptide is critical for Alzheimer's disease (AD) pathogenesis. Aβ peptide generation is initiated when β-secretase (BACE1) cleaves the amyloid precursor protein. De Meyer et al. re-affirm the putative role that the accumulation of Aβ peptide in cerebral spinal fluid (CSF) in a subject plays in the progression of symptoms, initially revealed as mild cognitive impairment, which ultimately leads to AD. *Arch Neurol.* 67(8):949-956 (2010). Aβ peptides generated from amyloid precursor protein (APP) by proteolytic cleavage, such as by aspartyl protease enzymes, including β-secretase (BACE) and γ-secretase, likely play a causal role in AD pathogenesis (Tanzi et al., *Cell* 120(4):545-555 (2005); Walsh et al., *Neuron* 44(1):181-193 (2004)). Although the precise mechanisms of Aβ toxicity are unclear, oligomeric forms of Aβ may contribute to cognitive decline by altering synaptic structure and function (Palop et al., *Nat. Neurosci.* 13(7): 812-818 (2010); Selkoe, *Behav. Brain Res.* 192(1):106-113 (2008); Shankar et al., *Nat. Med.* 14(8):837-842 (2008)). Transgenic mouse models that overexpress mutant APP and produce high levels of Aβ show amyloid plaque deposition, synaptic deficits, learning and memory impairments, and other behavioral abnormalities (Games et al., *Nature* 373: 523-527 (1995); Gotz et al., *Mol. Psychiatry* 9(7):664-683 (2004); Hsia et al., *Proc. Natl. Academy of Science* USA (96): 3228-3233, 1999; Hsiao et al., *Science* (274): 99-102, 1996, citing Harris et al, *Neuron* (68): 428-441, 2010).

For many years now, BACE1 has been a prime target for designing drugs to prevent or treat AD. Vassar et al., *Lancet Neurol.* 13:319-329 (2014). Several pharmaceutical companies are presently pursuing BACE1 inhibitors in human clinical trials. Id. at abstract.

For example, MK-8931, a small molecule inhibitor of BACE1, was the first molecule to enter phase I clinical trials. Yan, *Transl. Neurodegener.* 5(13):1-11 (2016) at page 4. MK-8931 was shown to have an excellent safety profile with no immediately noticeable side effects. Id. Merck was able to show that MK-8931 enters the brain and blocks β-secretase by showing that MK-8931 significantly reduced CSF Aβ peptide concentrations in a sustained and dose-dependent manner. Vassar et al., *Lancet Neurol.* 13:319-329 (2014) at page 323. MK-8931 is currently evaluated in a phase II/III clinical trial to assess the efficacy and safety of the compound for the treatment of AD patients with amnestic mild cognitive impairment (prodromal AD). Yan, *Transl. Neurodegener.* 5(13):1-11 (2016) at page 4.

Further, E2609, a BACE inhibitor identified by Eisai, showed significant reduction in Aβ peptide levels in the CSF and plasma in nonhuman primates. Yan, *Transl. Neurodegener.* 5(13):1-11 (2016) at page 7. E2609 did not show clinical significant safety concerns after repeated doses up to 200 mg in a phase I clinical trial. Id. After 14d dosing the Aβ peptide level reduction in the CSF was statistically significant compared to baseline (46.2% (25 mg), 61.9% (50 mg), 73.8% (100 mg), 79.9% (200 mg)). Id. In November 2014, Eisai stated that a phase II dose-finding study in patients with mild cognitive impairment (MCI) due to AD or prodromal AD and a positive amyloid PET-scan will be conducted in collaboration with Biogen.

Additionally, companies are also developing therapies targeting asymptomatic patients. JNJ-54861911, which was first developed by Shionogi & Co. in Japan and later in collaboration with Janssen, demonstrated an ability to cross the blood-brain barrier and to dose-dependently reduce Aβ peptide concentrations. Yan, *Transl. Neurodegener.* 5(13): 1-11 (2016) at pages 5-7. For example, an oral dose of 95 mg once daily achieved Aβ peptide reduction of up to 95% in CSF. Id. In October 2015, Janssen and Shionogi launched a phase trial targeting asymptomatic subjects that are at risk for developing Alzheimer's dementia. Id.

Similarly, Amgen and Novartis announced in late 2015 a collaboration to co-develop Novartis' BACE inhibitor CNP520. Yan, *Transl. Neurodegener.* 5(13):1-11 (2016) at page 8. The study that started in November 2015 is aimed at, inter alio, showing that CNP520 "can slow down the onset and progression of clinical symptoms associated with Alzheimer's disease (AD) in participants at the risk to develop clinical symptoms based on their age and genotype." https://clinicaltrials.govict2/show/NCT02565511 (last visited Oct. 23, 2016).

The compounds disclosed herein have been shown to modulate, and specifically inhibit the activity of the β-secretase enzymes as shown in Table 2 for specific examples disclosed herein, thereby reducing the generation of Aβ peptide. Accordingly, the compounds provided herein are useful for, for example, the prevention or treatment of β-secretase related diseases, including, but not limited to, AD. The compounds provided herein have the ability to modulate the activity of the β-secretase enzyme, thereby regulating the production of Aβ peptide and reducing the formation and deposition of Aβ peptide in both the cerebral spinal fluid as well as in the brain, resulting in a decrease of Aβ plaque in the brain.

More specifically, provided are the following uses for the compounds disclosed herein:

Provided are the compounds disclosed herein for reducing beta amyloid peptide levels in the cerebral spinal fluid of a subject.

Provided are the compounds disclosed herein for treating AD, cognitive impairment, or a combination thereof in a subject. In one embodiment, the compounds provided herein are useful for treating various stages and degrees of AD, including without limitation, mild, moderate and severe AD. In another embodiment, the compounds provided herein are useful for treating preclinical AD, mild cognitive impairment (MCI) due to AD, and dementia due to AD. In yet another embodiment, the compounds provided herein may be used to treat prodromal subjects.

Provided are the compounds disclosed herein for treating a neurological disorder selected from mild cognitive impairment, Down's syndrome, hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of AD, or a combination thereof in a subject.

Provided are the compounds disclosed herein for reducing formation of plaque in the brain of a subject.

As previously discussed, in certain embodiments, the compounds described herein are to be understood to include all stereoisomers, tautomers, isotopically-labelled forms thereof or pharmaceutically acceptable salts of any of the foregoing or solvates of any of the foregoing or amorphous and crystalline forms (polymorphs) of any of the foregoing. Accordingly, the scope of the methods and uses provided in the instant disclosure is to be understood to encompass also methods and uses employing all such forms.

Besides being useful for human treatment, the compounds provided herein may be useful for veterinary treatment of companion animals, exotic animals and farm animals, including mammals, rodents, and the like. For example, animals including horses, dogs, and cats may be treated with compounds provided herein.

Dosage, Formulation, and Route of Administration

The amount of compound(s) which is/are administered and the dosage regimen for treating neurological disorders and β-secretase mediated diseases with the compounds and/or compositions disclosed herein depends on a variety of factors, including the age, weight, sex and medical condition of the subject, the type of disease, the severity of the disease, the route and frequency of administration, and the particular compound employed. A daily dose of about 0.01 to 500 mg/kg, or in some embodiments, between about 0.01 and about 50 mg/kg, and in still other embodiments between about 0.01 and about 30 mg/kg body weight may be appropriate. In yet other embodiments, a daily dose of between about 0.1 and about 10 mg/kg body weight may be appropriate and should be useful for all uses disclosed herein. The daily dose can be administered a number of times a day such as from one to four doses per day.

While it may be possible to administer a compound disclosed herein alone in the uses described, the compound administered normally will be present as an active ingredient in a pharmaceutical composition. Thus, in another embodiment, provided herein is a pharmaceutical composition comprising a compound disclosed herein in combination with a pharmaceutically acceptable excipient, such as diluents, carriers, adjuvants and the like, and, if desired, other active ingredients. In one embodiment, a pharmaceutical composition may comprise a therapeutically effective amount of a compound disclosed herein.

The compound(s) disclosed herein may be administered by any suitable route in the form of a pharmaceutical composition adapted to such a route and in a dose effective for the treatment intended. The compounds and compositions present herein may, for example, be administered orally, mucosally, topically, rectally, pulmonarily, such as by inhalation spray, or parentally including intravascularly, intravenously, intraperitoneally, subcutaneously, intramuscularly, intrasternally, and by infusion techniques, in dosage unit formulations containing conventional pharmaceutically acceptable excipients such as carriers, adjuvants, and vehicles.

For oral administration, the pharmaceutical composition may be in the form of, for example, a tablet, capsule, suspension or liquid. The pharmaceutical composition is typically made in the form of a dosage unit containing a particular amount of the active ingredient. Examples of such dosage units are tablets or capsules. For example, these may contain an amount of active ingredient from about 1 to 2000 mg, from about 1 to 500 mg, and from about 5 to 150 mg.

For therapeutic purposes, the compounds provided herein are ordinarily combined with one or more diluents or other "excipients" appropriate to the indicated route of administration.

If orally administered on a per dose basis, the compounds provided herein may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other excipients and modes of administration are well and widely known in the pharmaceutical art. The active ingredient may also be administered by injection as a composition with suitable excipients including saline, dextrose, or water, and optionally comprising one or more of a cosolvent such as propylene glycol or emulsifier such as, for example, Tween 80. Such formulations may also include compounds such as a cyclodextrin (for example, Captisol).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and in some embodiments may be from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional excipients, such as preservatives, stabilizers, wetting agents, emulsifiers, buffers etc. Tablets and pills can additionally be prepared with enteric coatings. Such compositions may also comprise excipients, such as wetting, sweetening, flavoring, and perfuming agents. Accordingly, in yet another embodiment of the present disclosure, there is provided a method of manufacturing a medicament, the method comprising combining an amount of a compound according to Formula I with a pharmaceutically acceptable diluent to manufacture the medicament.

In yet another embodiment, the provided herein is a method of manufacturing a medicament for the treatment of AD, the method comprising combining an amount of a compound provided herein with a pharmaceutically acceptable excipient to manufacture the medicament.

Combinations

While the compounds disclosed herein can be dosed or administered as the sole active pharmaceutical agent, they can also be used in combination with one or more compounds provided herein or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound provided herein and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds provided herein may be in conjunction with additional therapies known to those skilled in the art in the prevention or treatment of β-secretase, γ-secretase and/or other reagents known in influence the formation and/or deposition of Aβ peptide, otherwise responsible for the formation of plaque in the brain.

If formulated as a fixed dose, such combination products employ the compounds disclosed herein within the accepted dosage ranges. The compounds provided herein may also be administered sequentially with other known medicinal agents. This disclosure is not limited in the sequence of administration; compounds provided herein may be administered either prior to, simultaneous with or after administration of the known anti-inflammatory agent.

The foregoing description is merely illustrative and is not intended to limit the disclosure to the described compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions.

All references, for example, a scientific publication or patent application publication, cited herein are incorporated herein by reference in their entirety and for all purposes to the same extent as if each reference was specifically and individually indicated to be incorporated by reference in its entirety for all purposes.

What is claimed is:

1. A compound of Formula I

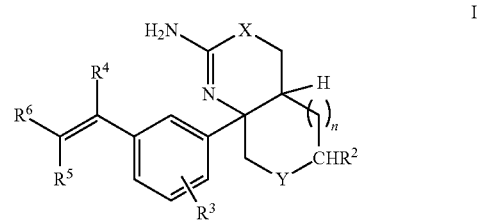

or a tautomer thereof, or a pharmaceutically acceptable salt of said compound or tautomer, wherein X is S or O;

Y is O or $NR^1$;

$R^1$ is $-C(O)C_{1-6}$alkyl, $-C(O)OC_{1-6}$alkyl, or 6-membered nitrogen-containing heteroaryl, wherein the $C_{1-6}$alkyl of $-C(O)C_{1-6}$alkyl and $-C(O)OC_{1-6}$alkyl is optionally substituted with 1 to 3 fluoro substituents, and wherein the heteroaryl is optionally substituted with 1 to 3 substituents independently selected from halogen, $C_{1-6}$alkyl, or $C_{1-6}$alkoxy;

$R^2$ is H or $C_{1-6}$alkyl, wherein the $C_{1-6}$alkyl is optionally substituted with 1 to 3 fluoro substituents;

$R^3$ is halogen;

$R^4$ is H or F;

one of $R^5$ and $R^6$ is F or H and the other of $R^5$ and $R^6$ is a 6-membered nitrogen-containing heteroaryl, which heteroaryl is optionally substituted with 1 to 3 substituents independently selected from halogen, $-CN$, $C_{1-6}$alkyl, $C_{1-6}$alkoxy, 2-propynyloxy, 2-butynyloxy, 3-butyn-2-yloxy, or (3-methyl-1,2,4-oxadiazol-5-yl)methoxy, wherein the $C_{1-6}$alkyl or $C_{1-6}$alkoxy is optionally substituted with 1 to 4 substituents independently selected from F or methoxy; and n is 0 or 1.

2. The compound according to claim 1, or a tautomer thereof, or a pharmaceutically acceptable salt of said compound or tautomer, wherein the compound of Formula I is a compound of Formula II

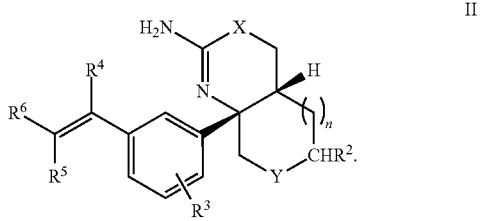

3. The compound according to claim 1, or a tautomer thereof, or a pharmaceutically acceptable salt of said compound or tautomer, wherein the compound of Formula I is a compound of Formula III

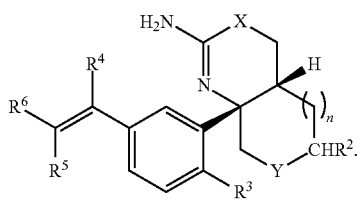

4. The compound according to claim 1, or a tautomer thereof, or a pharmaceutically acceptable salt of said compound or tautomer, wherein the compound of Formula I is a compound of Formula III'

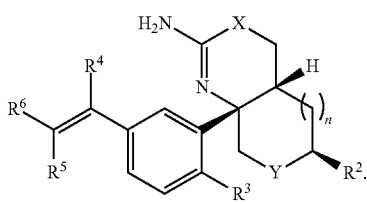

5. The compound according to claim 1, or a tautomer thereof, or a pharmaceutically acceptable salt of said compound or tautomer, wherein n is 0.

6. The compound according to claim 1, or a tautomer thereof, or a pharmaceutically acceptable salt of said compound or tautomer, wherein n is 1.

7. The compound according to claim 1, or a tautomer thereof, or a pharmaceutically acceptable salt of said compound or tautomer, wherein X is O.

8. The compound according to claim 1, or a tautomer thereof, or a pharmaceutically acceptable salt of said compound or tautomer, wherein X is S.

9. The compound according to claim 1, or a tautomer thereof, or a pharmaceutically acceptable salt of said compound or tautomer, wherein Y is O.

10. The compound according to claim 1, or a tautomer thereof, or a pharmaceutically acceptable salt of said compound or tautomer, wherein Y is $NR^1$.

11. The compound according to claim 1, or a tautomer thereof, or a pharmaceutically acceptable salt of said compound or tautomer, wherein $R^1$ is

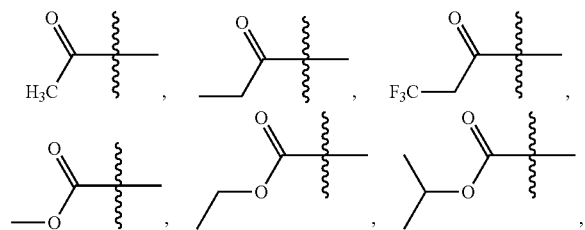

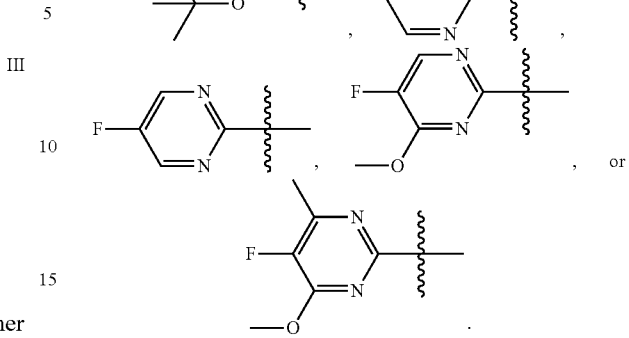

12. The compound according to claim 1, or a tautomer thereof, or a pharmaceutically acceptable salt of said compound or tautomer, wherein
$R^1$ is a 6-membered nitrogen-containing heteroaryl, wherein the heteroaryl is optionally substituted with 1 to 3 substituents independently selected from halogen, $C_{1-6}$alkyl, or $C_{1-6}$alkoxy.

13. The compound according to claim 1, or a tautomer thereof, or a pharmaceutically acceptable salt of said compound or tautomer, wherein
$R^1$ is pyrimidinyl optionally substituted with 1 to 3 substituents independently selected from halogen, $C_{1-6}$alkyl, or $C_{1-6}$alkoxy.

14. The compound according to claim 1, or a tautomer thereof, or a pharmaceutically acceptable salt of said compound or tautomer, wherein
$R^1$ is

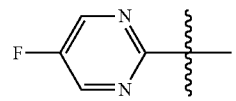

15. The compound according to claim 1, or a tautomer thereof, or a pharmaceutically acceptable salt of said compound or tautomer, wherein
$R^2$ is H, methyl, monofluoromethyl, difluoromethyl, or trifluoromethyl.

16. The compound according to claim 1, or a tautomer thereof, or a pharmaceutically acceptable salt of said compound or tautomer, wherein
$R^2$ is trifluoromethyl.

17. The compound according to claim 1, or a tautomer thereof, or a pharmaceutically acceptable salt of said compound or tautomer, wherein $R^3$ is F.

18. The compound according to claim 1, or a tautomer thereof, or a pharmaceutically acceptable salt of said compound or tautomer, wherein $R^5$ and $R^6$ is F or H and the other of $R^5$ and $R^6$ is pyridyl or pyrazinyl, which pyridyl or pyrazinyl is optionally substituted with 1 to 3 substituents independently selected from halogen, —CN, $C_{1-6}$alkyl, $C_{1-6}$alkoxy, 2-propynyloxy, 2-butynyloxy, 3-butyn-2-yloxy, or (3-methyl-1,2,4-oxadiazol-5-yl)methoxy,
wherein the $C_{1-6}$alkyl or $C_{1-6}$alkoxy is optionally substituted with 1 to 4 substituents independently selected from F or methoxy.

19. The compound according to claim 1, or a tautomer thereof, or a pharmaceutically acceptable salt of said compound or tautomer, wherein $R^5$ and $R^6$ is F or H and the other of $R^5$ and $R^6$ is pyridyl or pyrazinyl, which pyridyl or pyrazinyl is optionally substituted with 1 to 3 substituents independently selected from —CN, $C_{1-6}$alkyl, $C_{1-6}$alkoxy, 2-propynyloxy, 2-butynyloxy, 3-butyn-2-yloxy, or (3-methyl-1,2,4-oxadiazol-5-yl)methoxy, wherein the $C_{1-6}$alkyl or $C_{1-6}$alkoxy is optionally substituted with 1 to 4 substituents independently selected from F or methoxy.

20. The compound according to claim 1, or a tautomer thereof, or a pharmaceutically acceptable salt of said compound or tautomer, wherein one of $R^6$ and $R^5$ is

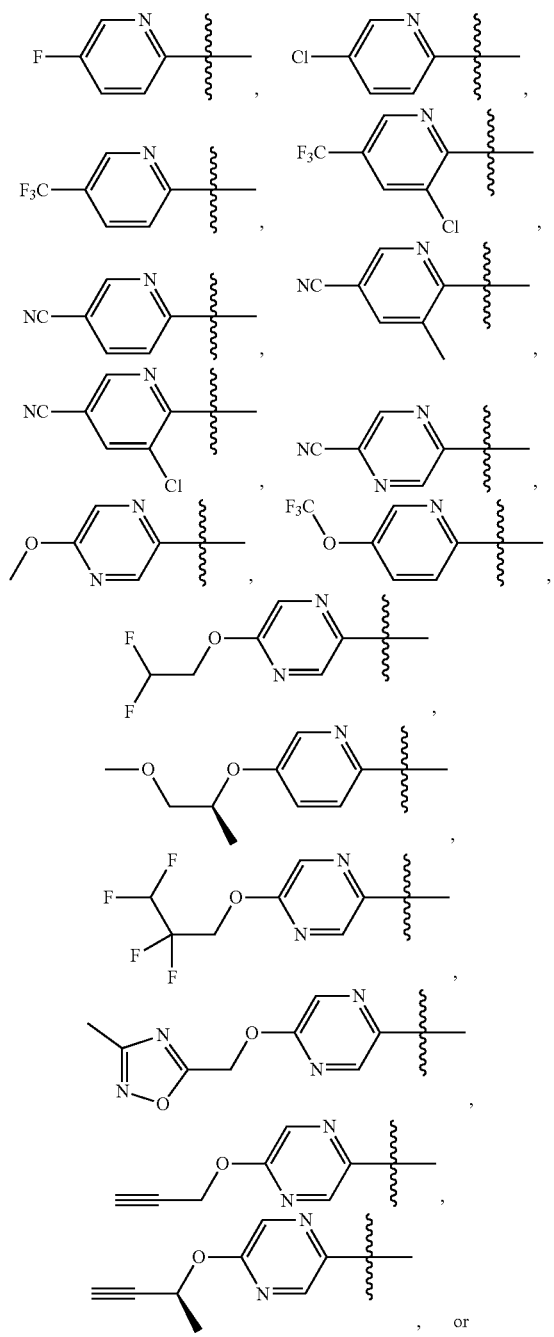

, or

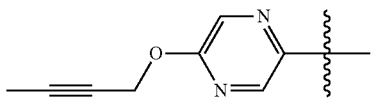

21. The compound according to claim 1, or a tautomer thereof, or a pharmaceutically acceptable salt of said compound or tautomer, wherein one of $R^6$ and $R^5$ is

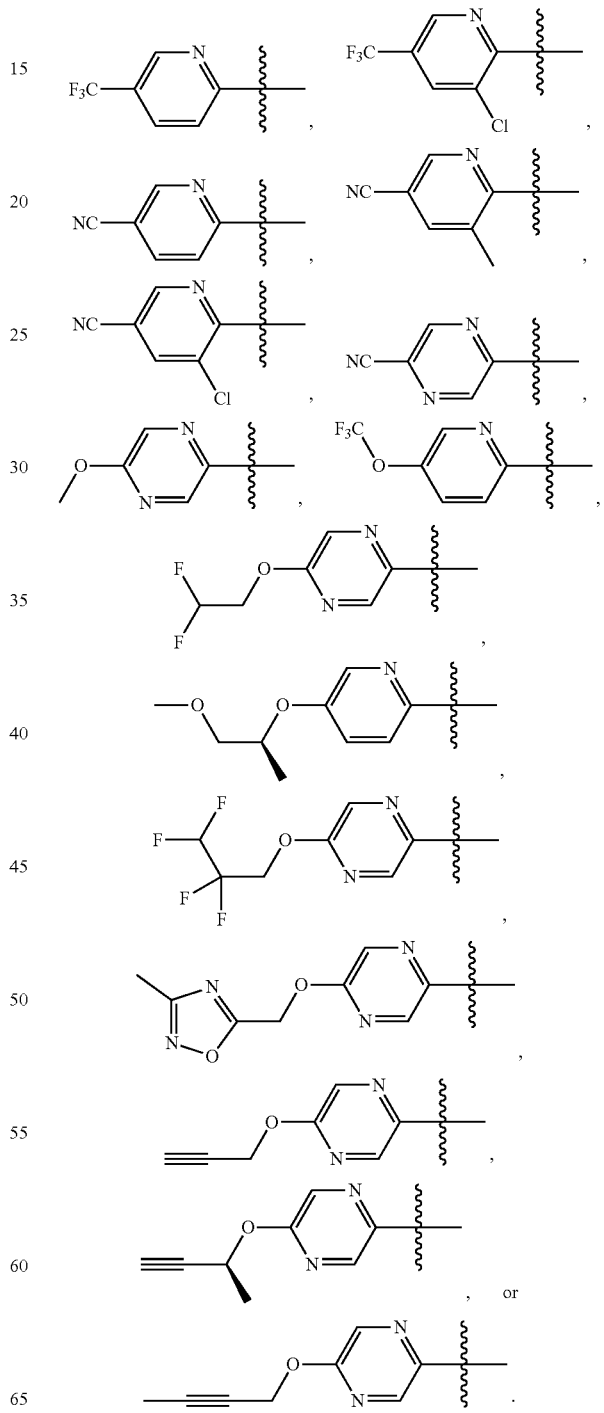

22. The compound according to claim 1, or a tautomer thereof, or a pharmaceutically acceptable salt of said compound or tautomer, wherein
$R^4$ is H and $R^3$ is H;
$R^4$ is H and $R^6$ is H;
$R^4$ is F and $R^5$ is H
$R^4$ is F and $R^6$ is H; or
$R^4$ is H and $R^6$ is F.

23. The compound according to claim 1, or a tautomer thereof, or a pharmaceutically acceptable salt of said compound or tautomer, wherein
$R^4$ is H; and
$R^5$ is F.

24. The compound of claim 1, or a tautomer thereof, or a pharmaceutically acceptable salt of said compound or tautomer, selected from
(4aS,7aR)-7a-(5-((Z)-2-(5-chloropyridin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;
(4aR,7aS)-7a-(5-((Z)-2-(5-chloropyridin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;
6-((Z)-2-(3-((4aR,7aS)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)nicotinonitrile;
6-((Z)-2-(3-((4aS,7aR)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)nicotinonitrile;
(4aR,7aR)-7a-(5-((Z)-2-(5-chloropyridin-2-yl)-2-fluorovinyl)-2-fluorophenyl)-4a,5,7,7a-tetrahydro-4H-furo[3,4-d][1,3]thiazin-2-amine;
(4aS,7aS)-7a-(5-((Z)-2-(5-chloropyridin-2-yl)-2-fluorovinyl)-2-fluorophenyl)-4a,5,7,7a-tetrahydro-4H-furo[3,4-d][1,3]thiazin-2-amine;
6-((Z)-2-(3-((4aR,7aR)-2-amino-4a,5,7,7a-tetrahydro-4H-furo[3,4-d][1,3]thiazin-7a-yl)-4-fluorophenyl)-1-fluorovinyl)nicotinonitrile;
6-((Z)-2-(3-((4aS,7aS)-2-amino-4a,5,7,7a-tetrahydro-4H-furo[3,4-d][1,3]thiazin-7a-yl)-4-fluorophenyl)-1-fluorovinyl)nicotinonitrile;
(4aR,7aS)-7a-(2-fluoro-5-((Z)-2-fluoro-2-(5-methoxypyrazin-2-yl)vinyl)phenyl)-6-(5-fluoropyrimidin-2-yl)-4,4a,5,6,7,7a-hexahydropyrrolo[3,4-d][1,3]thiazin-2-amine;
(4aR,7aS)-7a-(2-fluoro-5-((Z)-2-fluoro-2-(5-(prop-2-yn-1-yloxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;
(4aR,7aS)-7a-(2-fluoro-5-((Z)-2-fluoro-2-(5-((3-methyl-1,2,4-oxadiazol-5-yl)methoxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;
5-((Z)-2-(3-((4aR,7aS)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)pyrazine-2-carbonitrile;
(4aR,7aS)-7a-(2-fluoro-5-((Z)-2-fluoro-2-(5-(2,2,3,3-tetrafluoropropoxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;
(4aR,7aS)-7a-(5-((Z)-2-(5-(2,2-difluoroethoxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;
(4aR,7aS)-7a-(2-fluoro-5-((Z)-2-fluoro-2-(5-(((S)-1-methoxypropan-2-yl)oxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;
(4aR,7aS)-7a-(5-((Z)-2-(5-((S)-but-3-yn-2-yloxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;
(4aR,7aS)-tert-butyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;
(4aR,7aS)-7a-(5-((Z)-2-(5-(but-2-yn-1-yloxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;
1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)ethanone;
1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)-3,3,3-trifluoropropan-1-one;
(4aR,7aS)-7a-(2-fluoro-5-((Z)-2-fluoro-2-(5-(prop-2-yn-1-yloxy)pyrazin-2-yl)vinyl)phenyl)-6-(pyrimidin-2-yl)-4,4a,5,6,7,7a-hexahydropyrrolo[3,4-d][1,3]thiazin-2-amine;
(4aR,7aS)-methyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;
1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)propan-1-one;
(4aR,7aS)-ethyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;
(4aR,7aS)-isopropyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;
6-((Z)-2-(3-((4aR,5R,7aR)-2-amino-5-(trifluoromethyl)-4a,5,7,7a-tetrahydro-4H-furo[3,4-d][1,3]thiazin-7a-yl)-4-fluorophenyl)-1-fluorovinyl)nicotinonitrile;
6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)nicotinonitrile;
(4aS,5S,7aS)-7a-(2-fluoro-5-((Z)-2-fluoro-2-(5-(prop-2-ynyloxy)pyrazin-2-yl)vinyl)phenyl)-5-(trifluoromethyl)-4a,5,7,7a-tetrahydro-4H-furo[3,4-d][1,3]thiazin-2-amine;
5-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)pyrazine-2-carbonitrile;
(4aS,5S,7aS)-7a-(2-fluoro-5-((Z)-2-fluoro-2-(5-(trifluoromethoxy)pyridin-2-yl)vinyl)phenyl)-5-(trifluoromethyl)-4a,5,7,7a-tetrahydro-4H-furo[3,4-d][1,3]thiazin-2-amine;
6-((Z)-2-(3-((4aR,7aS)-2-amino-6-(5-fluoro-4-methoxy-6-methylpyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aS,5S,7aS)-2-amino-5-(fluoromethyl)-4a,5,7,7a-tetrahydro-4H-furo[3,4-d][1,3]thiazin-7a-yl)-4-fluorophenyl)-1-fluorovinyl)nicotinonitrile;

(4aS,5S,7aS)-7a-(2-fluoro-5-((Z)-2-fluoro-2-(5-fluoropyridin-2-yl)vinyl)phenyl)-5-(trifluoromethyl)-4a,5,7,7a-tetrahydro-4H-furo[3,4-d][1,3]thiazin-2-amine;

6-((Z)-2-(3-((4aR,5R,7aR)-2-amino-5-(fluoromethyl)-4a,5,7,7a-tetrahydro-4H-furo[3,4-d][1,3]thiazin-7a-yl)-4-fluorophenyl)-1-fluorovinyl)nicotinonitrile;

6-((Z)-2-(3-((4aR,7aS)-2-amino-6-(5-fluoro-4-methoxypyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aR,7aS)-2-amino-6-(pyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

(4aS,5S,7aS)-7a-(2-fluoro-5-((Z)-2-fluoro-2-(5-methoxypyrazin-2-yl)vinyl)phenyl)-5-(trifluoromethyl)-4a,5,7,7a-tetrahydro-4H-furo[3,4-d][1,3]thiazin-2-amine;

(4aS,5S,7aS)-7a-(5-((Z)-2-(3-chloro-5-(trifluoromethyl)pyridin-2-yl)-2-fluorovinyl)-2-fluorophenyl)-5-(trifluoromethyl)-4a,5,7,7a-tetrahydro-4H-furo[3,4-d][1,3]thiazin-2-amine;

6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)-5-methylnicotinonitrile;

(4aS,5S,7aS)-7a-(2-fluoro-5-((Z)-2-fluoro-2-(5-(trifluoromethyl)pyridin-2-yl)vinyl)phenyl)-5-(trifluoromethyl)-4a,5,7,7a-tetrahydro-4H-furo[3,4-d][1,3]thiazin-2-amine;

6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)-5-chloronicotinonitrile;

6-((Z)-2-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-1-fluorovinyl)nicotinonitrile;

6-((Z)-2-(3-((4aS,5R,7aR)-2-amino-5-(trifluoromethyl)-4a,5,7,7a-tetrahydro-4H-furo[3,4-d][1,3]oxazin-7a-yl)-4-fluorophenyl)-1-fluorovinyl)nicotinonitrile;

6-((Z)-2-(3-((4aS,5S,7aS)-2-amino-5-(difluoromethyl)-4a,5,7,7a-tetrahydro-4H-furo[3,4-d][1,3]thiazin-7a-yl)-4-fluorophenyl)-1-fluorovinyl)nicotinonitrile;

6-((Z)-2-(3-((4aR,5R,7aR)-2-amino-5-(difluoromethyl)-4a,5-dihydro-4H-furo[3,4-d][1,3]thiazin-7a(7H)-yl)-4-fluorophenyl)-1-fluorovinyl)nicotinonitrile; or (4aS,5S,7aS)-5-(difluoromethyl)-7a-(2-fluoro-5-((Z)-2-fluoro-2-(5-(trifluoromethyl)pyridin-2-yl)vinyl)phenyl)-4a,5,7,7a-tetrahydro-4H-furo[3,4-d][1,3]thiazin-2-amine.

25. The compound of claim 1, or a tautomer thereof, or a pharmaceutically acceptable salt of said compound or tautomer, selected from 6-((Z)-2-(3-((4aR,7aS)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aS,7aR)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aR,7aR)-2-amino-4a,5,7,7a-tetrahydro-4H-furo[3,4-d][1,3]thiazin-7a-yl)-4-fluorophenyl)-1-fluorovinyl)nicotinonitrile;

6-((Z)-2-(3-((4aS,7aS)-2-amino-4a,5,7,7a-tetrahydro-4H-furo[3,4-d][1,3]thiazin-7a-yl)-4-fluorophenyl)-1-fluorovinyl)nicotinonitrile;

(4aR,7aS)-7a-(2-fluoro-5-((Z)-2-fluoro-2-(5-methoxypyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(2-fluoro-5-((Z)-2-fluoro-2-(5-(prop-2-yn-1-yloxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(2-fluoro-5-((Z)-2-fluoro-2-(5-((3-methyl-1,2,4-oxadiazol-5-yl)methoxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

5-((Z)-2-(3-((4aR,7aS)-2-amino-6-(5-fluoropyrimidin-2-yl)-4,4a,5,6,7,7a-hexahydropyrrolo[3,4-d][1,3]thiazin-7a-yl)-4-fluorophenyl)-1-fluorovinyl)pyrazine-2-carbonitrile;

(4aR,7aS)-7a-(2-fluoro-5-((Z)-2-fluoro-2-(5-(2,2,3,3-tetrafluoropropoxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(5-((Z)-2-(5-(2,2-difluoroethoxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

(4aR,7aS)-7a-(2-fluoro-5-((Z)-2-fluoro-2-(5-(((S)-1-methoxypropan-2-yl)oxy)pyrazin-2-yl)vinyl)phenyl)-6-(5-fluoropyrimidin-2-yl)-4,4a,5,6,7,7a-hexahydropyrrolo[3,4-d][1,3]thiazin-2-amine;

(4aR,7aS)-7a-(5-((Z)-2-(5-((S)-but-3-yn-2-yloxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

(4aR,7aS)-tert-butyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

(4aR,7aS)-7a-(5-((Z)-2-(5-(but-2-yn-1-yloxy)pyrazin-2-yl)-2-fluorovinyl)-2-fluorophenyl)-6-(5-fluoropyrimidin-2-yl)-4,4a,5,6,7,7a-hexahydropyrrolo[3,4-d][1,3]thiazin-2-amine;

1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)ethanone;

1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)-3,3,3-trifluoropropan-1-one;

(4aR,7aS)-7a-(2-fluoro-5-((Z)-2-fluoro-2-(5-(prop-2-yn-1-yloxy)pyrazin-2-yl)vinyl)phenyl)-6-(pyrimidin-2-yl)-4,4a,5,6,7,7a-hexahydropyrrolo[3,4-d][1,3]thiazin-2-amine;

(4aR,7aS)-methyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

1-((4aR,7aS)-2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazin-6(4H)-yl)propan-1-one;

(4aR,7aS)-ethyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

(4aR,7aS)-isopropyl 2-amino-7a-(2-fluoro-5-((Z)-2-fluoro-2-(5-(prop-2-yn-1-yloxy)pyrazin-2-yl)vinyl)phenyl)-4a,5,7,7a-tetrahydropyrrolo[3,4-d][1,3]thiazine-6(4H)-carboxylate;

6-((Z)-2-(3-((4aR,5R,7aR)-2-amino-5-(trifluoromethyl)-4a,5,7,7a-tetrahydro-4H-furo[3,4-d][1,3]thiazin-7a-yl)-4-fluorophenyl)-1-fluorovinyl)nicotinonitrile;

6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)nicotinonitrile;

(4aS,5S,7aS)-7a-(2-fluoro-5-((Z)-2-fluoro-2-(5-(prop-2-ynyloxy)pyrazin-2-yl)vinyl)phenyl)-5-(trifluoromethyl)-4a,5,7,7a-tetrahydro-4H-furo[3,4-d][1,3]thiazin-2-amine;

5-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)pyrazine-2-carbonitrile;

(4aS,5S,7aS)-7a-(2-fluoro-5-((Z)-2-fluoro-2-(5-(trifluoromethoxy)pyridin-2-yl)vinyl)phenyl)-5-(trifluoromethyl)-4a,5,7,7a-tetrahydro-4H-furo[3,4-d][1,3]thiazin-2-amine;

6-((Z)-2-(3-((4aR,7aS)-2-amino-6-(5-fluoro-4-methoxy-6-methylpyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aS,5S,7aS)-2-amino-5-(fluoromethyl)-4a,5,7,7a-tetrahydro-4H-furo[3,4-d][1,3]thiazin-7a-yl)-4-fluorophenyl)-1-fluorovinyl)nicotinonitrile;

(4aS,5S,7aS)-7a-(2-fluoro-5-((Z)-2-fluoro-2-(5-fluoropyridin-2-yl)vinyl)phenyl)-5-(trifluoromethyl)-4a,5,7,7a-tetrahydro-4H-furo[3,4-d][1,3]thiazin-2-amine;

6-((Z)-2-(3-((4aR,5R,7aR)-2-amino-5-(fluoromethyl)-4a,5,7,7a-tetrahydro-4H-furo[3,4-d][1,3]thiazin-7a-yl)-4-fluorophenyl)-1-fluorovinyl)nicotinonitrile;

6-((Z)-2-(3-((4aR,7aS)-2-amino-6-(5-fluoro-4-methoxypyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

6-((Z)-2-(3-((4aR,7aS)-2-amino-6-(pyrimidin-2-yl)-4,4a,5,6,7,7a-hexahydropyrrolo[3,4-d][1,3]thiazin-7a-yl)-4-fluorophenyl)-1-fluorovinyl)nicotinonitrile;

(4aS,5S,7aS)-7a-(2-fluoro-5-((Z)-2-fluoro-2-(5-methoxypyrazin-2-yl)vinyl)phenyl)-5-(trifluoromethyl)-4a,5,7,7a-tetrahydro-4H-furo[3,4-d][1,3]thiazin-2-amine;

(4aS,5S,7aS)-7a-(5-((Z)-2-(3-chloro-5-(trifluoromethyl)pyridin-2-yl)-2-fluorovinyl)-2-fluorophenyl)-5-(trifluoromethyl)-4a,5,7,7a-tetrahydro-4H-furo[3,4-d][1,3]thiazin-2-amine;

6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)-5-methylnicotinonitrile;

(4aS,5S,7aS)-7a-(2-fluoro-5-((Z)-2-fluoro-2-(5-(trifluoromethyl)pyridin-2-yl)vinyl)phenyl)-5-(trifluoromethyl)-4a,5,7,7a-tetrahydro-4H-furo[3,4-d][1,3]thiazin-2-amine;

6-((Z)-2-(3-((4aS,5S,7aS)-2-amino-5-(trifluoromethyl)-4a,5,7,7a-tetrahydro-4H-furo[3,4-d][1,3]thiazin-7a-yl)-4-fluorophenyl)-1-fluorovinyl)-5-chloronicotinonitrile;

6-((Z)-2-(3-((4aR,5S,7aS)-2-amino-5-(trifluoromethyl)-4a,5,7,7a-tetrahydro-4H-furo[3,4-d][1,3]oxazin-7a-yl)-4-fluorophenyl)-1-fluorovinyl)nicotinonitrile;

6-((Z)-2-(3-((4aS,5R,7aR)-2-amino-5-(trifluoromethyl)-4a,5,7,7a-tetrahydro-4H-furo[3,4-d][1,3]oxazin-7a-yl)-4-fluorophenyl)-1-fluorovinyl)nicotinonitrile;

6-((Z)-2-(3-((4aS,5S,7aS)-2-amino-5-(difluoromethyl)-4a,5,7,7a-tetrahydro-4H-furo[3,4-d][1,3]thiazin-7a-yl)-4-fluorophenyl)-1-fluorovinyl)nicotinonitrile; or 6-((Z)-2-(3-((4aR,5R,7aR)-2-amino-5-(difluoromethyl)-4a,5-dihydro-4H-furo[3,4-d][1,3]thiazin-7a(7H)-yl)-4-fluorophenyl)-1-fluorovinyl)nicotinonitrile.

26. The compound of claim 1, or a tautomer thereof, or a pharmaceutically acceptable salt of said compound or tautomer, wherein the compound is

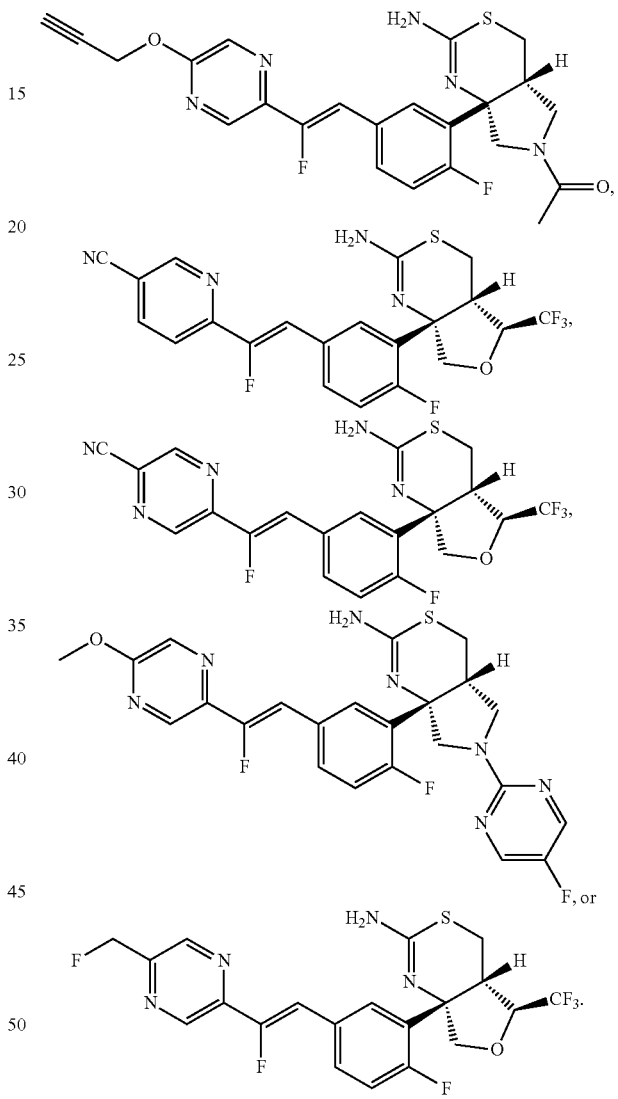

27. A pharmaceutical composition comprising the compound according to claim 1, or a tautomer thereof, or a pharmaceutically acceptable salt of said compound or tautomer, and a pharmaceutically acceptable excipient.

28. A method of reducing beta amyloid peptide levels in the cerebral spinal fluid of a subject in need thereof, the method comprising administering to the subject a therapeutically effective amount of the compound according to claim 1, or a tautomer thereof, or a pharmaceutically acceptable salt of said compound or tautomer.

29. A method of reducing the formation of plaque on the brain of a subject in need thereof, the method comprising administering to the subject a therapeutically effective amount of the compound according to claim 1, or a tautomer thereof, or a pharmaceutically acceptable salt of said compound or tautomer.

\* \* \* \* \*